US012037601B2

(12) United States Patent
Chapman et al.

(10) Patent No.: US 12,037,601 B2
(45) Date of Patent: Jul. 16, 2024

(54) METHOD OF INACTIVATING A FEL D1 GENE USING CRISPR

(71) Applicant: Indoor Biotechnologies Inc., Charlottesville, VA (US)

(72) Inventors: Martin D. Chapman, Charlottesville, VA (US); Olya Spassibojko, Marlboro, NJ (US)

(73) Assignee: Indoor Biotechnologies Inc., Charlottesville, VA (US)

( * ) Notice: Subject to any disclaimer, the term of this patent is extended or adjusted under 35 U.S.C. 154(b) by 0 days.

(21) Appl. No.: 16/082,157

(22) PCT Filed: Mar. 3, 2017

(86) PCT No.: PCT/US2017/020609
§ 371 (c)(1),
(2) Date: Sep. 4, 2018

(87) PCT Pub. No.: WO2017/152023
PCT Pub. Date: Sep. 8, 2017

(65) Prior Publication Data
US 2019/0330660 A1    Oct. 31, 2019

Related U.S. Application Data

(60) Provisional application No. 62/303,686, filed on Mar. 4, 2016.

(51) Int. Cl.
| | | |
|---|---|---|
| C12N 5/00 | (2006.01) | |
| A01K 67/0276 | (2024.01) | |
| C12N 15/11 | (2006.01) | |
| C12N 15/90 | (2006.01) | |

(52) U.S. Cl.
CPC ........ *C12N 15/907* (2013.01); *A01K 67/0276* (2013.01); *C12N 15/11* (2013.01); *A01K 2217/075* (2013.01); *A01K 2227/10* (2013.01); *A01K 2267/02* (2013.01); *C12N 2310/20* (2017.05); *C12N 2800/80* (2013.01)

(58) Field of Classification Search
CPC ................................................. A01K 67/0276
USPC ........................................................... 800/8
See application file for complete search history.

(56) References Cited

U.S. PATENT DOCUMENTS

| | | |
|---|---|---|
| 6,697,669 B2 | 2/2004 | Dev et al. |
| 8,697,359 B1 | 4/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 10,626,417 B2 * | 4/2020 | Avner .................. C12N 15/873 |
| 2003/0177512 A1 | 9/2003 | Avner |
| 2004/0141994 A1 | 7/2004 | Weller et al. |
| 2009/0298168 A1 | 12/2009 | Avner et al. |
| 2011/0023156 A1 | 1/2011 | Bedell et al. |
| 2012/0142110 A1 | 6/2012 | Avner et al. |
| 2012/0192298 A1 | 7/2012 | Weinstein et al. |
| 2014/0068797 A1 | 3/2014 | Doudna et al. |
| 2014/0134739 A1 | 5/2014 | Avner |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0248702 A1 | 9/2014 | Zhang et al. |
| 2014/0256046 A1 | 9/2014 | Zhang et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0287938 A1 | 9/2014 | Zhang et al. |

(Continued)

FOREIGN PATENT DOCUMENTS

| | | |
|---|---|---|
| CA | 2369672 | 6/2010 |
| JP | 2013500018 A | 1/2013 |

(Continued)

OTHER PUBLICATIONS

Sartore, Vet. Sci., 2017, vol. 4, No. 63, p. 1-5.*
Gomez (Theriogenology, 2010, vol. 74, p. 498-515).*
Ezashi (Annual Rev. Animal Biosci., 2016, vol. 4, p. 223-253).*
Dutton (Stem Cells and Develop., 2019, vol. 28, No. 19, p. 1299-1309).*
Yin (Biol. Reproduction, 2008, vol. 78, p. 425-431).*
Gomez (Cloning and Stem Cells, 2009, vol. 11, No. 1, p. 167-175).*
Cong (Sci., 2013, vol. 339, No. 6121, p. 819-823).*
Gronlund (Int Arch Allergy Immunol, 2010, vol. 151, p. 265-274).*
Pereyra-Bonnet (Reprod., Fertility and Develop., 2008, vol. 20, p. 741-749).*

(Continued)

*Primary Examiner* — Michael C Wilson
(74) *Attorney, Agent, or Firm* — New River Valley IP Law, P.C.; Michele L. Mayberry; Ashley M. Gates

(57) ABSTRACT

Compositions and methods for genetically modifying felines or feline cells are described. The compositions and methods are useful for knocking out all or a portion of a Fel d 1 gene from a feline genome. Feline cells and organisms in which all or a portion of the Fel d 1 gene is knocked out are also described. The compositions and methods may include reagents and procedures for CRISPR-Cas9-mediated genomic editing of Fel d 1.

1 Claim, 9 Drawing Sheets

Specification includes a Sequence Listing.

(56) References Cited

U.S. PATENT DOCUMENTS

| | | |
|---|---|---|
| 2014/0310830 A1 | 10/2014 | Zhang et al. |
| 2014/0335620 A1 | 11/2014 | Zhang et al. |
| 2014/0357530 A1 | 12/2014 | Zhang et al. |
| 2015/0020223 A1 | 1/2015 | Zhang et al. |
| 2015/0031134 A1 | 1/2015 | Zhang et al. |
| 2015/0079681 A1 | 3/2015 | Zhang |
| 2015/0184139 A1 | 7/2015 | Zhang et al. |
| 2015/0203872 A1 | 7/2015 | Zhang |
| 2015/0232882 A1 | 8/2015 | Zhang et al. |
| 2015/0232883 A1 | 8/2015 | Dahlman et al. |
| 2015/0247150 A1 | 9/2015 | Zhang et al. |
| 2015/0291965 A1 | 10/2015 | Zhang et al. |
| 2015/0291966 A1 | 10/2015 | Zhang et al. |
| 2015/0344908 A1 | 12/2015 | Avner |
| 2015/0356239 A1 | 12/2015 | Zhang et al. |
| 2017/0107540 A1 | 4/2017 | Avner |
| 2020/0008405 A1* | 1/2020 | Avner ............... C12N 5/0696 |

FOREIGN PATENT DOCUMENTS

| | | |
|---|---|---|
| KR | 2018022465 * | 6/2018 |
| WO | 2007113633 A2 | 10/2007 |
| WO | 2010053472 A1 | 5/2010 |
| WO | 2013142578 A1 | 9/2013 |
| WO | 2014131833 A1 | 9/2014 |
| WO | 2015048577 A2 | 4/2015 |
| WO | 2017124022 A3 | 9/2017 |
| WO | 2017152023 A1 | 9/2017 |

OTHER PUBLICATIONS

Cho (Cellular Reprogramming, 2010, vol. 12, No. 9, p. 739-747).*
Callaway, Nature, Jan. 2015, vol. 252, vol. 517, p. 252-253.*
KR 2018022465 translation, 2018.*
Mettelman (Virology, 2019, vol. 537, p. 226-236).*
Brackett (Allergy, 2020, vol. 75, p. 59-60).*
Brackett (Frontiers in allergy, 2021, vol. 2, p. 821107).*
Brackett (J Allergy Clin Immunol., 2021, vol. 147, AB175).*
Allerca: The Former Hypoallergenic Pets Creator; http://allerca.com/; Accessed as early as Dec. 7, 2015.
Aronovich, E.L., The Sleeping Beauty transposon system: a non-viral vector for gene therapy, Hum Mol Genet. Apr. 15, 2011; 20(R1): R14-R20.
ATCC; Manassas, Virginia; https://www.atcc.org; Accessed as early as Mar. 4, 2016.
Atschul, S. F., et al., Basic Local Alignment Search Tool, J Molec Biol 215:403 (1990).
Bahassi and Stambrook, Next-generation sequencing technologies: breaking the sound barrier of human genetics, Mutagenesis, Sep. 2014; 29(5):303-10).
Blessing et al., Overexpression of bone morphogenetic protein-6 (BMP-6) in the epidermis of transgenic mice: inhibition or stimulation of proliferation depending on the pattern of transgene expression and formation of psoriatic lesions. J. Cell. Biol., 135, 227-39 (1993).
Blessing et al., Transgenic mice as a model to study the role of TGF-13-related molecules in hair follicles Genes. Devel., 7, 204-15. (1993).
Byrne et al., Probing keratinocyte and differentiation specificity of the human K5 promoter in vitro and in transgenic mice, Mol. Cell. Biol., 13, 3176-90 (1993).
Chapman et al., The European Union Create Project: A model for international standardization of allergy diagnostics and vaccines, J Allergy Clin Immunol, 122(5):882-889 (2008).
Cong et al., Multiplex Genome Engineering Using CRISPR/Cas Systems, Science Feb. 15, 2013: 339 (6121), 819-823.
Co-pending International Application PCT/US2017/020609, filed Mar. 3, 2017, published as WO/2017/152023 on Sep. 8, 2017.
Co-pending International Application PCT/US2017/020609, International Preliminary Report on Patentability, Sep. 4, 2018, 19 pages.
Co-pending International Application PCT/US2017/020609, International Search Report and Written Opinion, Jul. 20, 2017, 26 pages.
CRISPR Design. Zhang Lab, Massachusetts Institute of Technology; Cambridge, MA; http://crispr.mit.edu/; Accessed as early as Mar. 4, 2016.
CRISPR Plasmids and Resources; http://www.addgene.org/crispr/; Addgene; Cambridge, MA; Accessed as early as Dec. 7, 2015.
Denning C, and Priddle, H, New frontiers in gene targeting and cloning: success, application and challenges in domesticanimals and human embryonic stem cells, Reproduction (2003) 126, 1-11.
Devereux, J., et al., A comprehensive set of sequence analysis programs for the VAX, Nucleic Acids Research 12 (1):387 (1984).
Doudna JA and Charpentier E, The new frontier of genome engineering with CRISPR-Cas9, Science, 2014, 346:6213, 1258096-1-9.
Dr. Feng Zhang; The Broad Institute; Cambridge MA; http://www.genomeengineering.org/crispr/; Accessed as early as Mar. 4, 2016.
E-CRISP; Design of CRISPR constructs; German Cancer Research Center; Heidelberg, Germany; http://www.e-crisp.org/E-CRISP/; Accessed as early as Mar. 4, 2016.
Grada and Weinbrecht, Next-Generation Sequencing: Methodology and Application, Journal of Investigative Dermatology (2013) 133, e11.
Grönlund et al., Formation of Disulfide Bonds and Homodimers of the Major Cat Allergen Fel d 1 Equivalent to the Natural Allergen by Expression in *Escherichia coli*, J. Biol. Chem., vol. 278, No. 41, pp. 40144-40141 (Oct. 10, 2003).
Grönlund et al., The Major Cat Allergen, Fel d 1, in Diagnosis and Therapy, Int Arch Allergy Immunol (2010), 151:265-274.
Hsu et al, DNA targeting specificity of RNA-guided Cas9 nucleases, Nature Biotechnology 31, 827-832 (2013).
Integrated DNA Technologies; Skokie, Illinois; https://www.idtdna.com/pages/home; Accessed as early as Dec. 7, 2015.
Isolation of High-molecular-weight (genomic) DNA from Mammalian Cells using Proteinase K and Phenol; http://www.unc.edu/depts/marzluff/Marzluff/Protocols_files/Isolation%20of%20genomic%20DNA%20from%20tissue%20culture%20cells.pdf; Accessed as early as Mar. 4, 2016.
Jinek et al., A Programmable Dual-RNA-Guided DNA Endonuclease in Adaptive Bacterial Immunity, Science 337, 816 (2012).
Kaiser L, Velickovic TC, Badia-Martinez D, Adedoyin J, Thunberg S, Hallén D, Berndt K, Grönlund H, Gafvelin G, van Hage M, Achour A. Structural characterization of the tetrameric form of the major cat allergen Fel d 1. J Mol Biol. Jul. 20, 2007;370(4):714-27.
Metzger, D. & Feil, R. Engineering the mouse genome by site-specific recombination. Curr. Opin. Biotechnol. (1999) 10, 470-476.
Morgenstern, et al., Amino acid sequence of Fel dl, the major allergen of the domestic cat: Protein sequence analysis and cDNA cloning, Proc Natl Acad Sci USA, 88(21):9690-9694 (1991).
Ola Germaniuk; Isolation of Total DNA From Mammalian Cells; http://groups.molbiosci.northwestern.edu/morimoto/research/Protocols/IV.%20DNA/B.%20Prep%20of%20DNA/B3.%20Isolation%20of%20total%20DNA%20.pdf; Accessed as early as Mar. 4, 2016.
Pontius, J.U., Initial sequence and comparative analysis of the cat genome, Genome Res. 17 (11), 1675-1689 (2007)).
Preparation of Genomic DNA; http://www4.utsouthwestern.edu/trosslab/protocols/southern_blot/preparation_of_genomic_dna.pdf; Accessed as early as Mar. 4, 2016.
Ran et al., Genome engineering using the CRISPR-Cas9 system, Nat Protoc. Nov. 8, 2013(11): 2281-2308.
Shin et al., A cat cloned by nuclear transplantation: This kitten's coat-coloration pattern is not a carbon copy of its genome donor's, Nature, vol. 415 (2002), 859.
The Broad Institute; Cambridge MA; https://www.broadinstitute.org/; Accessed as early as Mar. 4, 2016.
Wang et al., "One-Step Generation of Mice Carrying Mutations in Multiple Genes by CRISPR/Cas-Mediated Genome Engineering", Cell, 153(4): 910-918, 2013.
Wang, B, and Zhou, J, Specific genetic modifications of domestic animals by gene targeting and animal cloning, Reproductive Biology and Endocrinology (2003), 1:103.

(56) References Cited

OTHER PUBLICATIONS

Wongsrikeao et al., Antiviral restriction factor transgenesis in the domestic cat, Nat Methods.; 8(10): 853-859 (2011).
Yang et al., "One-Step Generation of Mice Carrying Reporter and Conditional Alleles by CRISPR/Cas-Mediated Genome Engineering", Cell, 154(6):1370-1379, 2013.
Yanni Lin, et al., CRISPR/Cas9 systems have off-target activity with insertions or deletions between target DNA and guide RNA sequences, Nucleic Acids Research, vol. 42, Issue 11, Jun. 17, 2014, pp. 7473-7485, https://doi.org/10.1093/nar/gku402.
Co-pending European Application No. 17760881.7, Communication Pursuant to Rules 161(2) and 162 EPC dated Oct. 25, 2018, 3 pages.
Co-pending European Application No. 17760881.7, Communication Pursuant to Rules 70(2) and 70a(2) EPC, dated Sep. 19, 2019, 1 page.
Co-pending European Application No. 17760881.7, Extended European Search Report, dated Aug. 30, 2019, 3 pages.
Co-pending European Application No. 17760881.7, Response to Sep. 19, 2019 Office Action, dated Mar. 27, 2020, 21 pages.
Carillo, H. & Lipton, D., The Multiple Sequence Alignment Problem in Biology, Siam J Applied Math 48:1073 (1988).
Co-pending Canadian Application No. 3,016,571, official filing date Mar. 3, 2017, see also WO2017/152023.
Co-pending European Application No. 17760881.7, official filing date Mar. 3, 2017, see also WO2017/152023.
Co-pending Japanese Application No. 2018-566187, official filing date Mar. 3, 2017, see also WO2017/152023.
Griffith, IJ et al. Expression and Genomic Structure of the Genes Encoding Fdl, The Major Allergen from the Domestic Cat. Gene. Apr. 15, 1992; vol. 113, No. 2; pp. 263-268.
Heigwer, F., Kerr, G. & Boutros, M. , E-CRISP: fast CRISPR target site identification. Nat. Methods 11, 122-123 (2014).
Kaiser L, Grönlund H, Sandalova T, Ljunggren HG, van Hage-Hamsten M., Achour A, Schneider G, The Crystal Structure of the Major Cat Allergen Fel d 1, a Member of the Secretoglobin Family, J. of Biological Chem., vol. 278, No. 39, Issue of Sep. 26, pp. 37730-37735, 2003.
Kalesnikoff J. & Galli S.J., "Nipping cat allergy with fusion proteins", Nature Medicine vol. 11, pp. 381-382 (2005).
Chen, Y. et al., "Engineering Human Stem Cell Lines with Inducible Gene Knockout using CRISPR/Cas9", 2015, Cell Stem Cell 17, 233-244.
Cui, C. et al., 2015, "Gene targeting by TALEN-induced homologous recombination in goats directs production of □-lactoglobulin-free, high-human lactoferrin milk", Scientific Reports, 5:10482.
Ezashi, T. et al., 2015, "Pluripotent Stem Cells from Domesticated Mammals", Annu. Rev. Anim. Biosci., 4:8.1-8.31.
Gomez, M. C. et al., 2004, "Birth of African Wildcat Cloned Kittens Born from Domestic Cats", Cloning and Stem Cells, vol. 6, No. 3, 247-258.
Gomez, M. C. et al., 2009, "Generation of Domestic Transgenic Cloned Kittens Using Lentivirus Vectors", Cloning and Stem Cells, 11(1): 167-175.
Gomez, M. C. et al., 2010, "Derivation of cat embryonic stem-like cells from in vitro-produced blastocysts on homologous and heterologous feeder cells", Theriogenology 74, 498-515.
Grens, Kerry. "Felis Enigmaticus." The Scientist, Jan. 2007, pp. 33-39.
Ni, W. et al., 2014, "Efficient Gene Knockout in Goats Using CRISPR/Cas9 System", PLoS ONE 9(9): e106718.
Paquet, Dominik et al. Efficient introduction of specific homozygous and heterozygous mutations using CRISPR/Cas9. May 5, 2016. Nature, vol. 533, pp. 125-129, and methods and enhanced data figures, 18 pages.
Pope, C.E. et al., 2006, "In vitro production and transfer of cat embryos in the 21st century", Theriogenology, 66, 59-71.
R. Verma et al., "Nanog is an Essential Factor for Induction of Pluripotency in Somatic Cells from Endangered Felids", BioResearch Open Access, vol. 2, No. 1, Feb. 2013, 72-76.
Si, Lihui et al. Generation of two ERF gene knockout human embryonic stem cell lines using CRISPR/Cas9 system. Stem Cell Research, 41, 2019, 101644, 4 pages.
Verma, R. et al., 2012, "Inducing pluripotency in somatic cells from the snow leopard (*Panthera uncia*), an endangered felid", Theriogenology, 77, 220-228.
Yin, X J et al., 2005, "Cats cloned from fetal and adult somatic cells by nuclear transfer", Reproduction, 129, 245-249.
Zhou, Wenjun et al. Generation of beta-lactoglobulin knock-out goats using CRISPR/Cas9. Oct. 10, 2017. PLoS ONE 12(10): e0186056.
(Chapman, Martin D. et al.) U.S. Appl. No. 62/303,686, filed Mar. 4, 2016, (110 pages).
Co-pending European Application No. 17760881.7, Communication Pursuant to Rule 94(3) EPC, dated Oct. 30, 2020, (5 pages).
Brackett, Nicole et al. "CRISPR Gene Editing of the Major Cat Allergen, Fel d 1", Poster, 2020.
Brackett, Nicole et al. "Gene Editing the Major Cat Allergen, Fel d 1, Using CRISPR-Cas9", Journal of Allergy and Clinical Immunology, vol. 145, Issue 2, Feb. 2020, p. AB156, 2 pages.
Co-pending European Application No. 17760881.7, Response to Oct. 30, 2020 Communication Pursuant to Rule 94(3) EPC, filed Mar. 8, 2021, 36 pages.
Co-pending Japanese Application No. 2018-566187, Office Action dated Mar. 19, 2021 (5 pages) and English Translation (7 pages).
Gupta, Rajat M. et al. "Expanding the genetic editing tool kit: ZFNs, TALENs, and CRISPR-Cas9", J Clin Invest. 2014; 124(10):4154-4161.
Satyaraj, Ebenezer et al. "Keep the cat, change the care pathway: A transformational approach to managing Fel d 1, the major cat allergen", Allergy 2019;74(Suppl. 107):5-17.
Slunt, Jeffrey B. et al. "IgE antibodies to recombinant forms of Fel d I: Dichotomy between fluid-phase and solid-phase binding studies", J Allergy Clin Immunol, Jun. 1995, 1221-1228.
Wynn, Gina "Scientists Are Poised to Pounce on Cat Allergies", Spring Summer Issue 2020, Fisher Science Education, 3 pages.
Co-pending European Application No. 17760881.7, Communication Pursuant to Article 94(3) EPC dated Apr. 5, 2022, 4 pages.
Co-pending European Application No. 17760881.7, Response to Apr. 5, 2022 Communication Pursuant to Article 94 (3) EPC with Declaration, Aug. 15, 2022, 7 pages.
Co-Pending Japanese Application No. 2022-082658, filed May 19, 2022, Japanese Translation as filed with Voluntary Amendment (303 pages) with English Translation of Amended Claims, filed Jun. 17, 2022 (14 pages).
Co-Pending Japanese Application No. 2022-082658, filed May 19, 2022, Specification, Claims, Figures, and Sequence Listing, 273 pages.
Li et al. "Excision of Expanded GAA Repeats Alleviates the Molecular Phenotype of Friedreich's Ataxia." Mol Ther. Jun. 2015; 23(6): 1055-1065.
Chapman, M. D. et al. "Monoclonal antibodies to the major feline allergen Fel d I. II. Single step affinity purification of Fel d I, N-terminal sequence analysis, and development of a sensitive two-site immunoassay to assess Fel d I exposure." J. Immunol. Feb. 1, 1988, 140 (3) 812-818, abstract only, 4 pages.
Co-pending Japanese Application No. 2018-566187, Decision of Rejection dated Jan. 21, 2022 (9 pages) and English Translation (11 pages).
Co-pending Japanese Application No. 2018-566187, Response to Mar. 19, 2021 Office Action, Filed Sep. 21, 2021 (33 pages) and English Translation (17 pages).
De Groot, H. et al. "Monoclonal antibodies to the major feline allergen Fel d I: I. Serologic and biologic activity of affinity-purified Fel d I and of Fel d I-depleted extract," Journal of Allergy and Clinical Immunology, vol. 82, Issue 5, Part 1, Nov. 1988, pp. 778-786, abstract only, 3 pages.
Lowenstein, H. et al. "Identification and Clinical Significance of Allergenic Molecules of Cat Origin", Allergy, vol. 40, Issue 6, p. 430-441, abstract only, 2 pages.
Ohman Jr., J. et al. "Antibody responses following immunotherapy with cat pelt extract", Journal of Allergy and Clinical Immunology, vol. 69, Issue 3, Mar. 1982, p. 319-326, abstract only, 2 pages.

(56) References Cited

OTHER PUBLICATIONS

Van Ree, R. et al. "Purified natural and recombinant Fel d 1 and cat albumin in in vitro diagnostics for cat allergy", Journal of Allergy and Clinical Immunology, vol. 104, Issue 6, Dec. 1999, pp. 1223-1230, abstract only, 2 pages.

* cited by examiner

- DESIGN OF crRNAs AND SELECT TARGET SEQS
  - AIM FOR TARGETING THE MORE CONSERVED PORTION OF GENOME SEQUENCES
  - SAMPLE crRNA pair 1: 1, 2 - TARGET FLANKING REGIONS OF FEL D 1 SEQUENCES (ONE UPSTREAM OF CHAIN 2, ONE DOWNSTREAM OF CHAIN 1)
    - 1: GGTGTCTGGATTCCAGCTTT (SEQ ID NO: 680)
    - 2: ACCTTGCCCAGAGTGAGACC (SEQ ID NO: 254)
  - SAMPLE crRNA pair 2: 3, 4 - TARTET INTERNAL REGIONS OF FEL D 1 GENES (ONE INTERNAL TO CHIAN 2, ONE INTERNAL TO CHAIN 1)
    - 3: GACTAGTCCATCCAAGACCC (SEQ ID NO: 851)
    - 4: CAATGCACGACCTGTAGTAT (SEQ ID NO: 266)
  - THE SAMPLE crRNAs CAN ALSO BE MIXED AND MATCHED INTO OPPOSITE PAIRS: 1/4 AND 2/3 (BUT NOT 1/3 AND 2/4 PROBABLY, BECAUSE THE DISTNCES BETWEEN THOSE ONLY COVER ~ ONE EXON)

*FIG. 4A*

- APPROACH USING Cas9 NICKASE:
  - crRNA PAIRS 1A/1B AND 2A/2B: TARGET FLANKING REGIONS OF FEL D 1 SEQUENCES (FOUR crRNAs TOTAL, FOR USE WITH NICKASE)
  - crRNA PAIRS 3A/3B AND 4A/4B: TARGET INTERNAL REGIONS OF FEL D 1 GENES (FOUR crRNAs TOTAL, FOR USE WITH NICKASE)

*FIG. 4B*

METHOD OF INACTIVATING A FEL D1 GENE USING CRISPR

CROSS-REFERENCE TO RELATED APPLICATIONS

This application is a National Stage application under 35 USC § 371 of International Application No. PCT/US17/20609, filed Mar. 3, 2017, which application relies on the disclosure of and claims priority to and the benefit of the filing date of U.S. Provisional Application No. 62/303,686, filed Mar. 4, 2016, the disclosures of each of which are hereby incorporated by reference herein in their entireties.

SEQUENCE LISTING

The instant application contains a Sequence Listing which has been submitted electronically in ASCII format and is hereby incorporated by reference in its entirety. Said ASCII copy, created on Mar. 2, 2017, is named WR-IB-101-PCT_SL.txt and is 192,603 bytes in size.

BACKGROUND OF THE INVENTION

Field of the Invention

The present invention generally relates to compositions and methods for genetically modifying felines or feline cells. More particularly, the present invention relates to compositions and methods for knocking out all or a portion of a Fel d 1 gene from a feline genome, as well as feline cells and organisms in which all or a portion of the Fel d 1 gene is knocked out.

Description of Related Art

Allergy and asthma have become increasingly prevalent in modern society. Common allergens come from a variety of different sources, ranging from dust mites to foods. Household pets are another typical source of allergens, and some (e.g. cat and dog) are commonly found in homes without pets. However, household pets play a significant role in people's daily lives, providing company and comfort to a variety of individuals of all ages and backgrounds, many of whom are allergic to their pets but could not bear to give them up. Cat allergens, in particular, are a common health concern for numerous patients, and the allergens are essentially ubiquitous in society. Particles of cat allergens readily become airborne and remain for hours, and the allergen also sticks to surfaces such as fabrics, resulting in its transmission from a cat-owning household to the rest of the world. Significant levels of cat allergens can be found in offices, stores, or schools, regardless of whether a cat has been present in that environment, due to such high transmission rates of the allergens.

Allergy to cats affects 10-15% of adults and 1 out of 7 children between the ages of 6-19. Symptoms of patients suffering from cat allergy may range from rhinoconjunctivitis to severe asthma. Though multiple cat allergens have been identified, up to 95% of patients have IgE antibodies specific to the major allergen from cat, Fel d 1. Fel d 1 is recognized by 60-90% of an allergic individual's total IgE antibodies.

Fel d 1 is a protein of the secretoglobin family, and exists as a tetramer that is 35 kD in molecular weight. The tetrameric protein is composed of two heterodimers, each of which consists of two antiparallel chains linked by three disulfide bonds, each encoded by a different gene. See Grönlund et al., Formation of Disulfide Bonds and Homodimers of the Major Cat Allergen Fel d 1 Equivalent to the Natural Allergen by Expression in *Escherichia coli*, J. Biol. Chem., Vol. 278, No. 41, pp. 40144-40141 (Oct. 10, 2003). The gene encoding chain 1 (for which the protein product is 70 amino acids (8 kD)) and chain 2 (92 amino acids (10 kD)) are arranged symmetrically in the feline genome, starting in a narrow region and extending outwards, encoded by opposite strands of the DNA (see Grönlund et al., The Major Cat Allergen, Fel d 1, in Diagnosis and Therapy, Int Arch Allergy Immunol (2010), 151:265-274 and Morgenstern, et al., Amino acid sequence of Fel dI, the major allergen of the domestic cat: Protein sequence analysis and cDNA cloning, Proc Natl Acad Sci USA, 88(21):9690-9694 (1991). The two genes are located in a genomic span of less than 10,000 base pairs.

Analysis of sequence and structural homology suggests that Fel d 1 is most closely related to Androgen-Binding Proteins (especially those of the mouse and yak) and other uteroglobin allergens (such as those produced by bats and rabbits). The Fel d 1 protein binds Ca' ions, and based on its structure, also contains two internal cavities that could bind steroid ligands. Additionally, it has been hypothesized that Fel d 1 may play a role in protecting the epithelium or have anti-inflammatory properties. However, despite years of studying Fel d 1, the biological function of the Fel d 1 protein remains unknown.

In the cat, Fel d 1 is produced by the sebaceous glands of the skin, as well as by the salivary, perianal, and lachrymal glands. Fel d 1 is transferred to the fur from saliva, through grooming, and from skin. Kittens are known to produce less Fel d 1 than adult cats, and females produce lower levels of Fel d 1 compared to males. Neutered cats also produce significantly less Fel d 1 than unaltered cats. When dried Fel d 1 particles on dander and cat hair become airborne, they can remain airborne for hours. Humans come in contact with Fel d 1 either by inhalation of these particles, or through direct contact with a cat. The immune system response to Fel d 1 is IgE-antibody mediated. When the Fel d 1 protein binds to receptors on immune cells, it results in the release of pro-inflammatory agents including cytokines and histamines, which stimulate the allergy symptoms. There is also evidence that Fel d 1 has gelatin- and fibronectin-degrading activity and, like other uteroglobins, is an inhibitor to the activity of phospholipase A2, but these additional properties have not been directly linked to the immune response.

Attempts to mitigate the amount of Fel d 1 present in the environment of cat-allergic patients have included limiting cats' access to bedrooms, frequent vacuuming or steam cleaning, and even regular cat washing. Additionally, the use of High-Efficiency Particulate Air (HEPA) filters has been shown to decrease the amount of airborne allergen present in the environment. Still, these methods cannot completely eliminate Fel d 1, and symptoms of severely allergic patients may persist, often for a long time after the cat has been in the environment due to trace amounts of allergen remaining.

Some individuals allergic to cats opt to search for animals specifically tested and proven to produce lower levels of Fel d 1, but selective breeding can only reduce an animal's allergens by so much, and perhaps not enough for severely allergic patients. Further, animals selectively bred for low allergen levels are extremely time-consuming and costly to produce. Additionally, extensive in-breeding of animal lineages can result in increased coincidence of rare genetic mutations, and consequently, severe genetic disease. So, while the practice of selective breeding may be practical in the short-term, it is unsustainable as a long-term solution to generating hypoallergenic animals.

Related efforts in this area include those described in U.S. Patent Application Publication Nos. 2003/0177512 and 2011/0023156, each incorporated by reference in their entireties. Yet, there remains a need in the art for improved methods and compositions that address these issues.

SUMMARY OF THE INVENTION

The present invention provides compositions and methods for selective deletion of one or more Fel d 1 genes in a cell of a cat, such as a domestic house cat (Fells catus). The one or more Fel d 1 genes may include chain 1, chain 2, or both chain 1 and chain 2.

In embodiments, the present invention provides compositions and methods for targeting a Fel d 1 genomic sequence in a cat cell. In one aspect of this embodiment, the invention provides a plurality of polynucleotide sequences that can be used in a CRISPR-Cas9 system to target Fel d 1 for genome editing. The polynucleotides may include any sgRNA that may have utility in a CRISPR-Cas9 system for targeted deletion of Fel d 1 or a portion thereof from the genome of a cat cell.

Embodiments of the invention provide a chimeric guide RNA (sgRNA) comprising a first polynucleotide and a second polynucleotide. The first polynucleotide is a crRNA. The second polynucleotide is a tracrRNA. The crRNA (first polynucleotide) is selected such that it is capable of binding to a portion of one strand of DNA located in a target DNA region. The complement of that strand is referred to herein as the sgRNA Target Sequence, which is identical in sequence to the crRNA. The sgRNA Target Sequence may also be referred to herein as the crRNA target sequence since it is the crRNA portion of the sgRNA that directs the sgRNA to the target DNA site. As used herein, "identical in sequence" means that the crRNA has the same sequence as the sgRNA Target Sequence, but that the crRNA contains uracil (U) in place of thymine (T). The sgRNA Target Sequence is a portion of a Fel d 1 genomic sequence or a flanking region, wherein the portion is 5' of a PAM sequence consisting of NGG, wherein N=A, T, C, or G.

In embodiments, the first polynucleotide of the sgRNA (crRNA) is identical in sequence to a portion of Fel d 1 chain 1 genomic sequence or 3' flanking region 1 kb in length or a portion of Fel d 1 chain 2 or a 5' flanking region 1 kb in length.

In embodiments, the first polynucleotide of the sgRNA (crRNA) is identical in sequence to a portion of the sequence set forth in SEQ ID NO: 1226 or SEQ ID NO: 1227, or is substantially complementary to a portion of the sequence set forth in SEQ ID NO: 1226 or SEQ ID NO: 1227.

In embodiments, the first polynucleotide of the sgRNA (crRNA) is 18-22 nucleotides in length, such as 18, 19, 20, 21, or 22 nucleotides in length.

In embodiments, the first polynucleotide of the sgRNA (crRNA) is identical in sequence to a DNA sequence set forth in SEQ ID NOS: 1-1225 (exemplary sgRNA Target Sequences).

In embodiments, the first polynucleotide of the sgRNA is a crRNA that is at least 60%, 65%, 70%, 75%, 80%, 85%, 90%, 95%, 96%, 97%, 98%, or 99% identical in sequence to a DNA sequence set forth in SEQ ID NOS: 1-1225.

In embodiments, the first polynucleotide of the sgRNA (crRNA) is located 5' of the second polynucleotide of the sgRNA (tracrRNA).

Embodiments of the invention include a chimeric DNA molecule encoding any chimeric guide RNA described herein.

In embodiments, the chimeric DNA molecule comprises a first polynucleotide and a second polynucleotide. The first polynucleotide of the chimeric DNA molecule is identical to a portion of a Fel d 1 genomic sequence or a flanking region, wherein the portion is 5' of a PAM sequence consisting of NGG, wherein N=A, T, C, or G. The second polynucleotide encodes a tracrRNA.

In embodiments, the first polynucleotide of the chimeric DNA molecule is identical to a portion of Fel d 1 chain 1 genomic sequence or 3' flanking region 1 kb in length or a portion of Fel d 1 chain 2 or a 5' flanking region 1 kb in length.

In embodiments, the first polynucleotide of the chimeric DNA molecule is identical to a portion of the sequence set forth in SEQ ID NO: 1226 or SEQ ID NO: 1227, or is substantially complementary to a portion of the sequence set forth in SEQ ID NO: 1226 or SEQ ID NO: 1227.

In embodiments, the first polynucleotide of the chimeric DNA molecule is identical to a DNA sequence set forth in SEQ ID NOS: 1-1225.

In embodiments, the first polynucleotide of the chimeric DNA molecule is at least 60%, 65%, 70%, 75%, 80%, 85%, 90%, 95%, 96%, 97%, 98%, or 99% identical to a DNA sequence set forth in SEQ ID NOS: 1-1225.

In embodiments, the second polynucleotide of the chimeric DNA molecule comprises a sequence set forth in SEQ ID NOS:1228-1233 or a fragment thereof, and the second polynucleotide of the sgRNA (tracrRNA) is selected to be identical in sequence to a DNA sequence set forth in SEQ ID NOS:1228-1233 or a fragment thereof.

Embodiments of the invention include an expression construct comprising any chimeric DNA molecule described herein, operably linked to a promoter. The promoter may be a Pol III promoter such as a U6 promoter.

Embodiments of the invention include recombinant vectors comprising any expression construct described herein. Additionally, recombinant vectors of the invention may include a second expression construct comprising a polynucleotide encoding Cas9 operably linked to a promoter. The promoter of the second expression construct may be a constitutive mammalian promoter, an inducible promoter, or a tissue-specific promoter.

Embodiments of the invention include host cells comprising any recombinant vector described herein. In embodiments, the host cells lack expression of Fel d 1 protein or a portion thereof, and/or lack all or a portion of the genomic sequence which encodes Fel d 1 protein. In some embodiments, the host cell produces a hypoallergenic variant of Fel d 1 protein.

Embodiments of the invention include a cell line derived from any host cell described herein. In some aspects of the invention, the cell line is immortalized.

Embodiments of the invention include a method of deleting all or a portion of a Fel d 1 genomic sequence from a feline cell. The method comprises introducing at least a first and second chimeric guide RNA and a Cas9 protein into a feline cell. Each chimeric guide RNA comprises a first polynucleotide and a second polynucleotide such that the first polynucleotide is a unique crRNA that is selected to be identical in sequence to a portion of a Fel d 1 genomic sequence that is selected as an sgRNA target sequence and the second polynucleotide is a tracrRNA. The first chimeric guide RNA and second chimeric guide RNA direct the Cas9 protein to produce a first and second double stranded break in a portion of Fel d 1 genomic sequence or a flanking region such that upon repair of the first and second double stranded breaks, an intervening portion comprising a Fel d 1 genomic sequence is removed from the genome of the feline cell.

In embodiments, the crRNA of the first chimeric guide RNA is identical in sequence to a portion of a Fel d 1 genomic sequence that is located 5' of Fel d 1 chain 2 genomic sequence and the crRNA of the second chimeric guide RNA is identical in sequence to a Fel d 1 genomic sequence that is located 3' of Fel d 1 chain 1.

In embodiments, the crRNA of the first chimeric guide RNA is identical in sequence to a portion of a Fel d 1 genomic sequence that is located internal to a portion of a Fel d 1 chain 2 genomic sequence and the crRNA of the second chimeric guide RNA is identical in sequence to a Fel d 1 genomic sequence that is located internal to Fel d 1 chain 1 genomic sequence.

In embodiments, the crRNA of the first chimeric guide RNA is identical in sequence to a portion of a Fel d 1 genomic sequence that is located 5' of Fel d 1 chain 2 genomic sequence and the crRNA of the second chimeric guide RNA is identical in sequence to a portion of a Fel d 1 genomic sequence that is located internal to Fel d 1 chain 1 genomic sequence.

In embodiments, the crRNA of the first chimeric guide RNA is identical in sequence to a portion of a Fel d 1 genomic sequence that is located internal to Fel d 1 chain 2 genomic sequence and the crRNA of the second chimeric guide RNA is identical in sequence to a portion of a Fel d 1 genomic sequence that is located 3' of Fel d 1 chain 1 genomic sequence.

In embodiments, the portion of the Fel d 1 genomic sequences are chosen from the DNA sequences set forth in SEQ ID NOS: 1-1225.

Additional embodiments include a method of deleting all or a portion of a Fel d 1 genomic sequence from a cell. The method comprises introducing a first and second pair of chimeric guide RNAs (sgRNAs) and a Cas9 nickase into a feline cell. Each chimeric guide RNA comprises a first polynucleotide and a second polynucleotide such that the first polynucleotide is a unique crRNA identical in sequence to a portion of a Fel d 1 genomic sequence selected as an sgRNA target sequence and the second polynucleotide is a tracrRNA. The first pair of chimeric guide RNAs direct the Cas9 nickase to produce a first pair of single stranded breaks in a first portion of Fel d 1 genomic sequence or a flanking region and the second pair of chimeric guide RNAs direct the Cas9 nickase to produce a second pair of single stranded breaks in a second portion of Fel d 1 genomic sequence or a flanking region such that upon repair of the first and second pair of single stranded breaks, an intervening portion comprising a Fel d 1 genomic sequence is removed from the genome of the feline cell.

In embodiments, the first pair of chimeric guide RNAs are selected to be capable of base pairing with a genomic sequence that is located 5' of Fel d 1 chain 2 genomic sequence and the second pair of chimeric guide RNAs are selected to be capable of base pairing with a genomic sequence that is located 3' of Fel d 1 chain 1 genomic sequence.

In embodiments, the first pair of chimeric guide RNAs are selected to be capable of base pairing with a genomic sequence that is located internal to Fel d 1 chain 2 genomic sequence and the second pair of chimeric guide RNAs are selected to be capable of base pairing with a genomic sequence that is located internal to Fel d 1 chain 1 genomic sequence.

In embodiments, the first pair of chimeric guide RNAs are selected to be capable of base pairing with a genomic sequence that is located 5' of Fel d 1 chain 2 genomic sequence and the second pair of chimeric guide RNAs are selected to be capable of base pairing with a genomic sequence that is located internal to Fel d 1 chain 1 genomic sequence.

In embodiments, the first pair of chimeric guide RNAs are selected to be capable of base pairing with a genomic sequence that is located internal to Fel d 1 chain 2 genomic sequence and the second pair of chimeric guide RNAs are selected to be capable of base pairing with a genomic sequence that is located 3' of Fel d 1 chain 1 genomic sequence.

In embodiments, the portion of the Fel d 1 genomic sequence selected as the sgRNA Target Sequence is chosen from the DNA sequences set forth in SEQ ID NOS: 1-1225. In embodiments, the sgRNA Target Sequence is the complement of the portion of the Fel d 1 genomic sequence that the chimeric guide RNAs are selected to be capable of base pairing with.

In embodiments of the methods described herein, chimeric guide RNAs and Cas9 protein are introduced directly into the cell as ribonucleoprotein complexes.

In embodiments of the methods described herein, chimeric guide RNAs and Cas9 protein are introduced indirectly into the cell by way of one or more expression cassettes.

In embodiments, the first and second chimeric guide RNAs and Cas9 protein are introduced indirectly into the cell by way of one or more vectors.

Embodiments include a method of treating a cat, such as administering a recombinant vector to a cat that is wild-type for Fel d 1 expression. The recombinant vector encodes at least a first and second chimeric guide RNA and a Cas9 protein. Each chimeric guide RNA (sgRNA) comprises a first polynucleotide and a second polynucleotide such that the first polynucleotide is a unique crRNA that is selected to be encoded by a portion of a Fel d 1 genomic sequence selected as an sgRNA target sequence and the second polynucleotide is a tracrRNA. The first chimeric guide RNA and second chimeric guide RNA direct the Cas9 protein to produce a first and second double stranded break in a portion of Fel d 1 genomic sequence or a flanking region such that upon repair of the first and second double stranded breaks, an intervening portion comprising a Fel d 1 genomic sequence is removed from the genome.

In embodiments, the recombinant vector is a viral vector such as a lentiviral vector. Further, in embodiments, the recombinant vector comprises a tissue-specific or inducible promoter driving Cas9 expression.

Further, the recombinant vector can be administered systemically, or to specific tissues such as salivary gland or skin tissue.

Further, in embodiments of methods of the invention, Fel d 1 protein expression is impaired or absent in skin, salivary glands, perianal glands, or lachrymal glands.

Additional embodiments of the invention include methods of producing a cat in which Fel d 1 expression is impaired or absent.

In one embodiment, the method comprises culturing any of the cell lines or host cells described herein, placing a single engineered cell or host cell into an enucleated ovum to create a cloned embryo, implanting the cloned embryo into a recipient female cat, and allowing the cloned embryo to mature into a cat.

In another embodiment, the method comprises culturing a cat oocyte, introducing into the cat oocyte a pair of guide RNAs and the Cas9 protein, wherein the guide RNAs are designed to be encoded by a Fel d 1 genomic sequence of a 5' or 3' flanking region, fertilizing the oocyte with cat sperm to create an embryo, culturing the embryo in vitro, implanting the embryo into a recipient female cat, and allowing the embryo to mature into a cat.

Additional embodiments include transgenic or knock-out cats produced according to any method described herein.

An embodiment of the invention includes a cat lacking a portion of a Fel d 1 genomic sequence which results in impaired or absent expression of Fel d 1 protein. In embodiments, the Fel d 1 protein or a portion thereof is expressed but is hypoallergenic in humans.

In some embodiments, all or a portion of the Fel d 1 genomic sequence is deleted from somatic cells. In some embodiments, all or a portion of the Fel d 1 genomic sequence is deleted from germline cells. In some embodiments, all or a portion of the Fel d 1 genomic sequence is deleted from both somatic cells and germline cells. In some embodiments, at least 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 kb of a Fel d 1 genomic sequence, including 5' and or 3' flanking regions, is deleted.

Another embodiment of the invention includes F1 progeny of a male and female cat embodiment described herein.

BRIEF DESCRIPTION OF THE DRAWINGS

The accompanying drawings illustrate certain aspects of embodiments of the present invention, and should not be used to limit the invention. Together with the written description the drawings serve to explain certain principles of the invention.

FIG. 4A is an outline of a strategy for designing sgRNAs for use with Cas9 according to an embodiment of the invention.

FIG. 4B is an outline of a strategy for designing sgRNAs for use with Cas9 nickase according to an embodiment of the invention.

DETAILED DESCRIPTION OF VARIOUS EMBODIMENTS OF THE INVENTION

Figure 1:
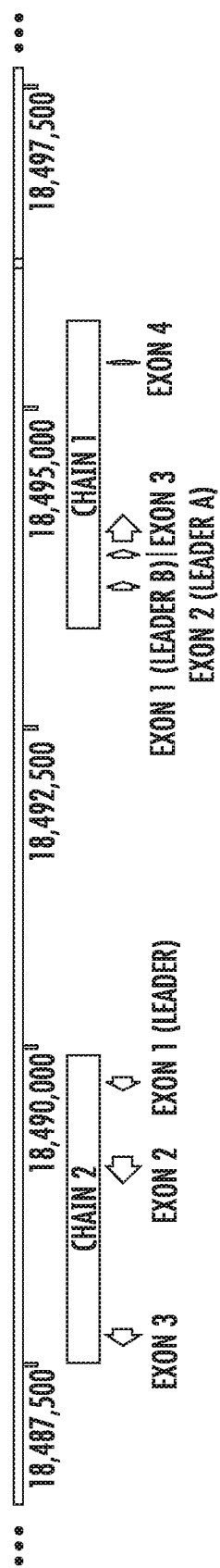
FIG. 1 is a genomic map of *Felis catus* Fel d genomic region, chains 1 and 2.

Reference will now be made in detail to various exemplary embodiments of the invention. It is to be understood that the following discussion of exemplary embodiments is not intended as a limitation on the invention. Rather, the following discussion is provided to give the reader a more detailed understanding of certain aspects and features of the invention.

The present invention provides compositions and methods for selective deletion of genomic DNA encoding one or more Fel d 1 genes in cat cells and ultimately in a living cat. The composition and methods are useful for precise genomic engineering to selectively eliminate production of Fel d 1, resulting in a domestic cat that no longer produces this key allergen.

Embodiments of methodologies of the present invention include those based on CRISPR-Cas9 mediated gene editing, which is known in the art (see Cong et al., Multiplex Genome Engineering Using CRISPR/Cas Systems, Science 15 Feb. 2013: 339 (6121), 819-823 "Cong et al., 2013"; Ran et al., Genome engineering using the CRISPR-Cas9 system, Nat Protoc. 2013 Nov. 8(11): 2281-2308 ("Ran et al., 2013"); Doudna J A and Charpentier E, The new frontier of genome engineering with CRISPR-Cas9, Science, 2014, 346:6213, 1258096-1-9; and Jinek et al., A Programmable Dual-RNA—Guided DNA Endonuclease in Adaptive Bacterial Immunity, Science 337, 816 (2012) ("Jinek, 2012")). Briefly, CRISPR is an RNA-guided genomic editing system that employs a bacterially derived protein (Cas9) and a synthetic guide RNA to introduce a double strand break at a specific location within the genome. By transfecting a cell with the Cas9 protein along with a specially designed guide RNA (gRNA, or sgRNA) that directs the cut through hybridization with its matching genomic sequence, site-specific cleavage of genomic DNA can be introduced into a cell. Upon repair of the double-strand break by the cell's DNA repair systems, errors can be introduced to generate a knockout of a particular gene. Additionally, an engineered Cas9 protein (Cas9 "nickase") functions similarly except it introduces single-stranded breaks instead of double-stranded breaks.

The details of the backbone vectors, other reagents for SpCas9 genome engineering system, and protocols can be found in the Cong and Ran publications referenced above, as well as the website for Dr. Feng Zhang at the Broad Institute (http://www.genome-engineering.org/crispr/). Features of the system such as the amino acid sequence of *Streptococcus pyogenes* Cas9 (for example, see public Accession No. Q99ZW2 (NCBI)) and sequence of the tracrRNA (see Jinek, 2012) are publicly available. Exemplary DNA sequences encoding *Streptococcus pyogenes* tracrRNA or fragments thereof are set forth in SEQ ID NOS: 1228-1233. Reagents, cloning vectors, and kits for guide RNA and Cas9 expression and associated assays are available from commercial vendors such as GenScript, BioRad, Thermo-Fisher, Sigma- Aldrich, OriGene, and Clontech. Additionally, CRISPR plasmids (including those from the Zhang lab) have been deposited at and are available from Addgene (Cambridge, MA), a non-profit plasmid repository, and a number of protocols and resources are available on the Addgene web site (http://www.addgene.org/crispr/).

In addition, background information on CRISPR-mediated gene editing can be found in U.S. Pat. Nos. 8,697,359; 8,795,965; 8,865,406; 8,871,445; 8,889,356; 8,889,418; 8,906,616; 8,932,814; 8,945,839; 8,993,233; 8,999,641 as well as U.S. Patent Application Publication Nos. 2014/0068797; 2014/0170753; 2014/0179006; 2014/0179770; 2014/0186843; 2014/0186919; 2014/0186958; 2014/0189896; 2014/0227787; 2014/0234972; 2014/0242664; 2014/0242699; 2014/0242700; 2014/0248702; 2014/0256046; 2014/0273231; 2014/0273232; 2014/0273234; 2014/0287938; 2014/0310830; 2014/0335620; 2014/0357530; 2015/0020223; 2015/0031134; 2015/0079681; 2015/0184139; 2015/0203872; 2015/0232882; 2015/0232883; 2015/0247150; 2015/0291965; 2015/0291966; 2015/0356239; the disclosures of these patents and published applications are hereby incorporated by reference herein in their entireties.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

In aspects of the invention the terms "guide RNA", "single guide RNA", "synthetic guide RNA", "sgRNA", and "chimeric guide RNA" are used interchangeably and refer to a chimeric polynucleotide sequence comprising a "guide sequence" and a "tracr sequence".

The term "guide sequence" may be used interchangeably with the terms "guide" or "CRISPR-targeting RNA" or "crRNA". In general, the guide sequence refers to the polynucleotide sequence within the guide RNA that is selected to hybridize with a corresponding DNA molecule at a specific location and is capable of directing sequence-specific binding of a CRISPR complex at that target location within the DNA molecule. In some embodiments, the degree of complementarity between a guide sequence and the corresponding sequence to which it will bind, when optimally aligned using a suitable alignment algorithm, is about or more than about 50%, 60%, 75%, 80%, 85%, 90%, 95%, 97.5%, 99%, or more. In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. In some embodiments, the guide sequence is about 5 to 40, 10 to 30, 15 to 25, 16 to 24, 17 to 23, 18 to 22, or 19 to 21, or 20 nucleotides in length. Preferably, the guide sequence is 18-22 nucleotides in length. The ability of a guide sequence to direct sequence-specific binding of a CRISPR complex at a target DNA location may be assessed by any suitable assay.

The term "tracrRNA" or "tracr sequence" refers to a portion of the guide RNA that acts as a scaffold between the crRNA and Cas9 endonuclease. Exemplary polynucleotides encoding tracrRNA are set forth in SEQ ID NOS: 1228-1233. Thus, suitable tracrRNA have a polynucleotide sequence that is identical in sequence to the polynucleotides in SEQ ID NOS: 1228-1233 or a fragment thereof. In some embodiments, the tracrRNA, or polynucleotides encoding tracrRNA may be about 50, 55, 60, 65, 70, 75, 80, 85, 90, 95, or 100 nucleotides in length.

The term "CRISPR" refers to Clustered Regularly Interspaced Short Palindromic Repeats, a series of short direct repeats in the genome of select bacteria and archaea that are interspaced with short spacer sequences of plasmid or viral origins.

The terms "CRISPR complex" and "CRISPR-Cas" refer to a specific system of adaptive immunity in select bacteria and archaea mediated by RNA and nucleases which enable the organisms to respond to and eliminate invading genetic material.

The term "Cas9" or "Cas9 endonuclease" (also known as COG3513, Csx12, Cas5, or Csn1) refers to a CRISPR-associated protein with two nuclease domains that uses a crRNA:tracRNA duplex for site-specific double-stranded cleavage of DNA. In aspects of the invention, the terms may refer to a wild-type Cas9 protein, or any variant, including mutants, homologs, orthologs, that mediate RNA-guided double-stranded or single-stranded cleavage of DNA.

The term "Cas9 nickase" refers to a Cas9 endonuclease that is engineered so that one of its nuclease domains is non-functional so that its activity is limited to single-stranded cleavage of DNA.

The term "target sequence" refers to a specific region of DNA (such as a genomic DNA sequence) that is the target of a guide RNA. A DNA strand within this region hybridizes with the crRNA portion of the guide RNA. The sgRNA Target Sequence is a polynucleotide sequence located in this target DNA region. In embodiments, the crRNA is selected to hybridize (otherwise referred to as binding or base pairing) with the polynucleotide sequence that is the complement of the sgRNA Target Sequence.

As used herein the term "wild type" is a term of the art understood by skilled persons and means the typical form of an organism, strain, gene or characteristic as it occurs in nature as distinguished from mutant or variant forms.

As used herein the term "variant" should be taken to mean the exhibition of qualities that have a pattern that deviates from what occurs in nature. "Variant" DNA molecules are DNA molecules containing minor changes in a native sequence, i.e., changes in which one or more nucleotides of a native sequence is deleted, added, and/or substituted. Variant DNA molecules can be produced, for example, by standard DNA mutagenesis techniques or by chemically synthesizing the variant DNA molecule or a portion thereof. Such variants preferably do not change the reading frame of the protein-coding region of the polynucleotide and can encode a protein having no change, a reduction, or an increase in a desired biological activity. "Variant" peptides or proteins are those which include changes in the amino acid sequence include substitutions, deletions, and/or insertions.

The terms "non-naturally occurring" or "engineered" or "genetically-engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature.

"Complementarity" refers to the ability of a nucleic acid to form hydrogen bond(s) with another nucleic acid sequence by either traditional Watson-Crick base pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

A "gene," as used herein, refers to a DNA region (including exons and introns) encoding a gene product, as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites, and locus control regions. According to certain aspects, any portion of the Fel d 1 gene which results in disruption of Fel d 1 protein synthesis may be targeted by the compositions and methods of the invention. As understood herein, a "Fel d 1 gene" can be used interchangeably with a "Fel d 1 genomic sequence".

The terms "polypeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

As used herein, "identity" is a measure of the identity of nucleotide sequences or amino acid sequences compared to a reference nucleotide or amino acid sequence. In general, the sequences are aligned so that the highest order match is obtained. "Identity" per se has an art-recognized meaning and can be calculated using published techniques. (See, e.g., Computational Molecular Biology, Lesk, A. M., ed., Oxford University Press, New York (1988); Biocomputing: Informatics And Genome Projects, Smith, D. W., ed., Academic Press, New York (1993); Computer Analysis of Sequence Data, Part I, Griffin, A. M., and Griffin, H. G., eds., Humana Press, New Jersey (1994); von Heinje, G., Sequence Analysis In Molecular Biology, Academic Press (1987); and Sequence Analysis Primer, Gribskov, M. and Devereux, J., eds., M Stockton Press, New York (1991)). While there exists several methods to measure identity between two polynucleotide or polypeptide sequences, the term "identity" is well known to skilled artisans (Carillo, H. & Lipton, D., Siam J Applied Math 48:1073 (1988)). Methods commonly employed to determine identity or similarity between two sequences include, but are not limited to, those disclosed in Guide to Huge Computers, Martin J. Bishop, ed., Academic Press, San Diego (1994) and Carillo, H. & Lipton, D., Siam Applied Math 48:1073 (1988). Computer programs may also contain methods and algorithms that calculate identity and similarity. Examples of computer program methods to determine identity and similarity between two sequences include, but are not limited to, GCG program package (Devereux, J., et al., Nucleic Acids Research 12(i):387 (1984)), BLASTP, ExPASy, BLASTN, FASTA (Atschul, S. F., et al., J Molec Biol 215:403 (1990)) and FASTDB. Examples of methods to determine identity and similarity are discussed in Michaels, G. and Garian, R., Current Protocols in Protein Science, Vol 1, John Wiley & Sons, Inc. (2000), which is incorporated by reference. In one embodiment of the present invention, the algorithm used to determine identity between two or more polypeptides is BLASTP.

As used herein, a sequence is "substantially identical" if it at least 60%, 65%, 70%, 75%, 80%, 85%, 90%, 95%, 97%, 98%, 99%, or 100% identical to a reference sequence.

"Operably Linked." A first nucleic-acid sequence is "operably linked" with a second nucleic-acid sequence when the first nucleic-acid sequence is placed in a functional relationship with the second nucleic-acid sequence. For instance, a promoter is operably linked to a coding sequence if the promoter affects the transcription or expression of the coding sequence. Generally, operably linked DNA sequences are contiguous and, where necessary to join two protein coding regions, in reading frame.

A cell, tissue, organ, or organism into which has been introduced a foreign polynucleotide, such as a recombinant vector, is considered "transformed", "transfected", or "transgenic." A "transgenic" or "transformed" cell or organism also includes progeny of the cell or organism.

As used herein, "knockout" refers to a cell or organism in which a gene product is eliminated or any procedure resulting in such elimination. In certain aspects of the invention, a "knockout" can result from insertions, deletions, substitutions, frameshift mutations, and the like, that result from the compositions and methods described herein. As used herein, "knockout" may also refer to a genetically-engineered cell or organism in which a portion of DNA (such as genomic DNA) is removed. The term "knockout" as it refers to a gene is intended to mean removal or all or a portion of the DNA associated with that gene. In certain aspects, the compositions and methods of the invention have utility for knocking out all or a portion of a Fel d 1 gene.

As used herein, "hypoallergenic" means designed to reduce or minimize the possibility of an allergic response. In certain aspects of the invention, a hypoallergenic cat may result from "knockout" of the cat allergen Fel d 1. However, this invention contemplates that the compositions and methods may produce Fel d 1 hypoallergenicity through a variety of mechanisms, including any change in Fel d 1 two-dimensional or three-dimensional structure that results in reduced IgE reactivity.

Compositions of the invention include one or more guide RNAs and one or more DNA sequences encoding guide RNAs that may direct site-specific cleavage of a Fel d 1 genomic sequence, or any flanking portion that is 5' or 3' of the Fel d 1 genomic sequence. By identifying appropriate target sequences in the cat genome, guide RNAs or DNA sequences encoding guide RNAs may be identified. Candidate guide RNA target sequences may be identified from published genomic data or by isolating genomic DNA from a feline tissue or cell sample and sequencing the genomic DNA. In an embodiment, SEQ ID NOS: 1-1225 represent 1225 candidate target sequences in the cat genome which may be the site of site-specific double stranded cleavage of a Fel d 1 genomic sequence or any adjacent 5' or 3' flanking region. The candidate target sequences may be identified in silico through one or more algorithms implemented by a computer processor, or manually.

Methods of the invention include, in embodiments, screening guide RNAs for efficacy in initiating genomic editing of Fel d 1 through in vitro techniques, which may include high-throughput screening. Upon identification of guide RNAs having efficacy in vitro, active guide RNAs can be introduced into a host cell, and the engineered host cell can be used as a basis for cloning a cat that lacks expression of the Fel d 1 protein.

Methods of the invention include cloning using engineered host cells as donor cells in cloning by nuclear transfer. For example, feline skin cells or adult fibroblast cells can be cultured and transfected with vectors encoding guide RNAs and Cas9. Upon confirmation of knock-out of Fel d 1, a single donor cell is placed into enucleated ova. Cloned embryos are cultured and then surgically transferred to a surrogate queen. Additionally, this invention contemplates additional methods of creating Fel d 1 knockout cells or animals, such as through direct gamete genetic modification, or manipulation of embryonic stem cells. Alternatively, viral vectors encoding guide RNAs and Cas9 can be administered to wild-type cats to excise Fel d 1 genomic sequences in vivo. The vectors can be administered systemically or to specific Fel d 1 expressing tissues.

Also included in embodiments of the invention are transgenic cats that are knockouts for Fel d 1 (or a portion thereof) as a result of method of the invention. The cats have reduced expression of Fel d 1 or a portion thereof, and may be hypoallergenic or non-allergenic for Fel d 1. The cats have Fel d 1 knocked out in somatic cells and in the germline and are thus able to pass this characteristic to progeny.

As an alternative to CRISPR-Cas9 genomic editing, the present invention contemplates the use of other methods of genomic editing, knockdown, or silencing known in the art, including knockout by homologous recombination, knock-out by Cre-lox system, or knockdown by RNA interference. For example, homologous recombination involves design of a disruption construct, deletion of the Fel d 1 gene in embryonic stem cells, injection of the engineered stem cells into an embryo, implantation of embryos, screening for kittens (heterozygous Fel d 1 Δ), and breeding of heterozygotes to obtain homozygotes. Genetic engineering through a Cre-lox system involves homologous recombination to insert lox sites around an exon or full Fel d 1 gene, and then transfection and expression of Cre recombinase (see Metzger, D. & Feil, R. Engineering the mouse genome by site-specific recombination. Curr. Opin. Biotechnol. 10, 470-476). RNA interference involves introduction of siRNA to target the native cellular machinery to prevent translation or induce degradation of specific mRNAs. These techniques are known in the art and have been reviewed (see Lodish, Molecular Cell Biology, W.H. Freeman and Company, New York). Additionally, embodiments of the invention contemplate inducible knockouts, tissue-specific knockouts, genome editing using zinc finger nucleases (see U.S. Patent Application Publication No. 2011/0023156), and Cas9 variations such as epigenetic silencing (dCas9 fused to a DNA methyltransferase).

Example: Culture of Cell Lines

*Felis catus* cell lines can be obtained from American Type Culture Collection (ATCC; Manassas, Virginia) and cultured according to protocols known the art, including the ATCC® Animal Cell Culture Guide available on the ATCC website. Examples of cell lines that may be available include CRFK (ATCC® CCL-94™), Fcwf-4 [Fcwf] (ATCC® CRL-2787™), FC77.T (ATCC® CRL-6105_FL™), PG-4 (S+L−) (ATCC® CRL-2032®), MYA-1 (ATCC® CRL-2417™), F1B [F1B(N)] (ATCC® CRL-6168™), G355-5 (ATCC® CRL-2033 ™) Fc2Lu (ATCC® CCL-217™), FC114E.Tr (ATCC® CRL-6167™), FC47 (ATCC® CRL-6094™), FeT-J (ATCC® CRL-11967™), F25 (ATCC® CRL-6566™), Fc3Tg (ATCC® CCL-176™), FeLV-3281 (ATCC® CRL-9116™), FC83.Res (ATCC® CRL-6567™), AK-D (ATCC® CCL-150™), FC2.K (ATCC® CRL-6126™), FL74-UCD-1 (ATCC® CRL-8012™), FeT-1C (ATCC® CRL-11968™).

Example: Primary Cell Culture

Primary cell lines may be established from tissue samples or biopsies of cat tissue. Examples include bone marrow biopsies, endoscopic biopsies, skin puncture biopsies and needle biopsy procedures including fine needle aspiration, core needle biopsies, vacuum-assisted biopsies, and image-guided biopsies. These would be performed according to standard protocols used when taking a biopsy for pathology, except a portion of the tissue sample would either be immediately put in culture or cryopreserved with the use of a cryoprotectant, such as DMSO or glycerol, for later culturing. Thus, the biopsy procedures need not be elaborated here.

The cells from the portion of the biopsy may be cultured through a variety of methods known for tissue culture and primary cell culture. For example, for primary cell culture, the tissue sample may be first dissected to remove fatty and necrotic cells. Then, the tissue sample may be subject to enzymatic or mechanical disaggregation. The dispersed cells may then be incubated, and the media changed to remove loose debris and unattached cells. Because primary cells are anchorage-dependent, adherent cells, they require a surface in order to grow properly in vitro. In one embodiment, the cells are cultured in two-dimensional (2D) cultures. Typically, a plastic uncoated vessel such as a flask or petri dish is used, and the cells are bathed in a complete cell culture media, composed of a basal medium supplemented with appropriate growth factors and cytokines. During establishment of primary cultures, it may be useful to include an antibiotic in the growth medium to inhibit contamination introduced from the host tissue. Various protocols for culturing primary cells are known and a variety of resources are available, including the ATCC® Primary Cell Culture Guide, available on the American Type Culture Collection website.

Example: Extraction of Genomic DNA

Genomic DNA can be isolated from tissue culture cells according to various protocols known in the art. For example, in one example of such a procedure, *Felis catus* cells are cultured in a monolayer are trypsinized and counted. The cells are pelleted by centrifuging 5 minutes at 500×g at 4 degrees, washed in ice cold PBS and re-pelleted. The cells are resuspended in 1 volume of digestion buffer (1 ml digestion buffer/$10^8$ cells. Samples are incubated at 50° C. for 12-18 hours while rotating, extracted with phenol/chloroform/isoamyl alcohol, and centrifuged 10 minutes at 1700×g. The aqueous layer is transferred to a new tube, and ½ volume of 7.5 M ammonium acetate and 2 volumes of 100% ethanol may be added. The DNA is pelleted by spinning 2 minutes at 1700×g and washed with 70% ethanol; the ethanol is then decanted and allowed to air dry. The DNA is resuspended at 1 mg/ml in TE buffer. If necessary, the sample is shaken gently at room temperature to 65° C. to facilitate resuspension (~1 g mammalian cells yields 2 mg DNA). 10% SDS is added to a final concentration of 0.1% and RNAse A to a final concentration of 1 µg/mL. The sample is incubated for 1 hour at 37° C. The sample is then phenol/chloroform extracted and ethanol precipitated.

Digestion Buffer:
100 mM NaCl
10 mM Tris [pH 8.0]
25 mM EDTA [pH 8.0]
0.5% SDS
0.1 mg/mL proteinase K

Example: Sequencing

Genomic DNA isolated from a direct biopsy sample, cryopreserved biopsy sample, or a cultured cell sample can be subject to sequencing analysis. Various sequencing approaches are known, including Sanger (or dideoxy) method, Maxam-Gilbert, Primer Walking, and Shotgun Sequencing. Preferred are next-generation sequencing methods (also known as high-throughput sequencing), which include a number of different sequencing methods including Illumina (Solexa) sequencing, Roche 454 sequencing, Ion torrent: Proton/PGM sequencing, and SOLiD sequencing. Such next-generation techniques have been reviewed in the literature (see Grada and Weinbrecht, Next-Generation Sequencing: Methodology and Application Journal of Investigative Dermatology (2013) 133, e11; and Bahassi and Stambrook, Next-generation sequencing technologies: breaking the sound barrier of human genetics, Mutagenesis, 2014 September; 29(5):303-10). Next generation sequence methods may encompass whole genome, whole exome, and partial genome or exome sequencing methods. Whole exome sequencing covers the protein-coding regions of the genome, which represents just over 1% of the genome.

Example: Design of Guide Sequences

In embodiments, a guide sequence of the invention is selected to target one or more Fel d 1 genomic sequences. The guide sequence may target a chain 1 or chain 2 genomic sequences on either strand of genomic DNA, or any region that is 5' or 3' of chain 1 or chain 2. In preferred embodiments, at least one pair of guide RNAs is chosen to excise a portion of genomic DNA between the pair.

Additionally, embodiments of the invention contemplate selection of guide RNA sequences to target flanking regions of Fel d 1 sequences and/or target internal regions of Fel d 1 sequences, or both. Thus, the guide RNAs may be selected to target one or more exons, or may be selected to completely excise Fel d 1 genomic DNA. For example, in one embodiment, genomic DNA encoding one or more exons of chain 1, chain 2, or both, is targeted. In another embodiment, exon 1 of chain 1 is targeted. In another embodiment, exon 2 of chain 1 is targeted. In another embodiment, exon 3 of chain 1 is targeted. In another embodiment, exon 1 of chain 2 is targeted. In another embodiment, exon 2 of chain 2 is targeted. In another embodiment, exon 3 of chain 2 is targeted. In another embodiment, multiple exons of chain 1, chain 2, or both chain 1 and chain 2 are targeted. In another embodiment, a region that is 5' or 3' flanking of chain 1 or chain 2 is targeted. In another embodiment, two flanking regions of Fel d 1 genes (e.g. one upstream of chain 2, another downstream of chain 1) are targeted. In embodiments of the invention, 5' or 3' flanking regions that are 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, or 10 kb or more in length are targeted. In another embodiment, two internal regions of Fel d 1 genes (e.g. one internal to chain 2, one internal to chain 1) are targeted. The guide RNAs may be selected to target one or more exons, or may be selected to completely excise Fel d 1 genomic DNA. In another embodiment, a guide RNA is selected to target and inactivate a regulatory element such as the promotor of a Fel d 1 genomic sequence.

Embodiments of the invention further contemplate selection of guide sequences based on predicted "on-target" activity. The guide sequences are selected to bind to one or more target sequences with minimal potential for "off-target" activity. Thus, the guide sequences should be designed to match the target sequence with minimal homology to other regions of the genome.

Additional embodiments of the invention contemplate selection of guide sequence through identification of Promoter Adjacent Motif (PAM) sequences in the genomic region to be targeted. The PAM sequences are short sequences recognized by the CRISPR complex and may vary depending on the species of Cas9. In one embodiment, the PAM sequence is specific to a *S. pyogenes* Cas9 and consists of the sequence NGG, wherein N is any nucleotide. The target sequences are chosen to be upstream (or 5') of the PAM sequence.

For example, in one embodiment of a method for designing a guide sequences a PAM (NGG) sequence is identified in a Fel d 1 genomic sequence or a region flanking 5' or 3' of the genomic sequence. Then, a specified number of nucleotides is counted upstream (or 5') of the PAM sequence to determine the 5' start of the actual guide RNA sequence. In one embodiment, the start of the target sequence is 20 nucleotides upstream of the PAM sequence. Additional considerations that may increase efficacy at target sequences include a G at position 1 (from the 5' end of the sequence) and an A or T at position 17. Additionally, it is preferred that conserved regions of Fel d 1 genomic sequence are targeted. Finally, the actual guide sequence is determined by selecting an RNA sequence that is complementary to the target sequence.

In one embodiment, the guide sequences are designed from Fel d 1 genomic sequences available in the literature or in GenBank (such as the *Felis catus* isolate Cinnamon breed Abyssinian chromosome E2, whole genome shotgun sequence, public Accession Number CM001392; see also Pontius, J. U., Initial sequence and comparative analysis of the cat genome, Genome Res. 17 (11), 1675-1689 (2007)). In another embodiment, the guide sequences are designed from sequencing data from one or more feline cell lines. The feline cell lines may be primary cell cultures, including those available commercially or those established from feline tissue samples.

Figure 2A:
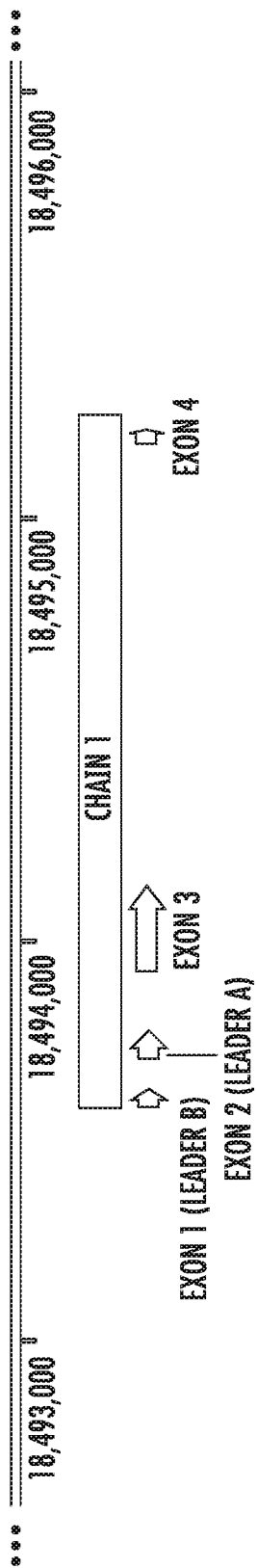
FIG. 2A is a genomic map of *Felis catus* Fel d 1 chain 1.
Figure 2B:
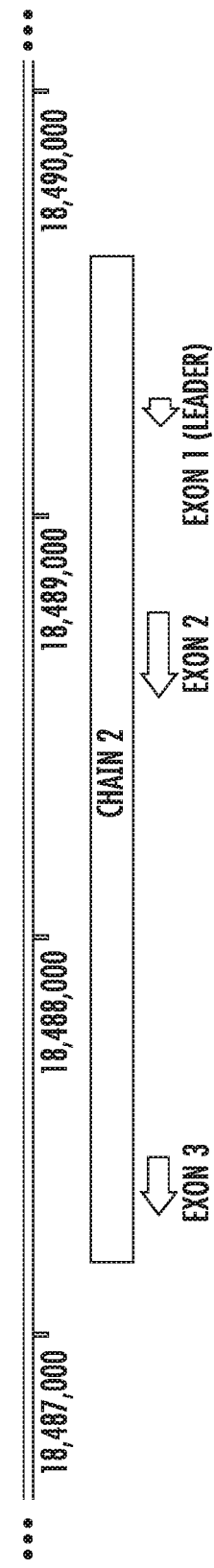
FIG. 2B is a genomic map of *Felis catus* Fel d 1 chain 2.

For example, FIG. 1 show a map of a 49.4 kilobase region of the *Felis catus* genome that comprises chain 1 and chain 2 coding regions. FIGS. 2A and 2B show a close-up map of chain 1 and chain 2 coding regions, respectively. The maps of FIGS. 1, 2A, and 2B show various features such as exons.

Figure 3:
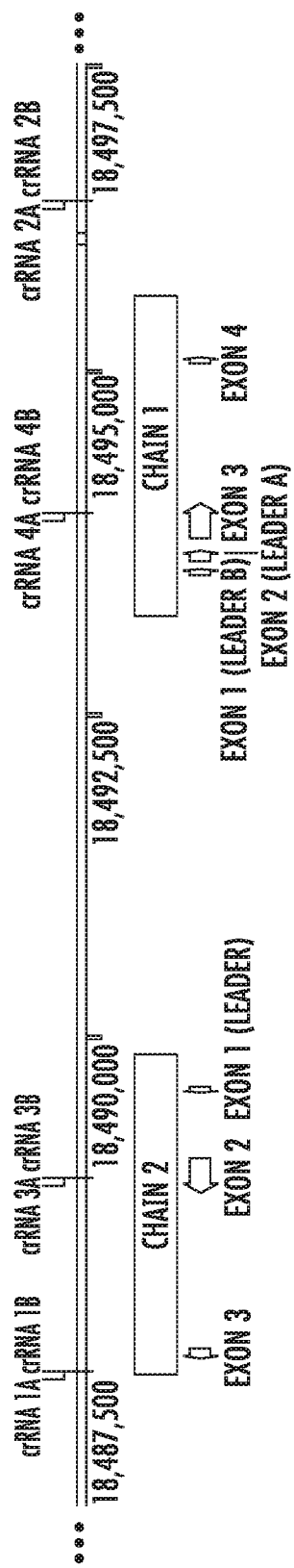
FIG. 3 is a genomic map of *Felis catus* Fel d genomic region, chains 1 and 2, showing exemplary sgRNA target regions.

FIG. 3 shows the map of FIG. 1 with specific target regions for guide RNAs (or more particularly, the crRNA portion of the sgRNAs). In this case, eight crRNA target sites are listed ("A" representing a target site for one strand of DNA and "B" representing a corresponding target site on the complementary strand). The table below shows the relative location of the (crRNA) target sites.

TABLE 1

Exemplary crRNA Target Sites and Location

| crRNA Target Site | Location |
| --- | --- |
| crRNA 1A, 1B | 5' of chain 2 |
| crRNA 2A, 2B | 3' of chain 1 |
| crRNA 3A, 3B | internal to chain 2 |
| crRNA 4A, 4B | internal to chain 1 |

Additionally, the following table shows exemplary strategies for designing pairs of guide RNAs and in particular for selecting target portions of the Fel d 1 genomic region.

TABLE 2

Exemplary Strategies for Two-Site Cleavage of Fel d 1 Genomic DNA

| 1st site | 2nd site |
| --- | --- |
| 5' of chain 2 | 3' of chain 1 |
| internal to chain 2 | internal to chain 1 |
| 5' of chain 2 | internal to chain 1 |
| internal to chain 2 | 3' of chain 1 |

Strategies which target as large a portion of the Fel d 1 genes as possible are preferred. For example, removing a portion of the Fel d 1 gene(s) that would in turn eliminate any potential allergic response is highly desired. One particular strategy could include choosing crRNA target sequence(s) toward the outside of the Fel d 1 region, whether the entire region is deleted or the beginning portion of the region is deleted. Thus, preferred embodiments include target sites that are 5' and 3' of the entire Fel d 1 genomic region, but removing any portion of the genomic region that would result in a reduced or eliminated allergic response is also possible. As an alternative strategy, beginning portions of chain 1 and chain 2 can be targeted so that neither chain is expressed.

Accordingly, pairs of crRNAs can be chosen according to the above strategy to target specific sites, such as according to the following table:

TABLE 3

Exemplary crRNA Target Sites for Cas9

| 1st site | 2nd site |
| --- | --- |
| 1A | 2B |
| 1B | 2A |
| 1A | 2A |
| 1B | 2B |
| 3A | 4B |
| 3B | 4A |
| 3A | 4A |
| 3B | 4B |
| 1A | 4B |
| 1B | 4A |
| 1A | 4A |
| 1B | 4B |
| 3A | 2B |
| 3B | 2A |
| 3A | 2A |
| 3B | 2B |

Additionally, FIG. 4A shows an exemplary strategy for selecting the crRNA portion of the guide RNAs for disruption of Fel d 1 expression.

Alternatively, if a Cas9 "nickase" is used, a total of four crRNAs would be chosen (as this would require two pairs of single-stranded breaks), such as shown in the following table. Such a strategy is also shown in FIG. 4B.

TABLE 4

Exemplary crRNA Target Sites for Cas9 Nickase

| 1st site | 2nd site | 3rd site | 4th site |
| --- | --- | --- | --- |
| 1A | 1B | 2A | 2B |
| 3A | 3B | 4A | 4B |
| 1A | 1B | 4A | 4B |
| 3A | 3B | 2A | 2B |

However, the crRNA target sites shown in FIG. 3 are merely exemplary. The target sites can be chosen to excise a Fel d 1 genomic sequence or associated region that is anywhere from about 0.01 kb to 50 kb in length, including at least about 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, and 49 kb in length.

Table 5 shows exemplary target DNA sequences for the sites discussed above, as well as the corresponding crRNA sequences.

TABLE 5

Exemplary crRNA Target Site Sequences

| crRNA Target Site | DNA Sequence | PAM | crRNA |
|---|---|---|---|
| 1A | ggtgtctggattccagcttt (SEQ ID NO: 680) | AGG | ggugucuggauuccagcuuu (SEQ ID NO: 1234) |
| 1B | ctgttctttacacctaaagc (SEQ ID NO: 1166) | TGG | cguucuuuacaccuaaagc (SEQ ID NO: 1235) |
| 2A | accttgcccagagtgagacc (SEQ ID NO: 254) | TGG | accuugcccagagugagacc (SEQ ID NO: 1236) |
| 2B | ccaagagccaggtctcactc (SEQ ID NO: 532) | TGG | ccaagagccaggucucacuc (SEQ ID NO: 1237) |
| 3A | gactagtccatccaagaccc (SEQ ID NO: 851) | TGG | gacuaguccauccaagaccc (SEQ ID NO: 1238) |
| 3B | cggactcttatccagggtct (SEQ ID NO: 1158) | TGG | cggacucuuauccaggggucu (SEQ ID NO: 1239) |
| 4A | caatgcacgacctgtagtat (SEQ ID NO: 266) | TGG | caaugcacgaccuguaguau (SEQ ID NO: 1240) |
| 4B | ctggcatttgccaatactac (SEQ ID NO: 361) | AGG | cuggcauuugccaauacuac (SEQ ID NO: 1241) |

In embodiments, the crRNA targets are chosen to induce any appropriate mutation that results in disrupted, reduced, or eliminated expression of Fel d 1, including insertions, deletions, frameshift mutations, and the like.

In some embodiments, a single crRNA target site is chosen to introduce disruptions that render the Fel d 1 gene non-functional. For example, double-stranded breaks at a single target site introduced by Cas9 are repaired by non-homologous end joining (NHEJ), which can result in the insertion and deletion of a few base pairs which can introduce frameshift mutations which effectively knock-out the Fel d 1 gene by shifting the reading frame. In another example, a piece of DNA ("donor") whose ends are identical to the region of interest (i.e. Fel d 1 genomic sequence) is introduced, along with a sgRNA and Cas9 nuclease. As a result of repair by homology-directed repair (HDR), the donor DNA is introduced into the genome resulting in introduction of a foreign sequence into the Fel d 1 genomic sequence which effectively "knocks in" the foreign DNA. The foreign DNA sequence can be inserted so that the entire region is rendered non-functional, or that the foreign DNA sequence is expressed. The foreign DNA sequence may include, for example, an epitope tag (such as c-myc) or a reporter (such as green fluorescent protein (GFP)) and/or a non-functional Fel d 1 gene. Such procedures have been reviewed (see Wang et al., One-Step Generation of Mice Carrying Mutations in Multiple Genes by CRISPR/Cas-Mediated Genome Engineering, 153(4): 910-918, 2013; Yang et al., One-Step Generation of Mice Carrying Reporter and Conditional Alleles by CRISPR/Cas-Mediated Genome Engineering, 154(6):1370-1379, 2013).

Example: In Silico Identification of Guide RNA Target Sequences

A program that identifies guide RNA Target Sequences from a particular genomic sequence was used to identify a list of candidate guide RNA Target Sequences. The program is available on the Broad Institute website (http://www.broadinstitute.org/rnai/public/analysis-tools/sgrna-design). The genomic sequences of Fel d 1 chain 1 and chain 2, with 1 kb additional sequence on either side of them, were submitted separately to the program. For chain 1, the total length of the target sequence was 4516 base pairs (full sequence is set forth in SEQ ID NO: 1226), and for chain 2 the total length was 4416 base pairs (full sequence is set forth in SEQ ID NO: 1227). Additional parameters are provided in the table below (definitions can be found below):

TABLE 6

| Quota | Target Taxon | PAM Policy | Target Window Policy | Initial Spacing Requirement | Off-Target Match Ruleset Version | Off-Target Tier Policy | Off-Target Match Bin Policy |
|---|---|---|---|---|---|---|---|
| 8 | 9506 | NGG | 5-65 | 5 | 1 | 1 | 5.20.100 |

Quota = Desired number of candidate sgRNA sequences to pick for this target.
Target Taxon = Taxon of the target gene.
PAM Policy = Currently limited to NGG only.
Target Window Policy = Portion of the target region (as defined by Target Mode) which is preferentially targeted (given as a percent range, e.g. 5-65 means target the region between the 5th and 65th percentile of the target region).
Initial Spacing Requirement = When possible, pick sgRNA sequences which are separated by a certain distance (measured here in terms of percentage of the length of the entire target region). This is called "Initial" because, this requirement is relaxed in subsequent picking "rounds" if the quota is not met after examining all candidate sgRNAs for the target.
Off-Target Match Rule Set Version ("CFD score") = Method of calculating an off-target match, or "CFD" (Cutting Frequency Determination) score; currently there is only one off-target rule set ("1").
Off-Target Tier Policy = Method used to categorize off-target matches into "Tiers"; currently there is only one such policy ("1"), which breaks down as follows: Tier I: protein-coding regions; Tier II: any position within the transcribed sequence of a coding gene (intron or exon); Tier III: any position within the transcribed sequence of a non-coding gene; Tier IV: positions not contained in any gene (i.e. not transcribed).
Off-Target Match Bin Policy = Thresholds used to categorize off-target matches into "Match Bins" according to CFD score. There are four bins notated by three thresholds in increasing numerical order, separated by periods. Threshold values are in hundredths. For example, "5.20.100" represents the following 4 bins: Bin I: CFD = 1.0, Bin II: 1.0 > CFD ≥ 0.2, Bin III: 0.2 > CFD ≥ 0.05, Bin IV: 0.05 > CFD.

SEQ ID NOS: 1-1225 lists exemplary target sequences obtained from the above procedure. In general, the sequences were obtained from the corresponding chain (chain 1 or chain 2) and strand (sense or antisense) in which the target sequence is found, using a PAM Sequence of NGG, where N=A, C, G, or T. A total of 1428 target sequences were identified (795 for chain 1 and 633 for chain 2); however there were duplicates in this initial set so that 1225 of the 1428 are unique sequences and are set forth as SEQ ID NOS: 1-1225. With respect to the 1225 unique sequences, Table 7 represents the correspondence with SEQ ID NOS, Fel D 1 chain, strand, and the PAM sequence used to identify the sequences.

TABLE 7

| Sequences | Chain | Strand | PAM Sequence |
|---|---|---|---|
| SEQ ID NOS: 1-105 | 1 | sense | AGG |
| SEQ ID NOS: 106-123 | 1 | sense | CGG |
| SEQ ID NOS: 124-248 | 1 | sense | GGG |
| SEQ ID NOS: 249-323 | 1 | sense | TGG |
| SEQ ID NOS: 324-400 | 1 | antisense | AGG |
| SEQ ID NOS: 400-412 | 1 | antisense | CGG |
| SEQ ID NOS: 413-509 | 1 | antisense | GGG |
| SEQ ID NOS: 510-593 | 1 | antisense | TGG |
| SEQ ID NOS: 594-702 | 2 | sense | AGG |
| SEQ ID NOS: 703-718 | 2 | sense | CGG |
| SEQ ID NOS: 719-803 | 2 | sense | GGG |
| SEQ ID NOS: 804-881 | 2 | sense | TGG |
| SEQ ID NOS: 882-985 | 2 | antisense | AGG |
| SEQ ID NOS: 986-1008 | 2 | antisense | CGG |
| SEQ ID NOS: 1009-1118 | 2 | antisense | GGG |
| SEQ ID NOS: 1119-1225 | 2 | antisense | TGG |

Target sequences are located in the target DNA region and are referred to herein as the sgRNA Target Sequences. Corresponding crRNAs are identical in sequence to the target sequences. For example, appropriate crRNAs corresponding to the sgRNA Target Sequences provided in SEQ ID NOS: 1-1225 can include: AAAAAAAAAAUAAAGUGACC (SEQ ID NO: 1242) (crRNA encoded by target sequence of SEQ ID NO: 1); AAAAAUGACAGAAGAGGAUA (SEQ ID NO: 1243) (crRNA encoded by target sequence of SEQ ID NO: 2), etc.

Additionally, it is possible to rank the guide RNA target sequences according to an algorithm that predicts off-target and on-target effects. For example, algorithms can rank and pick candidate sgRNA sequences for the targets provided, while attempting to maximize on-target activity and minimizing off-target activity, if a reference genome is available. For example, the Broad Institute tool uses "Rule Set 2" (developed in conjunction with the Azimuth project at Microsoft Research) to model sgRNA on-target activity, and the CFD (Cutting Frequency Determination) score to evaluate off-target sites.

Additional tools for identifying guide RNA Target Sequences include those found at http://crispr.mit.edu/ (see Hsu et al, DNA targeting specificity of RNA-guided Cas9 nucleases, Nature Biotechnology 31, 827-832 (2013)) and http://www.e-crisp.org/ (see Heigwer, F., Kerr, G. & Boutros, M., E-CRISP: fast CRISPR target site identification. Nat. Methods 11, 122-123 (2014)).

Example: Oligonucleotide Synthesis

Once guide RNA Target Sequences have been identified, DNA oligonucleotide sequences encoding guide RNAs and Cas9 may be synthesized. For example, the oligonucleotide sequences may be identical to any of the sgRNA Target Sequences set forth in SEQ ID NOS: 1-1225. In other embodiments, the oligonucleotide is at least 60%, 65%, 70%, 75%, 80%, 85%, 90%, or 95% identical to a sgRNA Target Sequence set forth in SEQ ID NOS: 1-1225. In specific aspects of the invention, the oligonucleotide encoding the crRNA portion of the guide RNA will be a 18-mer to 22-mer, such as a 20-mer, that is at least 60%, 65%, 70%, 75%, 80%, 85%, 90%, or 95% identical to the 20-mers set forth in SEQ ID NOS: 1-1225. Chemical synthesis of polynucleotides can be performed, for example, on commercial automated oligonucleotide synthesizers. Additionally, the oligonucleotide sequences may encode a tracrRNA portion. Examples of such tracrRNA-encoding oligonucleotides are set forth in SEQ ID NOS: 1228-1233. Further, oligonucleotides may be synthesized to encode any Cas9 protein or variant with dual or single endonuclease activity.

Example: Cloning into Vectors

General protocols for cloning include those found in Sambrook, Molecular Cloning: A Laboratory Manual, Cold Spring Harbor Press, Cold Spring Harbor, New York. For example, oligonucleotides encoding Cas9 and a pair of guide RNAs can be cloned into a single vector, or two separate vectors (one encoding Cas9 and one encoding the pair of guide RNAs). Protocols for such guide RNA and Cas9 cloning have been described (see Ran et al., 2013).

The vectors may be a plasmid or other recombinant vector which contains a promoter capable of expression of a transcript in mammalian cells, one or more cloning sites, a selectable marker for selection of transfected cells (e.g. Neomycin, Puromycin, Hydromycin, Zeocin/Bleo), and optionally a tag such as an epitope tag (e.g. FLAG, HA, Myc, 6×His), protein purification tag (GST), or localization tag (GFP). Alternatively, the vectors may be viral vectors. Such viral vectors, and particularly retroviral vectors, have been used in a wide variety of gene delivery applications in cells, as well as living animal subjects. Viral vectors that can be used include, but are not limited to, retrovirus, adeno-associated virus, pox, baculovirus, vaccinia, herpes simplex, Epstein-Barr, adenovirus, geminivirus, and caulimovirus vectors. Additional examples of viral vectors include lentiviral vectors such as those based on HIV or FIV. Non-viral vectors include plasmids, liposomes, electrically charged lipids (cytofectins), DNA-protein complexes, and biopolymers. An example of a non-viral vector system is the Sleeping Beauty transposon system, which has been reviewed (see Aronovich, E. L., The Sleeping Beauty transposon system: a non-viral vector for gene therapy, Hum Mol Genet. 2011 Apr. 15; 20(R1): R14-R20). In addition to a nucleic acid, a vector may also comprise one or more regulatory regions, and/or selectable markers useful in selecting, measuring, and monitoring nucleic acid transfer results (transfer to which tissues, duration of expression, etc.).

Examples of commercially-available mammalian expression vectors include p3xFLAG-CMV™ (Sigma Aldrich), p3xFLAG-Myc-CMV™ (Sigma Aldrich), pBI-CMV (Clontech), pcDNA™3.1 (Life Technologies), pCMV-Tag (Agilent Technologies), pIRES (Clontech), and others.

In aspects of the invention, vectors that may be used in the inventive methods may employ any of the following:
1) An RNA pol III promoter (such as a U6 promoter) for guide RNA expression.
2) A constitutive mammalian cell promoter for expression of Cas 9.
3) A nuclear localization signal (NLS) for directing Cas9 into the nucleus.
4) A Green-Fluorescent Protein (GFP) tag.
5) A tracrRNA sequence (gRNA scaffold).
6) A site for cloning a guide sequence (crRNA) oligonucleotide upstream of the tracrRNA sequence (G(N) 20 gRNA) by way of restriction enzyme digestion.
7) One or more selectable markers.

Figure 5A:
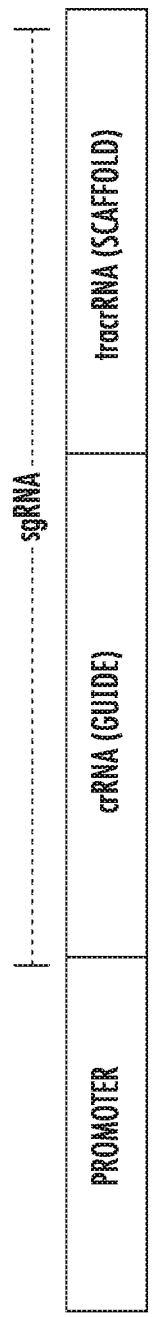
FIG. 5A is a schematic diagram of a guide RNA expression cassette according to an embodiment of the invention.
Figure 5B:
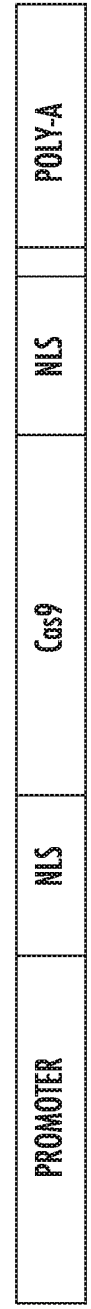
FIG. 5B is a schematic diagram of a Cas9 expression cassette according to an embodiment of the invention.

FIGS. 5A and 5B show examples of two basic expression cassettes for independent use or for incorporating into vectors. FIG. 5A shows an expression cassette comprising (from 5' to 3') a promoter and a chimeric DNA polynucleotide comprising a polynucleotide encoding a crRNA and a polynucleotide encoding a tracrRNA. Together the crRNA and tracrRNA make up the guide RNA that directs the Cas9 protein to a specific site in the genome. The promoter shown in FIG. 5A can be a pol III promoter such as a U6 promoter.

FIG. 5B shows an expression cassette comprising a promoter located 5' of a polynucleotide encoding Cas9. The Cas9 encoding sequence is flanked by two nuclear localization signals (NLS). Additionally, the codons of the Cas9 encoding sequence can be optimized for expression in a species of interest (i.e. *Felis catus* cells). At the 3' end of the expression cassette is a polynucleotide sequence encoding a poly-adenylation site. However, in other embodiments, such as use in lentiviral vectors, the nuclear localization signals may not be needed. One who is skilled in the art of molecular biology can customize the expression cassettes according to the requirements for a particular application. The promoter may be a mammalian promoter, an inducible promoter, a tissue-specific promoter, or the like.

Examples of animal and mammalian promoters known in the art include, but are not limited to, the SV40 early (SV40e) promoter region, the promoter contained in the 3' long terminal repeat (LTR) of Rous sarcoma virus (RSV), the promoters of the E1A or major late promoter (MLP) genes of adenoviruses (Ad), the cytomegalovirus (CMV) early promoter, the herpes simplex virus (HSV) thymidine kinase (TK) promoter, a baculovirus IE1 promoter, an elongation factor 1 alpha (EF1) promoter, a phosphoglycerate kinase (PGK) promoter, a ubiquitin (Ubc) promoter, an albumin promoter, the regulatory sequences of the mouse metallothionein-L promoter and transcriptional control regions, the ubiquitous promoters (HPRT, vimentin, beta-actin, tubulin and the like), the promoters of the intermediate filaments (desmin, neurofilaments, keratin, GFAP, and the like), the promoters of therapeutic genes (of the MDR, CFTR or factor VIII type, and the like), pathogenesis or disease related-promoters, and promoters that exhibit tissue specificity and have been utilized in transgenic animals, such as the elastase I gene control region which is active in pancreatic acinar cells; insulin gene control region active in pancreatic beta cells, immunoglobulin gene control region active in lymphoid cells, mouse mammary tumor virus control region active in testicular, breast, lymphoid and mast cells; albumin gene, Apo AI and Apo AII control regions active in liver, alpha-fetoprotein gene control region active in liver, alpha 1-antitrypsin gene control region active in the liver, beta-globin gene control region active in myeloid cells, myelin basic protein gene control region active in oligodendrocyte cells in the brain, myosin light chain-2 gene control region active in skeletal muscle, and gonadotropic releasing hormone gene control region active in the hypothalamus, pyruvate kinase promoter, villin promoter, promoter of the fatty acid binding intestinal protein, promoter of the smooth muscle cell beta-actin, and the like. In addition, these expression sequences may be modified by addition of enhancer or regulatory sequences and the like.

Other types of promoters that may be used in the expression cassettes may include, without limitation, tissue-specific promoters, inducible promotors, light-regulated promoters, developmental-specific promoters, and the like.

As an example of tissue-specific promoters which may be useful according to the inventive methods, salivary gland-specific promoters such as parotid secretory protein (PSP) promoter, proline-rich protein (PRP) promoter, and salivary amylase promoter are described in Canadian Patent No. CA2369672C. Skin-specific promoters, such as keratin promoters for epidermal expression have also been described (see Blessing et al., Genes. Devel., 7, 204-15 (1993); Blessing et al., J. Cell. Biol., 135, 227-39 (1993); and Byrne et al., Mol., Cell. Biol., 13, 3176-90 (1993)). Other skin-specific promoters include E-cadherin, elastin or alpha-1 collagen promoters. These and other tissue-specific promoters known in the art may be useful for tissue-specific deletion of Fel d 1 expression.

Inducible promoters activate a level of gene expression that is dependent on the level of a ligand that is present to activate the promoter. Examples of inducible promoters are known in the art, and include those activated by tetracycline (TET-ON), rapamycin or its derivatives, or various steroidal ligands (e.g., glucocorticoid, estrogen, progestin, retinoid, or ecdysone) or analogs or mimetics thereof. Inducible promoter systems that are commercially available include the T-REx™ System (ThermoFisher Scientific, Waltham, MA) which is a mammalian expression system based on the binding of tetracycline to the Tet repressor and derepression of the promoter controlling expression of the gene of interest, as well as the Tet-On 3G Tetracycline-Inducible Gene Expression Systems (Clontech Laboratories, Inc., Mountain View, CA).

Figure 6A:
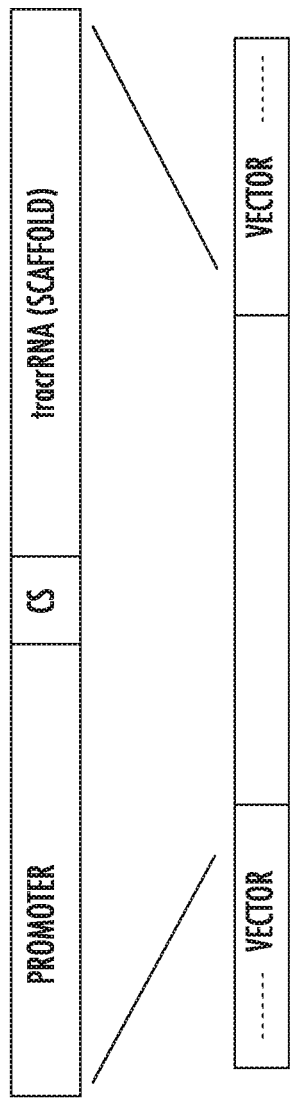
FIG. 6A is a schematic diagram of a vector comprising a cloning site for insertion of an oligonucleotide encoding a crRNA upstream of a polynucleotide encoding a tracrRNA according to an embodiment of the invention.
Figure 6B:
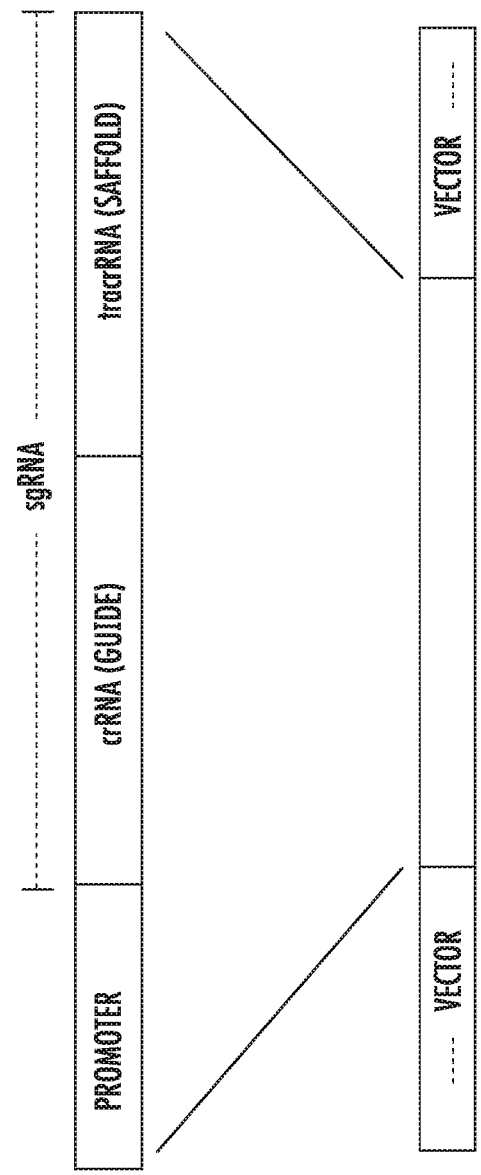
FIG. 6B is a schematic diagram of the vector of FIG. 6A with a crRNA cloned into the vector according to an embodiment of the invention.

FIG. 6A shows a recombinant vector useful for cloning an oligonucleotide encoding a custom crRNA for expression of a guide RNA. The vector comprises (from 5' to 3') a promoter, a cloning site, and a polynucleotide encoding the tracr/scaffold portion of the guide RNA. For example, any of the 1225 polynucleotides set forth in SEQ ID NOS: 1-1225 can be synthesized as 20-mers and flanked with bases to match the restriction enzyme sites in the cloning site and cloned into the vector. FIG. 6B shows the vector of FIG. 6A with an oligonucleotide with a sequence chosen from one of the sequences set forth in SEQ ID NOS:1-1225 cloned into the vector to complete the expression cassette.

Figure 7:
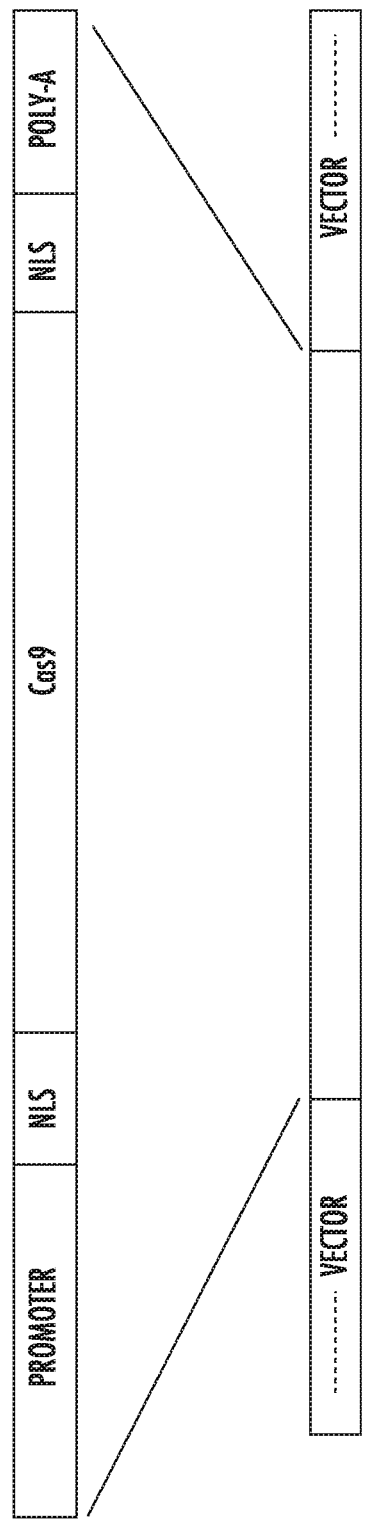
FIG. 7 is a schematic diagram of a vector comprising a Cas9 expression cassette according to an embodiment of the invention.

FIG. 7 shows a vector with the expression cassette of FIG. 5B.

Figure 8A:
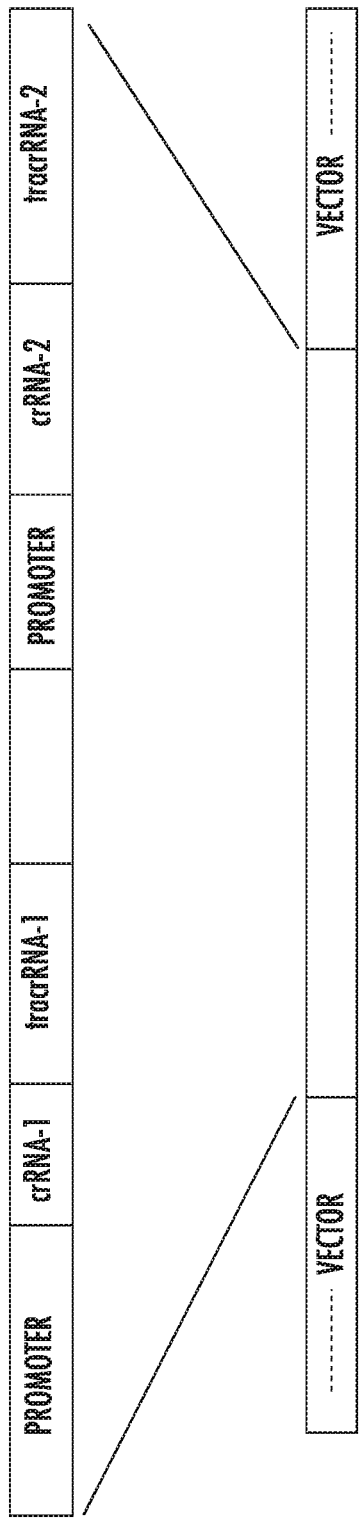
FIG. 8A is a schematic diagram of a vector comprising two guide RNA expression cassettes according to an embodiment of the invention.
Figure 8B:
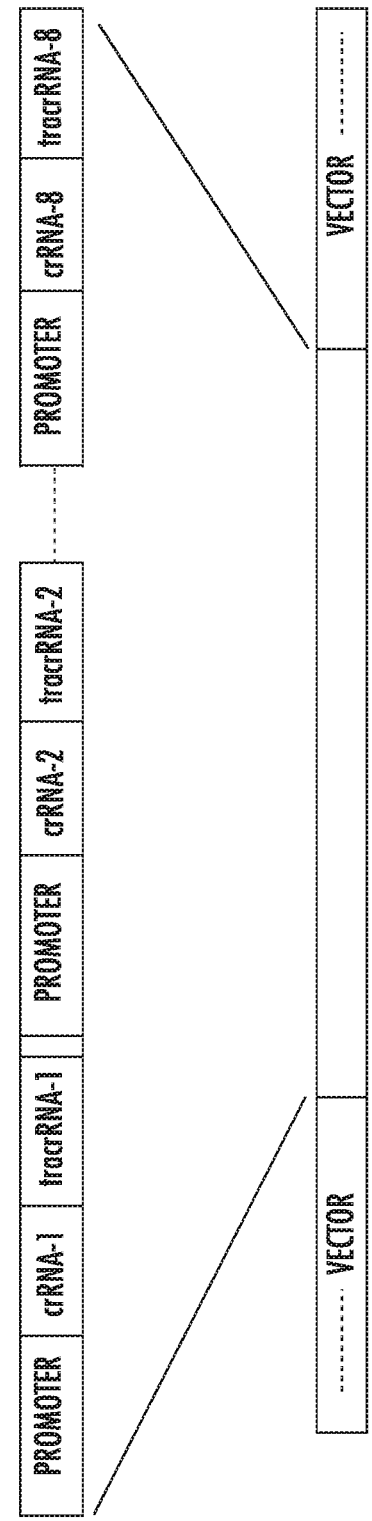
FIG. 8B is a schematic diagram of a vector comprising up to 8 guide RNA expression cassettes according to an embodiment of the invention.
Figure 9A:
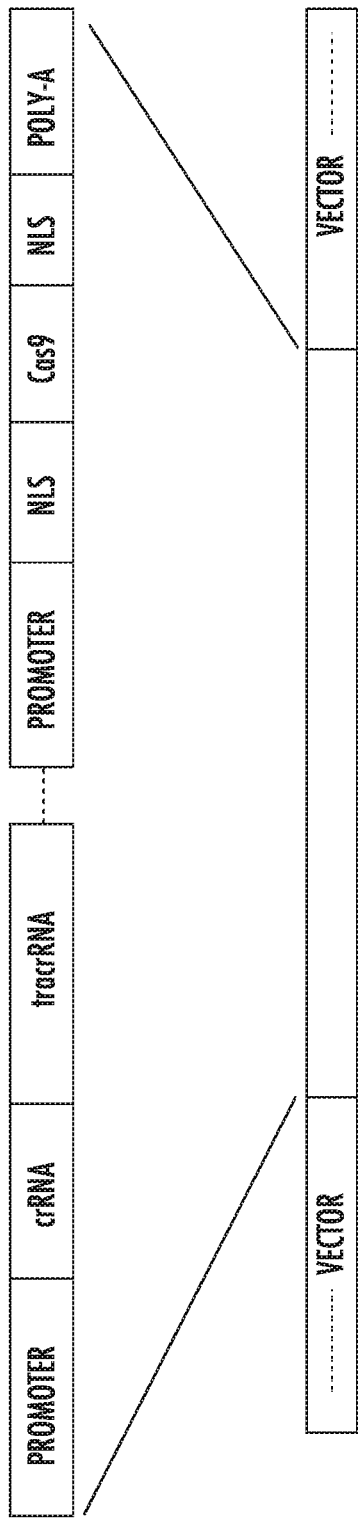
FIG. 9A is a schematic diagram of a vector comprising a guide RNA expression cassette and a Cas9 expression cassette according to embodiments of the invention.
Figure 9B:
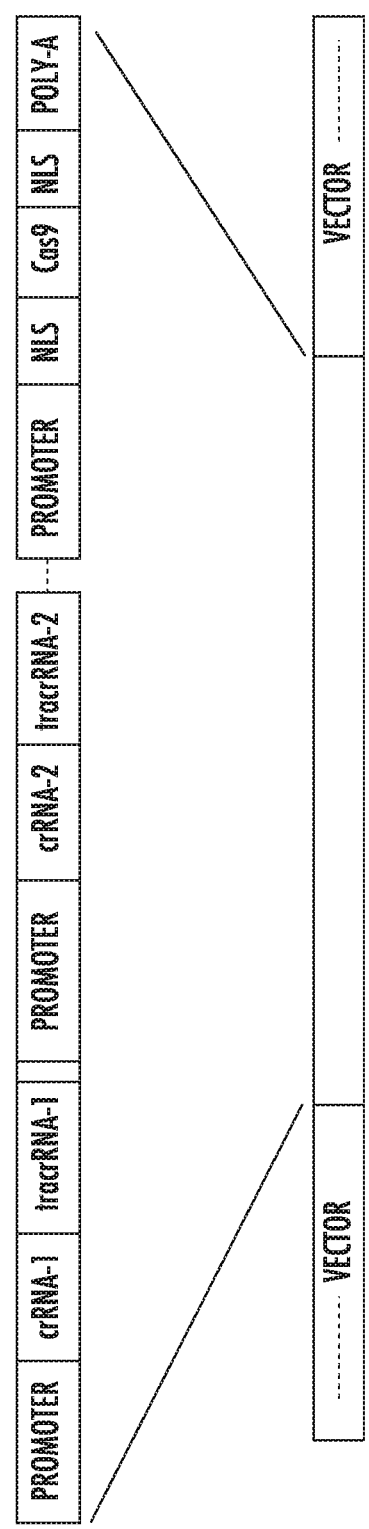
FIG. 9B is a schematic diagram of a vector comprising a two guide RNA expression cassettes and a Cas9 expression cassette according to embodiments of the invention.

Additionally, vectors containing multiple expression cassettes are possible for multiplex gene targeting. For example, FIG. 8A shows a vector capable of expressing two guide RNAs, while FIG. 8B shows a vector capable of expressing up to 8 guide RNAs. Additionally, expression cassette encoding guide RNAs and Cas9 may be provided in separate vectors or the same vector. For example, FIG. 9A shows a vector capable of expressing a single guide RNA and Cas9, while FIG. 9B shows a vector capable of expressing a pair of guide RNAs and Cas9.

Additionally, a number of publicly-available vectors can be used for one or two-vector systems of guideRNA and Cas9 expression. Examples of commercially-available Cas9 vectors include pSpCas9 BB-2A-GFP (PX458), pLentiCRISPR v2, pLentiGuide-Puro, pGS-gRNA pGS-gRNA-Neo, pAAV SpCas9 acceptor (PX552) (GenScript, Piscataway, NJ). Non-profit plasmid repositories such as Addgene are another source of vectors capable of expressing guideRNAs and Cas9.

Example: Testing of Guide RNA Sequences

Guide RNA sequences may be tested for activity prior to testing in cell culture through routine methods. For example, in some embodiments, guide RNA sequences of interest are first synthesized by in vitro transcription. Next, individual guide RNA sequences may be tested in vitro to determine their efficacy. For example, in one embodiment, a target sequence may be synthesized and amplified by PCR to create a template. In a preferred embodiment, the genomic DNA target sequence of the particular cat cell line to be used in the implementation of the inventive methods is directly amplified by PCR to create the template. This ensures that the results would be representative of what would happen in the cell line of interest. The template may then be combined with a guide RNA of interest and a Cas9 nuclease. The efficiency with which Cas9 nuclease cleaves the template can then be measured using agarose gel electrophoresis. Such testing is available from commercially available kits (In Vitro Transcription and Screening Kits for sgRNA, Clontech Laboratories Inc, Mountain View, CA).

Alternatively or in addition, guide RNA sequences are tested in cell culture. Guide RNAs can be delivered to cells as either PCR amplicons containing an expression cassette or guide RNA-expressing plasmids. In addition to PCR and plasmid-based delivery methods, Cas9 and sgRNAs can be introduced into cells as mRNA and RNA, respectively. Alternatively, cultured cells can be transfected with Cas9 proteins and synthetic guide RNA oligonucleotides using conventional lipofection reagents. This generally involves: 1) assembly of a ribonuclear protein complex (RNP) by duplexing crRNA and tracrRNA oligos and mixing with Cas9 protein 2) reverse transfecting the RNP complex in cultured cells by way of transfection reagent.

For example, in one embodiment, 20-mer oligonucleotides encoding a pair of guide sequences may be synthesized into commercially available Cas9 vectors (all-in-one vector) and prepared for transfection into feline cell lines. Alternatively, the pair of guide sequences and Cas9 may be cloned into separate vectors (two-vector system). The following is an exemplary protocol for testing guide RNA sequences in cell culture.

Feline host cells are cultured in Eagle's Minimum Essential Medium supplied with fetal bovine serum to a final concentration of 10%. The cultures are incubated at 37° C. and subcultured when cell concentration is between 6 and $7 \times 10^4$ cells/cm'. The cells are then seeded $4\text{-}6 \times 10^4$ cells/cm$^2$ in cell culture plate one day before transfection.

Guide RNA and Cas9 are introduced into feline host cells using standard methods. Vectors containing DNA encoding guide RNA and Cas9 may be introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter. Two to three days after transfection, the cell pool can be analyzed directly by Sanger sequencing, NGS (Next Generation Sequencing) and/or Surveyor assay. Sanger sequencing of the target region can detect overlapping peaks at close region of double strand break (DSB), if small insertion or deletion (indel) mutations are introduced. Surveyor assay (or T7E1 assay) uses enzymes of mismatch-specific DNA endonucleases to detect indel mutations at the targeted loci. By targeting and digesting mismatched heteroduplex double-strand DNA, this assay produces two or more smaller fragments, depending on number of mismatched sites on the region analyzed.

Transfected cells can be selected using antibiotic resistance or a GFP reporter if they are present on the Cas9 expression plasmid. Transfected cells (with or without selection) can be plated into 96 well plates at 1 cell/well density for cloning. This procedure can be also conducted using diluted host cell line on 10 cm plate to form colonies, which can be picked up and transferred to 24 well plate for future usage.

After expansion of the clones, the cells in each clone can be analyzed by Sanger sequencing to identify the clones harboring a mutation at the target region. Sequencing trace files will show overlapping peaks at regions where double strand breaks have been repaired by introducing small indels.

Alternatively, knock-out cell lines can be confirmed by Western Blot if a specific antibody is available, or through ELISA or other immunoassay.

Additionally, high throughput screening assays can be developed which assess guide RNA efficacy. Briefly, feline cells may be cultured in 96-well or 384-well plates. A library of sgRNA vectors may than be used to transfect the cells (two sgRNA sequences per well). After transfection the cells may be prepared for PCR based on amplification of an internal Fel d 1 sequence to confirm efficacy of each vector design, where successful knockout results in lack of amplification and vice versa. Alternatively or in addition, a cell line that expresses Fel d 1 can be used for the assay, and the cell media can be assayed for the Fel d 1 protein using an immunological-based assay such as a Radio Immune Assay (MA) or ELISA.

Creating Transgenic Cats

Once the efficacy of guide RNAs for Cas9-mediated knock out of Fel d 1 is confirmed, such guide RNAs can be used with Cas9 to create a transgenic cat. General procedures for gene targeting and animal cloning are available (see Denning C, and Priddle, H, New frontiers in gene targeting and cloning: success, application and challenges in domestic animals and human embryonic stem cells, Reproduction (2003) 126, 1-11; and Wang, B, and Zhou, J, Specific genetic modifications of domestic animals by gene targeting and animal cloning, Reproductive Biology and Endocrinology (2003), 1:103). The following Examples describe three different methodologies for creating Fel d 1 knockout cats.

Example: Cloning a Genetically Engineered Fel d 1 Knockout Cat by Nuclear Transfer The following Example is adapted from Shin et al., A cat cloned by nuclear transplantation: This kitten's coat-coloration pattern is not a carbon copy of its genome donor's, Nature, Vol 415 (2002), 859 and Supplementary Information.

Oocyte Recovery and In Vitro Oocyte Maturation

Reproductive tracts from queens greater than 6 months of age are collected from routine ovariohysterectomy at local veterinary clinics. Ovaries are removed from the tract, rinsed in TL-Hepes, and then minced with a scalpel blade to release immature ova. For in vitro maturation, cat ova are then cultured in TCM 199 with Earle's salts supplemented with 0.36 mM pyruvate, 2.0 mM L-glutamine, 2.28 mM calcium lactate, 1.13 mM cysteine, 1% of a solution containing 10,000 U/ml Penicillin G, 10,000 µg/ml Streptomycin (P/S), 10 ng/ml EGF, 1 IU/ml hCG, 0.5 IU/ml eCG and 3 mg/ml fatty acid free BSA (IVM medium) for 24-30 hrs under 5% $CO_2$, 5% $O_2$, and 90% $N_2$ gas and humidified air atmosphere at 38° C.

Enucleation

Following in vitro maturation, cumulus cells are removed from the ova by gently pipetting for 3 minutes in Hepes-buffered TCM 199 supplemented with 0.1% hyluronidase. After removal of cumulus cells, the oocytes are placed in a petri dish containing Hepes-buffered TCM 199 supplemented with 3 mg/ml fatty acid free BSA, 15.0 µg/ml cytochalasin B and 5 µg/ml Hoechst 33342, and enucleated using a beveled glass pipette mounted on Narshige micromanipulators while viewing with a Zeiss Microscope. Enucleation is confirmed by observation under UV light.

Cell Culture and Preparation of Donor Cells

Skin cells or adult fibroblast cells from a donor cat are isolated and cultured in an appropriate mammalian cell culture medium, supplemented with 10% FBS for 2-5 days at 37° C. in an atmosphere of 5% $CO_2$ and air. The cells are then transfected with a vector comprising an expression cassette encoding Cas9 and a pair of guide RNAs (one designed to target the 5' flanking region of chain 2, and one designed to target the 3' flanking region of chain 1). sgRNA Target Sequences are for example chosen from those set forth in SEQ ID NOS: 1-1225. A sequencing assay or assay for Fel d 1 expression is performed on a portion of the cells to confirm knockout of Fel d 1 or a portion thereof. The cells are passaged multiple times then collected, frozen, and stored in liquid nitrogen. Three to 5 days prior to nuclear transfer the cell line is thawed and maintained in 4-well dishes (Nunc, Denmark) in DMEM/F12, supplemented with 10% FCS+1% P/S at 37° C. in an atmosphere of in 5% $CO_2$ and air.

Nuclear Transfer, Electrofusion and Oocyte Activation

For nuclear transfer, the engineered Fel d 1 knockout donor cells are removed from the incubator, trypsinized using a 1% trypsin-EDTA solution, and placed into a petri dish containing $Ca^{2+}$, $Mg^{2+}$ free D-PBS with 0.3% BSA. Micromanipulation is then used to place a single nuclear donor cell into the perivitelline space of enucleated ova.

For electrofusion, the ovum/cell couplets are equilibrated in 0.3 M mannitol solution containing 0.1 mM $Mg^{2+}$, then transferred to an electrofusion chamber containing the same medium. Cell fusion is induced by applying 2, 3.0 kV/cm 25 µsec DC pulses delivered by a BTX Electrocell Manipulator 200 (BTX, San Diego, CA). The couplets are then removed from the fusion chamber, washed and incubated in TCM 199 supplemented with 0.3% BSA and 5.0 µg/ml cytochalasin B, at 38° C. in and atmosphere of 5% $CO_2$ and air. Two hours after electrofusion, fused couplets are removed from the incubator and equilibrated in 0.3 mM mannitol containing 0.1 mM $Ca^{2+}$ and 0.1 mM $Mg^{2+}$, then placed into a fusion chamber containing the same medium and electropulsed by applying 2×, 1.0 KV/cm 50 µsec pulses, 5 seconds apart. The ova are then removed from the fusion chamber, washed, and incubated for 6-7 hrs in TCM 199 supplemented with 0.3% BSA, 10 µg/ml cycloheximide and 5 µg/ml cytochalasin B in a 5% $CO_2$, 5% $O_2$, 90% $N_2$ gas mixture in humidified air at 38° C. Cloned embryos are then cultured in modified Tyrode's solution supplemented with 0.36 mM pyruvate, 1.0 mM L-glutamine, 2.28 mM calcium lactate, 1% non-essential amino acids (NEAA) and 3 mg/ml fatty acid free BSA (IVC 1 medium) for 1-3 days.

Synchronization of Recipient Females and Embryo Transfer

Cloned embryos are surgically transferred into the oviducts of recipient queens. Estrus synchronization of recipient queens is attained using the same hormone injection regimen described above. Following embryo transfer, trans-abdominal ultrasonography is utilized to monitor for pregnancy.

Cloned kittens are reared to 6 months of age. Samples of saliva are tested for the production of Fel d 1 according to an ELISA assay. Additionally, kittens are anesthetized and a biopsy of the salivary gland is taken. Salivary gland explants are grown in organ culture dishes in DMEM with 10% FCS on filter paper. The explants are subject to genomic DNA extraction as described above and PCR and sequence analysis. ELISA testing of saliva samples shows no detectable Fel d 1 in comparison to controls, and PCR and sequencing analysis confirm complete disruption of chain 1 and chain 2 Fel d 1 genomic DNA.

Alternatively or in addition to ELISA testing, Western Blot Analysis can be used to confirm lack of Fel d 1 production in saliva or explant samples.

Example: Cloning a Genetically Engineered Fel d 1 Knockout Cat by Direct Gamete Genetic Modification The following Example is adapted from Wongsrikeao et al., Antiviral restriction factor transgenesis in the domestic cat, Nat Methods.; 8(10): 853-859 (2011), incorporated by reference herein in its entirety. The skilled artisan can supplement this Example with specific details provided in the Wongsrikeao manuscript and Supplemental Materials.

Gametes from both domestic sexes are obtained without added animal procedures by micro-dissecting gonads discarded after spaying or neutering. In vitro matured grade I and II domestic cat oocytes are subjected to perivitelline space microinjection (PVSMI) with 100 picoliters of concentrated lentiviral vector. The lentiviral vector includes expression cassettes for two guide RNAs (one designed to target the 5' flanking region of chain 2, and one designed to target the 3' flanking region of chain 1) as well as Cas9. Injection is timed 10-12 h before or 10-12 hr after in vitro fertilization (IVF) with feline sperm. The embryos are then cultured and selected for implantation from cleaved, post-IVF oocytes and are transferred into surgically exposed fallopian tubes at 48-72 hours after lentiviral vector transduction. The transfers are performed in hormonally synchronized queens prepared by a 14/10 hour light/dark environment. Queens are administered PMSG on day −4, and HCG on day −1 with respect to lentiviral vector transduction and are mated ad lib from the day of HCG injection until the day before embryo transfer with a vasectomized, azoospermia-verified tomcat to induce ovulation and corpus luteum formation. At surgery follicles are punctured with a needle if not naturally ovulated. The implanted embryos are allowed to develop in utero. Skin and salivary gland samples from kittens are assessed for Fel d 1 protein expression and genomic deletion. The results show complete knockout of Fel d 1, and complete lack of production of this allergen.

Example: Cloning a Genetically Engineered Fel d 1 Knockout Cat by Embryonic Stem Cell Manipulation Embryonic stem cells of a cat are cultured and transfected with a vector comprising an expression cassette encoding Cas9 and a pair of guide RNAs (one chosen to target an interior region of chain 2, and one chosen to target a 3' flanking region of chain 1). Sequencing analysis may be performed on a sample of the culture to confirm knockout of all or a portion of a Fel d 1 genomic sequence. The embryonic stem cells may then be transferred to a blastocyst by aggregation or injection. Manipulated embryos are then transferred to a pseudopregnant female recipient cat and allowed to mature. The resulting offspring are heterozygotes for the Fel d 1 knockout. Heterozygotes are then cross-bred to produce homozygotes for the Fel d 1 knockout.

Detailed procedures for embryonic stem cell derivation, culture, manipulation, and implantation are known in the art and are described in U.S. Patent Application Publication No. 2003/0177512, incorporated by reference. The skilled artisan can supplement this Example with specific details provided in the '512 Patent Application Publication.

Example: Treatment of Salivary Glands of an Adult Wild-Type Cat

An FIV-based vector is genetically engineered to include expression cassettes encoding Cas9 and a pair of guide RNAs selected to target two of the guide RNA target sequences set forth in SEQ ID NOS: 1-1225. The guide RNAs are selected to target flanking regions of Fel d 1 sequences (e.g., one upstream of chain 2, one downstream of chain 1). The expression cassettes are driven by a salivary-gland specific promoter (salivary amylase promoter) to minimize the potential for systemic effects. Viral particles are produced by the transfection of 293 T cells with transfer vector, packaging vector, and envelope vector. Supernatants are collected 48 and 72 h post-transfection. Viral particles are concentrated 100-fold from pooled supernatants spun in an ultracentrifuge resuspended in PBS. Viral titers of the FIV-based vector are determined by FACS analysis of 293 T cells infected with diluted viral supernatant.

A 12 month-old male domestic cat is given a combination of Dexmedetomidine (0.025-0.0375 mg/kg IM)+Butorphanol (0.4-0.6 mg/kg IM)+Ketamine (5-7.5 mg/kg IM). The cat's salivary glands are cannulated through their ducts using an extended polyethylene tube. The cannulated glands are repeatedly inoculated with the FIV-based vector. The cannulas are then removed and the cat is allowed to recovery from the procedure.

At 1 week, 2 weeks, and 1 month post-procedure, samples of saliva are tested for the production of Fel d 1 according to Western Blot Analysis. Additionally, the cat is re-anesthetized and a biopsy of the salivary gland is taken. Salivary gland explants are grown in organ culture dishes in DMEM with 10% FCS on filter paper. The explants are subject to genomic DNA extraction as described above and PCR and sequencing analysis. Western blot analysis of saliva samples show no Fel d 1 immunoreactivity in comparison to controls, and PCR sequencing analysis, or Surveyor Assay to confirm complete excision of chain 1 and chain 2 Fel d 1 genomic DNA.

Example: Treatment of Skin of an Adult Wild-Type Cat

An FIV-based vector is genetically engineered to include expression cassettes encoding Cas9 and a pair of guide RNAs that are selected to target internal regions of Fel d 1 sequences (e.g., one internal to chain 1 and one internal to chain 2). The guide RNAs, and in particular the crRNA portion of the sgRNA, can be chosen based on the sgRNA Target Sequences provided in SEQ ID NOS: 1-1225. The expression cassettes are driven by a skin-specific promoter (keratin promoter) to minimize the potential for systemic effects. Viral particles of the FIV-based vector are produced as described in the previous example. The FIV-based vector is then injected intradermally into a 3 year-old female domestic cat using a 34 gauge needle. Alternatively, the cat is shaved to expose the skin and the FIV-based vector of the previous example is topically applied in a formulation that includes a permeation enhancer such as alcohols (e.g., methanol), alkyl methyl sulfoxides (e.g., DMSO), pyrrolidones (e.g., 2-pyrrolidone), surfactants, urea, glycerol monolaurate, polyethylene glycol monolaurate, glycerol monolaurate, docainehydrochloride, hydrocortisone, menthol, or methyl salicylate. Optionally, the skin is subject to reversible electroporation to enhance uptake of the vector according to established methods, such as those described in U.S. Pat. No. 6,697,669, incorporated by reference.

At 1 week, 2 weeks, and 1 month post-procedure, samples of skin are biopsied and subject to analysis of Fel d 1 expression or genomic deletion as described in the previous example. The results show no Fel d 1 immunoreactivity in comparison to controls and confirm excision of Fel d 1 genomic DNA at the target sequences.

Example: Systemic Treatment of a Juvenile Wild-Type Cat

A catheter is placed in the cephalic vein of a 6 month old cat using a 22 gauge needle. An FIV-based vector is genetically engineered to include expression cassettes encoding Cas9 and a pair of guide RNAs selected to target two of the guide RNA target sequences set forth in SEQ ID NOS: 1-1225. The guide RNAs are selected to target flanking regions of Fel d 1 sequences (e.g., one upstream of chain 2, one downstream of chain 1). Viral particles of the FIV-based vector are produced as described previously. The expression cassettes for Cas9 are optionally driven by promoters for keratin and amylase, which limit expression to skin and salivary glands, respectively. The FIV-based vector is administered intravenously once a day for 5 consecutive days. At 1 month, 3 months, and 6 months post-procedure, samples of skin and salivary gland are biopsied and subject to analysis of Fel d 1 expression or genomic deletion as described in the previous examples. The results show no Fel d 1 immunoreactivity in comparison to controls and confirm complete excision of chain 1 and chain 2 Fel d 1 genomic DNA.

Example: Inactivation of Fel d 1 by Knock-In of Green Fluorescent Protein

A plasmid donor (400 ng), with two homology arms on each side flanking a green fluorescent protein (GFP) reporter is introduced into cat zygotes along with a vector encoding Cas9 and a guide RNA. Each of the homology arms is around 800 bp. The sgRNA and plasmid donor are designed to insert the GFP reporter in place of the Fel d 1 promoter and the Chain 1 and Chain 2 start codons. The plasmid donor would be used as a template in the process of HDR for sealing the double-stranded break in the DNA. In this way, the coding sequence of GFP in between the homology arms would take the place of the promoter region and start codons, when the break is repaired. A stop codon is included in the plasmid donor after the GFP reporter gene sequence so that only the GFP sequence is expressed. After injection of the vectors into zygotes, in vitro differentiated blastocysts are explanted into culture to derive embryonic stem cells. PCR genotyping and sequencing is used to identify embryonic stem cell lines carrying a correctly targeted insert. GFP expression is confirmed via a microplate fluorescence reader using appropriate excitation and emission filter settings. Cat zygotes with the correct insertion are then allowed to develop into embryos, which are implanted into recipient female cats and allowed to develop to term. The live-born kittens are confirmed to express GFP and also lack Fel d 1 expression as described in previous examples.

Example: Confirmation of Fel d 1 Hypoallergenicity

Allergy testing can be performed on a group of confirmed human Fel d 1 allergy sufferers to confirm success of Fel d 1 knockout procedures in producing a Fel d 1 hypoallergenic phenotype. For example, cat hair or saliva may be collected from a Fel d 1 knockout cat and an extract of the hair or saliva may be prepared and used as an inoculant in skin testing procedures (skin prick, intradermal, or skin patch testing). The results can be compared to a standardized cat hair extract indicated in skin testing diagnosis such as Greer's Standardized Cat Hair (GREER®, Lenoir, NC). Lack of an allergic response (e.g., swelling, redness, hives, sneezing, breathing difficulties, asthma, itchy skin, runny nose, stuffy nose, coughing, and/or eye irritation) can confirm that the particular Fel d 1 knockout results in a hypoallergenic phenotype.

Alternatively or in addition, serum samples from confirmed human Fel d 1 allergy sufferers may be collected and various in vitro immunoassays measuring IgE reactivity as well as allergenic activity known in the art may be performed using the aforementioned inoculants as test samples. For example, the ability of such test samples to inhibit the binding of Fel d 1 protein to IgE antibodies can be tested by way of a radioallergosorbent test (RAST) inhibition assay. Also, the activity of such test samples in a histamine release assay using the stripped basophil technique can be assessed and compared to that of Fel d 1 (see Chapman et al., The European Union CREATE Project: A model for international standardization of allergy diagnostics and vaccines, *J Allergy Clin Immunol*, 122(5):882-889 (2008)).

The present invention has been described with reference to particular embodiments having various features. In light of the disclosure provided above, it will be apparent to those skilled in the art that various modifications and variations can be made in the practice of the present invention without departing from the scope or spirit of the invention. For example, while the present disclosure, in embodiments, discusses genomic editing in *Felis catus* (the domestic house cat), the present invention contemplates compositions and methods for removal of Fel d 1 from any wild or domesticated feline, including those of genera *Acinonyx, Caracal, Calopuma, Felts, Leopardus, Leplailurus, Lynx, Olocolobus, Pardofelis, Prionailurus,* and *Profelis*. Additionally, one skilled in the art can recognize that the methods provided in this disclosure may be modified to target and remove other cat allergens. One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. A method of inactivating a Fel d 1 gene in an isolated *Felis catus* cell, the method comprising:

introducing i) a pair of gRNAs and ii) Cas9 into an isolated *Felis catus* cell such that an endogenous Fel d 1 gene is inactivated, wherein the pair of gRNAs comprises the nucleic acid sequences of:

a) SEQ ID NO: 1234, 1235, 1238 or 1239; and
b) SEQ ID NO: 1236, 1237, 1240 or 1241.

* * * * *

SEQUENCE LISTING

<160> NUMBER OF SEQ ID NOS: 1243

<210> SEQ ID NO 1
<211> LENGTH: 20
<212> TYPE: DNA
<213> ORGANISM: Felis catus

<400> SEQUENCE: 1
aaaaaaaaaa taaagtgacc                                                    20

<210> SEQ ID NO 2
<211> LENGTH: 20
<212> TYPE: DNA
<213> ORGANISM: Felis catus

<400> SEQUENCE: 2
aaaaatgaca gaagaggata                                                    20

<210> SEQ ID NO 3
<211> LENGTH: 20
<212> TYPE: DNA
<213> ORGANISM: Felis catus

<400> SEQUENCE: 3
aaaagggttc caggctgggg                                                    20

<210> SEQ ID NO 4
<211> LENGTH: 20
<212> TYPE: DNA
<213> ORGANISM: Felis catus

<400> SEQUENCE: 4
aaagttcttg ggcttacaga                                                    20

<210> SEQ ID NO 5
<211> LENGTH: 20
<212> TYPE: DNA
<213> ORGANISM: Felis catus

<400> SEQUENCE: 5
aaataaagtg accaggtgac                                                    20

<210> SEQ ID NO 6
<211> LENGTH: 20
<212> TYPE: DNA
<213> ORGANISM: Felis catus

<400> SEQUENCE: 6
aaatactgag agagaggagg                                                    20

<210> SEQ ID NO 7
<211> LENGTH: 20
<212> TYPE: DNA
<213> ORGANISM: Felis catus

<400> SEQUENCE: 7
aaatttgccc agccgtgaag                                                    20

<210> SEQ ID NO 8
<211> LENGTH: 20
<212> TYPE: DNA
<213> ORGANISM: Felis catus

<400> SEQUENCE: 8

```
aacagtatag agaaactcaa                                              20

<210> SEQ ID NO 9
<211> LENGTH: 20
<212> TYPE: DNA
<213> ORGANISM: Felis catus

<400> SEQUENCE: 9
aagacgggga aggggagcca                                              20

<210> SEQ ID NO 10
<211> LENGTH: 20
<212> TYPE: DNA
<213> ORGANISM: Felis catus

<400> SEQUENCE: 10
aagcagaaag gagacccgtg                                              20

<210> SEQ ID NO 11
<211> LENGTH: 20
<212> TYPE: DNA
<213> ORGANISM: Felis catus

<400> SEQUENCE: 11
aaggacacag attatgacga                                              20

<210> SEQ ID NO 12
<211> LENGTH: 20
<212> TYPE: DNA
<213> ORGANISM: Felis catus

<400> SEQUENCE: 12
acacagatta tgacgaaggc                                              20

<210> SEQ ID NO 13
<211> LENGTH: 20
<212> TYPE: DNA
<213> ORGANISM: Felis catus

<400> SEQUENCE: 13
actgcagggc ttcccccagg                                              20

<210> SEQ ID NO 14
<211> LENGTH: 20
<212> TYPE: DNA
<213> ORGANISM: Felis catus

<400> SEQUENCE: 14
agaaaggaga cccgtgaggg                                              20

<210> SEQ ID NO 15
<211> LENGTH: 20
<212> TYPE: DNA
<213> ORGANISM: Felis catus

<400> SEQUENCE: 15
agaagagggg cggggcaggg                                              20

<210> SEQ ID NO 16
<211> LENGTH: 20
<212> TYPE: DNA
<213> ORGANISM: Felis catus
```

```
<400> SEQUENCE: 16
agagaggatg atggaagggg                                              20

<210> SEQ ID NO 17
<211> LENGTH: 20
<212> TYPE: DNA
<213> ORGANISM: Felis catus

<400> SEQUENCE: 17
agattcagga gactggctca                                              20

<210> SEQ ID NO 18
<211> LENGTH: 20
<212> TYPE: DNA
<213> ORGANISM: Felis catus

<400> SEQUENCE: 18
agcaggtata aaagggttcc                                              20

<210> SEQ ID NO 19
<211> LENGTH: 20
<212> TYPE: DNA
<213> ORGANISM: Felis catus

<400> SEQUENCE: 19
agggctccag aatcagattc                                              20

<210> SEQ ID NO 20
<211> LENGTH: 20
<212> TYPE: DNA
<213> ORGANISM: Felis catus

<400> SEQUENCE: 20
aggggttcta acaccttccc                                              20

<210> SEQ ID NO 21
<211> LENGTH: 20
<212> TYPE: DNA
<213> ORGANISM: Felis catus

<400> SEQUENCE: 21
aggtaaatat caggaaccta                                              20

<210> SEQ ID NO 22
<211> LENGTH: 20
<212> TYPE: DNA
<213> ORGANISM: Felis catus

<400> SEQUENCE: 22
agtagatgca gaaaagcagc                                              20

<210> SEQ ID NO 23
<211> LENGTH: 20
<212> TYPE: DNA
<213> ORGANISM: Felis catus

<400> SEQUENCE: 23
agtggcaaca gctcgtgcaa                                              20

<210> SEQ ID NO 24
<211> LENGTH: 20
<212> TYPE: DNA
<213> ORGANISM: Felis catus
```

```
<400> SEQUENCE: 24
atctgttgac tcggggactt                                            20

<210> SEQ ID NO 25
<211> LENGTH: 20
<212> TYPE: DNA
<213> ORGANISM: Felis catus

<400> SEQUENCE: 25
atcttcaaac tgtttgcact                                            20

<210> SEQ ID NO 26
<211> LENGTH: 20
<212> TYPE: DNA
<213> ORGANISM: Felis catus

<400> SEQUENCE: 26
atgaaggtct ttcaaaaggg                                            20

<210> SEQ ID NO 27
<211> LENGTH: 20
<212> TYPE: DNA
<213> ORGANISM: Felis catus

<400> SEQUENCE: 27
atggaagggg aggggagggg                                            20

<210> SEQ ID NO 28
<211> LENGTH: 20
<212> TYPE: DNA
<213> ORGANISM: Felis catus

<400> SEQUENCE: 28
caaacctcag atagcttgaa                                            20

<210> SEQ ID NO 29
<211> LENGTH: 20
<212> TYPE: DNA
<213> ORGANISM: Felis catus

<400> SEQUENCE: 29
cacagcaagt gtagggagtg                                            20

<210> SEQ ID NO 30
<211> LENGTH: 20
<212> TYPE: DNA
<213> ORGANISM: Felis catus

<400> SEQUENCE: 30
caccccaccc aaaggtgaga                                            20

<210> SEQ ID NO 31
<211> LENGTH: 20
<212> TYPE: DNA
<213> ORGANISM: Felis catus

<400> SEQUENCE: 31
caccctccca tatgtgaccc                                            20

<210> SEQ ID NO 32
<211> LENGTH: 20
<212> TYPE: DNA
```

```
<213> ORGANISM: Felis catus

<400> SEQUENCE: 32
cacctgccac tgcatcatga                                         20

<210> SEQ ID NO 33
<211> LENGTH: 20
<212> TYPE: DNA
<213> ORGANISM: Felis catus

<400> SEQUENCE: 33
cacttctgag catggcggga                                         20

<210> SEQ ID NO 34
<211> LENGTH: 20
<212> TYPE: DNA
<213> ORGANISM: Felis catus

<400> SEQUENCE: 34
cagagccctc aagacgggga                                         20

<210> SEQ ID NO 35
<211> LENGTH: 20
<212> TYPE: DNA
<213> ORGANISM: Felis catus

<400> SEQUENCE: 35
cagcatgtag gggagggctc                                         20

<210> SEQ ID NO 36
<211> LENGTH: 20
<212> TYPE: DNA
<213> ORGANISM: Felis catus

<400> SEQUENCE: 36
cagcatgtag gggagggttc                                         20

<210> SEQ ID NO 37
<211> LENGTH: 20
<212> TYPE: DNA
<213> ORGANISM: Felis catus

<400> SEQUENCE: 37
catcacttgg cctcagtgtc                                         20

<210> SEQ ID NO 38
<211> LENGTH: 20
<212> TYPE: DNA
<213> ORGANISM: Felis catus

<400> SEQUENCE: 38
ccaagagaga ggatgatgga                                         20

<210> SEQ ID NO 39
<211> LENGTH: 20
<212> TYPE: DNA
<213> ORGANISM: Felis catus

<400> SEQUENCE: 39
ccaccagctt gggggtctgc                                         20

<210> SEQ ID NO 40
<211> LENGTH: 20
```

```
<212> TYPE: DNA
<213> ORGANISM: Felis catus

<400> SEQUENCE: 40
ccaccggctt gggggtctgc                                                   20

<210> SEQ ID NO 41
<211> LENGTH: 20
<212> TYPE: DNA
<213> ORGANISM: Felis catus

<400> SEQUENCE: 41
ccatgaatca tatgcttgtt                                                   20

<210> SEQ ID NO 42
<211> LENGTH: 20
<212> TYPE: DNA
<213> ORGANISM: Felis catus

<400> SEQUENCE: 42
ccctggtcca cagcaagtgt                                                   20

<210> SEQ ID NO 43
<211> LENGTH: 20
<212> TYPE: DNA
<213> ORGANISM: Felis catus

<400> SEQUENCE: 43
cccttccctg ggaatctggg                                                   20

<210> SEQ ID NO 44
<211> LENGTH: 20
<212> TYPE: DNA
<213> ORGANISM: Felis catus

<400> SEQUENCE: 44
cctactgttg cagccacagc                                                   20

<210> SEQ ID NO 45
<211> LENGTH: 20
<212> TYPE: DNA
<213> ORGANISM: Felis catus

<400> SEQUENCE: 45
cctgatgaag gtctttcaaa                                                   20

<210> SEQ ID NO 46
<211> LENGTH: 20
<212> TYPE: DNA
<213> ORGANISM: Felis catus

<400> SEQUENCE: 46
cctgtctggg gggtctgctc                                                   20

<210> SEQ ID NO 47
<211> LENGTH: 20
<212> TYPE: DNA
<213> ORGANISM: Felis catus

<400> SEQUENCE: 47
cgccatggct ggggaagtag                                                   20

<210> SEQ ID NO 48
```

<210> SEQ ID NO 48
<211> LENGTH: 20
<212> TYPE: DNA
<213> ORGANISM: Felis catus

<400> SEQUENCE: 48
ctcaaatact gagagagagg                                               20

<210> SEQ ID NO 49
<211> LENGTH: 20
<212> TYPE: DNA
<213> ORGANISM: Felis catus

<400> SEQUENCE: 49
ctcaagggag gccactgagc                                               20

<210> SEQ ID NO 50
<211> LENGTH: 20
<212> TYPE: DNA
<213> ORGANISM: Felis catus

<400> SEQUENCE: 50
ctcctccctc cacagccccc                                               20

<210> SEQ ID NO 51
<211> LENGTH: 20
<212> TYPE: DNA
<213> ORGANISM: Felis catus

<400> SEQUENCE: 51
ctgagagaga ggaggagggg                                               20

<210> SEQ ID NO 52
<211> LENGTH: 20
<212> TYPE: DNA
<213> ORGANISM: Felis catus

<400> SEQUENCE: 52
ctggcggtgc ctcctggaaa                                               20

<210> SEQ ID NO 53
<211> LENGTH: 20
<212> TYPE: DNA
<213> ORGANISM: Felis catus

<400> SEQUENCE: 53
ctgtgatcat tttggtgaag                                               20

<210> SEQ ID NO 54
<211> LENGTH: 20
<212> TYPE: DNA
<213> ORGANISM: Felis catus

<400> SEQUENCE: 54
cttcattccc tgggtcccag                                               20

<210> SEQ ID NO 55
<211> LENGTH: 20
<212> TYPE: DNA
<213> ORGANISM: Felis catus

<400> SEQUENCE: 55
gaacctgggc accagcatgt                                               20

```
<210> SEQ ID NO 56
<211> LENGTH: 20
<212> TYPE: DNA
<213> ORGANISM: Felis catus

<400> SEQUENCE: 56
gacattggcc atcattcggg                                              20

<210> SEQ ID NO 57
<211> LENGTH: 20
<212> TYPE: DNA
<213> ORGANISM: Felis catus

<400> SEQUENCE: 57
gacccccagg gtctggccgg                                              20

<210> SEQ ID NO 58
<211> LENGTH: 20
<212> TYPE: DNA
<213> ORGANISM: Felis catus

<400> SEQUENCE: 58
gaggtgctat taaagtgacc                                              20

<210> SEQ ID NO 59
<211> LENGTH: 20
<212> TYPE: DNA
<213> ORGANISM: Felis catus

<400> SEQUENCE: 59
gatattcctg tgtctgcctg                                              20

<210> SEQ ID NO 60
<211> LENGTH: 20
<212> TYPE: DNA
<213> ORGANISM: Felis catus

<400> SEQUENCE: 60
gatatttctg tgtctgcctg                                              20

<210> SEQ ID NO 61
<211> LENGTH: 20
<212> TYPE: DNA
<213> ORGANISM: Felis catus

<400> SEQUENCE: 61
gattatgacg aaggcagggc                                              20

<210> SEQ ID NO 62
<211> LENGTH: 20
<212> TYPE: DNA
<213> ORGANISM: Felis catus

<400> SEQUENCE: 62
gcacgtcatg gggacaggag                                              20

<210> SEQ ID NO 63
<211> LENGTH: 20
<212> TYPE: DNA
<213> ORGANISM: Felis catus

<400> SEQUENCE: 63
gcactgcccc catggtagca                                              20
```

```
<210> SEQ ID NO 64
<211> LENGTH: 20
<212> TYPE: DNA
<213> ORGANISM: Felis catus

<400> SEQUENCE: 64
gcagagcaca cgacggtccc                                               20

<210> SEQ ID NO 65
<211> LENGTH: 20
<212> TYPE: DNA
<213> ORGANISM: Felis catus

<400> SEQUENCE: 65
gcagccacag caggtataaa                                               20

<210> SEQ ID NO 66
<211> LENGTH: 20
<212> TYPE: DNA
<213> ORGANISM: Felis catus

<400> SEQUENCE: 66
gctattaaag tgaccaggtg                                               20

<210> SEQ ID NO 67
<211> LENGTH: 20
<212> TYPE: DNA
<213> ORGANISM: Felis catus

<400> SEQUENCE: 67
ggaagaatgt gtcctgatga                                               20

<210> SEQ ID NO 68
<211> LENGTH: 20
<212> TYPE: DNA
<213> ORGANISM: Felis catus

<400> SEQUENCE: 68
ggaggagggg agggagaag                                                20

<210> SEQ ID NO 69
<211> LENGTH: 20
<212> TYPE: DNA
<213> ORGANISM: Felis catus

<400> SEQUENCE: 69
ggaggccact gagcaggtca                                               20

<210> SEQ ID NO 70
<211> LENGTH: 20
<212> TYPE: DNA
<213> ORGANISM: Felis catus

<400> SEQUENCE: 70
ggagtccaga ggtcataagc                                               20

<210> SEQ ID NO 71
<211> LENGTH: 20
<212> TYPE: DNA
<213> ORGANISM: Felis catus

<400> SEQUENCE: 71
ggatgatgga aggggagggg                                               20
```

<210> SEQ ID NO 72
<211> LENGTH: 20
<212> TYPE: DNA
<213> ORGANISM: Felis catus

<400> SEQUENCE: 72
ggcccaccac tctgaccccc 20

<210> SEQ ID NO 73
<211> LENGTH: 20
<212> TYPE: DNA
<213> ORGANISM: Felis catus

<400> SEQUENCE: 73
ggcgtggtca agaagcagaa 20

<210> SEQ ID NO 74
<211> LENGTH: 20
<212> TYPE: DNA
<213> ORGANISM: Felis catus

<400> SEQUENCE: 74
ggctgaggaa aggttcccag 20

<210> SEQ ID NO 75
<211> LENGTH: 20
<212> TYPE: DNA
<213> ORGANISM: Felis catus

<400> SEQUENCE: 75
gggcagggag ggacgagggg 20

<210> SEQ ID NO 76
<211> LENGTH: 20
<212> TYPE: DNA
<213> ORGANISM: Felis catus

<400> SEQUENCE: 76
gggcggggca gggagggacg 20

<210> SEQ ID NO 77
<211> LENGTH: 20
<212> TYPE: DNA
<213> ORGANISM: Felis catus

<400> SEQUENCE: 77
ggggagaaga ggggcggggc 20

<210> SEQ ID NO 78
<211> LENGTH: 20
<212> TYPE: DNA
<213> ORGANISM: Felis catus

<400> SEQUENCE: 78
gggtctgctc agggcagtgc 20

<210> SEQ ID NO 79
<211> LENGTH: 20
<212> TYPE: DNA
<213> ORGANISM: Felis catus

<400> SEQUENCE: 79
gtcacccaga tgagtgggcc                                            20

<210> SEQ ID NO 80
<211> LENGTH: 20
<212> TYPE: DNA
<213> ORGANISM: Felis catus

<400> SEQUENCE: 80
gtcatgggga caggagagga                                            20

<210> SEQ ID NO 81
<211> LENGTH: 20
<212> TYPE: DNA
<213> ORGANISM: Felis catus

<400> SEQUENCE: 81
gtctgctgaa cttacactgc                                            20

<210> SEQ ID NO 82
<211> LENGTH: 20
<212> TYPE: DNA
<213> ORGANISM: Felis catus

<400> SEQUENCE: 82
gtgagggagg agagaatggc                                            20

<210> SEQ ID NO 83
<211> LENGTH: 20
<212> TYPE: DNA
<213> ORGANISM: Felis catus

<400> SEQUENCE: 83
gtgaggggca ccccacccaa                                            20

<210> SEQ ID NO 84
<211> LENGTH: 20
<212> TYPE: DNA
<213> ORGANISM: Felis catus

<400> SEQUENCE: 84
gtgagttcga gccccgcgtc                                            20

<210> SEQ ID NO 85
<211> LENGTH: 20
<212> TYPE: DNA
<213> ORGANISM: Felis catus

<400> SEQUENCE: 85
gtggagcacg tcatggggac                                            20

<210> SEQ ID NO 86
<211> LENGTH: 20
<212> TYPE: DNA
<213> ORGANISM: Felis catus

<400> SEQUENCE: 86
tacactgcag ggcttccccc                                            20

<210> SEQ ID NO 87
<211> LENGTH: 20
<212> TYPE: DNA
<213> ORGANISM: Felis catus

<400> SEQUENCE: 87
tagcttgaaa ggtaaatatc                              20

<210> SEQ ID NO 88
<211> LENGTH: 20
<212> TYPE: DNA
<213> ORGANISM: Felis catus

<400> SEQUENCE: 88
tattaaagtg accaggtgac                              20

<210> SEQ ID NO 89
<211> LENGTH: 20
<212> TYPE: DNA
<213> ORGANISM: Felis catus

<400> SEQUENCE: 89
tcaagctttg gggctggccc                              20

<210> SEQ ID NO 90
<211> LENGTH: 20
<212> TYPE: DNA
<213> ORGANISM: Felis catus

<400> SEQUENCE: 90
tcaaggtcac atgtaatgac                              20

<210> SEQ ID NO 91
<211> LENGTH: 20
<212> TYPE: DNA
<213> ORGANISM: Felis catus

<400> SEQUENCE: 91
tcaggagact ggctcaaggg                              20

<210> SEQ ID NO 92
<211> LENGTH: 20
<212> TYPE: DNA
<213> ORGANISM: Felis catus

<400> SEQUENCE: 92
tcattttggt gaagaggctg                              20

<210> SEQ ID NO 93
<211> LENGTH: 20
<212> TYPE: DNA
<213> ORGANISM: Felis catus

<400> SEQUENCE: 93
tctgctcagg gcagtgcagg                              20

<210> SEQ ID NO 94
<211> LENGTH: 20
<212> TYPE: DNA
<213> ORGANISM: Felis catus

<400> SEQUENCE: 94
tctggggaca cagattctcc                              20

<210> SEQ ID NO 95
<211> LENGTH: 20
<212> TYPE: DNA
<213> ORGANISM: Felis catus

```
<400> SEQUENCE: 95
tcttgatctg gggtggaagt                                               20

<210> SEQ ID NO 96
<211> LENGTH: 20
<212> TYPE: DNA
<213> ORGANISM: Felis catus

<400> SEQUENCE: 96
tgagcatggc gggaagggga                                               20

<210> SEQ ID NO 97
<211> LENGTH: 20
<212> TYPE: DNA
<213> ORGANISM: Felis catus

<400> SEQUENCE: 97
tgatgcaaaa atgacagaag                                               20

<210> SEQ ID NO 98
<211> LENGTH: 20
<212> TYPE: DNA
<213> ORGANISM: Felis catus

<400> SEQUENCE: 98
tgcctcaaat actgagagag                                               20

<210> SEQ ID NO 99
<211> LENGTH: 20
<212> TYPE: DNA
<213> ORGANISM: Felis catus

<400> SEQUENCE: 99
tgcctcacat accaagagag                                               20

<210> SEQ ID NO 100
<211> LENGTH: 20
<212> TYPE: DNA
<213> ORGANISM: Felis catus

<400> SEQUENCE: 100
tgggcaccag catgtagggg                                               20

<210> SEQ ID NO 101
<211> LENGTH: 20
<212> TYPE: DNA
<213> ORGANISM: Felis catus

<400> SEQUENCE: 101
tggtagcaag gggagtccag                                               20

<210> SEQ ID NO 102
<211> LENGTH: 20
<212> TYPE: DNA
<213> ORGANISM: Felis catus

<400> SEQUENCE: 102
ttaagcgtcc ggcttcagcc                                               20

<210> SEQ ID NO 103
<211> LENGTH: 20
<212> TYPE: DNA
<213> ORGANISM: Felis catus
```

<400> SEQUENCE: 103
ttctgagaag cagcccagag                                                    20

<210> SEQ ID NO 104
<211> LENGTH: 20
<212> TYPE: DNA
<213> ORGANISM: Felis catus

<400> SEQUENCE: 104
ttgagaccag accatcttca                                                    20

<210> SEQ ID NO 105
<211> LENGTH: 20
<212> TYPE: DNA
<213> ORGANISM: Felis catus

<400> SEQUENCE: 105
ttggtgaaga ggctgaggaa                                                    20

<210> SEQ ID NO 106
<211> LENGTH: 20
<212> TYPE: DNA
<213> ORGANISM: Felis catus

<400> SEQUENCE: 106
agcagcccag agaggcctgg                                                    20

<210> SEQ ID NO 107
<211> LENGTH: 20
<212> TYPE: DNA
<213> ORGANISM: Felis catus

<400> SEQUENCE: 107
aggggagggg agaagagggg                                                    20

<210> SEQ ID NO 108
<211> LENGTH: 20
<212> TYPE: DNA
<213> ORGANISM: Felis catus

<400> SEQUENCE: 108
agtgaccagg tgacaggact                                                    20

<210> SEQ ID NO 109
<211> LENGTH: 20
<212> TYPE: DNA
<213> ORGANISM: Felis catus

<400> SEQUENCE: 109
caggctctgg gctgatggct                                                    20

<210> SEQ ID NO 110
<211> LENGTH: 20
<212> TYPE: DNA
<213> ORGANISM: Felis catus

<400> SEQUENCE: 110
cagggcactt ctgagcatgg                                                    20

<210> SEQ ID NO 111
<211> LENGTH: 20
<212> TYPE: DNA

<213> ORGANISM: Felis catus

<400> SEQUENCE: 111
cttggacaga gccctcaaga   20

<210> SEQ ID NO 112
<211> LENGTH: 20
<212> TYPE: DNA
<213> ORGANISM: Felis catus

<400> SEQUENCE: 112
gaagcagtct ggcttttcct   20

<210> SEQ ID NO 113
<211> LENGTH: 20
<212> TYPE: DNA
<213> ORGANISM: Felis catus

<400> SEQUENCE: 113
gcagaaaagc agcaggtctt   20

<210> SEQ ID NO 114
<211> LENGTH: 20
<212> TYPE: DNA
<213> ORGANISM: Felis catus

<400> SEQUENCE: 114
gctcaacgct gcttggccac   20

<210> SEQ ID NO 115
<211> LENGTH: 20
<212> TYPE: DNA
<213> ORGANISM: Felis catus

<400> SEQUENCE: 115
ggcgcagtcg gttaagcgtc   20

<210> SEQ ID NO 116
<211> LENGTH: 20
<212> TYPE: DNA
<213> ORGANISM: Felis catus

<400> SEQUENCE: 116
ggctgacatt ggccatcatt   20

<210> SEQ ID NO 117
<211> LENGTH: 20
<212> TYPE: DNA
<213> ORGANISM: Felis catus

<400> SEQUENCE: 117
gggcaggagc caccagagac   20

<210> SEQ ID NO 118
<211> LENGTH: 20
<212> TYPE: DNA
<213> ORGANISM: Felis catus

<400> SEQUENCE: 118
gggcgcctgg gtggcgcagt   20

<210> SEQ ID NO 119
<211> LENGTH: 20

<212> TYPE: DNA
<213> ORGANISM: Felis catus

<400> SEQUENCE: 119
ggtagcgtca tctgttgact                                                    20

<210> SEQ ID NO 120
<211> LENGTH: 20
<212> TYPE: DNA
<213> ORGANISM: Felis catus

<400> SEQUENCE: 120
ggtgagaagg tgatgagcaa                                                    20

<210> SEQ ID NO 121
<211> LENGTH: 20
<212> TYPE: DNA
<213> ORGANISM: Felis catus

<400> SEQUENCE: 121
tcagccaggt cacgatctcg                                                    20

<210> SEQ ID NO 122
<211> LENGTH: 20
<212> TYPE: DNA
<213> ORGANISM: Felis catus

<400> SEQUENCE: 122
tctgaccccc agggtctggc                                                    20

<210> SEQ ID NO 123
<211> LENGTH: 20
<212> TYPE: DNA
<213> ORGANISM: Felis catus

<400> SEQUENCE: 123
tggttacgca gagcacacga                                                    20

<210> SEQ ID NO 124
<211> LENGTH: 20
<212> TYPE: DNA
<213> ORGANISM: Felis catus

<400> SEQUENCE: 124
aaaagcagca ggtcttcggt                                                    20

<210> SEQ ID NO 125
<211> LENGTH: 20
<212> TYPE: DNA
<213> ORGANISM: Felis catus

<400> SEQUENCE: 125
aaagcagcag gtcttcggtg                                                    20

<210> SEQ ID NO 126
<211> LENGTH: 20
<212> TYPE: DNA
<213> ORGANISM: Felis catus

<400> SEQUENCE: 126
aaaggaagaa gccagttggg                                                    20

<210> SEQ ID NO 127

```
<211> LENGTH: 20
<212> TYPE: DNA
<213> ORGANISM: Felis catus

<400> SEQUENCE: 127
aaagggttcc aggctgggga                                               20

<210> SEQ ID NO 128
<211> LENGTH: 20
<212> TYPE: DNA
<213> ORGANISM: Felis catus

<400> SEQUENCE: 128
aacctgggca ccagcatgta                                               20

<210> SEQ ID NO 129
<211> LENGTH: 20
<212> TYPE: DNA
<213> ORGANISM: Felis catus

<400> SEQUENCE: 129
aagagagagg atgatggaag                                               20

<210> SEQ ID NO 130
<211> LENGTH: 20
<212> TYPE: DNA
<213> ORGANISM: Felis catus

<400> SEQUENCE: 130
aagctgtcac ccagatgagt                                               20

<210> SEQ ID NO 131
<211> LENGTH: 20
<212> TYPE: DNA
<213> ORGANISM: Felis catus

<400> SEQUENCE: 131
aatactgaga gagaggagga                                               20

<210> SEQ ID NO 132
<211> LENGTH: 20
<212> TYPE: DNA
<213> ORGANISM: Felis catus

<400> SEQUENCE: 132
aatgctctca gcgtgctggt                                               20

<210> SEQ ID NO 133
<211> LENGTH: 20
<212> TYPE: DNA
<213> ORGANISM: Felis catus

<400> SEQUENCE: 133
aatttgccca gccgtgaaga                                               20

<210> SEQ ID NO 134
<211> LENGTH: 20
<212> TYPE: DNA
<213> ORGANISM: Felis catus

<400> SEQUENCE: 134
acagcaagtg tagggagtga                                               20
```

-continued

```
<210> SEQ ID NO 135
<211> LENGTH: 20
<212> TYPE: DNA
<213> ORGANISM: Felis catus

<400> SEQUENCE: 135
accctcccat atgtgaccca                                               20

<210> SEQ ID NO 136
<211> LENGTH: 20
<212> TYPE: DNA
<213> ORGANISM: Felis catus

<400> SEQUENCE: 136
acctgccact gcatcatgaa                                               20

<210> SEQ ID NO 137
<211> LENGTH: 20
<212> TYPE: DNA
<213> ORGANISM: Felis catus

<400> SEQUENCE: 137
acctgggcac cagcatgtag                                               20

<210> SEQ ID NO 138
<211> LENGTH: 20
<212> TYPE: DNA
<213> ORGANISM: Felis catus

<400> SEQUENCE: 138
actgccccca tggtagcaag                                               20

<210> SEQ ID NO 139
<211> LENGTH: 20
<212> TYPE: DNA
<213> ORGANISM: Felis catus

<400> SEQUENCE: 139
acttctgagc atggcgggaa                                               20

<210> SEQ ID NO 140
<211> LENGTH: 20
<212> TYPE: DNA
<213> ORGANISM: Felis catus

<400> SEQUENCE: 140
agactcgcac agaactccct                                               20

<210> SEQ ID NO 141
<211> LENGTH: 20
<212> TYPE: DNA
<213> ORGANISM: Felis catus

<400> SEQUENCE: 141
agagccctca agacggggaa                                               20

<210> SEQ ID NO 142
<211> LENGTH: 20
<212> TYPE: DNA
<213> ORGANISM: Felis catus

<400> SEQUENCE: 142
agaggatgat ggaagggag                                                20
```

```
<210> SEQ ID NO 143
<211> LENGTH: 20
<212> TYPE: DNA
<213> ORGANISM: Felis catus

<400> SEQUENCE: 143
agaggtcata agcaggttgt                                              20

<210> SEQ ID NO 144
<211> LENGTH: 20
<212> TYPE: DNA
<213> ORGANISM: Felis catus

<400> SEQUENCE: 144
agcagaaagg agacccgtga                                              20

<210> SEQ ID NO 145
<211> LENGTH: 20
<212> TYPE: DNA
<213> ORGANISM: Felis catus

<400> SEQUENCE: 145
agcatgtagg ggagggctca                                              20

<210> SEQ ID NO 146
<211> LENGTH: 20
<212> TYPE: DNA
<213> ORGANISM: Felis catus

<400> SEQUENCE: 146
agcatgtagg ggagggttca                                              20

<210> SEQ ID NO 147
<211> LENGTH: 20
<212> TYPE: DNA
<213> ORGANISM: Felis catus

<400> SEQUENCE: 147
agcctacccc tcaagctttg                                              20

<210> SEQ ID NO 148
<211> LENGTH: 20
<212> TYPE: DNA
<213> ORGANISM: Felis catus

<400> SEQUENCE: 148
aggagaaaga cgccatggct                                              20

<210> SEQ ID NO 149
<211> LENGTH: 20
<212> TYPE: DNA
<213> ORGANISM: Felis catus

<400> SEQUENCE: 149
aggaggggag gggagaagag                                              20

<210> SEQ ID NO 150
<211> LENGTH: 20
<212> TYPE: DNA
<213> ORGANISM: Felis catus

<400> SEQUENCE: 150
agggcacttc tgagcatggc                                              20
```

<210> SEQ ID NO 151
<211> LENGTH: 20
<212> TYPE: DNA
<213> ORGANISM: Felis catus

<400> SEQUENCE: 151
atacatactg aaaagttctt                                              20

<210> SEQ ID NO 152
<211> LENGTH: 20
<212> TYPE: DNA
<213> ORGANISM: Felis catus

<400> SEQUENCE: 152
atactgagag agaggaggag                                              20

<210> SEQ ID NO 153
<211> LENGTH: 20
<212> TYPE: DNA
<213> ORGANISM: Felis catus

<400> SEQUENCE: 153
atgatggaag gggaggggag                                              20

<210> SEQ ID NO 154
<211> LENGTH: 20
<212> TYPE: DNA
<213> ORGANISM: Felis catus

<400> SEQUENCE: 154
caaaggaaga agccagttgg                                              20

<210> SEQ ID NO 155
<211> LENGTH: 20
<212> TYPE: DNA
<213> ORGANISM: Felis catus

<400> SEQUENCE: 155
caagagagag gatgatggaa                                              20

<210> SEQ ID NO 156
<211> LENGTH: 20
<212> TYPE: DNA
<213> ORGANISM: Felis catus

<400> SEQUENCE: 156
cacagattat gacgaaggca                                              20

<210> SEQ ID NO 157
<211> LENGTH: 20
<212> TYPE: DNA
<213> ORGANISM: Felis catus

<400> SEQUENCE: 157
cactgccccc atggtagcaa                                              20

<210> SEQ ID NO 158
<211> LENGTH: 20
<212> TYPE: DNA
<213> ORGANISM: Felis catus

<400> SEQUENCE: 158
cagcaagtgt agggagtgag 20

<210> SEQ ID NO 159
<211> LENGTH: 20
<212> TYPE: DNA
<213> ORGANISM: Felis catus

<400> SEQUENCE: 159
cagccacagc aggtataaaa 20

<210> SEQ ID NO 160
<211> LENGTH: 20
<212> TYPE: DNA
<213> ORGANISM: Felis catus

<400> SEQUENCE: 160
cagcctaccc ctcaagcttt 20

<210> SEQ ID NO 161
<211> LENGTH: 20
<212> TYPE: DNA
<213> ORGANISM: Felis catus

<400> SEQUENCE: 161
ccatggctgg ggaagtagag 20

<210> SEQ ID NO 162
<211> LENGTH: 20
<212> TYPE: DNA
<213> ORGANISM: Felis catus

<400> SEQUENCE: 162
cctgccactg catcatgaag 20

<210> SEQ ID NO 163
<211> LENGTH: 20
<212> TYPE: DNA
<213> ORGANISM: Felis catus

<400> SEQUENCE: 163
cctggtccac agcaagtgta 20

<210> SEQ ID NO 164
<211> LENGTH: 20
<212> TYPE: DNA
<213> ORGANISM: Felis catus

<400> SEQUENCE: 164
cgagccccgc gtcaggctct 20

<210> SEQ ID NO 165
<211> LENGTH: 20
<212> TYPE: DNA
<213> ORGANISM: Felis catus

<400> SEQUENCE: 165
cgctgcttgg ccaccagctt 20

<210> SEQ ID NO 166
<211> LENGTH: 20
<212> TYPE: DNA
<213> ORGANISM: Felis catus

<400> SEQUENCE: 166
cgctgcttgg ccaccggctt					20

<210> SEQ ID NO 167
<211> LENGTH: 20
<212> TYPE: DNA
<213> ORGANISM: Felis catus

<400> SEQUENCE: 167
ctattaaagt gaccaggtga					20

<210> SEQ ID NO 168
<211> LENGTH: 20
<212> TYPE: DNA
<213> ORGANISM: Felis catus

<400> SEQUENCE: 168
ctcaaaggaa gaagccagtt					20

<210> SEQ ID NO 169
<211> LENGTH: 20
<212> TYPE: DNA
<213> ORGANISM: Felis catus

<400> SEQUENCE: 169
ctcagggcag tgcaggaggg					20

<210> SEQ ID NO 170
<211> LENGTH: 20
<212> TYPE: DNA
<213> ORGANISM: Felis catus

<400> SEQUENCE: 170
ctcatttgtc ttcattccct					20

<210> SEQ ID NO 171
<211> LENGTH: 20
<212> TYPE: DNA
<213> ORGANISM: Felis catus

<400> SEQUENCE: 171
ctccaccatg gcccttccct					20

<210> SEQ ID NO 172
<211> LENGTH: 20
<212> TYPE: DNA
<213> ORGANISM: Felis catus

<400> SEQUENCE: 172
ctctctgtgg agcacgtcat					20

<210> SEQ ID NO 173
<211> LENGTH: 20
<212> TYPE: DNA
<213> ORGANISM: Felis catus

<400> SEQUENCE: 173
ctgaggaaag gttcccagag					20

<210> SEQ ID NO 174
<211> LENGTH: 20
<212> TYPE: DNA
<213> ORGANISM: Felis catus

```
<400> SEQUENCE: 174
ctgatgaagg tctttcaaaa                                                    20

<210> SEQ ID NO 175
<211> LENGTH: 20
<212> TYPE: DNA
<213> ORGANISM: Felis catus

<400> SEQUENCE: 175
ctgcagggct tcccccagga                                                    20

<210> SEQ ID NO 176
<211> LENGTH: 20
<212> TYPE: DNA
<213> ORGANISM: Felis catus

<400> SEQUENCE: 176
ctgccactgc atcatgaagg                                                    20

<210> SEQ ID NO 177
<211> LENGTH: 20
<212> TYPE: DNA
<213> ORGANISM: Felis catus

<400> SEQUENCE: 177
ctgctcaggg cagtgcagga                                                    20

<210> SEQ ID NO 178
<211> LENGTH: 20
<212> TYPE: DNA
<213> ORGANISM: Felis catus

<400> SEQUENCE: 178
ctgcttggcc accagcttgg                                                    20

<210> SEQ ID NO 179
<211> LENGTH: 20
<212> TYPE: DNA
<213> ORGANISM: Felis catus

<400> SEQUENCE: 179
ctgcttggcc accggcttgg                                                    20

<210> SEQ ID NO 180
<211> LENGTH: 20
<212> TYPE: DNA
<213> ORGANISM: Felis catus

<400> SEQUENCE: 180
ctggggacac agattctcca                                                    20

<210> SEQ ID NO 181
<211> LENGTH: 20
<212> TYPE: DNA
<213> ORGANISM: Felis catus

<400> SEQUENCE: 181
ctgtctgggg ggtctgctca                                                    20

<210> SEQ ID NO 182
<211> LENGTH: 20
<212> TYPE: DNA
<213> ORGANISM: Felis catus
```

```
<400> SEQUENCE: 182
cttctgagca tggcgggaag                                               20

<210> SEQ ID NO 183
<211> LENGTH: 20
<212> TYPE: DNA
<213> ORGANISM: Felis catus

<400> SEQUENCE: 183
cttgttagga agagcctcct                                               20

<210> SEQ ID NO 184
<211> LENGTH: 20
<212> TYPE: DNA
<213> ORGANISM: Felis catus

<400> SEQUENCE: 184 gaagagggc ggggcaggga                                                20

<210> SEQ ID NO 185
<211> LENGTH: 20
<212> TYPE: DNA
<213> ORGANISM: Felis catus

<400> SEQUENCE: 185
gaagtagagg ggatcatgtg                                               20

<210> SEQ ID NO 186
<211> LENGTH: 20
<212> TYPE: DNA
<213> ORGANISM: Felis catus

<400> SEQUENCE: 186
gactcgcaca gaactccctg                                               20

<210> SEQ ID NO 187
<211> LENGTH: 20
<212> TYPE: DNA
<213> ORGANISM: Felis catus

<400> SEQUENCE: 187
gagagagagg aggaggggag                                               20

<210> SEQ ID NO 188
<211> LENGTH: 20
<212> TYPE: DNA
<213> ORGANISM: Felis catus

<400> SEQUENCE: 188
gagaggatga tggaagggga                                               20

<210> SEQ ID NO 189
<211> LENGTH: 20
<212> TYPE: DNA
<213> ORGANISM: Felis catus

<400> SEQUENCE: 189
gagcatggcg ggaaggggaa                                               20

<210> SEQ ID NO 190
<211> LENGTH: 20
<212> TYPE: DNA
```

<213> ORGANISM: Felis catus

<400> SEQUENCE: 190
gagccctcaa gacggggaag					20

<210> SEQ ID NO 191
<211> LENGTH: 20
<212> TYPE: DNA
<213> ORGANISM: Felis catus

<400> SEQUENCE: 191
gaggagggga ggggagaaga					20

<210> SEQ ID NO 192
<211> LENGTH: 20
<212> TYPE: DNA
<213> ORGANISM: Felis catus

<400> SEQUENCE: 192
gaggtcataa gcaggttgtg					20

<210> SEQ ID NO 193
<211> LENGTH: 20
<212> TYPE: DNA
<213> ORGANISM: Felis catus

<400> SEQUENCE: 193
gagtccacta gctaagcact					20

<210> SEQ ID NO 194
<211> LENGTH: 20
<212> TYPE: DNA
<213> ORGANISM: Felis catus

<400> SEQUENCE: 194
gatgatggaa ggggagggga					20

<210> SEQ ID NO 195
<211> LENGTH: 20
<212> TYPE: DNA
<213> ORGANISM: Felis catus

<400> SEQUENCE: 195
gatgttgacc tattcctgat					20

<210> SEQ ID NO 196
<211> LENGTH: 20
<212> TYPE: DNA
<213> ORGANISM: Felis catus

<400> SEQUENCE: 196
gattcaggag actggctcaa					20

<210> SEQ ID NO 197
<211> LENGTH: 20
<212> TYPE: DNA
<213> ORGANISM: Felis catus

<400> SEQUENCE: 197
gccatggctg gggaagtaga					20

<210> SEQ ID NO 198
<211> LENGTH: 20

```
<212> TYPE: DNA
<213> ORGANISM: Felis catus

<400> SEQUENCE: 198
gcccaccact ctgaccccca                                          20

<210> SEQ ID NO 199
<211> LENGTH: 20
<212> TYPE: DNA
<213> ORGANISM: Felis catus

<400> SEQUENCE: 199
gcctctgacg cctgtctggg                                          20

<210> SEQ ID NO 200
<211> LENGTH: 20
<212> TYPE: DNA
<213> ORGANISM: Felis catus

<400> SEQUENCE: 200
gcggggcagg gagggacgag                                          20

<210> SEQ ID NO 201
<211> LENGTH: 20
<212> TYPE: DNA
<213> ORGANISM: Felis catus

<400> SEQUENCE: 201
gctcagggca gtgcaggagg                                          20

<210> SEQ ID NO 202
<211> LENGTH: 20
<212> TYPE: DNA
<213> ORGANISM: Felis catus

<400> SEQUENCE: 202
gctgacattg gccatcattc                                          20

<210> SEQ ID NO 203
<211> LENGTH: 20
<212> TYPE: DNA
<213> ORGANISM: Felis catus

<400> SEQUENCE: 203
gctgaggaaa ggttcccaga                                          20

<210> SEQ ID NO 204
<211> LENGTH: 20
<212> TYPE: DNA
<213> ORGANISM: Felis catus

<400> SEQUENCE: 204
gctgccttgc tcttgatctg                                          20

<210> SEQ ID NO 205
<211> LENGTH: 20
<212> TYPE: DNA
<213> ORGANISM: Felis catus

<400> SEQUENCE: 205
gctgcttggc caccagcttg                                          20

<210> SEQ ID NO 206
```

```
<211> LENGTH: 20
<212> TYPE: DNA
<213> ORGANISM: Felis catus

<400> SEQUENCE: 206
gctgcttggc caccggcttg                                              20

<210> SEQ ID NO 207
<211> LENGTH: 20
<212> TYPE: DNA
<213> ORGANISM: Felis catus

<400> SEQUENCE: 207
ggaaggggag gggaggggag                                              20

<210> SEQ ID NO 208
<211> LENGTH: 20
<212> TYPE: DNA
<213> ORGANISM: Felis catus

<400> SEQUENCE: 208
ggaagtagag gggatcatgt                                              20

<210> SEQ ID NO 209
<211> LENGTH: 20
<212> TYPE: DNA
<213> ORGANISM: Felis catus

<400> SEQUENCE: 209
ggacgagggg aggtgagatg                                              20

<210> SEQ ID NO 210
<211> LENGTH: 20
<212> TYPE: DNA
<213> ORGANISM: Felis catus

<400> SEQUENCE: 210
ggagaaagac gccatggctg                                              20

<210> SEQ ID NO 211
<211> LENGTH: 20
<212> TYPE: DNA
<213> ORGANISM: Felis catus

<400> SEQUENCE: 211
ggcggggcag ggagggacga                                              20

<210> SEQ ID NO 212
<211> LENGTH: 20
<212> TYPE: DNA
<213> ORGANISM: Felis catus

<400> SEQUENCE: 212
ggctgccttg ctcttgatct                                              20

<210> SEQ ID NO 213
<211> LENGTH: 20
<212> TYPE: DNA
<213> ORGANISM: Felis catus

<400> SEQUENCE: 213
gggacgaggg gaggtgagat                                              20
```

```
<210> SEQ ID NO 214
<211> LENGTH: 20
<212> TYPE: DNA
<213> ORGANISM: Felis catus

<400> SEQUENCE: 214
gggagaagag gggcggggca                                               20

<210> SEQ ID NO 215
<211> LENGTH: 20
<212> TYPE: DNA
<213> ORGANISM: Felis catus

<400> SEQUENCE: 215
gggaggggag aagagggggcg                                              20

<210> SEQ ID NO 216
<211> LENGTH: 20
<212> TYPE: DNA
<213> ORGANISM: Felis catus

<400> SEQUENCE: 216
gggcaccagc atgtagggga                                               20

<210> SEQ ID NO 217
<211> LENGTH: 20
<212> TYPE: DNA
<213> ORGANISM: Felis catus

<400> SEQUENCE: 217
ggggagggga gaagaggggc                                               20

<210> SEQ ID NO 218
<211> LENGTH: 20
<212> TYPE: DNA
<213> ORGANISM: Felis catus

<400> SEQUENCE: 218
ggggttctaa caccttccca                                               20

<210> SEQ ID NO 219
<211> LENGTH: 20
<212> TYPE: DNA
<213> ORGANISM: Felis catus

<400> SEQUENCE: 219
ggtaaatatc aggaacctaa                                               20

<210> SEQ ID NO 220
<211> LENGTH: 20
<212> TYPE: DNA
<213> ORGANISM: Felis catus

<400> SEQUENCE: 220
gtagcgtcat ctgttgactc                                               20

<210> SEQ ID NO 221
<211> LENGTH: 20
<212> TYPE: DNA
<213> ORGANISM: Felis catus

<400> SEQUENCE: 221
gtataaaagg gttccaggct                                               20
```

```
<210> SEQ ID NO 222
<211> LENGTH: 20
<212> TYPE: DNA
<213> ORGANISM: Felis catus

<400> SEQUENCE: 222
gtctgggaca tgagtgtctg                                               20

<210> SEQ ID NO 223
<211> LENGTH: 20
<212> TYPE: DNA
<213> ORGANISM: Felis catus

<400> SEQUENCE: 223
gtgagaaggt gatgagcaac                                               20

<210> SEQ ID NO 224
<211> LENGTH: 20
<212> TYPE: DNA
<213> ORGANISM: Felis catus

<400> SEQUENCE: 224
gtgcctctga cgcctgtctg                                               20

<210> SEQ ID NO 225
<211> LENGTH: 20
<212> TYPE: DNA
<213> ORGANISM: Felis catus

<400> SEQUENCE: 225
tagcgtcatc tgttgactcg                                               20

<210> SEQ ID NO 226
<211> LENGTH: 20
<212> TYPE: DNA
<213> ORGANISM: Felis catus

<400> SEQUENCE: 226 tataaaggg ttccaggctg                                                20

<210> SEQ ID NO 227
<211> LENGTH: 20
<212> TYPE: DNA
<213> ORGANISM: Felis catus

<400> SEQUENCE: 227
tattaaagtg accaggtgag                                               20

<210> SEQ ID NO 228
<211> LENGTH: 20
<212> TYPE: DNA
<213> ORGANISM: Felis catus

<400> SEQUENCE: 228
tcaaaggaag aagccagttg                                               20

<210> SEQ ID NO 229
<211> LENGTH: 20
<212> TYPE: DNA
<213> ORGANISM: Felis catus

<400> SEQUENCE: 229
tcaagagacg actagaacct                                               20
```

```
<210> SEQ ID NO 230
<211> LENGTH: 20
<212> TYPE: DNA
<213> ORGANISM: Felis catus

<400> SEQUENCE: 230
tcattcggga ggcctgactt                                          20

<210> SEQ ID NO 231
<211> LENGTH: 20
<212> TYPE: DNA
<213> ORGANISM: Felis catus

<400> SEQUENCE: 231
tcgtgttctc gtgcttctct                                          20

<210> SEQ ID NO 232
<211> LENGTH: 20
<212> TYPE: DNA
<213> ORGANISM: Felis catus

<400> SEQUENCE: 232
tctctgtgga gcacgtcatg                                          20

<210> SEQ ID NO 233
<211> LENGTH: 20
<212> TYPE: DNA
<213> ORGANISM: Felis catus

<400> SEQUENCE: 233
tctgctgaac ttacactgca                                          20

<210> SEQ ID NO 234
<211> LENGTH: 20
<212> TYPE: DNA
<213> ORGANISM: Felis catus

<400> SEQUENCE: 234
tgaaggtctt tcaaaaggga                                          20

<210> SEQ ID NO 235
<211> LENGTH: 20
<212> TYPE: DNA
<213> ORGANISM: Felis catus

<400> SEQUENCE: 235
tgaccaggtg aggggcgcct                                          20

<210> SEQ ID NO 236
<211> LENGTH: 20
<212> TYPE: DNA
<213> ORGANISM: Felis catus

<400> SEQUENCE: 236
tgagagagag gaggagggga                                          20

<210> SEQ ID NO 237
<211> LENGTH: 20
<212> TYPE: DNA
<213> ORGANISM: Felis catus

<400> SEQUENCE: 237
```

```
tgcagggctt cccccaggag                                               20

<210> SEQ ID NO 238
<211> LENGTH: 20
<212> TYPE: DNA
<213> ORGANISM: Felis catus

<400> SEQUENCE: 238
tgcctctgac gcctgtctgg                                               20

<210> SEQ ID NO 239
<211> LENGTH: 20
<212> TYPE: DNA
<213> ORGANISM: Felis catus

<400> SEQUENCE: 239
tgctcagggc agtgcaggag                                               20

<210> SEQ ID NO 240
<211> LENGTH: 20
<212> TYPE: DNA
<213> ORGANISM: Felis catus

<400> SEQUENCE: 240
tggaagggga ggggaggggα                                               20

<210> SEQ ID NO 241
<211> LENGTH: 20
<212> TYPE: DNA
<213> ORGANISM: Felis catus

<400> SEQUENCE: 241
tggacagagc cctcaagacg                                               20

<210> SEQ ID NO 242
<211> LENGTH: 20
<212> TYPE: DNA
<213> ORGANISM: Felis catus

<400> SEQUENCE: 242
tggcccttcc ctgggaatct                                               20

<210> SEQ ID NO 243
<211> LENGTH: 20
<212> TYPE: DNA
<213> ORGANISM: Felis catus

<400> SEQUENCE: 243
tggggacaca gattctccag                                               20

<210> SEQ ID NO 244
<211> LENGTH: 20
<212> TYPE: DNA
<213> ORGANISM: Felis catus

<400> SEQUENCE: 244
tggggtggaa gtaggtgtct                                               20

<210> SEQ ID NO 245
<211> LENGTH: 20
<212> TYPE: DNA
<213> ORGANISM: Felis catus

<400> SEQUENCE: 245
```
tgtctgggac atgagtgtct                                              20

<210> SEQ ID NO 246
<211> LENGTH: 20
<212> TYPE: DNA
<213> ORGANISM: Felis catus

<400> SEQUENCE: 246
tgtgcctctg acgcctgtct                                              20

<210> SEQ ID NO 247
<211> LENGTH: 20
<212> TYPE: DNA
<213> ORGANISM: Felis catus

<400> SEQUENCE: 247
ttcattccct gggtcccaga                                              20

<210> SEQ ID NO 248
<211> LENGTH: 20
<212> TYPE: DNA
<213> ORGANISM: Felis catus

<400> SEQUENCE: 248
ttggacagag ccctcaagac                                              20

<210> SEQ ID NO 249
<211> LENGTH: 20
<212> TYPE: DNA
<213> ORGANISM: Felis catus

<400> SEQUENCE: 249
aaagctgtca cccagatgag                                              20

<210> SEQ ID NO 250
<211> LENGTH: 20
<212> TYPE: DNA
<213> ORGANISM: Felis catus

<400> SEQUENCE: 250
aacagctcgt gcaaaggccc                                              20

<210> SEQ ID NO 251
<211> LENGTH: 20
<212> TYPE: DNA
<213> ORGANISM: Felis catus

<400> SEQUENCE: 251
aatttcagtt ctgaaattac                                              20

<210> SEQ ID NO 252
<211> LENGTH: 20
<212> TYPE: DNA
<213> ORGANISM: Felis catus

<400> SEQUENCE: 252
accagagacc ggcctccttt                                              20

<210> SEQ ID NO 253
<211> LENGTH: 20
<212> TYPE: DNA
<213> ORGANISM: Felis catus

```
<400> SEQUENCE: 253
acccgtgagg gaggagagaa                                              20

<210> SEQ ID NO 254
<211> LENGTH: 20
<212> TYPE: DNA
<213> ORGANISM: Felis catus

<400> SEQUENCE: 254
accttgccca gagtgagacc                                              20

<210> SEQ ID NO 255
<211> LENGTH: 20
<212> TYPE: DNA
<213> ORGANISM: Felis catus

<400> SEQUENCE: 255
acgctgcttg gccaccagct                                              20

<210> SEQ ID NO 256
<211> LENGTH: 20
<212> TYPE: DNA
<213> ORGANISM: Felis catus

<400> SEQUENCE: 256
acgctgcttg gccaccggct                                              20

<210> SEQ ID NO 257
<211> LENGTH: 20
<212> TYPE: DNA
<213> ORGANISM: Felis catus

<400> SEQUENCE: 257
actcaaagga agaagccagt                                              20

<210> SEQ ID NO 258
<211> LENGTH: 20
<212> TYPE: DNA
<213> ORGANISM: Felis catus

<400> SEQUENCE: 258
agaagcagcc cagagaggcc                                              20

<210> SEQ ID NO 259
<211> LENGTH: 20
<212> TYPE: DNA
<213> ORGANISM: Felis catus

<400> SEQUENCE: 259
agaggcctgg cggtgcctcc                                              20

<210> SEQ ID NO 260
<211> LENGTH: 20
<212> TYPE: DNA
<213> ORGANISM: Felis catus

<400> SEQUENCE: 260
agccccgccc cacttccccg                                              20

<210> SEQ ID NO 261
<211> LENGTH: 20
<212> TYPE: DNA
<213> ORGANISM: Felis catus
```

```
<400> SEQUENCE: 261
aggaagagcc tcctgggcag                                               20

<210> SEQ ID NO 262
<211> LENGTH: 20
<212> TYPE: DNA
<213> ORGANISM: Felis catus

<400> SEQUENCE: 262
agggacgagg ggaggtgaga                                               20

<210> SEQ ID NO 263
<211> LENGTH: 20
<212> TYPE: DNA
<213> ORGANISM: Felis catus

<400> SEQUENCE: 263
atcattcggg aggcctgact                                               20

<210> SEQ ID NO 264
<211> LENGTH: 20
<212> TYPE: DNA
<213> ORGANISM: Felis catus

<400> SEQUENCE: 264 atgcccttc cctgggaatc                                                20

<210> SEQ ID NO 265
<211> LENGTH: 20
<212> TYPE: DNA
<213> ORGANISM: Felis catus

<400> SEQUENCE: 265
atgtaatgac aggctgacat                                               20

<210> SEQ ID NO 266
<211> LENGTH: 20
<212> TYPE: DNA
<213> ORGANISM: Felis catus

<400> SEQUENCE: 266
caatgcacga cctgtagtat                                               20

<210> SEQ ID NO 267
<211> LENGTH: 20
<212> TYPE: DNA
<213> ORGANISM: Felis catus

<400> SEQUENCE: 267
cagaactccc tggggactga                                               20

<210> SEQ ID NO 268
<211> LENGTH: 20
<212> TYPE: DNA
<213> ORGANISM: Felis catus

<400> SEQUENCE: 268
cagaatcaga ttcaggagac                                               20

<210> SEQ ID NO 269
<211> LENGTH: 20
<212> TYPE: DNA
```

```
<213> ORGANISM: Felis catus

<400> SEQUENCE: 269
cagaggtcat aagcaggttg                                              20

<210> SEQ ID NO 270
<211> LENGTH: 20
<212> TYPE: DNA
<213> ORGANISM: Felis catus

<400> SEQUENCE: 270
cagtgtcagg ccctcagctc                                              20

<210> SEQ ID NO 271
<211> LENGTH: 20
<212> TYPE: DNA
<213> ORGANISM: Felis catus

<400> SEQUENCE: 271
catacatact gaaaagttct                                              20

<210> SEQ ID NO 272
<211> LENGTH: 20
<212> TYPE: DNA
<213> ORGANISM: Felis catus

<400> SEQUENCE: 272
cataccaaga gagaggatga                                              20

<210> SEQ ID NO 273
<211> LENGTH: 20
<212> TYPE: DNA
<213> ORGANISM: Felis catus

<400> SEQUENCE: 273
ccactctgac ccccagggtc                                              20

<210> SEQ ID NO 274
<211> LENGTH: 20
<212> TYPE: DNA
<213> ORGANISM: Felis catus

<400> SEQUENCE: 274
ccagagtgag acctggctct                                              20

<210> SEQ ID NO 275
<211> LENGTH: 20
<212> TYPE: DNA
<213> ORGANISM: Felis catus

<400> SEQUENCE: 275
ccaggctgct caacgctgct                                              20

<210> SEQ ID NO 276
<211> LENGTH: 20
<212> TYPE: DNA
<213> ORGANISM: Felis catus

<400> SEQUENCE: 276
ccaggtgagg ggcgcctggg                                              20

<210> SEQ ID NO 277
<211> LENGTH: 20
```

```
<212> TYPE: DNA
<213> ORGANISM: Felis catus

<400> SEQUENCE: 277
cccaggccac agaagcagtc                                            20

<210> SEQ ID NO 278
<211> LENGTH: 20
<212> TYPE: DNA
<213> ORGANISM: Felis catus

<400> SEQUENCE: 278
cctcatttgt cttcattccc                                            20

<210> SEQ ID NO 279
<211> LENGTH: 20
<212> TYPE: DNA
<213> ORGANISM: Felis catus

<400> SEQUENCE: 279
cctgtgtccc tggcatcact                                            20

<210> SEQ ID NO 280
<211> LENGTH: 20
<212> TYPE: DNA
<213> ORGANISM: Felis catus

<400> SEQUENCE: 280
cgcgtcaggc tctgggctga                                            20

<210> SEQ ID NO 281
<211> LENGTH: 20
<212> TYPE: DNA
<213> ORGANISM: Felis catus

<400> SEQUENCE: 281
ctcatgtttg ttctccacca                                            20

<210> SEQ ID NO 282
<211> LENGTH: 20
<212> TYPE: DNA
<213> ORGANISM: Felis catus

<400> SEQUENCE: 282
ctcgtgcaaa ggccctggcg                                            20

<210> SEQ ID NO 283
<211> LENGTH: 20
<212> TYPE: DNA
<213> ORGANISM: Felis catus

<400> SEQUENCE: 283
ctcgtgttct cgtgcttctc                                            20

<210> SEQ ID NO 284
<211> LENGTH: 20
<212> TYPE: DNA
<213> ORGANISM: Felis catus

<400> SEQUENCE: 284
ctgatggcac ctatgacatc                                            20

<210> SEQ ID NO 285
```

```
<211> LENGTH: 20
<212> TYPE: DNA
<213> ORGANISM: Felis catus

<400> SEQUENCE: 285
ctgccttcca aacagccaga                                          20

<210> SEQ ID NO 286
<211> LENGTH: 20
<212> TYPE: DNA
<213> ORGANISM: Felis catus

<400> SEQUENCE: 286
ctgggaggag aaagacgcca                                          20

<210> SEQ ID NO 287
<211> LENGTH: 20
<212> TYPE: DNA
<213> ORGANISM: Felis catus

<400> SEQUENCE: 287
ctggggtgga agtaggtgtc                                          20

<210> SEQ ID NO 288
<211> LENGTH: 20
<212> TYPE: DNA
<213> ORGANISM: Felis catus

<400> SEQUENCE: 288
ctgtgcctct gacgcctgtc                                          20

<210> SEQ ID NO 289
<211> LENGTH: 20
<212> TYPE: DNA
<213> ORGANISM: Felis catus

<400> SEQUENCE: 289
gaaaagcagc aggtcttcgg                                          20

<210> SEQ ID NO 290
<211> LENGTH: 20
<212> TYPE: DNA
<213> ORGANISM: Felis catus

<400> SEQUENCE: 290
gaaatggagc actgccccca                                          20

<210> SEQ ID NO 291
<211> LENGTH: 20
<212> TYPE: DNA
<213> ORGANISM: Felis catus

<400> SEQUENCE: 291
gaatgctctc agcgtgctgg                                          20

<210> SEQ ID NO 292
<211> LENGTH: 20
<212> TYPE: DNA
<213> ORGANISM: Felis catus

<400> SEQUENCE: 292
gagacctggc tcttggccta                                          20
```

```
<210> SEQ ID NO 293
<211> LENGTH: 20
<212> TYPE: DNA
<213> ORGANISM: Felis catus

<400> SEQUENCE: 293
gaggagaaag acgccatggc                                              20

<210> SEQ ID NO 294
<211> LENGTH: 20
<212> TYPE: DNA
<213> ORGANISM: Felis catus

<400> SEQUENCE: 294
gcaggtcttc ggtggggcgc                                              20

<210> SEQ ID NO 295
<211> LENGTH: 20
<212> TYPE: DNA
<213> ORGANISM: Felis catus

<400> SEQUENCE: 295
gccggaggct acttctgaaa                                              20

<210> SEQ ID NO 296
<211> LENGTH: 20
<212> TYPE: DNA
<213> ORGANISM: Felis catus

<400> SEQUENCE: 296
gcctctccag cacgtgagac                                              20

<210> SEQ ID NO 297
<211> LENGTH: 20
<212> TYPE: DNA
<213> ORGANISM: Felis catus

<400> SEQUENCE: 297
gccttgctct tgatctgggg                                              20

<210> SEQ ID NO 298
<211> LENGTH: 20
<212> TYPE: DNA
<213> ORGANISM: Felis catus

<400> SEQUENCE: 298
gcttgttagg aagagcctcc                                              20

<210> SEQ ID NO 299
<211> LENGTH: 20
<212> TYPE: DNA
<213> ORGANISM: Felis catus

<400> SEQUENCE: 299
ggagaatgct ctcagcgtgc                                              20

<210> SEQ ID NO 300
<211> LENGTH: 20
<212> TYPE: DNA
<213> ORGANISM: Felis catus

<400> SEQUENCE: 300
ggatgttgac ctattcctga                                              20
```

```
<210> SEQ ID NO 301
<211> LENGTH: 20
<212> TYPE: DNA
<213> ORGANISM: Felis catus

<400> SEQUENCE: 301
gggaagtaga ggggatcatg                                              20

<210> SEQ ID NO 302
<211> LENGTH: 20
<212> TYPE: DNA
<213> ORGANISM: Felis catus

<400> SEQUENCE: 302
gggctgcctt gctcttgatc                                              20

<210> SEQ ID NO 303
<211> LENGTH: 20
<212> TYPE: DNA
<213> ORGANISM: Felis catus

<400> SEQUENCE: 303
gggtatctct gtgatcattt                                              20

<210> SEQ ID NO 304
<211> LENGTH: 20
<212> TYPE: DNA
<213> ORGANISM: Felis catus

<400> SEQUENCE: 304
ggtataaaag ggttccaggc                                              20

<210> SEQ ID NO 305
<211> LENGTH: 20
<212> TYPE: DNA
<213> ORGANISM: Felis catus

<400> SEQUENCE: 305
gtcaagagac gactagaacc                                              20

<210> SEQ ID NO 306
<211> LENGTH: 20
<212> TYPE: DNA
<213> ORGANISM: Felis catus

<400> SEQUENCE: 306
gtgaccaggt gagggcgcc                                               20

<210> SEQ ID NO 307
<211> LENGTH: 20
<212> TYPE: DNA
<213> ORGANISM: Felis catus

<400> SEQUENCE: 307
gtgtctggga catgagtgtc                                              20

<210> SEQ ID NO 308
<211> LENGTH: 20
<212> TYPE: DNA
<213> ORGANISM: Felis catus

<400> SEQUENCE: 308 taccccctcaa gctttgggc                                              20
```

<210> SEQ ID NO 309
<211> LENGTH: 20
<212> TYPE: DNA
<213> ORGANISM: Felis catus

<400> SEQUENCE: 309
tactggtgtc agctgacact                                               20

<210> SEQ ID NO 310
<211> LENGTH: 20
<212> TYPE: DNA
<213> ORGANISM: Felis catus

<400> SEQUENCE: 310
tagactcgca cagaactccc                                               20

<210> SEQ ID NO 311
<211> LENGTH: 20
<212> TYPE: DNA
<213> ORGANISM: Felis catus

<400> SEQUENCE: 311
tcagcctacc cctcaagctt                                               20

<210> SEQ ID NO 312
<211> LENGTH: 20
<212> TYPE: DNA
<213> ORGANISM: Felis catus

<400> SEQUENCE: 312
tcatagatga agactcaccc                                               20

<210> SEQ ID NO 313
<211> LENGTH: 20
<212> TYPE: DNA
<213> ORGANISM: Felis catus

<400> SEQUENCE: 313
tcccagggca cttctgagca                                               20

<210> SEQ ID NO 314
<211> LENGTH: 20
<212> TYPE: DNA
<213> ORGANISM: Felis catus

<400> SEQUENCE: 314
tcgagccccg cgtcaggctc                                               20

<210> SEQ ID NO 315
<211> LENGTH: 20
<212> TYPE: DNA
<213> ORGANISM: Felis catus

<400> SEQUENCE: 315
tctccaccat ggcccttccc                                               20

<210> SEQ ID NO 316
<211> LENGTH: 20
<212> TYPE: DNA
<213> ORGANISM: Felis catus

<400> SEQUENCE: 316
tctctctctc tctctctctg                                             20

<210> SEQ ID NO 317
<211> LENGTH: 20
<212> TYPE: DNA
<213> ORGANISM: Felis catus

<400> SEQUENCE: 317
tctctctgtg gagcacgtca                                             20

<210> SEQ ID NO 318
<211> LENGTH: 20
<212> TYPE: DNA
<213> ORGANISM: Felis catus

<400> SEQUENCE: 318
tctgtgtaat ccctcccctc                                             20

<210> SEQ ID NO 319
<211> LENGTH: 20
<212> TYPE: DNA
<213> ORGANISM: Felis catus

<400> SEQUENCE: 319
tgacaaatat gttgagcaag                                             20

<210> SEQ ID NO 320
<211> LENGTH: 20
<212> TYPE: DNA
<213> ORGANISM: Felis catus

<400> SEQUENCE: 320
tgagtccact agctaagcac                                             20

<210> SEQ ID NO 321
<211> LENGTH: 20
<212> TYPE: DNA
<213> ORGANISM: Felis catus

<400> SEQUENCE: 321
tgcaggccct cctgtgtccc                                             20

<210> SEQ ID NO 322
<211> LENGTH: 20
<212> TYPE: DNA
<213> ORGANISM: Felis catus

<400> SEQUENCE: 322
tgggctgatg gctcggagcc                                             20

<210> SEQ ID NO 323
<211> LENGTH: 20
<212> TYPE: DNA
<213> ORGANISM: Felis catus

<400> SEQUENCE: 323
ttgtatctcc agagagataa                                             20

<210> SEQ ID NO 324
<211> LENGTH: 20
<212> TYPE: DNA
<213> ORGANISM: Felis catus

<400> SEQUENCE: 324 acccccaga caggcgtcag                                              20

<210> SEQ ID NO 325
<211> LENGTH: 20
<212> TYPE: DNA
<213> ORGANISM: Felis catus

<400> SEQUENCE: 325
acgagctgtt gccactgccc                                              20

<210> SEQ ID NO 326
<211> LENGTH: 20
<212> TYPE: DNA
<213> ORGANISM: Felis catus

<400> SEQUENCE: 326
acttgaggag ttaagagaaa                                              20

<210> SEQ ID NO 327
<211> LENGTH: 20
<212> TYPE: DNA
<213> ORGANISM: Felis catus

<400> SEQUENCE: 327
acttgctcaa catatttgtc                                              20

<210> SEQ ID NO 328
<211> LENGTH: 20
<212> TYPE: DNA
<213> ORGANISM: Felis catus

<400> SEQUENCE: 328
agaaagcgtc cagatgtcat                                              20

<210> SEQ ID NO 329
<211> LENGTH: 20
<212> TYPE: DNA
<213> ORGANISM: Felis catus

<400> SEQUENCE: 329
agaatggccc tctgggaccc                                              20

<210> SEQ ID NO 330
<211> LENGTH: 20
<212> TYPE: DNA
<213> ORGANISM: Felis catus

<400> SEQUENCE: 330
agacagagca tgagcagggg                                              20

<210> SEQ ID NO 331
<211> LENGTH: 20
<212> TYPE: DNA
<213> ORGANISM: Felis catus

<400> SEQUENCE: 331
agatcaaaag cgtcaccctt                                              20

<210> SEQ ID NO 332
<211> LENGTH: 20
<212> TYPE: DNA
<213> ORGANISM: Felis catus

```
<400> SEQUENCE: 332
agccccaaag cttgagggt                                                    20

<210> SEQ ID NO 333
<211> LENGTH: 20
<212> TYPE: DNA
<213> ORGANISM: Felis catus

<400> SEQUENCE: 333
agctagcaag taccaaaagg                                                   20

<210> SEQ ID NO 334
<211> LENGTH: 20
<212> TYPE: DNA
<213> ORGANISM: Felis catus

<400> SEQUENCE: 334
agctgttgcc actgcccagg                                                   20

<210> SEQ ID NO 335
<211> LENGTH: 20
<212> TYPE: DNA
<213> ORGANISM: Felis catus

<400> SEQUENCE: 335
aggaactgac gtttggagat                                                   20

<210> SEQ ID NO 336
<211> LENGTH: 20
<212> TYPE: DNA
<213> ORGANISM: Felis catus

<400> SEQUENCE: 336
agtcaggaag gccagagctg                                                   20

<210> SEQ ID NO 337
<211> LENGTH: 20
<212> TYPE: DNA
<213> ORGANISM: Felis catus

<400> SEQUENCE: 337
agtgatgcca gggacacagg                                                   20

<210> SEQ ID NO 338
<211> LENGTH: 20
<212> TYPE: DNA
<213> ORGANISM: Felis catus

<400> SEQUENCE: 338
atagcacctc aggcagacac                                                   20

<210> SEQ ID NO 339
<211> LENGTH: 20
<212> TYPE: DNA
<213> ORGANISM: Felis catus

<400> SEQUENCE: 339
atcctctctc ttggtatgtg                                                   20

<210> SEQ ID NO 340
<211> LENGTH: 20
<212> TYPE: DNA
<213> ORGANISM: Felis catus
```

```
<400> SEQUENCE: 340
atttgtcagg ggttcccatc                                          20

<210> SEQ ID NO 341
<211> LENGTH: 20
<212> TYPE: DNA
<213> ORGANISM: Felis catus

<400> SEQUENCE: 341
caacagtagg gcagggtggg                                          20

<210> SEQ ID NO 342
<211> LENGTH: 20
<212> TYPE: DNA
<213> ORGANISM: Felis catus

<400> SEQUENCE: 342
cacagctagc aagtaccaaa                                          20

<210> SEQ ID NO 343
<211> LENGTH: 20
<212> TYPE: DNA
<213> ORGANISM: Felis catus

<400> SEQUENCE: 343
caccctgggt cacatatggg                                          20

<210> SEQ ID NO 344
<211> LENGTH: 20
<212> TYPE: DNA
<213> ORGANISM: Felis catus

<400> SEQUENCE: 344
cactgaggcc aagtgatgcc                                          20

<210> SEQ ID NO 345
<211> LENGTH: 20
<212> TYPE: DNA
<213> ORGANISM: Felis catus

<400> SEQUENCE: 345
cagaatcgga aacaggctcc                                          20

<210> SEQ ID NO 346
<211> LENGTH: 20
<212> TYPE: DNA
<213> ORGANISM: Felis catus

<400> SEQUENCE: 346
cagaatggca gggcaggggg                                          20

<210> SEQ ID NO 347
<211> LENGTH: 20
<212> TYPE: DNA
<213> ORGANISM: Felis catus

<400> SEQUENCE: 347
cagccatctg gctgtttgga                                          20

<210> SEQ ID NO 348
<211> LENGTH: 20
<212> TYPE: DNA
```

```
<213> ORGANISM: Felis catus

<400> SEQUENCE: 348
caggggaggg gcagagagag                                              20

<210> SEQ ID NO 349
<211> LENGTH: 20
<212> TYPE: DNA
<213> ORGANISM: Felis catus

<400> SEQUENCE: 349 cagggttcc catcaggaat                                               20

<210> SEQ ID NO 350
<211> LENGTH: 20
<212> TYPE: DNA
<213> ORGANISM: Felis catus

<400> SEQUENCE: 350
cataggtgcc atcagtcccc                                              20

<210> SEQ ID NO 351
<211> LENGTH: 20
<212> TYPE: DNA
<213> ORGANISM: Felis catus

<400> SEQUENCE: 351
catatgggag ggtgatgaga                                              20

<210> SEQ ID NO 352
<211> LENGTH: 20
<212> TYPE: DNA
<213> ORGANISM: Felis catus

<400> SEQUENCE: 352
ccaagtgatg ccagggacac                                              20

<210> SEQ ID NO 353
<211> LENGTH: 20
<212> TYPE: DNA
<213> ORGANISM: Felis catus

<400> SEQUENCE: 353
ccagggaatg aagacaaatg                                              20

<210> SEQ ID NO 354
<211> LENGTH: 20
<212> TYPE: DNA
<213> ORGANISM: Felis catus

<400> SEQUENCE: 354
ccccttcatg atgcagtggc                                              20

<210> SEQ ID NO 355
<211> LENGTH: 20
<212> TYPE: DNA
<213> ORGANISM: Felis catus

<400> SEQUENCE: 355
ccctacactt gctgtggacc                                              20

<210> SEQ ID NO 356
<211> LENGTH: 20
```

<212> TYPE: DNA
<213> ORGANISM: Felis catus

<400> SEQUENCE: 356
cctgagcaga cccccagac        20

<210> SEQ ID NO 357
<211> LENGTH: 20
<212> TYPE: DNA
<213> ORGANISM: Felis catus

<400> SEQUENCE: 357
cctgctgtgg ctgcaacagt        20

<210> SEQ ID NO 358
<211> LENGTH: 20
<212> TYPE: DNA
<213> ORGANISM: Felis catus

<400> SEQUENCE: 358 cctttttgaaa gaccttcatc       20

<210> SEQ ID NO 359
<211> LENGTH: 20
<212> TYPE: DNA
<213> ORGANISM: Felis catus

<400> SEQUENCE: 359
ctcctctctc tcagtatttg        20

<210> SEQ ID NO 360
<211> LENGTH: 20
<212> TYPE: DNA
<213> ORGANISM: Felis catus

<400> SEQUENCE: 360
ctctctggag atacaatccg        20

<210> SEQ ID NO 361
<211> LENGTH: 20
<212> TYPE: DNA
<213> ORGANISM: Felis catus

<400> SEQUENCE: 361
ctggcatttg ccaatactac        20

<210> SEQ ID NO 362
<211> LENGTH: 20
<212> TYPE: DNA
<213> ORGANISM: Felis catus

<400> SEQUENCE: 362
cttaaccgac tgcgccaccc        20

<210> SEQ ID NO 363
<211> LENGTH: 20
<212> TYPE: DNA
<213> ORGANISM: Felis catus

<400> SEQUENCE: 363
ctttctcctc ccagattccc        20

<210> SEQ ID NO 364

```
<211> LENGTH: 20
<212> TYPE: DNA
<213> ORGANISM: Felis catus

<400> SEQUENCE: 364
cttttccagg aggcaccgcc                                               20

<210> SEQ ID NO 365
<211> LENGTH: 20
<212> TYPE: DNA
<213> ORGANISM: Felis catus

<400> SEQUENCE: 365
gaactgcctg ggggctgtgg                                               20

<210> SEQ ID NO 366
<211> LENGTH: 20
<212> TYPE: DNA
<213> ORGANISM: Felis catus

<400> SEQUENCE: 366
gagagagaca gagcatgagc                                               20

<210> SEQ ID NO 367
<211> LENGTH: 20
<212> TYPE: DNA
<213> ORGANISM: Felis catus

<400> SEQUENCE: 367
gagctgaggg cctgacactg                                               20

<210> SEQ ID NO 368
<211> LENGTH: 20
<212> TYPE: DNA
<213> ORGANISM: Felis catus

<400> SEQUENCE: 368
gaggagatgt atgtgtgggc                                               20

<210> SEQ ID NO 369
<211> LENGTH: 20
<212> TYPE: DNA
<213> ORGANISM: Felis catus

<400> SEQUENCE: 369
gaggcacaga atggcagggc                                               20

<210> SEQ ID NO 370
<211> LENGTH: 20
<212> TYPE: DNA
<213> ORGANISM: Felis catus

<400> SEQUENCE: 370
gcaagagagt ctcccaagtc                                               20

<210> SEQ ID NO 371
<211> LENGTH: 20
<212> TYPE: DNA
<213> ORGANISM: Felis catus

<400> SEQUENCE: 371
gccaggtctc actctgggca                                               20
```

```
<210> SEQ ID NO 372
<211> LENGTH: 20
<212> TYPE: DNA
<213> ORGANISM: Felis catus

<400> SEQUENCE: 372
gctgtttgga aggcagccag                                              20

<210> SEQ ID NO 373
<211> LENGTH: 20
<212> TYPE: DNA
<213> ORGANISM: Felis catus

<400> SEQUENCE: 373
ggagacacag aatcggaaac                                              20

<210> SEQ ID NO 374
<211> LENGTH: 20
<212> TYPE: DNA
<213> ORGANISM: Felis catus

<400> SEQUENCE: 374
ggctcccctt ccccgtcttg                                              20

<210> SEQ ID NO 375
<211> LENGTH: 20
<212> TYPE: DNA
<213> ORGANISM: Felis catus

<400> SEQUENCE: 375
gggctggttg tgtcttggtg                                              20

<210> SEQ ID NO 376
<211> LENGTH: 20
<212> TYPE: DNA
<213> ORGANISM: Felis catus

<400> SEQUENCE: 376
ggggtggaat atggaacttg                                              20

<210> SEQ ID NO 377
<211> LENGTH: 20
<212> TYPE: DNA
<213> ORGANISM: Felis catus

<400> SEQUENCE: 377
gggtcagagt ggtgggccat                                              20

<210> SEQ ID NO 378
<211> LENGTH: 20
<212> TYPE: DNA
<213> ORGANISM: Felis catus

<400> SEQUENCE: 378
ggtcacttta atagcacctc                                              20

<210> SEQ ID NO 379
<211> LENGTH: 20
<212> TYPE: DNA
<213> ORGANISM: Felis catus

<400> SEQUENCE: 379
gtctaacatc cttttccagg                                              20
```

```
<210> SEQ ID NO 380
<211> LENGTH: 20
<212> TYPE: DNA
<213> ORGANISM: Felis catus

<400> SEQUENCE: 380
gtgctggaga ggctggagtc                                              20

<210> SEQ ID NO 381
<211> LENGTH: 20
<212> TYPE: DNA
<213> ORGANISM: Felis catus

<400> SEQUENCE: 381
tatgtgaggc acagaatggc                                              20

<210> SEQ ID NO 382
<211> LENGTH: 20
<212> TYPE: DNA
<213> ORGANISM: Felis catus

<400> SEQUENCE: 382
tccaccccag atcaagagca                                              20

<210> SEQ ID NO 383
<211> LENGTH: 20
<212> TYPE: DNA
<213> ORGANISM: Felis catus

<400> SEQUENCE: 383
tccagtctca cgtgctggag                                              20

<210> SEQ ID NO 384
<211> LENGTH: 20
<212> TYPE: DNA
<213> ORGANISM: Felis catus

<400> SEQUENCE: 384
tcccctacat gctggtgccc                                              20

<210> SEQ ID NO 385
<211> LENGTH: 20
<212> TYPE: DNA
<213> ORGANISM: Felis catus

<400> SEQUENCE: 385
tcctcccaga ttcccaggga                                              20

<210> SEQ ID NO 386
<211> LENGTH: 20
<212> TYPE: DNA
<213> ORGANISM: Felis catus

<400> SEQUENCE: 386
tctcaactta cggattttc                                               20

<210> SEQ ID NO 387
<211> LENGTH: 20
<212> TYPE: DNA
<213> ORGANISM: Felis catus

<400> SEQUENCE: 387
tcttttctgg gggagtgctc                                              20
```

<210> SEQ ID NO 388
<211> LENGTH: 20
<212> TYPE: DNA
<213> ORGANISM: Felis catus

<400> SEQUENCE: 388
tgcctggggg ctgtggaggg                                           20

<210> SEQ ID NO 389
<211> LENGTH: 20
<212> TYPE: DNA
<213> ORGANISM: Felis catus

<400> SEQUENCE: 389
tgcgtctaac atccttttcc                                           20

<210> SEQ ID NO 390
<211> LENGTH: 20
<212> TYPE: DNA
<213> ORGANISM: Felis catus

<400> SEQUENCE: 390
tgctcagaag tgccctggga                                           20

<210> SEQ ID NO 391
<211> LENGTH: 20
<212> TYPE: DNA
<213> ORGANISM: Felis catus

<400> SEQUENCE: 391
tggagaggct ggagtcagga                                           20

<210> SEQ ID NO 392
<211> LENGTH: 20
<212> TYPE: DNA
<213> ORGANISM: Felis catus

<400> SEQUENCE: 392
tgggccagcc ccaaagcttg                                           20

<210> SEQ ID NO 393
<211> LENGTH: 20
<212> TYPE: DNA
<213> ORGANISM: Felis catus

<400> SEQUENCE: 393
tgggccatag gccaagagcc                                           20

<210> SEQ ID NO 394
<211> LENGTH: 20
<212> TYPE: DNA
<213> ORGANISM: Felis catus

<400> SEQUENCE: 394
tgtggctgca acagtagggc                                           20

<210> SEQ ID NO 395
<211> LENGTH: 20
<212> TYPE: DNA
<213> ORGANISM: Felis catus

<400> SEQUENCE: 395

```
ttctgcttct tgaccacgcc                                              20

<210> SEQ ID NO 396
<211> LENGTH: 20
<212> TYPE: DNA
<213> ORGANISM: Felis catus

<400> SEQUENCE: 396
ttgcatcaac gcagttcttc                                              20

<210> SEQ ID NO 397
<211> LENGTH: 20
<212> TYPE: DNA
<213> ORGANISM: Felis catus

<400> SEQUENCE: 397
ttggaaggca gccagagggg                                              20

<210> SEQ ID NO 398
<211> LENGTH: 20
<212> TYPE: DNA
<213> ORGANISM: Felis catus

<400> SEQUENCE: 398
tttacctttc aagctatctg                                              20

<210> SEQ ID NO 399
<211> LENGTH: 20
<212> TYPE: DNA
<213> ORGANISM: Felis catus

<400> SEQUENCE: 399
tttcagaact gaaattttct                                              20

<210> SEQ ID NO 400
<211> LENGTH: 20
<212> TYPE: DNA
<213> ORGANISM: Felis catus

<400> SEQUENCE: 400
tttctaggtt gactggggaa                                              20

<210> SEQ ID NO 401
<211> LENGTH: 20
<212> TYPE: DNA
<213> ORGANISM: Felis catus

<400> SEQUENCE: 401
agcaagtacc aaaaggaggc                                              20

<210> SEQ ID NO 402
<211> LENGTH: 20
<212> TYPE: DNA
<213> ORGANISM: Felis catus

<400> SEQUENCE: 402
cagaccacgg ggaagtgggg                                              20

<210> SEQ ID NO 403
<211> LENGTH: 20
<212> TYPE: DNA
<213> ORGANISM: Felis catus

<400> SEQUENCE: 403
```
catcagccca gagcctgacg                                                    20

<210> SEQ ID NO 404
<211> LENGTH: 20
<212> TYPE: DNA
<213> ORGANISM: Felis catus

<400> SEQUENCE: 404
gagagaggga gacacagaat                                                    20

<210> SEQ ID NO 405
<211> LENGTH: 20
<212> TYPE: DNA
<213> ORGANISM: Felis catus

<400> SEQUENCE: 405
gatcgtgacc tggctgaagc                                                    20

<210> SEQ ID NO 406
<211> LENGTH: 20
<212> TYPE: DNA
<213> ORGANISM: Felis catus

<400> SEQUENCE: 406
gatggtctgg tctcaactta                                                    20

<210> SEQ ID NO 407
<211> LENGTH: 20
<212> TYPE: DNA
<213> ORGANISM: Felis catus

<400> SEQUENCE: 407
ggcgaattta ggtcagacca                                                    20

<210> SEQ ID NO 408
<211> LENGTH: 20
<212> TYPE: DNA
<213> ORGANISM: Felis catus

<400> SEQUENCE: 408
gggcctgcag accccccaagc                                                   20

<210> SEQ ID NO 409
<211> LENGTH: 20
<212> TYPE: DNA
<213> ORGANISM: Felis catus

<400> SEQUENCE: 409
taggtcaaca tccctcttca                                                    20

<210> SEQ ID NO 410
<211> LENGTH: 20
<212> TYPE: DNA
<213> ORGANISM: Felis catus

<400> SEQUENCE: 410
tccatttcag aagtagcctc                                                    20

<210> SEQ ID NO 411
<211> LENGTH: 20
<212> TYPE: DNA
<213> ORGANISM: Felis catus -continued

```
<400> SEQUENCE: 411
tgacgcgggg ctcgaactca                                               20

<210> SEQ ID NO 412
<211> LENGTH: 20
<212> TYPE: DNA
<213> ORGANISM: Felis catus

<400> SEQUENCE: 412
tgccattctc tcctccctca                                               20

<210> SEQ ID NO 413
<211> LENGTH: 20
<212> TYPE: DNA
<213> ORGANISM: Felis catus

<400> SEQUENCE: 413
aaatgagggt tttttttttgg                                              20

<210> SEQ ID NO 414
<211> LENGTH: 20
<212> TYPE: DNA
<213> ORGANISM: Felis catus

<400> SEQUENCE: 414
aacagtaggg cagggtggga                                               20

<210> SEQ ID NO 415
<211> LENGTH: 20
<212> TYPE: DNA
<213> ORGANISM: Felis catus

<400> SEQUENCE: 415
aactgcctgg gggctgtgga                                               20

<210> SEQ ID NO 416
<211> LENGTH: 20
<212> TYPE: DNA
<213> ORGANISM: Felis catus

<400> SEQUENCE: 416
aacttttcag tatgtatggt                                               20

<210> SEQ ID NO 417
<211> LENGTH: 20
<212> TYPE: DNA
<213> ORGANISM: Felis catus

<400> SEQUENCE: 417
aagacctggc ccactcatct                                               20

<210> SEQ ID NO 418
<211> LENGTH: 20
<212> TYPE: DNA
<213> ORGANISM: Felis catus

<400> SEQUENCE: 418
aatgagggtt ttttttttggg                                              20

<210> SEQ ID NO 419
<211> LENGTH: 20
<212> TYPE: DNA
<213> ORGANISM: Felis catus
```

-continued

```
<400> SEQUENCE: 419
acaaatgagg gttttttttt                                          20

<210> SEQ ID NO 420
<211> LENGTH: 20
<212> TYPE: DNA
<213> ORGANISM: Felis catus

<400> SEQUENCE: 420
acagagcatg agcaggggag                                          20

<210> SEQ ID NO 421
<211> LENGTH: 20
<212> TYPE: DNA
<213> ORGANISM: Felis catus

<400> SEQUENCE: 421
accctggggg tcagagtggt                                          20

<210> SEQ ID NO 422
<211> LENGTH: 20
<212> TYPE: DNA
<213> ORGANISM: Felis catus

<400> SEQUENCE: 422
accctgggtc acatatggga                                          20

<210> SEQ ID NO 423
<211> LENGTH: 20
<212> TYPE: DNA
<213> ORGANISM: Felis catus

<400> SEQUENCE: 423
actgaggcca agtgatgcca                                          20

<210> SEQ ID NO 424
<211> LENGTH: 20
<212> TYPE: DNA
<213> ORGANISM: Felis catus

<400> SEQUENCE: 424
acttttcagt atgtatggtg                                          20

<210> SEQ ID NO 425
<211> LENGTH: 20
<212> TYPE: DNA
<213> ORGANISM: Felis catus

<400> SEQUENCE: 425
agaatggcag ggcaggggga                                          20

<210> SEQ ID NO 426
<211> LENGTH: 20
<212> TYPE: DNA
<213> ORGANISM: Felis catus

<400> SEQUENCE: 426
agaccacggg gaagtggggc                                          20

<210> SEQ ID NO 427
<211> LENGTH: 20
<212> TYPE: DNA
```

<213> ORGANISM: Felis catus

<400> SEQUENCE: 427
agagagacag agcatgagca  20

<210> SEQ ID NO 428
<211> LENGTH: 20
<212> TYPE: DNA
<213> ORGANISM: Felis catus

<400> SEQUENCE: 428
agcctccggc cagaccctgg  20

<210> SEQ ID NO 429
<211> LENGTH: 20
<212> TYPE: DNA
<213> ORGANISM: Felis catus

<400> SEQUENCE: 429
aggcacagaa tggcagggca  20

<210> SEQ ID NO 430
<211> LENGTH: 20
<212> TYPE: DNA
<213> ORGANISM: Felis catus

<400> SEQUENCE: 430
aggcaccgcc aggcctctct  20

<210> SEQ ID NO 431
<211> LENGTH: 20
<212> TYPE: DNA
<213> ORGANISM: Felis catus

<400> SEQUENCE: 431
aggggagggg cagagagaga  20

<210> SEQ ID NO 432
<211> LENGTH: 20
<212> TYPE: DNA
<213> ORGANISM: Felis catus

<400> SEQUENCE: 432 agggttttt tttggggggg  20

<210> SEQ ID NO 433
<211> LENGTH: 20
<212> TYPE: DNA
<213> ORGANISM: Felis catus

<400> SEQUENCE: 433
aggtcagacc acggggaagt  20

<210> SEQ ID NO 434
<211> LENGTH: 20
<212> TYPE: DNA
<213> ORGANISM: Felis catus

<400> SEQUENCE: 434
agtggtggaa tatacaccct  20

<210> SEQ ID NO 435
<211> LENGTH: 20

```
<212> TYPE: DNA
<213> ORGANISM: Felis catus

<400> SEQUENCE: 435
agttcagcag actcttttct                                                   20

<210> SEQ ID NO 436
<211> LENGTH: 20
<212> TYPE: DNA
<213> ORGANISM: Felis catus

<400> SEQUENCE: 436
atacaccctg ggtcacatat                                                   20

<210> SEQ ID NO 437
<211> LENGTH: 20
<212> TYPE: DNA
<213> ORGANISM: Felis catus

<400> SEQUENCE: 437
ataggtgcca tcagtcccca                                                   20

<210> SEQ ID NO 438
<211> LENGTH: 20
<212> TYPE: DNA
<213> ORGANISM: Felis catus

<400> SEQUENCE: 438
atatgggagg gtgatgagaa                                                   20

<210> SEQ ID NO 439
<211> LENGTH: 20
<212> TYPE: DNA
<213> ORGANISM: Felis catus

<400> SEQUENCE: 439
atcacagaga taccccctcct                                                  20

<210> SEQ ID NO 440
<211> LENGTH: 20
<212> TYPE: DNA
<213> ORGANISM: Felis catus

<400> SEQUENCE: 440
atcagcccag agcctgacgc                                                   20

<210> SEQ ID NO 441
<211> LENGTH: 20
<212> TYPE: DNA
<213> ORGANISM: Felis catus

<400> SEQUENCE: 441
atgagggttt tttttggggg                                                   20

<210> SEQ ID NO 442
<211> LENGTH: 20
<212> TYPE: DNA
<213> ORGANISM: Felis catus

<400> SEQUENCE: 442
atgtgaggca cagaatggca                                                   20

<210> SEQ ID NO 443
```

```
<211> LENGTH: 20
<212> TYPE: DNA
<213> ORGANISM: Felis catus

<400> SEQUENCE: 443
caaatgaggg ttttttttg                                                    20

<210> SEQ ID NO 444
<211> LENGTH: 20
<212> TYPE: DNA
<213> ORGANISM: Felis catus

<400> SEQUENCE: 444
caacatccct cttcacggct                                                   20

<210> SEQ ID NO 445
<211> LENGTH: 20
<212> TYPE: DNA
<213> ORGANISM: Felis catus

<400> SEQUENCE: 445
caagagccag gtctcactct                                                   20

<210> SEQ ID NO 446
<211> LENGTH: 20
<212> TYPE: DNA
<213> ORGANISM: Felis catus

<400> SEQUENCE: 446
caagcagcgt tgagcagcct                                                   20

<210> SEQ ID NO 447
<211> LENGTH: 20
<212> TYPE: DNA
<213> ORGANISM: Felis catus

<400> SEQUENCE: 447
cacagagata cccctcctgg                                                   20

<210> SEQ ID NO 448
<211> LENGTH: 20
<212> TYPE: DNA
<213> ORGANISM: Felis catus

<400> SEQUENCE: 448
caccttctca cctttgggtg                                                   20

<210> SEQ ID NO 449
<211> LENGTH: 20
<212> TYPE: DNA
<213> ORGANISM: Felis catus

<400> SEQUENCE: 449
cagggaatga agacaaatga                                                   20

<210> SEQ ID NO 450
<211> LENGTH: 20
<212> TYPE: DNA
<213> ORGANISM: Felis catus

<400> SEQUENCE: 450
ccagactgct tctgtggcct                                                   20
```

```
<210> SEQ ID NO 451
<211> LENGTH: 20
<212> TYPE: DNA
<213> ORGANISM: Felis catus

<400> SEQUENCE: 451
cctacacttg ctgtggacca                                          20

<210> SEQ ID NO 452
<211> LENGTH: 20
<212> TYPE: DNA
<213> ORGANISM: Felis catus

<400> SEQUENCE: 452
cctcccagat tcccagggaa                                          20

<210> SEQ ID NO 453
<211> LENGTH: 20
<212> TYPE: DNA
<213> ORGANISM: Felis catus

<400> SEQUENCE: 453
cgaatttagg tcagaccacg                                          20

<210> SEQ ID NO 454
<211> LENGTH: 20
<212> TYPE: DNA
<213> ORGANISM: Felis catus

<400> SEQUENCE: 454
cgagtctagc agcagttggg                                          20

<210> SEQ ID NO 455
<211> LENGTH: 20
<212> TYPE: DNA
<213> ORGANISM: Felis catus

<400> SEQUENCE: 455
ctcatcacct tctcacctt                                           20

<210> SEQ ID NO 456
<211> LENGTH: 20
<212> TYPE: DNA
<213> ORGANISM: Felis catus

<400> SEQUENCE: 456
ctgcaacagt agggcagggt                                          20

<210> SEQ ID NO 457
<211> LENGTH: 20
<212> TYPE: DNA
<213> ORGANISM: Felis catus

<400> SEQUENCE: 457
ctgctgtggc tgcaacagta                                          20

<210> SEQ ID NO 458
<211> LENGTH: 20
<212> TYPE: DNA
<213> ORGANISM: Felis catus

<400> SEQUENCE: 458
ctgcttctca gaactgcctg                                          20
```

```
<210> SEQ ID NO 459
<211> LENGTH: 20
<212> TYPE: DNA
<213> ORGANISM: Felis catus

<400> SEQUENCE: 459
ctgtttggaa ggcagccaga                                          20

<210> SEQ ID NO 460
<211> LENGTH: 20
<212> TYPE: DNA
<213> ORGANISM: Felis catus

<400> SEQUENCE: 460
cttgctcaac atatttgtca                                          20

<210> SEQ ID NO 461
<211> LENGTH: 20
<212> TYPE: DNA
<213> ORGANISM: Felis catus

<400> SEQUENCE: 461
cttttcagta tgtatggtgg                                          20

<210> SEQ ID NO 462
<211> LENGTH: 20
<212> TYPE: DNA
<213> ORGANISM: Felis catus

<400> SEQUENCE: 462
gaaattttct aggttgactg                                          20

<210> SEQ ID NO 463
<211> LENGTH: 20
<212> TYPE: DNA
<213> ORGANISM: Felis catus

<400> SEQUENCE: 463
gaatggccct ctgggaccca                                          20

<210> SEQ ID NO 464
<211> LENGTH: 20
<212> TYPE: DNA
<213> ORGANISM: Felis catus

<400> SEQUENCE: 464
gacagagcat gagcagggga                                          20

<210> SEQ ID NO 465
<211> LENGTH: 20
<212> TYPE: DNA
<213> ORGANISM: Felis catus

<400> SEQUENCE: 465
gaccacgggg aagtggggcg                                          20

<210> SEQ ID NO 466
<211> LENGTH: 20
<212> TYPE: DNA
<213> ORGANISM: Felis catus

<400> SEQUENCE: 466
gactccccct tgctaccatgg                                         20
```

```
<210> SEQ ID NO 467
<211> LENGTH: 20
<212> TYPE: DNA
<213> ORGANISM: Felis catus

<400> SEQUENCE: 467
gagagacaga gcatgagcag                                                  20

<210> SEQ ID NO 468
<211> LENGTH: 20
<212> TYPE: DNA
<213> ORGANISM: Felis catus

<400> SEQUENCE: 468
gagagagaga gatccctct                                                   20

<210> SEQ ID NO 469
<211> LENGTH: 20
<212> TYPE: DNA
<213> ORGANISM: Felis catus

<400> SEQUENCE: 469
gaggcacaga atggccctct                                                  20

<210> SEQ ID NO 470
<211> LENGTH: 20
<212> TYPE: DNA
<213> ORGANISM: Felis catus

<400> SEQUENCE: 470
gagggaggag atgtatgtgt                                                  20

<210> SEQ ID NO 471
<211> LENGTH: 20
<212> TYPE: DNA
<213> ORGANISM: Felis catus

<400> SEQUENCE: 471
gagggttttt ttttgggggg                                                  20

<210> SEQ ID NO 472
<211> LENGTH: 20
<212> TYPE: DNA
<213> ORGANISM: Felis catus

<400> SEQUENCE: 472
gcacagaatg gcagggcagg                                                  20

<210> SEQ ID NO 473
<211> LENGTH: 20
<212> TYPE: DNA
<213> ORGANISM: Felis catus

<400> SEQUENCE: 473
gccatgctca gaagtgccct                                                  20

<210> SEQ ID NO 474
<211> LENGTH: 20
<212> TYPE: DNA
<213> ORGANISM: Felis catus

<400> SEQUENCE: 474
```
gccattctct cctccctcac                                          20

<210> SEQ ID NO 475
<211> LENGTH: 20
<212> TYPE: DNA
<213> ORGANISM: Felis catus

<400> SEQUENCE: 475
gcgaatttag gtcagaccac                                          20

<210> SEQ ID NO 476
<211> LENGTH: 20
<212> TYPE: DNA
<213> ORGANISM: Felis catus

<400> SEQUENCE: 476
gcgagtctag cagcagttgg                                          20

<210> SEQ ID NO 477
<211> LENGTH: 20
<212> TYPE: DNA
<213> ORGANISM: Felis catus

<400> SEQUENCE: 477
gctccccttc cccgtcttga                                          20

<210> SEQ ID NO 478
<211> LENGTH: 20
<212> TYPE: DNA
<213> ORGANISM: Felis catus

<400> SEQUENCE: 478
gctgcttctc agaactgcct                                          20

<210> SEQ ID NO 479
<211> LENGTH: 20
<212> TYPE: DNA
<213> ORGANISM: Felis catus

<400> SEQUENCE: 479
ggactcccct tgctaccatg                                          20

<210> SEQ ID NO 480
<211> LENGTH: 20
<212> TYPE: DNA
<213> ORGANISM: Felis catus

<400> SEQUENCE: 480
ggcacagaat ggcagggcag                                          20

<210> SEQ ID NO 481
<211> LENGTH: 20
<212> TYPE: DNA
<213> ORGANISM: Felis catus

<400> SEQUENCE: 481
ggccagcccc aaagcttgag                                          20

<210> SEQ ID NO 482
<211> LENGTH: 20
<212> TYPE: DNA
<213> ORGANISM: Felis catus

<400> SEQUENCE: 482
gggccagccc caaagcttga                                                       20

<210> SEQ ID NO 483
<211> LENGTH: 20
<212> TYPE: DNA
<213> ORGANISM: Felis catus

<400> SEQUENCE: 483
gggggagtgc tcaggtggtg                                                       20

<210> SEQ ID NO 484
<211> LENGTH: 20
<212> TYPE: DNA
<213> ORGANISM: Felis catus

<400> SEQUENCE: 484
ggtcagacca cggggaagtg                                                       20

<210> SEQ ID NO 485
<211> LENGTH: 20
<212> TYPE: DNA
<213> ORGANISM: Felis catus

<400> SEQUENCE: 485
gtagcctccg gccagaccct                                                       20

<210> SEQ ID NO 486
<211> LENGTH: 20
<212> TYPE: DNA
<213> ORGANISM: Felis catus

<400> SEQUENCE: 486
gtcaggaagg ccagagctga                                                       20

<210> SEQ ID NO 487
<211> LENGTH: 20
<212> TYPE: DNA
<213> ORGANISM: Felis catus

<400> SEQUENCE: 487
gtgatgccag ggacacagga                                                       20

<210> SEQ ID NO 488
<211> LENGTH: 20
<212> TYPE: DNA
<213> ORGANISM: Felis catus

<400> SEQUENCE: 488
gtgcgagtct agcagcagtt                                                       20

<210> SEQ ID NO 489
<211> LENGTH: 20
<212> TYPE: DNA
<213> ORGANISM: Felis catus

<400> SEQUENCE: 489
gtggctgcaa cagtagggca                                                       20

<210> SEQ ID NO 490
<211> LENGTH: 20
<212> TYPE: DNA
<213> ORGANISM: Felis catus

```
<400> SEQUENCE: 490
gttcagcaga ctcttttctg                                              20

<210> SEQ ID NO 491
<211> LENGTH: 20
<212> TYPE: DNA
<213> ORGANISM: Felis catus

<400> SEQUENCE: 491
tagcctccgg ccagaccctg                                              20

<210> SEQ ID NO 492
<211> LENGTH: 20
<212> TYPE: DNA
<213> ORGANISM: Felis catus

<400> SEQUENCE: 492
tcacagagat acccctcctg                                              20

<210> SEQ ID NO 493
<211> LENGTH: 20
<212> TYPE: DNA
<213> ORGANISM: Felis catus

<400> SEQUENCE: 493
tcaccttctc acctttgggt                                              20

<210> SEQ ID NO 494
<211> LENGTH: 20
<212> TYPE: DNA
<213> ORGANISM: Felis catus

<400> SEQUENCE: 494
tcagcccaga gcctgacgcg                                              20

<210> SEQ ID NO 495
<211> LENGTH: 20
<212> TYPE: DNA
<213> ORGANISM: Felis catus

<400> SEQUENCE: 495
tctaggttga ctggggaaag                                              20

<210> SEQ ID NO 496
<211> LENGTH: 20
<212> TYPE: DNA
<213> ORGANISM: Felis catus

<400> SEQUENCE: 496
tctgcttctt gaccacgcca                                              20

<210> SEQ ID NO 497
<211> LENGTH: 20
<212> TYPE: DNA
<213> ORGANISM: Felis catus

<400> SEQUENCE: 497
tgaaattttc taggttgact                                              20

<210> SEQ ID NO 498
<211> LENGTH: 20
<212> TYPE: DNA
<213> ORGANISM: Felis catus
```

```
<400> SEQUENCE: 498
tgagggtttt tttttggggg                                              20

<210> SEQ ID NO 499
<211> LENGTH: 20
<212> TYPE: DNA
<213> ORGANISM: Felis catus

<400> SEQUENCE: 499
tgcgagtcta gcagcagttg                                              20

<210> SEQ ID NO 500
<211> LENGTH: 20
<212> TYPE: DNA
<213> ORGANISM: Felis catus

<400> SEQUENCE: 500
tgcttctcag aactgcctgg                                              20

<210> SEQ ID NO 501
<211> LENGTH: 20
<212> TYPE: DNA
<213> ORGANISM: Felis catus

<400> SEQUENCE: 501
tggaaggcag ccagagggga                                              20

<210> SEQ ID NO 502
<211> LENGTH: 20
<212> TYPE: DNA
<213> ORGANISM: Felis catus

<400> SEQUENCE: 502
tggactcccc ttgctaccat                                              20

<210> SEQ ID NO 503
<211> LENGTH: 20
<212> TYPE: DNA
<213> ORGANISM: Felis catus

<400> SEQUENCE: 503
tgggggagtg ctcaggtggt                                              20

<210> SEQ ID NO 504
<211> LENGTH: 20
<212> TYPE: DNA
<213> ORGANISM: Felis catus

<400> SEQUENCE: 504
tgtttggaag gcagccagag                                              20

<210> SEQ ID NO 505
<211> LENGTH: 20
<212> TYPE: DNA
<213> ORGANISM: Felis catus

<400> SEQUENCE: 505
ttcaatgttt atttattttt                                              20

<210> SEQ ID NO 506
<211> LENGTH: 20
<212> TYPE: DNA
```

<213> ORGANISM: Felis catus

<400> SEQUENCE: 506
ttcagcagac tctttctgg                                    20

<210> SEQ ID NO 507
<211> LENGTH: 20
<212> TYPE: DNA
<213> ORGANISM: Felis catus

<400> SEQUENCE: 507
ttctaggttg actggggaaa                                   20

<210> SEQ ID NO 508
<211> LENGTH: 20
<212> TYPE: DNA
<213> ORGANISM: Felis catus

<400> SEQUENCE: 508
ttgctcaaca tatttgtcag                                   20

<210> SEQ ID NO 509
<211> LENGTH: 20
<212> TYPE: DNA
<213> ORGANISM: Felis catus

<400> SEQUENCE: 509
tttctcctcc cagattccca                                   20

<210> SEQ ID NO 510
<211> LENGTH: 20
<212> TYPE: DNA
<213> ORGANISM: Felis catus

<400> SEQUENCE: 510
aaaaggaggc cggtctctgg                                   20

<210> SEQ ID NO 511
<211> LENGTH: 20
<212> TYPE: DNA
<213> ORGANISM: Felis catus

<400> SEQUENCE: 511
aaatatcatt tccccccaac                                   20

<210> SEQ ID NO 512
<211> LENGTH: 20
<212> TYPE: DNA
<213> ORGANISM: Felis catus

<400> SEQUENCE: 512
aacgcagttc ttcaggtttc                                   20

<210> SEQ ID NO 513
<211> LENGTH: 20
<212> TYPE: DNA
<213> ORGANISM: Felis catus

<400> SEQUENCE: 513
aagtcaggcc tcccgaatga                                   20

<210> SEQ ID NO 514
<211> LENGTH: 20

```
<212> TYPE: DNA
<213> ORGANISM: Felis catus

<400> SEQUENCE: 514
aagttcagca gactcttttc                                              20

<210> SEQ ID NO 515
<211> LENGTH: 20
<212> TYPE: DNA
<213> ORGANISM: Felis catus

<400> SEQUENCE: 515
accaaaagga ggccggtctc                                              20

<210> SEQ ID NO 516
<211> LENGTH: 20
<212> TYPE: DNA
<213> ORGANISM: Felis catus

<400> SEQUENCE: 516
agagaaaagg aactgacgtt                                              20

<210> SEQ ID NO 517
<211> LENGTH: 20
<212> TYPE: DNA
<213> ORGANISM: Felis catus

<400> SEQUENCE: 517
agagagagag agatcccctc                                              20

<210> SEQ ID NO 518
<211> LENGTH: 20
<212> TYPE: DNA
<213> ORGANISM: Felis catus

<400> SEQUENCE: 518
agattcccag ggaagggcca                                              20

<210> SEQ ID NO 519
<211> LENGTH: 20
<212> TYPE: DNA
<213> ORGANISM: Felis catus

<400> SEQUENCE: 519
aggtctcact ctgggcaagg                                              20

<210> SEQ ID NO 520
<211> LENGTH: 20
<212> TYPE: DNA
<213> ORGANISM: Felis catus

<400> SEQUENCE: 520
agtagcctcc ggccagaccc                                              20

<210> SEQ ID NO 521
<211> LENGTH: 20
<212> TYPE: DNA
<213> ORGANISM: Felis catus

<400> SEQUENCE: 521
atcaccttct cacctttggg                                              20

<210> SEQ ID NO 522
```

```
<211> LENGTH: 20
<212> TYPE: DNA
<213> ORGANISM: Felis catus

<400> SEQUENCE: 522
atctatgaca ttggaagacc                                              20

<210> SEQ ID NO 523
<211> LENGTH: 20
<212> TYPE: DNA
<213> ORGANISM: Felis catus

<400> SEQUENCE: 523
atgtgacctt gaagatggtc                                              20

<210> SEQ ID NO 524
<211> LENGTH: 20
<212> TYPE: DNA
<213> ORGANISM: Felis catus

<400> SEQUENCE: 524
attacatgtg accttgaaga                                              20

<210> SEQ ID NO 525
<211> LENGTH: 20
<212> TYPE: DNA
<213> ORGANISM: Felis catus

<400> SEQUENCE: 525
caagaacttt tcagtatgta                                              20

<210> SEQ ID NO 526
<211> LENGTH: 20
<212> TYPE: DNA
<213> ORGANISM: Felis catus

<400> SEQUENCE: 526
cacaacctgc ttatgacctc                                              20

<210> SEQ ID NO 527
<211> LENGTH: 20
<212> TYPE: DNA
<213> ORGANISM: Felis catus

<400> SEQUENCE: 527
cagacagcca tctggctgtt                                              20

<210> SEQ ID NO 528
<211> LENGTH: 20
<212> TYPE: DNA
<213> ORGANISM: Felis catus

<400> SEQUENCE: 528
cagggcaggg ggagggcttt                                              20

<210> SEQ ID NO 529
<211> LENGTH: 20
<212> TYPE: DNA
<213> ORGANISM: Felis catus

<400> SEQUENCE: 529
caggtgctcc ctccccagcc                                              20
```

```
<210> SEQ ID NO 530
<211> LENGTH: 20
<212> TYPE: DNA
<213> ORGANISM: Felis catus

<400> SEQUENCE: 530
cagtatgtat ggtgggggag                                               20

<210> SEQ ID NO 531
<211> LENGTH: 20
<212> TYPE: DNA
<213> ORGANISM: Felis catus

<400> SEQUENCE: 531
cagtctcctg aatctgattc                                               20

<210> SEQ ID NO 532
<211> LENGTH: 20
<212> TYPE: DNA
<213> ORGANISM: Felis catus

<400> SEQUENCE: 532
ccaagagcca ggtctcactc                                               20

<210> SEQ ID NO 533
<211> LENGTH: 20
<212> TYPE: DNA
<213> ORGANISM: Felis catus

<400> SEQUENCE: 533
ccaagcagcg ttgagcagcc                                               20

<210> SEQ ID NO 534
<211> LENGTH: 20
<212> TYPE: DNA
<213> ORGANISM: Felis catus

<400> SEQUENCE: 534
ccacccaggc gccctcacc                                                20

<210> SEQ ID NO 535
<211> LENGTH: 20
<212> TYPE: DNA
<213> ORGANISM: Felis catus

<400> SEQUENCE: 535
ccagaccctg ggggtcagag                                               20

<210> SEQ ID NO 536
<211> LENGTH: 20
<212> TYPE: DNA
<213> ORGANISM: Felis catus

<400> SEQUENCE: 536
cccctctact tccccagcca                                               20

<210> SEQ ID NO 537
<211> LENGTH: 20
<212> TYPE: DNA
<213> ORGANISM: Felis catus

<400> SEQUENCE: 537
cctaacaagc atatgattca                                               20
```

```
<210> SEQ ID NO 538
<211> LENGTH: 20
<212> TYPE: DNA
<213> ORGANISM: Felis catus

<400> SEQUENCE: 538
cctgcagacc cccaagccgg                                              20

<210> SEQ ID NO 539
<211> LENGTH: 20
<212> TYPE: DNA
<213> ORGANISM: Felis catus

<400> SEQUENCE: 539
cctgcagacc cccaagctgg                                              20

<210> SEQ ID NO 540
<211> LENGTH: 20
<212> TYPE: DNA
<213> ORGANISM: Felis catus

<400> SEQUENCE: 540
ccttccatca tcctctctct                                              20

<210> SEQ ID NO 541
<211> LENGTH: 20
<212> TYPE: DNA
<213> ORGANISM: Felis catus

<400> SEQUENCE: 541
cgccatgctc agaagtgccc                                              20

<210> SEQ ID NO 542
<211> LENGTH: 20
<212> TYPE: DNA
<213> ORGANISM: Felis catus

<400> SEQUENCE: 542
cggaccgcga gatcgtgacc                                              20

<210> SEQ ID NO 543
<211> LENGTH: 20
<212> TYPE: DNA
<213> ORGANISM: Felis catus

<400> SEQUENCE: 543
ctcactccct acacttgctg                                              20

<210> SEQ ID NO 544
<211> LENGTH: 20
<212> TYPE: DNA
<213> ORGANISM: Felis catus

<400> SEQUENCE: 544
ctgaaatttt ctaggttgac                                              20

<210> SEQ ID NO 545
<211> LENGTH: 20
<212> TYPE: DNA
<213> ORGANISM: Felis catus

<400> SEQUENCE: 545
ctgaaccctc ccctacatgc                                              20
```

```
<210> SEQ ID NO 546
<211> LENGTH: 20
<212> TYPE: DNA
<213> ORGANISM: Felis catus

<400> SEQUENCE: 546
ctgagccctc ccctacatgc                                              20

<210> SEQ ID NO 547
<211> LENGTH: 20
<212> TYPE: DNA
<213> ORGANISM: Felis catus

<400> SEQUENCE: 547
ctggactccc cttgctacca                                              20

<210> SEQ ID NO 548
<211> LENGTH: 20
<212> TYPE: DNA
<213> ORGANISM: Felis catus

<400> SEQUENCE: 548
ctgggggagt gctcaggtgg                                              20

<210> SEQ ID NO 549
<211> LENGTH: 20
<212> TYPE: DNA
<213> ORGANISM: Felis catus

<400> SEQUENCE: 549
cttgaccgag tcctgtcacc                                              20

<210> SEQ ID NO 550
<211> LENGTH: 20
<212> TYPE: DNA
<213> ORGANISM: Felis catus

<400> SEQUENCE: 550
ctttcaagct atctgaggtt                                              20

<210> SEQ ID NO 551
<211> LENGTH: 20
<212> TYPE: DNA
<213> ORGANISM: Felis catus

<400> SEQUENCE: 551
gaaaagccag actgcttctg                                              20

<210> SEQ ID NO 552
<211> LENGTH: 20
<212> TYPE: DNA
<213> ORGANISM: Felis catus

<400> SEQUENCE: 552
gaaacccagt gcttagctag                                              20

<210> SEQ ID NO 553
<211> LENGTH: 20
<212> TYPE: DNA
<213> ORGANISM: Felis catus

<400> SEQUENCE: 553
```

-continued

| | |
|---|---|
| gaacccttttt atacctgctg | 20 |

<210> SEQ ID NO 554
<211> LENGTH: 20
<212> TYPE: DNA
<213> ORGANISM: Felis catus

<400> SEQUENCE: 554

| | |
|---|---|
| gaactttttca gtatgtatgg | 20 |

<210> SEQ ID NO 555
<211> LENGTH: 20
<212> TYPE: DNA
<213> ORGANISM: Felis catus

<400> SEQUENCE: 555

| | |
|---|---|
| gaagacctgg cccactcatc | 20 |

<210> SEQ ID NO 556
<211> LENGTH: 20
<212> TYPE: DNA
<213> ORGANISM: Felis catus

<400> SEQUENCE: 556

| | |
|---|---|
| gaagatccag tctcacgtgc | 20 |

<210> SEQ ID NO 557
<211> LENGTH: 20
<212> TYPE: DNA
<213> ORGANISM: Felis catus

<400> SEQUENCE: 557

| | |
|---|---|
| gaatatcatt tccccccaac | 20 |

<210> SEQ ID NO 558
<211> LENGTH: 20
<212> TYPE: DNA
<213> ORGANISM: Felis catus

<400> SEQUENCE: 558

| | |
|---|---|
| gacaaatgag ggttttttttt | 20 |

<210> SEQ ID NO 559
<211> LENGTH: 20
<212> TYPE: DNA
<213> ORGANISM: Felis catus

<400> SEQUENCE: 559

| | |
|---|---|
| gaccctgggg gtcagagtgg | 20 |

<210> SEQ ID NO 560
<211> LENGTH: 20
<212> TYPE: DNA
<213> ORGANISM: Felis catus

<400> SEQUENCE: 560

| | |
|---|---|
| gagccccctt catgatgcag | 20 |

<210> SEQ ID NO 561
<211> LENGTH: 20
<212> TYPE: DNA
<213> ORGANISM: Felis catus

<400> SEQUENCE: 561
gaggcaccgc caggcctctc                                              20

<210> SEQ ID NO 562
<211> LENGTH: 20
<212> TYPE: DNA
<213> ORGANISM: Felis catus

<400> SEQUENCE: 562
gagtgctcag gtggtgggga                                              20

<210> SEQ ID NO 563
<211> LENGTH: 20
<212> TYPE: DNA
<213> ORGANISM: Felis catus

<400> SEQUENCE: 563
gagtggtgga atatacaccc                                              20

<210> SEQ ID NO 564
<211> LENGTH: 20
<212> TYPE: DNA
<213> ORGANISM: Felis catus

<400> SEQUENCE: 564
gatcacagag ataccctcc                                               20

<210> SEQ ID NO 565
<211> LENGTH: 20
<212> TYPE: DNA
<213> ORGANISM: Felis catus

<400> SEQUENCE: 565
gccagactgc ttctgtggcc                                              20

<210> SEQ ID NO 566
<211> LENGTH: 20
<212> TYPE: DNA
<213> ORGANISM: Felis catus

<400> SEQUENCE: 566
gctcatcacc ttctcacctt                                              20

<210> SEQ ID NO 567
<211> LENGTH: 20
<212> TYPE: DNA
<213> ORGANISM: Felis catus

<400> SEQUENCE: 567
gctgcaacag tagggcaggg                                              20

<210> SEQ ID NO 568
<211> LENGTH: 20
<212> TYPE: DNA
<213> ORGANISM: Felis catus

<400> SEQUENCE: 568
gctgggcaaa tttcacaatc                                              20

<210> SEQ ID NO 569
<211> LENGTH: 20
<212> TYPE: DNA
<213> ORGANISM: Felis catus

```
<400> SEQUENCE: 569
ggagggagga gatgtatgtg                                              20

<210> SEQ ID NO 570
<211> LENGTH: 20
<212> TYPE: DNA
<213> ORGANISM: Felis catus

<400> SEQUENCE: 570
ggctgcttct cagaactgcc                                              20

<210> SEQ ID NO 571
<211> LENGTH: 20
<212> TYPE: DNA
<213> ORGANISM: Felis catus

<400> SEQUENCE: 571
gtcaacagat gacgctacct                                              20

<210> SEQ ID NO 572
<211> LENGTH: 20
<212> TYPE: DNA
<213> ORGANISM: Felis catus

<400> SEQUENCE: 572
gtctcacgtg ctggagaggc                                              20

<210> SEQ ID NO 573
<211> LENGTH: 20
<212> TYPE: DNA
<213> ORGANISM: Felis catus

<400> SEQUENCE: 573
gttttttttt gggggggggg                                              20

<210> SEQ ID NO 574
<211> LENGTH: 20
<212> TYPE: DNA
<213> ORGANISM: Felis catus

<400> SEQUENCE: 574
taggtcagac cacggggaag                                              20

<210> SEQ ID NO 575
<211> LENGTH: 20
<212> TYPE: DNA
<213> ORGANISM: Felis catus

<400> SEQUENCE: 575
tatacaccct gggtcacata                                              20

<210> SEQ ID NO 576
<211> LENGTH: 20
<212> TYPE: DNA
<213> ORGANISM: Felis catus

<400> SEQUENCE: 576
tatgtatggt gggggagtgg                                              20

<210> SEQ ID NO 577
<211> LENGTH: 20
<212> TYPE: DNA
<213> ORGANISM: Felis catus
```

```
<400> SEQUENCE: 577
tattcacacc attatctctc                                                  20

<210> SEQ ID NO 578
<211> LENGTH: 20
<212> TYPE: DNA
<213> ORGANISM: Felis catus

<400> SEQUENCE: 578
tcaacatccc tcttcacggc                                                  20

<210> SEQ ID NO 579
<211> LENGTH: 20
<212> TYPE: DNA
<213> ORGANISM: Felis catus

<400> SEQUENCE: 579
tcagaactgc ctgggggctg                                                  20

<210> SEQ ID NO 580
<211> LENGTH: 20
<212> TYPE: DNA
<213> ORGANISM: Felis catus

<400> SEQUENCE: 580
tcagtatttg aggcacagaa                                                  20

<210> SEQ ID NO 581
<211> LENGTH: 20
<212> TYPE: DNA
<213> ORGANISM: Felis catus

<400> SEQUENCE: 581
tctagcagca gttgggggc                                                   20

<210> SEQ ID NO 582
<211> LENGTH: 20
<212> TYPE: DNA
<213> ORGANISM: Felis catus

<400> SEQUENCE: 582
tgaggcacag aatggccctc                                                  20

<210> SEQ ID NO 583
<211> LENGTH: 20
<212> TYPE: DNA
<213> ORGANISM: Felis catus

<400> SEQUENCE: 583
tgagtcttca tctatgacat                                                  20

<210> SEQ ID NO 584
<211> LENGTH: 20
<212> TYPE: DNA
<213> ORGANISM: Felis catus

<400> SEQUENCE: 584
tgggaaggtg ttagaacccc                                                  20

<210> SEQ ID NO 585
<211> LENGTH: 20
<212> TYPE: DNA
```

```
<213> ORGANISM: Felis catus

<400> SEQUENCE: 585
tgtgcgagtc tagcagcagt                                              20

<210> SEQ ID NO 586
<211> LENGTH: 20
<212> TYPE: DNA
<213> ORGANISM: Felis catus

<400> SEQUENCE: 586
tgtgtccttg acctgctcag                                              20

<210> SEQ ID NO 587
<211> LENGTH: 20
<212> TYPE: DNA
<213> ORGANISM: Felis catus

<400> SEQUENCE: 587
ttcccaggga agggccatgg                                              20

<210> SEQ ID NO 588
<211> LENGTH: 20
<212> TYPE: DNA
<213> ORGANISM: Felis catus

<400> SEQUENCE: 588
ttggatgtca gacagccatc                                              20

<210> SEQ ID NO 589
<211> LENGTH: 20
<212> TYPE: DNA
<213> ORGANISM: Felis catus

<400> SEQUENCE: 589 ttgggggggct ggttgtgtct                                             20

<210> SEQ ID NO 590
<211> LENGTH: 20
<212> TYPE: DNA
<213> ORGANISM: Felis catus

<400> SEQUENCE: 590
ttggtatgtg aggcacagaa                                              20

<210> SEQ ID NO 591
<211> LENGTH: 20
<212> TYPE: DNA
<213> ORGANISM: Felis catus

<400> SEQUENCE: 591
tttcaatgtt tatttatttt                                              20

<210> SEQ ID NO 592
<211> LENGTH: 20
<212> TYPE: DNA
<213> ORGANISM: Felis catus

<400> SEQUENCE: 592
tttctggggg agtgctcagg                                              20

<210> SEQ ID NO 593
<211> LENGTH: 20
```

```
<212> TYPE: DNA
<213> ORGANISM: Felis catus

<400> SEQUENCE: 593
tttggggggg gggtggaata                                        20

<210> SEQ ID NO 594
<211> LENGTH: 20
<212> TYPE: DNA
<213> ORGANISM: Felis catus

<400> SEQUENCE: 594
aaaaatcaca ggagggtca                                         20

<210> SEQ ID NO 595
<211> LENGTH: 20
<212> TYPE: DNA
<213> ORGANISM: Felis catus

<400> SEQUENCE: 595
aaaacgtaaa gacagaaaat                                        20

<210> SEQ ID NO 596
<211> LENGTH: 20
<212> TYPE: DNA
<213> ORGANISM: Felis catus

<400> SEQUENCE: 596
aaaagaatca gcagagcagg                                        20

<210> SEQ ID NO 597
<211> LENGTH: 20
<212> TYPE: DNA
<213> ORGANISM: Felis catus

<400> SEQUENCE: 597
aaacatcagg ggggttctgc                                        20

<210> SEQ ID NO 598
<211> LENGTH: 20
<212> TYPE: DNA
<213> ORGANISM: Felis catus

<400> SEQUENCE: 598
aaagagataa aaatcacagg                                        20

<210> SEQ ID NO 599
<211> LENGTH: 20
<212> TYPE: DNA
<213> ORGANISM: Felis catus

<400> SEQUENCE: 599
aaagtgtcca acttcggctc                                        20

<210> SEQ ID NO 600
<211> LENGTH: 20
<212> TYPE: DNA
<213> ORGANISM: Felis catus

<400> SEQUENCE: 600 aacgttatt tttaagagag                                         20

<210> SEQ ID NO 601
```

```
<211> LENGTH: 20
<212> TYPE: DNA
<213> ORGANISM: Felis catus

<400> SEQUENCE: 601
aactgagagt tcctgcagaa                                              20

<210> SEQ ID NO 602
<211> LENGTH: 20
<212> TYPE: DNA
<213> ORGANISM: Felis catus

<400> SEQUENCE: 602
aactttctct ttcctgtgga                                              20

<210> SEQ ID NO 603
<211> LENGTH: 20
<212> TYPE: DNA
<213> ORGANISM: Felis catus

<400> SEQUENCE: 603
aataccactg agacacggag                                              20

<210> SEQ ID NO 604
<211> LENGTH: 20
<212> TYPE: DNA
<213> ORGANISM: Felis catus

<400> SEQUENCE: 604
aatgtttaaa taaataaata                                              20

<210> SEQ ID NO 605
<211> LENGTH: 20
<212> TYPE: DNA
<213> ORGANISM: Felis catus

<400> SEQUENCE: 605
acagaccgat ttctggagag                                              20

<210> SEQ ID NO 606
<211> LENGTH: 20
<212> TYPE: DNA
<213> ORGANISM: Felis catus

<400> SEQUENCE: 606
acaggaggat ggggctcaga                                              20

<210> SEQ ID NO 607
<211> LENGTH: 20
<212> TYPE: DNA
<213> ORGANISM: Felis catus

<400> SEQUENCE: 607
accagaagct tcccaaagcc                                              20

<210> SEQ ID NO 608
<211> LENGTH: 20
<212> TYPE: DNA
<213> ORGANISM: Felis catus

<400> SEQUENCE: 608
acccacgcac ctgtgccagg                                              20
```

```
<210> SEQ ID NO 609
<211> LENGTH: 20
<212> TYPE: DNA
<213> ORGANISM: Felis catus

<400> SEQUENCE: 609
acctcccttt gccatgtccc                                                    20

<210> SEQ ID NO 610
<211> LENGTH: 20
<212> TYPE: DNA
<213> ORGANISM: Felis catus

<400> SEQUENCE: 610
agaagaggag aagattctgg                                                    20

<210> SEQ ID NO 611
<211> LENGTH: 20
<212> TYPE: DNA
<213> ORGANISM: Felis catus

<400> SEQUENCE: 611
agaccctgaa ttgatacaga                                                    20

<210> SEQ ID NO 612
<211> LENGTH: 20
<212> TYPE: DNA
<213> ORGANISM: Felis catus

<400> SEQUENCE: 612
agagcaactc acatatatcc                                                    20

<210> SEQ ID NO 613
<211> LENGTH: 20
<212> TYPE: DNA
<213> ORGANISM: Felis catus

<400> SEQUENCE: 613
agagtgaatt aggtgaggac                                                    20

<210> SEQ ID NO 614
<211> LENGTH: 20
<212> TYPE: DNA
<213> ORGANISM: Felis catus

<400> SEQUENCE: 614
agcctgattg agagtgaatt                                                    20

<210> SEQ ID NO 615
<211> LENGTH: 20
<212> TYPE: DNA
<213> ORGANISM: Felis catus

<400> SEQUENCE: 615
agctccaaag gcctgtgggc                                                    20

<210> SEQ ID NO 616
<211> LENGTH: 20
<212> TYPE: DNA
<213> ORGANISM: Felis catus

<400> SEQUENCE: 616
agtgggggag gggcagagag                                                    20
```

```
<210> SEQ ID NO 617
<211> LENGTH: 20
<212> TYPE: DNA
<213> ORGANISM: Felis catus

<400> SEQUENCE: 617
agttggagct ccacatacca                                              20

<210> SEQ ID NO 618
<211> LENGTH: 20
<212> TYPE: DNA
<213> ORGANISM: Felis catus

<400> SEQUENCE: 618
ataggtactc tcccttaagg                                              20

<210> SEQ ID NO 619
<211> LENGTH: 20
<212> TYPE: DNA
<213> ORGANISM: Felis catus

<400> SEQUENCE: 619
atctgggaga gagtaagacg                                              20

<210> SEQ ID NO 620
<211> LENGTH: 20
<212> TYPE: DNA
<213> ORGANISM: Felis catus

<400> SEQUENCE: 620 atggggctg ggcctgggtg                                               20

<210> SEQ ID NO 621
<211> LENGTH: 20
<212> TYPE: DNA
<213> ORGANISM: Felis catus

<400> SEQUENCE: 621
atgtcccagg atctcctgcc                                              20

<210> SEQ ID NO 622
<211> LENGTH: 20
<212> TYPE: DNA
<213> ORGANISM: Felis catus

<400> SEQUENCE: 622
attctacgac taaaaacatc                                              20

<210> SEQ ID NO 623
<211> LENGTH: 20
<212> TYPE: DNA
<213> ORGANISM: Felis catus

<400> SEQUENCE: 623
caaaggaata gcagccatca                                              20

<210> SEQ ID NO 624
<211> LENGTH: 20
<212> TYPE: DNA
<213> ORGANISM: Felis catus

<400> SEQUENCE: 624
caaggtgcca ggtcaaccaa                                              20
```

<210> SEQ ID NO 625
<211> LENGTH: 20
<212> TYPE: DNA
<213> ORGANISM: Felis catus

<400> SEQUENCE: 625
cacaaaagaa tcagcagagc                                               20

<210> SEQ ID NO 626
<211> LENGTH: 20
<212> TYPE: DNA
<213> ORGANISM: Felis catus

<400> SEQUENCE: 626
cacataggta ctctcccetta                                              20

<210> SEQ ID NO 627
<211> LENGTH: 20
<212> TYPE: DNA
<213> ORGANISM: Felis catus

<400> SEQUENCE: 627
cagacggaac attttctatg                                               20

<210> SEQ ID NO 628
<211> LENGTH: 20
<212> TYPE: DNA
<213> ORGANISM: Felis catus

<400> SEQUENCE: 628
cagactccaa agcaggattc                                               20

<210> SEQ ID NO 629
<211> LENGTH: 20
<212> TYPE: DNA
<213> ORGANISM: Felis catus

<400> SEQUENCE: 629
cagcacttaa cggcaagtag                                               20

<210> SEQ ID NO 630
<211> LENGTH: 20
<212> TYPE: DNA
<213> ORGANISM: Felis catus

<400> SEQUENCE: 630
cagccatcaa ggtgggcaca                                               20

<210> SEQ ID NO 631
<211> LENGTH: 20
<212> TYPE: DNA
<213> ORGANISM: Felis catus

<400> SEQUENCE: 631
cagctttagg tgtaaagaac                                               20

<210> SEQ ID NO 632
<211> LENGTH: 20
<212> TYPE: DNA
<213> ORGANISM: Felis catus

<400> SEQUENCE: 632
caggcatgag ctgtcagcac                                           20

<210> SEQ ID NO 633
<211> LENGTH: 20
<212> TYPE: DNA
<213> ORGANISM: Felis catus

<400> SEQUENCE: 633
cagtagcatt gacttttgtg                                           20

<210> SEQ ID NO 634
<211> LENGTH: 20
<212> TYPE: DNA
<213> ORGANISM: Felis catus

<400> SEQUENCE: 634
ccagtgaggg aggcaagaag                                           20

<210> SEQ ID NO 635
<211> LENGTH: 20
<212> TYPE: DNA
<213> ORGANISM: Felis catus

<400> SEQUENCE: 635
ccccccccca gaagctccaa                                           20

<210> SEQ ID NO 636
<211> LENGTH: 20
<212> TYPE: DNA
<213> ORGANISM: Felis catus

<400> SEQUENCE: 636
ccctgccagg atgacattta                                           20

<210> SEQ ID NO 637
<211> LENGTH: 20
<212> TYPE: DNA
<213> ORGANISM: Felis catus

<400> SEQUENCE: 637
cctaaccgac tgagccaccc                                           20

<210> SEQ ID NO 638
<211> LENGTH: 20
<212> TYPE: DNA
<213> ORGANISM: Felis catus

<400> SEQUENCE: 638
cgtaaggtaa ttcgcacaca                                           20

<210> SEQ ID NO 639
<211> LENGTH: 20
<212> TYPE: DNA
<213> ORGANISM: Felis catus

<400> SEQUENCE: 639
cgtagctagg agctgcctcg                                           20

<210> SEQ ID NO 640
<211> LENGTH: 20
<212> TYPE: DNA
<213> ORGANISM: Felis catus

<400> SEQUENCE: 640

```
ctatttttcca actgtgcgta                                        20

<210> SEQ ID NO 641
<211> LENGTH: 20
<212> TYPE: DNA
<213> ORGANISM: Felis catus

<400> SEQUENCE: 641
ctcaggacgc ttgggcatgt                                         20

<210> SEQ ID NO 642
<211> LENGTH: 20
<212> TYPE: DNA
<213> ORGANISM: Felis catus

<400> SEQUENCE: 642
ctccctacta ggggagtctc                                         20

<210> SEQ ID NO 643
<211> LENGTH: 20
<212> TYPE: DNA
<213> ORGANISM: Felis catus

<400> SEQUENCE: 643
ctgctgcacg cgcaacgtga                                         20

<210> SEQ ID NO 644
<211> LENGTH: 20
<212> TYPE: DNA
<213> ORGANISM: Felis catus

<400> SEQUENCE: 644
ctgcttccct ctcaccctta                                         20

<210> SEQ ID NO 645
<211> LENGTH: 20
<212> TYPE: DNA
<213> ORGANISM: Felis catus

<400> SEQUENCE: 645
ctgggcctgg gtgaggggca                                         20

<210> SEQ ID NO 646
<211> LENGTH: 20
<212> TYPE: DNA
<213> ORGANISM: Felis catus

<400> SEQUENCE: 646
ctgggtgtgc acatggcgtg                                         20

<210> SEQ ID NO 647
<211> LENGTH: 20
<212> TYPE: DNA
<213> ORGANISM: Felis catus

<400> SEQUENCE: 647
cttcctggga agagagtctg                                         20

<210> SEQ ID NO 648
<211> LENGTH: 20
<212> TYPE: DNA
<213> ORGANISM: Felis catus
```

```
<400> SEQUENCE: 648
ctttgccaaa gaccaactgg                                          20

<210> SEQ ID NO 649
<211> LENGTH: 20
<212> TYPE: DNA
<213> ORGANISM: Felis catus

<400> SEQUENCE: 649
gaaggttggg gaggcgggga                                          20

<210> SEQ ID NO 650
<211> LENGTH: 20
<212> TYPE: DNA
<213> ORGANISM: Felis catus

<400> SEQUENCE: 650
gaagtgagac tctgaaccaa                                          20

<210> SEQ ID NO 651
<211> LENGTH: 20
<212> TYPE: DNA
<213> ORGANISM: Felis catus

<400> SEQUENCE: 651
gacaaagaga taaaaatcac                                          20

<210> SEQ ID NO 652
<211> LENGTH: 20
<212> TYPE: DNA
<213> ORGANISM: Felis catus

<400> SEQUENCE: 652
gacaaggctc ctacatgtgc                                          20

<210> SEQ ID NO 653
<211> LENGTH: 20
<212> TYPE: DNA
<213> ORGANISM: Felis catus

<400> SEQUENCE: 653
gacacgtgtg gtagaagaac                                          20

<210> SEQ ID NO 654
<211> LENGTH: 20
<212> TYPE: DNA
<213> ORGANISM: Felis catus

<400> SEQUENCE: 654
gagagaatag cccaaggaag                                          20

<210> SEQ ID NO 655
<211> LENGTH: 20
<212> TYPE: DNA
<213> ORGANISM: Felis catus

<400> SEQUENCE: 655
gagatcacca tgggaggtaa                                          20

<210> SEQ ID NO 656
<211> LENGTH: 20
<212> TYPE: DNA
<213> ORGANISM: Felis catus
```

```
<400> SEQUENCE: 656
gagcagggca aggatcagga                                               20

<210> SEQ ID NO 657
<211> LENGTH: 20
<212> TYPE: DNA
<213> ORGANISM: Felis catus

<400> SEQUENCE: 657
gagtgagata gagcagggca                                               20

<210> SEQ ID NO 658
<211> LENGTH: 20
<212> TYPE: DNA
<213> ORGANISM: Felis catus

<400> SEQUENCE: 658
gatagagcag ggcaaggatc                                               20

<210> SEQ ID NO 659
<211> LENGTH: 20
<212> TYPE: DNA
<213> ORGANISM: Felis catus

<400> SEQUENCE: 659
gatgacattt aagggactag                                               20

<210> SEQ ID NO 660
<211> LENGTH: 20
<212> TYPE: DNA
<213> ORGANISM: Felis catus

<400> SEQUENCE: 660
gattgagagt gaattaggtg                                               20

<210> SEQ ID NO 661
<211> LENGTH: 20
<212> TYPE: DNA
<213> ORGANISM: Felis catus

<400> SEQUENCE: 661
gatttgtgat aaacccactc                                               20

<210> SEQ ID NO 662
<211> LENGTH: 20
<212> TYPE: DNA
<213> ORGANISM: Felis catus

<400> SEQUENCE: 662
gcagagacct gcccactccc                                               20

<210> SEQ ID NO 663
<211> LENGTH: 20
<212> TYPE: DNA
<213> ORGANISM: Felis catus

<400> SEQUENCE: 663
gcagatgaga gaatagccca                                               20

<210> SEQ ID NO 664
<211> LENGTH: 20
<212> TYPE: DNA
```

<213> ORGANISM: Felis catus

<400> SEQUENCE: 664
gcagcgctat ccattccccc                                                    20

<210> SEQ ID NO 665
<211> LENGTH: 20
<212> TYPE: DNA
<213> ORGANISM: Felis catus

<400> SEQUENCE: 665
gcattctaga taatacacat                                                    20

<210> SEQ ID NO 666
<211> LENGTH: 20
<212> TYPE: DNA
<213> ORGANISM: Felis catus

<400> SEQUENCE: 666
gccacccagg cgccctgcc                                                     20

<210> SEQ ID NO 667
<211> LENGTH: 20
<212> TYPE: DNA
<213> ORGANISM: Felis catus

<400> SEQUENCE: 667
gcgcaacgtg aaggttgggg                                                    20

<210> SEQ ID NO 668
<211> LENGTH: 20
<212> TYPE: DNA
<213> ORGANISM: Felis catus

<400> SEQUENCE: 668
gctacaaatc actccctact                                                    20

<210> SEQ ID NO 669
<211> LENGTH: 20
<212> TYPE: DNA
<213> ORGANISM: Felis catus

<400> SEQUENCE: 669
gctccacata ccaaggtgcc                                                    20

<210> SEQ ID NO 670
<211> LENGTH: 20
<212> TYPE: DNA
<213> ORGANISM: Felis catus

<400> SEQUENCE: 670
gctgctagaa tgctctgctc                                                    20

<210> SEQ ID NO 671
<211> LENGTH: 20
<212> TYPE: DNA
<213> ORGANISM: Felis catus

<400> SEQUENCE: 671 ggaagcccctt cctactcttg                                                   20

<210> SEQ ID NO 672
<211> LENGTH: 20

```
<212> TYPE: DNA
<213> ORGANISM: Felis catus

<400> SEQUENCE: 672
ggacagatct acaccactac                                           20

<210> SEQ ID NO 673
<211> LENGTH: 20
<212> TYPE: DNA
<213> ORGANISM: Felis catus

<400> SEQUENCE: 673
ggagacacag actccaaagc                                           20

<210> SEQ ID NO 674
<211> LENGTH: 20
<212> TYPE: DNA
<213> ORGANISM: Felis catus

<400> SEQUENCE: 674
ggagctgcct cgagggcctc                                           20

<210> SEQ ID NO 675
<211> LENGTH: 20
<212> TYPE: DNA
<213> ORGANISM: Felis catus

<400> SEQUENCE: 675
ggctggtaac gctctaaatt                                           20

<210> SEQ ID NO 676
<211> LENGTH: 20
<212> TYPE: DNA
<213> ORGANISM: Felis catus

<400> SEQUENCE: 676
gggagtctga acaaccagtg                                           20

<210> SEQ ID NO 677
<211> LENGTH: 20
<212> TYPE: DNA
<213> ORGANISM: Felis catus

<400> SEQUENCE: 677
gggccgcgat cagtcagacc                                           20

<210> SEQ ID NO 678
<211> LENGTH: 20
<212> TYPE: DNA
<213> ORGANISM: Felis catus

<400> SEQUENCE: 678
gggtgcagct gcacgtagct                                           20

<210> SEQ ID NO 679
<211> LENGTH: 20
<212> TYPE: DNA
<213> ORGANISM: Felis catus

<400> SEQUENCE: 679
ggtgtaaaga acaggacagg                                           20

<210> SEQ ID NO 680
```

```
<211> LENGTH: 20
<212> TYPE: DNA
<213> ORGANISM: Felis catus

<400> SEQUENCE: 680
ggtgtctgga ttccagcttt                                              20

<210> SEQ ID NO 681
<211> LENGTH: 20
<212> TYPE: DNA
<213> ORGANISM: Felis catus

<400> SEQUENCE: 681
gtaaacttaa tcccaagagg                                              20

<210> SEQ ID NO 682
<211> LENGTH: 20
<212> TYPE: DNA
<213> ORGANISM: Felis catus

<400> SEQUENCE: 682
gtaaaggagt gagatagagc                                              20

<210> SEQ ID NO 683
<211> LENGTH: 20
<212> TYPE: DNA
<213> ORGANISM: Felis catus

<400> SEQUENCE: 683
gtcacccacg cacctgtgcc                                              20

<210> SEQ ID NO 684
<211> LENGTH: 20
<212> TYPE: DNA
<213> ORGANISM: Felis catus

<400> SEQUENCE: 684
gtctgaacaa ccagtgaggg                                              20

<210> SEQ ID NO 685
<211> LENGTH: 20
<212> TYPE: DNA
<213> ORGANISM: Felis catus

<400> SEQUENCE: 685
gtgggtctga gacccgtgtc                                              20

<210> SEQ ID NO 686
<211> LENGTH: 20
<212> TYPE: DNA
<213> ORGANISM: Felis catus

<400> SEQUENCE: 686
taaactcaac cttctaatct                                              20

<210> SEQ ID NO 687
<211> LENGTH: 20
<212> TYPE: DNA
<213> ORGANISM: Felis catus

<400> SEQUENCE: 687
tagaatgctc tgctcaggac                                              20
```

-continued

```
<210> SEQ ID NO 688
<211> LENGTH: 20
<212> TYPE: DNA
<213> ORGANISM: Felis catus

<400> SEQUENCE: 688
tagtccatga aaattattga                                                    20

<210> SEQ ID NO 689
<211> LENGTH: 20
<212> TYPE: DNA
<213> ORGANISM: Felis catus

<400> SEQUENCE: 689
tcacctgaga ctcatctgtc                                                    20

<210> SEQ ID NO 690
<211> LENGTH: 20
<212> TYPE: DNA
<213> ORGANISM: Felis catus

<400> SEQUENCE: 690
tcagtaaact taatcccaag                                                    20

<210> SEQ ID NO 691
<211> LENGTH: 20
<212> TYPE: DNA
<213> ORGANISM: Felis catus

<400> SEQUENCE: 691
tcttgactcc aagtagctcc                                                    20

<210> SEQ ID NO 692
<211> LENGTH: 20
<212> TYPE: DNA
<213> ORGANISM: Felis catus

<400> SEQUENCE: 692
tgaggacaaa gctcttggag                                                    20

<210> SEQ ID NO 693
<211> LENGTH: 20
<212> TYPE: DNA
<213> ORGANISM: Felis catus

<400> SEQUENCE: 693
tgagtcaccc ttaaattgcc                                                    20

<210> SEQ ID NO 694
<211> LENGTH: 20
<212> TYPE: DNA
<213> ORGANISM: Felis catus

<400> SEQUENCE: 694
tgcacacgtg caagtggggg                                                    20

<210> SEQ ID NO 695
<211> LENGTH: 20
<212> TYPE: DNA
<213> ORGANISM: Felis catus

<400> SEQUENCE: 695
tgggaagaga gtctgagggc                                                    20
```

```
<210> SEQ ID NO 696
<211> LENGTH: 20
<212> TYPE: DNA
<213> ORGANISM: Felis catus

<400> SEQUENCE: 696
tgggagagag taagacgagg                                            20

<210> SEQ ID NO 697
<211> LENGTH: 20
<212> TYPE: DNA
<213> ORGANISM: Felis catus

<400> SEQUENCE: 697
tgggcatgta ggcctcctca                                            20

<210> SEQ ID NO 698
<211> LENGTH: 20
<212> TYPE: DNA
<213> ORGANISM: Felis catus

<400> SEQUENCE: 698
tgtgctgtag agcggagcaa                                            20

<210> SEQ ID NO 699
<211> LENGTH: 20
<212> TYPE: DNA
<213> ORGANISM: Felis catus

<400> SEQUENCE: 699
tgtttggaga tcaccatggg                                            20

<210> SEQ ID NO 700
<211> LENGTH: 20
<212> TYPE: DNA
<213> ORGANISM: Felis catus

<400> SEQUENCE: 700
ttaggtgtaa agaacaggac                                            20

<210> SEQ ID NO 701
<211> LENGTH: 20
<212> TYPE: DNA
<213> ORGANISM: Felis catus

<400> SEQUENCE: 701
ttcctccacc agaactgaca                                            20

<210> SEQ ID NO 702
<211> LENGTH: 20
<212> TYPE: DNA
<213> ORGANISM: Felis catus

<400> SEQUENCE: 702
ttggggaggc ggggaaggaa                                            20

<210> SEQ ID NO 703
<211> LENGTH: 20
<212> TYPE: DNA
<213> ORGANISM: Felis catus

<400> SEQUENCE: 703
agacccctga ccggtgcctc                                            20
```

-continued

```
<210> SEQ ID NO 704
<211> LENGTH: 20
<212> TYPE: DNA
<213> ORGANISM: Felis catus

<400> SEQUENCE: 704
aggcaaatac cactgagaca                                                  20

<210> SEQ ID NO 705
<211> LENGTH: 20
<212> TYPE: DNA
<213> ORGANISM: Felis catus

<400> SEQUENCE: 705
caacgtgaag gttgggagg                                                   20

<210> SEQ ID NO 706
<211> LENGTH: 20
<212> TYPE: DNA
<213> ORGANISM: Felis catus

<400> SEQUENCE: 706
cagccggaga gacccctgac                                                  20

<210> SEQ ID NO 707
<211> LENGTH: 20
<212> TYPE: DNA
<213> ORGANISM: Felis catus

<400> SEQUENCE: 707
cagtcagacc aggatggaga                                                  20

<210> SEQ ID NO 708
<211> LENGTH: 20
<212> TYPE: DNA
<213> ORGANISM: Felis catus

<400> SEQUENCE: 708
ctgcttacat cccagacaga                                                  20

<210> SEQ ID NO 709
<211> LENGTH: 20
<212> TYPE: DNA
<213> ORGANISM: Felis catus

<400> SEQUENCE: 709
gaacacagac acggggcacc                                                  20

<210> SEQ ID NO 710
<211> LENGTH: 20
<212> TYPE: DNA
<213> ORGANISM: Felis catus

<400> SEQUENCE: 710
gcaccccagc ctgcctgttt                                                  20

<210> SEQ ID NO 711
<211> LENGTH: 20
<212> TYPE: DNA
<213> ORGANISM: Felis catus

<400> SEQUENCE: 711
```

```
gggcgcctgg gtggctcagt                                               20

<210> SEQ ID NO 712
<211> LENGTH: 20
<212> TYPE: DNA
<213> ORGANISM: Felis catus

<400> SEQUENCE: 712
gggctcagaa ggggcatcag                                               20

<210> SEQ ID NO 713
<211> LENGTH: 20
<212> TYPE: DNA
<213> ORGANISM: Felis catus

<400> SEQUENCE: 713
gtattctatg tgctgtagag                                               20

<210> SEQ ID NO 714
<211> LENGTH: 20
<212> TYPE: DNA
<213> ORGANISM: Felis catus

<400> SEQUENCE: 714
gttcagcttg agatcttcta                                               20

<210> SEQ ID NO 715
<211> LENGTH: 20
<212> TYPE: DNA
<213> ORGANISM: Felis catus

<400> SEQUENCE: 715
tcccgcacag aacacagaca                                               20

<210> SEQ ID NO 716
<211> LENGTH: 20
<212> TYPE: DNA
<213> ORGANISM: Felis catus

<400> SEQUENCE: 716
tcggttaaag tgtccaactt                                               20

<210> SEQ ID NO 717
<211> LENGTH: 20
<212> TYPE: DNA
<213> ORGANISM: Felis catus

<400> SEQUENCE: 717
tctcagcaga agagagcagc                                               20

<210> SEQ ID NO 718
<211> LENGTH: 20
<212> TYPE: DNA
<213> ORGANISM: Felis catus

<400> SEQUENCE: 718
tttacagaat cagcacttaa                                               20

<210> SEQ ID NO 719
<211> LENGTH: 20
<212> TYPE: DNA
<213> ORGANISM: Felis catus

<400> SEQUENCE: 719
```
aaaaagacgt cataaaaaat                                               20

<210> SEQ ID NO 720
<211> LENGTH: 20
<212> TYPE: DNA
<213> ORGANISM: Felis catus

<400> SEQUENCE: 720
aaaagacgtc ataaaaaatg                                               20

<210> SEQ ID NO 721
<211> LENGTH: 20
<212> TYPE: DNA
<213> ORGANISM: Felis catus

<400> SEQUENCE: 721
aaacattagt gaatagttgt                                               20

<210> SEQ ID NO 722
<211> LENGTH: 20
<212> TYPE: DNA
<213> ORGANISM: Felis catus

<400> SEQUENCE: 722
aaagaacagg acaggaggat                                               20

<210> SEQ ID NO 723
<211> LENGTH: 20
<212> TYPE: DNA
<213> ORGANISM: Felis catus

<400> SEQUENCE: 723
aaatacactg accagccctg                                               20

<210> SEQ ID NO 724
<211> LENGTH: 20
<212> TYPE: DNA
<213> ORGANISM: Felis catus

<400> SEQUENCE: 724
aacacagaca cggggcaccc                                               20

<210> SEQ ID NO 725
<211> LENGTH: 20
<212> TYPE: DNA
<213> ORGANISM: Felis catus

<400> SEQUENCE: 725
aacattagtg aatagttgtg                                               20

<210> SEQ ID NO 726
<211> LENGTH: 20
<212> TYPE: DNA
<213> ORGANISM: Felis catus

<400> SEQUENCE: 726
aacgtgaagg ttggggaggc                                               20

<210> SEQ ID NO 727
<211> LENGTH: 20
<212> TYPE: DNA
<213> ORGANISM: Felis catus

```
<400> SEQUENCE: 727
aagaacagga caggaggatg                                              20

<210> SEQ ID NO 728
<211> LENGTH: 20
<212> TYPE: DNA
<213> ORGANISM: Felis catus

<400> SEQUENCE: 728
aagagataaa aatcacagga                                              20

<210> SEQ ID NO 729
<211> LENGTH: 20
<212> TYPE: DNA
<213> ORGANISM: Felis catus

<400> SEQUENCE: 729
aagattctgg agggcgcgat                                              20

<210> SEQ ID NO 730
<211> LENGTH: 20
<212> TYPE: DNA
<213> ORGANISM: Felis catus

<400> SEQUENCE: 730
aagccaggga gtcccttcct                                              20

<210> SEQ ID NO 731
<211> LENGTH: 20
<212> TYPE: DNA
<213> ORGANISM: Felis catus

<400> SEQUENCE: 731
aagtcctgga gataagtatg                                              20

<210> SEQ ID NO 732
<211> LENGTH: 20
<212> TYPE: DNA
<213> ORGANISM: Felis catus

<400> SEQUENCE: 732
aatgggtgga caccatcctt                                              20

<210> SEQ ID NO 733
<211> LENGTH: 20
<212> TYPE: DNA
<213> ORGANISM: Felis catus

<400> SEQUENCE: 733
acacagacac ggggcacccg                                              20

<210> SEQ ID NO 734
<211> LENGTH: 20
<212> TYPE: DNA
<213> ORGANISM: Felis catus

<400> SEQUENCE: 734
acccttgggc tgttaagagt                                              20

<210> SEQ ID NO 735
<211> LENGTH: 20
<212> TYPE: DNA
<213> ORGANISM: Felis catus
```

```
<400> SEQUENCE: 735
acctgtttgg agatcaccat                                              20

<210> SEQ ID NO 736
<211> LENGTH: 20
<212> TYPE: DNA
<213> ORGANISM: Felis catus

<400> SEQUENCE: 736
acgtgaaggt tggggaggcg                                              20

<210> SEQ ID NO 737
<211> LENGTH: 20
<212> TYPE: DNA
<213> ORGANISM: Felis catus

<400> SEQUENCE: 737
acgtttattt ttaagagaga                                              20

<210> SEQ ID NO 738
<211> LENGTH: 20
<212> TYPE: DNA
<213> ORGANISM: Felis catus

<400> SEQUENCE: 738
agagataaaa atcacaggag                                              20

<210> SEQ ID NO 739
<211> LENGTH: 20
<212> TYPE: DNA
<213> ORGANISM: Felis catus

<400> SEQUENCE: 739
agattctgga gggcgcgatg                                              20

<210> SEQ ID NO 740
<211> LENGTH: 20
<212> TYPE: DNA
<213> ORGANISM: Felis catus

<400> SEQUENCE: 740
agccatcaag gtgggcacaa                                              20

<210> SEQ ID NO 741
<211> LENGTH: 20
<212> TYPE: DNA
<213> ORGANISM: Felis catus

<400> SEQUENCE: 741
aggaggatgg ggctcagaag                                              20

<210> SEQ ID NO 742
<211> LENGTH: 20
<212> TYPE: DNA
<213> ORGANISM: Felis catus

<400> SEQUENCE: 742
aggcatgagc tgtcagcaca                                              20

<210> SEQ ID NO 743
<211> LENGTH: 20
<212> TYPE: DNA
```

<213> ORGANISM: Felis catus

<400> SEQUENCE: 743
aggggagtct caggacgctt                                         20

<210> SEQ ID NO 744
<211> LENGTH: 20
<212> TYPE: DNA
<213> ORGANISM: Felis catus

<400> SEQUENCE: 744
agtagcattg acttttgtga                                         20

<210> SEQ ID NO 745
<211> LENGTH: 20
<212> TYPE: DNA
<213> ORGANISM: Felis catus

<400> SEQUENCE: 745
atattcgttg atggctatct                                         20

<210> SEQ ID NO 746
<211> LENGTH: 20
<212> TYPE: DNA
<213> ORGANISM: Felis catus

<400> SEQUENCE: 746
caaagaagca gaaaatggtg                                         20

<210> SEQ ID NO 747
<211> LENGTH: 20
<212> TYPE: DNA
<213> ORGANISM: Felis catus

<400> SEQUENCE: 747
cacacgtgca agtgggggag                                         20

<210> SEQ ID NO 748
<211> LENGTH: 20
<212> TYPE: DNA
<213> ORGANISM: Felis catus

<400> SEQUENCE: 748
cacagacacg gggcacccgg                                         20

<210> SEQ ID NO 749
<211> LENGTH: 20
<212> TYPE: DNA
<213> ORGANISM: Felis catus

<400> SEQUENCE: 749
cacgcgcaac gtgaaggttg                                         20

<210> SEQ ID NO 750
<211> LENGTH: 20
<212> TYPE: DNA
<213> ORGANISM: Felis catus

<400> SEQUENCE: 750
cagaaaatgg tggggcgcct                                         20

<210> SEQ ID NO 751
<211> LENGTH: 20

```
<212> TYPE: DNA
<213> ORGANISM: Felis catus

<400> SEQUENCE: 751
cagaagctcc aaaggcctgt                                              20

<210> SEQ ID NO 752
<211> LENGTH: 20
<212> TYPE: DNA
<213> ORGANISM: Felis catus

<400> SEQUENCE: 752
cagaccgatt tctggagaga                                              20

<210> SEQ ID NO 753
<211> LENGTH: 20
<212> TYPE: DNA
<213> ORGANISM: Felis catus

<400> SEQUENCE: 753
caggaggatg gggctcagaa                                              20

<210> SEQ ID NO 754
<211> LENGTH: 20
<212> TYPE: DNA
<213> ORGANISM: Felis catus

<400> SEQUENCE: 754
catcttgacg cccagctctt                                              20

<210> SEQ ID NO 755
<211> LENGTH: 20
<212> TYPE: DNA
<213> ORGANISM: Felis catus

<400> SEQUENCE: 755
ccaaagaagc agaaaatggt                                              20

<210> SEQ ID NO 756
<211> LENGTH: 20
<212> TYPE: DNA
<213> ORGANISM: Felis catus

<400> SEQUENCE: 756
ccagaagctt cccaaagcca                                              20

<210> SEQ ID NO 757
<211> LENGTH: 20
<212> TYPE: DNA
<213> ORGANISM: Felis catus

<400> SEQUENCE: 757
cccacgcacc tgtgccagga                                              20

<210> SEQ ID NO 758
<211> LENGTH: 20
<212> TYPE: DNA
<213> ORGANISM: Felis catus

<400> SEQUENCE: 758
cccgcacaga acacagacac                                              20

<210> SEQ ID NO 759
```

```
<211> LENGTH: 20
<212> TYPE: DNA
<213> ORGANISM: Felis catus

<400> SEQUENCE: 759
ccgcacagaa cacagacacg                                               20

<210> SEQ ID NO 760
<211> LENGTH: 20
<212> TYPE: DNA
<213> ORGANISM: Felis catus

<400> SEQUENCE: 760
cctgccagga tgacatttaa                                               20

<210> SEQ ID NO 761
<211> LENGTH: 20
<212> TYPE: DNA
<213> ORGANISM: Felis catus

<400> SEQUENCE: 761
ccttaaggaa gtaaatgcct                                               20

<210> SEQ ID NO 762
<211> LENGTH: 20
<212> TYPE: DNA
<213> ORGANISM: Felis catus

<400> SEQUENCE: 762
cgcttgcaca cgtgcaagtg                                               20

<210> SEQ ID NO 763
<211> LENGTH: 20
<212> TYPE: DNA
<213> ORGANISM: Felis catus

<400> SEQUENCE: 763
ctacaaatca ctccctacta                                               20

<210> SEQ ID NO 764
<211> LENGTH: 20
<212> TYPE: DNA
<213> ORGANISM: Felis catus

<400> SEQUENCE: 764
ctacgactaa aaacatcagg                                               20

<210> SEQ ID NO 765
<211> LENGTH: 20
<212> TYPE: DNA
<213> ORGANISM: Felis catus

<400> SEQUENCE: 765
cttctgtggt gatgaatcct                                               20

<210> SEQ ID NO 766
<211> LENGTH: 20
<212> TYPE: DNA
<213> ORGANISM: Felis catus

<400> SEQUENCE: 766
gaaatacact gaccagccct                                               20
```

```
<210> SEQ ID NO 767
<211> LENGTH: 20
<212> TYPE: DNA
<213> ORGANISM: Felis catus

<400> SEQUENCE: 767
gaagaggaga agattctgga                                               20

<210> SEQ ID NO 768
<211> LENGTH: 20
<212> TYPE: DNA
<213> ORGANISM: Felis catus

<400> SEQUENCE: 768
gacccctgac cggtgcctcc                                               20

<210> SEQ ID NO 769
<211> LENGTH: 20
<212> TYPE: DNA
<213> ORGANISM: Felis catus

<400> SEQUENCE: 769
gagcaactca catatatcca                                               20

<210> SEQ ID NO 770
<211> LENGTH: 20
<212> TYPE: DNA
<213> ORGANISM: Felis catus

<400> SEQUENCE: 770
gagtcaccct taaattgcca                                               20

<210> SEQ ID NO 771
<211> LENGTH: 20
<212> TYPE: DNA
<213> ORGANISM: Felis catus

<400> SEQUENCE: 771
gattctggag ggcgcgatgg                                               20

<210> SEQ ID NO 772
<211> LENGTH: 20
<212> TYPE: DNA
<213> ORGANISM: Felis catus

<400> SEQUENCE: 772
gcacacgtgc aagtggggga                                               20

<210> SEQ ID NO 773
<211> LENGTH: 20
<212> TYPE: DNA
<213> ORGANISM: Felis catus

<400> SEQUENCE: 773
gcacgcgcaa cgtgaaggtt                                               20

<210> SEQ ID NO 774
<211> LENGTH: 20
<212> TYPE: DNA
<213> ORGANISM: Felis catus

<400> SEQUENCE: 774
gccatcaagg tgggcacaag                                               20
```

```
<210> SEQ ID NO 775
<211> LENGTH: 20
<212> TYPE: DNA
<213> ORGANISM: Felis catus

<400> SEQUENCE: 775
gcgcgatggg ggctgggcct                                                20

<210> SEQ ID NO 776
<211> LENGTH: 20
<212> TYPE: DNA
<213> ORGANISM: Felis catus

<400> SEQUENCE: 776
gcgcttgcac acgtgcaagt                                                20

<210> SEQ ID NO 777
<211> LENGTH: 20
<212> TYPE: DNA
<213> ORGANISM: Felis catus

<400> SEQUENCE: 777
gctccaaagg cctgtgggca                                                20

<210> SEQ ID NO 778
<211> LENGTH: 20
<212> TYPE: DNA
<213> ORGANISM: Felis catus

<400> SEQUENCE: 778
gcttgcacac gtgcaagtgg                                                20

<210> SEQ ID NO 779
<211> LENGTH: 20
<212> TYPE: DNA
<213> ORGANISM: Felis catus

<400> SEQUENCE: 779
ggaatagcag ccatcaaggt                                                20

<210> SEQ ID NO 780
<211> LENGTH: 20
<212> TYPE: DNA
<213> ORGANISM: Felis catus

<400> SEQUENCE: 780
ggagtctgaa caaccagtga                                                20

<210> SEQ ID NO 781
<211> LENGTH: 20
<212> TYPE: DNA
<213> ORGANISM: Felis catus

<400> SEQUENCE: 781
ggcagggacc tggcacatgt                                                20

<210> SEQ ID NO 782
<211> LENGTH: 20
<212> TYPE: DNA
<213> ORGANISM: Felis catus

<400> SEQUENCE: 782
gggagagagt aagacgagga                                                20
```

<210> SEQ ID NO 783
<211> LENGTH: 20
<212> TYPE: DNA
<213> ORGANISM: Felis catus

<400> SEQUENCE: 783
gggcatgtag gcctcctcaa　　　　　　　　　　　　　　　　　　　　　　　　20

<210> SEQ ID NO 784
<211> LENGTH: 20
<212> TYPE: DNA
<213> ORGANISM: Felis catus

<400> SEQUENCE: 784
ggggcaaggt agctgagtct　　　　　　　　　　　　　　　　　　　　　　　　20

<210> SEQ ID NO 785
<211> LENGTH: 20
<212> TYPE: DNA
<213> ORGANISM: Felis catus

<400> SEQUENCE: 785
gggggctggg cctgggtgag　　　　　　　　　　　　　　　　　　　　　　　　20

<210> SEQ ID NO 786
<211> LENGTH: 20
<212> TYPE: DNA
<213> ORGANISM: Felis catus

<400> SEQUENCE: 786
gggtggctcc ctcaaccctt　　　　　　　　　　　　　　　　　　　　　　　　20

<210> SEQ ID NO 787
<211> LENGTH: 20
<212> TYPE: DNA
<213> ORGANISM: Felis catus

<400> SEQUENCE: 787
gtaaggtaat tcgcacacaa　　　　　　　　　　　　　　　　　　　　　　　　20

<210> SEQ ID NO 788
<211> LENGTH: 20
<212> TYPE: DNA
<213> ORGANISM: Felis catus

<400> SEQUENCE: 788
gtagctagga gctgcctcga　　　　　　　　　　　　　　　　　　　　　　　　20

<210> SEQ ID NO 789
<211> LENGTH: 20
<212> TYPE: DNA
<213> ORGANISM: Felis catus

<400> SEQUENCE: 789
gtcatgatct cacagtttgt　　　　　　　　　　　　　　　　　　　　　　　　20

<210> SEQ ID NO 790
<211> LENGTH: 20
<212> TYPE: DNA
<213> ORGANISM: Felis catus

<400> SEQUENCE: 790

```
gtggatcaag ccctgagaat                                               20

<210> SEQ ID NO 791
<211> LENGTH: 20
<212> TYPE: DNA
<213> ORGANISM: Felis catus

<400> SEQUENCE: 791
gtgggggagg ggcagagaga                                               20

<210> SEQ ID NO 792
<211> LENGTH: 20
<212> TYPE: DNA
<213> ORGANISM: Felis catus

<400> SEQUENCE: 792
gtgtggtaga agaacaggct                                               20

<210> SEQ ID NO 793
<211> LENGTH: 20
<212> TYPE: DNA
<213> ORGANISM: Felis catus

<400> SEQUENCE: 793
taaaggagtg agatagagca                                               20

<210> SEQ ID NO 794
<211> LENGTH: 20
<212> TYPE: DNA
<213> ORGANISM: Felis catus

<400> SEQUENCE: 794
taagtcctgg agataagtat                                               20

<210> SEQ ID NO 795
<211> LENGTH: 20
<212> TYPE: DNA
<213> ORGANISM: Felis catus

<400> SEQUENCE: 795
tacaaatcac tccctactag                                               20

<210> SEQ ID NO 796
<211> LENGTH: 20
<212> TYPE: DNA
<213> ORGANISM: Felis catus

<400> SEQUENCE: 796
tacgactaaa aacatcaggg                                               20

<210> SEQ ID NO 797
<211> LENGTH: 20
<212> TYPE: DNA
<213> ORGANISM: Felis catus

<400> SEQUENCE: 797
tctacgacta aaaacatcag                                               20

<210> SEQ ID NO 798
<211> LENGTH: 20
<212> TYPE: DNA
<213> ORGANISM: Felis catus

<400> SEQUENCE: 798
```
tgaacaatcc catgtgccct                                              20

<210> SEQ ID NO 799
<211> LENGTH: 20
<212> TYPE: DNA
<213> ORGANISM: Felis catus

<400> SEQUENCE: 799
tggagggcgc gatgggggct                                              20

<210> SEQ ID NO 800
<211> LENGTH: 20
<212> TYPE: DNA
<213> ORGANISM: Felis catus

<400> SEQUENCE: 800
tgggggctgg gcctgggtga                                              20

<210> SEQ ID NO 801
<211> LENGTH: 20
<212> TYPE: DNA
<213> ORGANISM: Felis catus

<400> SEQUENCE: 801
ttcctgggaa gagagtctga                                              20

<210> SEQ ID NO 802
<211> LENGTH: 20
<212> TYPE: DNA
<213> ORGANISM: Felis catus

<400> SEQUENCE: 802
ttctacgact aaaaacatca                                              20

<210> SEQ ID NO 803
<211> LENGTH: 20
<212> TYPE: DNA
<213> ORGANISM: Felis catus

<400> SEQUENCE: 803
ttctgtggtg atgaatcctg                                              20

<210> SEQ ID NO 804
<211> LENGTH: 20
<212> TYPE: DNA
<213> ORGANISM: Felis catus

<400> SEQUENCE: 804
aaaaaagacg tcataaaaaa                                              20

<210> SEQ ID NO 805
<211> LENGTH: 20
<212> TYPE: DNA
<213> ORGANISM: Felis catus

<400> SEQUENCE: 805
aaaatggtgg ggcgcctggg                                              20

<210> SEQ ID NO 806
<211> LENGTH: 20
<212> TYPE: DNA
<213> ORGANISM: Felis catus

<400> SEQUENCE: 806
aaagccaggg agtcccttcc                                           20

<210> SEQ ID NO 807
<211> LENGTH: 20
<212> TYPE: DNA
<213> ORGANISM: Felis catus

<400> SEQUENCE: 807
aaccctgggg ctgttaagag                                           20

<210> SEQ ID NO 808
<211> LENGTH: 20
<212> TYPE: DNA
<213> ORGANISM: Felis catus

<400> SEQUENCE: 808
aacctgtttg gagatcacca                                           20

<210> SEQ ID NO 809
<211> LENGTH: 20
<212> TYPE: DNA
<213> ORGANISM: Felis catus

<400> SEQUENCE: 809
aaggcctgtg ggcagggacc                                           20

<210> SEQ ID NO 810
<211> LENGTH: 20
<212> TYPE: DNA
<213> ORGANISM: Felis catus

<400> SEQUENCE: 810
aatattcgtt gatggctatc                                           20

<210> SEQ ID NO 811
<211> LENGTH: 20
<212> TYPE: DNA
<213> ORGANISM: Felis catus

<400> SEQUENCE: 811
aatctaggaa agtagtttat                                           20

<210> SEQ ID NO 812
<211> LENGTH: 20
<212> TYPE: DNA
<213> ORGANISM: Felis catus

<400> SEQUENCE: 812
acaacatttt tatccttctg                                           20

<210> SEQ ID NO 813
<211> LENGTH: 20
<212> TYPE: DNA
<213> ORGANISM: Felis catus

<400> SEQUENCE: 813
accaaagaag cagaaaatgg                                           20

<210> SEQ ID NO 814
<211> LENGTH: 20
<212> TYPE: DNA
<213> ORGANISM: Felis catus

```
<400> SEQUENCE: 814
acccatgcaa tattcgttga                                            20

<210> SEQ ID NO 815
<211> LENGTH: 20
<212> TYPE: DNA
<213> ORGANISM: Felis catus

<400> SEQUENCE: 815
accttaactg ctgcagtctg                                            20

<210> SEQ ID NO 816
<211> LENGTH: 20
<212> TYPE: DNA
<213> ORGANISM: Felis catus

<400> SEQUENCE: 816
actccaagta gctccaggtt                                            20

<210> SEQ ID NO 817
<211> LENGTH: 20
<212> TYPE: DNA
<213> ORGANISM: Felis catus

<400> SEQUENCE: 817
actcttgagg acaaagctct                                            20

<210> SEQ ID NO 818
<211> LENGTH: 20
<212> TYPE: DNA
<213> ORGANISM: Felis catus

<400> SEQUENCE: 818
acttaatccc aagaggaggt                                            20

<210> SEQ ID NO 819
<211> LENGTH: 20
<212> TYPE: DNA
<213> ORGANISM: Felis catus

<400> SEQUENCE: 819
agaaatacac tgaccagccc                                            20

<210> SEQ ID NO 820
<211> LENGTH: 20
<212> TYPE: DNA
<213> ORGANISM: Felis catus

<400> SEQUENCE: 820
agagttggaa atatgctacg                                            20

<210> SEQ ID NO 821
<211> LENGTH: 20
<212> TYPE: DNA
<213> ORGANISM: Felis catus

<400> SEQUENCE: 821
agcgcttgca cacgtgcaag                                            20

<210> SEQ ID NO 822
<211> LENGTH: 20
<212> TYPE: DNA
```

<213> ORGANISM: Felis catus

<400> SEQUENCE: 822
aggaatagca gccatcaagg                                               20

<210> SEQ ID NO 823
<211> LENGTH: 20
<212> TYPE: DNA
<213> ORGANISM: Felis catus

<400> SEQUENCE: 823
agggacctgg cacatgtggg                                               20

<210> SEQ ID NO 824
<211> LENGTH: 20
<212> TYPE: DNA
<213> ORGANISM: Felis catus

<400> SEQUENCE: 824
aggggcaagg tagctgagtc                                               20

<210> SEQ ID NO 825
<211> LENGTH: 20
<212> TYPE: DNA
<213> ORGANISM: Felis catus

<400> SEQUENCE: 825
atgtaggcct cctcaagggc                                               20

<210> SEQ ID NO 826
<211> LENGTH: 20
<212> TYPE: DNA
<213> ORGANISM: Felis catus

<400> SEQUENCE: 826
attaggtgag gacaggtgtc                                               20

<210> SEQ ID NO 827
<211> LENGTH: 20
<212> TYPE: DNA
<213> ORGANISM: Felis catus

<400> SEQUENCE: 827
caaaagaaat aacattgtat                                               20

<210> SEQ ID NO 828
<211> LENGTH: 20
<212> TYPE: DNA
<213> ORGANISM: Felis catus

<400> SEQUENCE: 828
caaagctctt ggagaggatg                                               20

<210> SEQ ID NO 829
<211> LENGTH: 20
<212> TYPE: DNA
<213> ORGANISM: Felis catus

<400> SEQUENCE: 829
caacagtaat tcatttccat                                               20

<210> SEQ ID NO 830
<211> LENGTH: 20

```
<212> TYPE: DNA
<213> ORGANISM: Felis catus

<400> SEQUENCE: 830
caggcaccag aacaacagag                                                   20

<210> SEQ ID NO 831
<211> LENGTH: 20
<212> TYPE: DNA
<213> ORGANISM: Felis catus

<400> SEQUENCE: 831
ccagaagctc caaaggcctg                                                   20

<210> SEQ ID NO 832
<211> LENGTH: 20
<212> TYPE: DNA
<213> ORGANISM: Felis catus

<400> SEQUENCE: 832
ccagctgccg cttaactttg                                                   20

<210> SEQ ID NO 833
<211> LENGTH: 20
<212> TYPE: DNA
<213> ORGANISM: Felis catus

<400> SEQUENCE: 833
ccatcttgac gcccagctct                                                   20

<210> SEQ ID NO 834
<211> LENGTH: 20
<212> TYPE: DNA
<213> ORGANISM: Felis catus

<400> SEQUENCE: 834
ccatgtagcc cctgactgca                                                   20

<210> SEQ ID NO 835
<211> LENGTH: 20
<212> TYPE: DNA
<213> ORGANISM: Felis catus

<400> SEQUENCE: 835
cccttaagga agtaaatgcc                                                   20

<210> SEQ ID NO 836
<211> LENGTH: 20
<212> TYPE: DNA
<213> ORGANISM: Felis catus

<400> SEQUENCE: 836
ccttctgtgg tgatgaatcc                                                   20

<210> SEQ ID NO 837
<211> LENGTH: 20
<212> TYPE: DNA
<213> ORGANISM: Felis catus

<400> SEQUENCE: 837
cgcgatcagt cagaccagga                                                   20

<210> SEQ ID NO 838
```

```
<211> LENGTH: 20
<212> TYPE: DNA
<213> ORGANISM: Felis catus

<400> SEQUENCE: 838
cgtgtggtag aagaacaggc                                               20

<210> SEQ ID NO 839
<211> LENGTH: 20
<212> TYPE: DNA
<213> ORGANISM: Felis catus

<400> SEQUENCE: 839
cgttctccac gtagcaatcc                                               20

<210> SEQ ID NO 840
<211> LENGTH: 20
<212> TYPE: DNA
<213> ORGANISM: Felis catus

<400> SEQUENCE: 840
ctagcccaca gaccgatttc                                               20

<210> SEQ ID NO 841
<211> LENGTH: 20
<212> TYPE: DNA
<213> ORGANISM: Felis catus

<400> SEQUENCE: 841
ctccttccct caaactatcc                                               20

<210> SEQ ID NO 842
<211> LENGTH: 20
<212> TYPE: DNA
<213> ORGANISM: Felis catus

<400> SEQUENCE: 842
ctcttatgtc cattgtgagt                                               20

<210> SEQ ID NO 843
<211> LENGTH: 20
<212> TYPE: DNA
<213> ORGANISM: Felis catus

<400> SEQUENCE: 843
ctgactgcat ggtctgtatg                                               20

<210> SEQ ID NO 844
<211> LENGTH: 20
<212> TYPE: DNA
<213> ORGANISM: Felis catus

<400> SEQUENCE: 844
ctggagggcg cgatgggggc                                               20

<210> SEQ ID NO 845
<211> LENGTH: 20
<212> TYPE: DNA
<213> ORGANISM: Felis catus

<400> SEQUENCE: 845
ctttgtggct agaacctgtt                                               20
```

-continued

```
<210> SEQ ID NO 846
<211> LENGTH: 20
<212> TYPE: DNA
<213> ORGANISM: Felis catus

<400> SEQUENCE: 846
gaaacattag tgaatagttg                                               20

<210> SEQ ID NO 847
<211> LENGTH: 20
<212> TYPE: DNA
<213> ORGANISM: Felis catus

<400> SEQUENCE: 847
gaacaggctg ggtgtgcaca                                               20

<210> SEQ ID NO 848
<211> LENGTH: 20
<212> TYPE: DNA
<213> ORGANISM: Felis catus

<400> SEQUENCE: 848
gaagaacttt ctctttcctg                                               20

<210> SEQ ID NO 849
<211> LENGTH: 20
<212> TYPE: DNA
<213> ORGANISM: Felis catus

<400> SEQUENCE: 849
gaagattctg gagggcgcga                                               20

<210> SEQ ID NO 850
<211> LENGTH: 20
<212> TYPE: DNA
<213> ORGANISM: Felis catus

<400> SEQUENCE: 850
gaatgggtgg acaccatcct                                               20

<210> SEQ ID NO 851
<211> LENGTH: 20
<212> TYPE: DNA
<213> ORGANISM: Felis catus

<400> SEQUENCE: 851
gactagtcca tccaagaccc                                               20

<210> SEQ ID NO 852
<211> LENGTH: 20
<212> TYPE: DNA
<213> ORGANISM: Felis catus

<400> SEQUENCE: 852
gactcatctg tcaggtgtac                                               20

<210> SEQ ID NO 853
<211> LENGTH: 20
<212> TYPE: DNA
<213> ORGANISM: Felis catus

<400> SEQUENCE: 853
gagagttcct gcagaaaggt                                               20
```

```
<210> SEQ ID NO 854
<211> LENGTH: 20
<212> TYPE: DNA
<213> ORGANISM: Felis catus

<400> SEQUENCE: 854
gatcaagccc tgagaatggg                                       20

<210> SEQ ID NO 855
<211> LENGTH: 20
<212> TYPE: DNA
<213> ORGANISM: Felis catus

<400> SEQUENCE: 855
gcaagaagag gagaagattc                                       20

<210> SEQ ID NO 856
<211> LENGTH: 20
<212> TYPE: DNA
<213> ORGANISM: Felis catus

<400> SEQUENCE: 856
gcaatcctgg atttttttca                                       20

<210> SEQ ID NO 857
<211> LENGTH: 20
<212> TYPE: DNA
<213> ORGANISM: Felis catus

<400> SEQUENCE: 857
gcagaaaatg gtggggcgcc                                       20

<210> SEQ ID NO 858
<211> LENGTH: 20
<212> TYPE: DNA
<213> ORGANISM: Felis catus

<400> SEQUENCE: 858
gcagaaccca agaacagcag                                       20

<210> SEQ ID NO 859
<211> LENGTH: 20
<212> TYPE: DNA
<213> ORGANISM: Felis catus

<400> SEQUENCE: 859
gctgtgacaa atgccagagt                                       20

<210> SEQ ID NO 860
<211> LENGTH: 20
<212> TYPE: DNA
<213> ORGANISM: Felis catus

<400> SEQUENCE: 860
ggacagaaga cctgagcgca                                       20

<210> SEQ ID NO 861
<211> LENGTH: 20
<212> TYPE: DNA
<213> ORGANISM: Felis catus

<400> SEQUENCE: 861
ggcgcgatgg gggctgggcc                                       20
```

<210> SEQ ID NO 862
<211> LENGTH: 20
<212> TYPE: DNA
<213> ORGANISM: Felis catus

<400> SEQUENCE: 862
gggcagggac ctggcacatg                                            20

<210> SEQ ID NO 863
<211> LENGTH: 20
<212> TYPE: DNA
<213> ORGANISM: Felis catus

<400> SEQUENCE: 863 gggggggttct gcaggactcc                                           20

<210> SEQ ID NO 864
<211> LENGTH: 20
<212> TYPE: DNA
<213> ORGANISM: Felis catus

<400> SEQUENCE: 864
ggtactctcc cttaaggagg                                            20

<210> SEQ ID NO 865
<211> LENGTH: 20
<212> TYPE: DNA
<213> ORGANISM: Felis catus

<400> SEQUENCE: 865
ggtcatgatc tcacagtttg                                            20

<210> SEQ ID NO 866
<211> LENGTH: 20
<212> TYPE: DNA
<213> ORGANISM: Felis catus

<400> SEQUENCE: 866
gtgaacaatc ccatgtgccc                                            20

<210> SEQ ID NO 867
<211> LENGTH: 20
<212> TYPE: DNA
<213> ORGANISM: Felis catus

<400> SEQUENCE: 867
taaagaacag gacaggagga                                            20

<210> SEQ ID NO 868
<211> LENGTH: 20
<212> TYPE: DNA
<213> ORGANISM: Felis catus

<400> SEQUENCE: 868 tagggagtc tcaggacgct                                             20

<210> SEQ ID NO 869
<211> LENGTH: 20
<212> TYPE: DNA
<213> ORGANISM: Felis catus

<400> SEQUENCE: 869

```
tcagaacctg gagcctgctt                                                   20

<210> SEQ ID NO 870
<211> LENGTH: 20
<212> TYPE: DNA
<213> ORGANISM: Felis catus

<400> SEQUENCE: 870
tcgcacacaa gggacacgtg                                                   20

<210> SEQ ID NO 871
<211> LENGTH: 20
<212> TYPE: DNA
<213> ORGANISM: Felis catus

<400> SEQUENCE: 871
tctaccaaag aagcagaaaa                                                   20

<210> SEQ ID NO 872
<211> LENGTH: 20
<212> TYPE: DNA
<213> ORGANISM: Felis catus

<400> SEQUENCE: 872
tgcacgcgca acgtgaaggt                                                   20

<210> SEQ ID NO 873
<211> LENGTH: 20
<212> TYPE: DNA
<213> ORGANISM: Felis catus

<400> SEQUENCE: 873
tgcactgaca gctcagaacc                                                   20

<210> SEQ ID NO 874
<211> LENGTH: 20
<212> TYPE: DNA
<213> ORGANISM: Felis catus

<400> SEQUENCE: 874
tgggtggctc cctcaaccct                                                   20

<210> SEQ ID NO 875
<211> LENGTH: 20
<212> TYPE: DNA
<213> ORGANISM: Felis catus

<400> SEQUENCE: 875
tgtcaggtgt actggatgta                                                   20

<210> SEQ ID NO 876
<211> LENGTH: 20
<212> TYPE: DNA
<213> ORGANISM: Felis catus

<400> SEQUENCE: 876
tgtggatcaa gccctgagaa                                                   20

<210> SEQ ID NO 877
<211> LENGTH: 20
<212> TYPE: DNA
<213> ORGANISM: Felis catus

<400> SEQUENCE: 877
```
ttaagtcctg gagataagta                                          20

<210> SEQ ID NO 878
<211> LENGTH: 20
<212> TYPE: DNA
<213> ORGANISM: Felis catus

<400> SEQUENCE: 878
ttattgaagg aaactcccag                                          20

<210> SEQ ID NO 879
<211> LENGTH: 20
<212> TYPE: DNA
<213> ORGANISM: Felis catus

<400> SEQUENCE: 879
ttgtgcccaa gtttaagtcc                                          20

<210> SEQ ID NO 880
<211> LENGTH: 20
<212> TYPE: DNA
<213> ORGANISM: Felis catus

<400> SEQUENCE: 880
tttctttgcc aaagaccaac                                          20

<210> SEQ ID NO 881
<211> LENGTH: 20
<212> TYPE: DNA
<213> ORGANISM: Felis catus

<400> SEQUENCE: 881
tttttcatgg ctgttctctc                                          20

<210> SEQ ID NO 882
<211> LENGTH: 20
<212> TYPE: DNA
<213> ORGANISM: Felis catus

<400> SEQUENCE: 882
aacagccatg aaaaaaatcc                                          20

<210> SEQ ID NO 883
<211> LENGTH: 20
<212> TYPE: DNA
<213> ORGANISM: Felis catus

<400> SEQUENCE: 883
aaccaggata gtttgaggga                                          20

<210> SEQ ID NO 884
<211> LENGTH: 20
<212> TYPE: DNA
<213> ORGANISM: Felis catus

<400> SEQUENCE: 884
aactactttc ctagattaga                                          20

<210> SEQ ID NO 885
<211> LENGTH: 20
<212> TYPE: DNA
<213> ORGANISM: Felis catus

```
<400> SEQUENCE: 885
aagcagtcct gggagtgggc                                          20

<210> SEQ ID NO 886
<211> LENGTH: 20
<212> TYPE: DNA
<213> ORGANISM: Felis catus

<400> SEQUENCE: 886
aatcacatac atgtaacccc                                          20

<210> SEQ ID NO 887
<211> LENGTH: 20
<212> TYPE: DNA
<213> ORGANISM: Felis catus

<400> SEQUENCE: 887
aatgtcaccc tggcaattta                                          20

<210> SEQ ID NO 888
<211> LENGTH: 20
<212> TYPE: DNA
<213> ORGANISM: Felis catus

<400> SEQUENCE: 888
acacctgaca gatgagtctc                                          20

<210> SEQ ID NO 889
<211> LENGTH: 20
<212> TYPE: DNA
<213> ORGANISM: Felis catus

<400> SEQUENCE: 889
acttccttct gtatcaattc                                          20

<210> SEQ ID NO 890
<211> LENGTH: 20
<212> TYPE: DNA
<213> ORGANISM: Felis catus

<400> SEQUENCE: 890
agagagagag aatccaaagc                                          20

<210> SEQ ID NO 891
<211> LENGTH: 20
<212> TYPE: DNA
<213> ORGANISM: Felis catus

<400> SEQUENCE: 891
agagcatggg gactggaggc                                          20

<210> SEQ ID NO 892
<211> LENGTH: 20
<212> TYPE: DNA
<213> ORGANISM: Felis catus

<400> SEQUENCE: 892
agagctttgt cctcaagagt                                          20

<210> SEQ ID NO 893
<211> LENGTH: 20
<212> TYPE: DNA
<213> ORGANISM: Felis catus
```

<400> SEQUENCE: 893
agatgggtga gagcagatgg                                              20

<210> SEQ ID NO 894
<211> LENGTH: 20
<212> TYPE: DNA
<213> ORGANISM: Felis catus

<400> SEQUENCE: 894
agcaccccat acttatctcc                                              20

<210> SEQ ID NO 895
<211> LENGTH: 20
<212> TYPE: DNA
<213> ORGANISM: Felis catus

<400> SEQUENCE: 895
agccttgtca gttctggtgg                                              20

<210> SEQ ID NO 896
<211> LENGTH: 20
<212> TYPE: DNA
<213> ORGANISM: Felis catus

<400> SEQUENCE: 896
agcgttacca gcccttgagg                                              20

<210> SEQ ID NO 897
<211> LENGTH: 20
<212> TYPE: DNA
<213> ORGANISM: Felis catus

<400> SEQUENCE: 897
agctaccttg ccccctcaccc                                             20

<210> SEQ ID NO 898
<211> LENGTH: 20
<212> TYPE: DNA
<213> ORGANISM: Felis catus

<400> SEQUENCE: 898
aggcaggctg gggtgcccgg                                              20

<210> SEQ ID NO 899
<211> LENGTH: 20
<212> TYPE: DNA
<213> ORGANISM: Felis catus

<400> SEQUENCE: 899
agggagaggt ttggagatgg                                              20

<210> SEQ ID NO 900
<211> LENGTH: 20
<212> TYPE: DNA
<213> ORGANISM: Felis catus

<400> SEQUENCE: 900
agggagtgat ttgtagccca                                              20

<210> SEQ ID NO 901
<211> LENGTH: 20
<212> TYPE: DNA

```
<213> ORGANISM: Felis catus

<400> SEQUENCE: 901
agtgggcagg tctctgcgga                                              20

<210> SEQ ID NO 902
<211> LENGTH: 20
<212> TYPE: DNA
<213> ORGANISM: Felis catus

<400> SEQUENCE: 902
agtttgaggg aaggagtagc                                              20

<210> SEQ ID NO 903
<211> LENGTH: 20
<212> TYPE: DNA
<213> ORGANISM: Felis catus

<400> SEQUENCE: 903
atcactgggg atgaggcatg                                              20

<210> SEQ ID NO 904
<211> LENGTH: 20
<212> TYPE: DNA
<213> ORGANISM: Felis catus

<400> SEQUENCE: 904
attaagttta ctgatggagg                                              20

<210> SEQ ID NO 905
<211> LENGTH: 20
<212> TYPE: DNA
<213> ORGANISM: Felis catus

<400> SEQUENCE: 905
attgagagca tggggactgg                                              20

<210> SEQ ID NO 906
<211> LENGTH: 20
<212> TYPE: DNA
<213> ORGANISM: Felis catus

<400> SEQUENCE: 906
atttttcttg ttgcacagtt                                              20

<210> SEQ ID NO 907
<211> LENGTH: 20
<212> TYPE: DNA
<213> ORGANISM: Felis catus

<400> SEQUENCE: 907
caaaatgggg attaagtgtg                                              20

<210> SEQ ID NO 908
<211> LENGTH: 20
<212> TYPE: DNA
<213> ORGANISM: Felis catus

<400> SEQUENCE: 908
cacatacaga ccatgcagtc                                              20

<210> SEQ ID NO 909
<211> LENGTH: 20
```

```
<212> TYPE: DNA
<213> ORGANISM: Felis catus

<400> SEQUENCE: 909
cacctaattc actctcaatc                                            20

<210> SEQ ID NO 910
<211> LENGTH: 20
<212> TYPE: DNA
<213> ORGANISM: Felis catus

<400> SEQUENCE: 910
cagcagttaa ggtgttcaag                                            20

<210> SEQ ID NO 911
<211> LENGTH: 20
<212> TYPE: DNA
<213> ORGANISM: Felis catus

<400> SEQUENCE: 911
cagctcaggt catgatctca                                            20

<210> SEQ ID NO 912
<211> LENGTH: 20
<212> TYPE: DNA
<213> ORGANISM: Felis catus

<400> SEQUENCE: 912
cagctgggag atcattgtcc                                            20

<210> SEQ ID NO 913
<211> LENGTH: 20
<212> TYPE: DNA
<213> ORGANISM: Felis catus

<400> SEQUENCE: 913
cattcagctc ctgcacatgt                                            20

<210> SEQ ID NO 914
<211> LENGTH: 20
<212> TYPE: DNA
<213> ORGANISM: Felis catus

<400> SEQUENCE: 914
ccaggattca tcaccacaga                                            20

<210> SEQ ID NO 915
<211> LENGTH: 20
<212> TYPE: DNA
<213> ORGANISM: Felis catus

<400> SEQUENCE: 915
cccaggcatt tacttcctta                                            20

<210> SEQ ID NO 916
<211> LENGTH: 20
<212> TYPE: DNA
<213> ORGANISM: Felis catus

<400> SEQUENCE: 916
cccttaaatg tcatcctggc                                            20

<210> SEQ ID NO 917
```

```
<211> LENGTH: 20
<212> TYPE: DNA
<213> ORGANISM: Felis catus

<400> SEQUENCE: 917
cctgggtggc tcagtcggtt                                          20

<210> SEQ ID NO 918
<211> LENGTH: 20
<212> TYPE: DNA
<213> ORGANISM: Felis catus

<400> SEQUENCE: 918
cgtaggattt ttttctttct                                          20

<210> SEQ ID NO 919
<211> LENGTH: 20
<212> TYPE: DNA
<213> ORGANISM: Felis catus

<400> SEQUENCE: 919
cgtcctgaga ctcccctagt                                          20

<210> SEQ ID NO 920
<211> LENGTH: 20
<212> TYPE: DNA
<213> ORGANISM: Felis catus

<400> SEQUENCE: 920
ctcagactct cttcccagga                                          20

<210> SEQ ID NO 921
<211> LENGTH: 20
<212> TYPE: DNA
<213> ORGANISM: Felis catus

<400> SEQUENCE: 921
ctctcaagtg gcgggcaaac                                          20

<210> SEQ ID NO 922
<211> LENGTH: 20
<212> TYPE: DNA
<213> ORGANISM: Felis catus

<400> SEQUENCE: 922
ctctgctgat tcttttgtga                                          20

<210> SEQ ID NO 923
<211> LENGTH: 20
<212> TYPE: DNA
<213> ORGANISM: Felis catus

<400> SEQUENCE: 923
ctctgttgtt ctggtgcctg                                          20

<210> SEQ ID NO 924
<211> LENGTH: 20
<212> TYPE: DNA
<213> ORGANISM: Felis catus

<400> SEQUENCE: 924
ctgatggagg agggtgagac                                          20
```

```
<210> SEQ ID NO 925
<211> LENGTH: 20
<212> TYPE: DNA
<213> ORGANISM: Felis catus

<400> SEQUENCE: 925
cttaaacttg ggcacaagta                                               20

<210> SEQ ID NO 926
<211> LENGTH: 20
<212> TYPE: DNA
<213> ORGANISM: Felis catus

<400> SEQUENCE: 926
cttaagggtg agagggaagc                                               20

<210> SEQ ID NO 927
<211> LENGTH: 20
<212> TYPE: DNA
<213> ORGANISM: Felis catus

<400> SEQUENCE: 927
cttacgcaca gttggaaaat                                               20

<210> SEQ ID NO 928
<211> LENGTH: 20
<212> TYPE: DNA
<213> ORGANISM: Felis catus

<400> SEQUENCE: 928
cttatttgaa aggccgaaac                                               20

<210> SEQ ID NO 929
<211> LENGTH: 20
<212> TYPE: DNA
<213> ORGANISM: Felis catus

<400> SEQUENCE: 929
ctttgtcctc aagagtagga                                               20

<210> SEQ ID NO 930
<211> LENGTH: 20
<212> TYPE: DNA
<213> ORGANISM: Felis catus

<400> SEQUENCE: 930
gaaatcggtc tgtgggctag                                               20

<210> SEQ ID NO 931
<211> LENGTH: 20
<212> TYPE: DNA
<213> ORGANISM: Felis catus

<400> SEQUENCE: 931
gactggaggc aggctgaatc                                               20

<210> SEQ ID NO 932
<211> LENGTH: 20
<212> TYPE: DNA
<213> ORGANISM: Felis catus

<400> SEQUENCE: 932
gagaatccaa agcaggctcc                                               20
```

<210> SEQ ID NO 933
<211> LENGTH: 20
<212> TYPE: DNA
<213> ORGANISM: Felis catus

<400> SEQUENCE: 933
gagagcagat ggagggacag                                        20

<210> SEQ ID NO 934
<211> LENGTH: 20
<212> TYPE: DNA
<213> ORGANISM: Felis catus

<400> SEQUENCE: 934
gagagtgcac acaagtggga                                        20

<210> SEQ ID NO 935
<211> LENGTH: 20
<212> TYPE: DNA
<213> ORGANISM: Felis catus

<400> SEQUENCE: 935
gagatcctgg gacatggcaa                                        20

<210> SEQ ID NO 936
<211> LENGTH: 20
<212> TYPE: DNA
<213> ORGANISM: Felis catus

<400> SEQUENCE: 936
gagcggaatc actggggatg                                        20

<210> SEQ ID NO 937
<211> LENGTH: 20
<212> TYPE: DNA
<213> ORGANISM: Felis catus

<400> SEQUENCE: 937
gaggaggcca acctttctgc                                        20

<210> SEQ ID NO 938
<211> LENGTH: 20
<212> TYPE: DNA
<213> ORGANISM: Felis catus

<400> SEQUENCE: 938
gagtatcgca tttgggaacc                                        20

<210> SEQ ID NO 939
<211> LENGTH: 20
<212> TYPE: DNA
<213> ORGANISM: Felis catus

<400> SEQUENCE: 939
gatagcgctg ccatgcgctc                                        20

<210> SEQ ID NO 940
<211> LENGTH: 20
<212> TYPE: DNA
<213> ORGANISM: Felis catus

<400> SEQUENCE: 940
gatggtgtcc acccattctc                                        20

<210> SEQ ID NO 941
<211> LENGTH: 20
<212> TYPE: DNA
<213> ORGANISM: Felis catus

<400> SEQUENCE: 941
gcagtcaggg gctacatggc                                               20

<210> SEQ ID NO 942
<211> LENGTH: 20
<212> TYPE: DNA
<213> ORGANISM: Felis catus

<400> SEQUENCE: 942
gctacgtgca gctgcacccc                                               20

<210> SEQ ID NO 943
<211> LENGTH: 20
<212> TYPE: DNA
<213> ORGANISM: Felis catus

<400> SEQUENCE: 943
ggaagcgtgg gaggcctggc                                               20

<210> SEQ ID NO 944
<211> LENGTH: 20
<212> TYPE: DNA
<213> ORGANISM: Felis catus

<400> SEQUENCE: 944
ggagctactt ggagtcaaga                                               20

<210> SEQ ID NO 945
<211> LENGTH: 20
<212> TYPE: DNA
<213> ORGANISM: Felis catus

<400> SEQUENCE: 945
gggaaggagt agcaggaaac                                               20

<210> SEQ ID NO 946
<211> LENGTH: 20
<212> TYPE: DNA
<213> ORGANISM: Felis catus

<400> SEQUENCE: 946
gggagccacc cacatgtgcc                                               20

<210> SEQ ID NO 947
<211> LENGTH: 20
<212> TYPE: DNA
<213> ORGANISM: Felis catus

<400> SEQUENCE: 947
gggattaagt ttactgatgg                                               20

<210> SEQ ID NO 948
<211> LENGTH: 20
<212> TYPE: DNA
<213> ORGANISM: Felis catus

<400> SEQUENCE: 948

```
gggggtgtgg gctgggctta                                              20

<210> SEQ ID NO 949
<211> LENGTH: 20
<212> TYPE: DNA
<213> ORGANISM: Felis catus

<400> SEQUENCE: 949
ggtagtggtg cttatttgaa                                              20

<210> SEQ ID NO 950
<211> LENGTH: 20
<212> TYPE: DNA
<213> ORGANISM: Felis catus

<400> SEQUENCE: 950
ggtgcccgga ggcaccggtc                                              20

<210> SEQ ID NO 951
<211> LENGTH: 20
<212> TYPE: DNA
<213> ORGANISM: Felis catus

<400> SEQUENCE: 951
ggtgtcagaa ttgcaggagt                                              20

<210> SEQ ID NO 952
<211> LENGTH: 20
<212> TYPE: DNA
<213> ORGANISM: Felis catus

<400> SEQUENCE: 952
gtaggatttt agccttccac                                              20

<210> SEQ ID NO 953
<211> LENGTH: 20
<212> TYPE: DNA
<213> ORGANISM: Felis catus

<400> SEQUENCE: 953
gtgagttcga gcggggcatc                                              20

<210> SEQ ID NO 954
<211> LENGTH: 20
<212> TYPE: DNA
<213> ORGANISM: Felis catus

<400> SEQUENCE: 954
gtggaggaat attgaaacta                                              20

<210> SEQ ID NO 955
<211> LENGTH: 20
<212> TYPE: DNA
<213> ORGANISM: Felis catus

<400> SEQUENCE: 955
gtgggctaga ggttcttgct                                              20

<210> SEQ ID NO 956
<211> LENGTH: 20
<212> TYPE: DNA
<213> ORGANISM: Felis catus

<400> SEQUENCE: 956
```
gttcggggtg tcagaattgc                    20

<210> SEQ ID NO 957
<211> LENGTH: 20
<212> TYPE: DNA
<213> ORGANISM: Felis catus

<400> SEQUENCE: 957
taaggtgttc aagaggcttg                    20

<210> SEQ ID NO 958
<211> LENGTH: 20
<212> TYPE: DNA
<213> ORGANISM: Felis catus

<400> SEQUENCE: 958
tagaaagcgt gttgactcgt                    20

<210> SEQ ID NO 959
<211> LENGTH: 20
<212> TYPE: DNA
<213> ORGANISM: Felis catus

<400> SEQUENCE: 959
tagagcgtta ccagcccttg                    20

<210> SEQ ID NO 960
<211> LENGTH: 20
<212> TYPE: DNA
<213> ORGANISM: Felis catus

<400> SEQUENCE: 960
taggtgactg acttcagctc                    20

<210> SEQ ID NO 961
<211> LENGTH: 20
<212> TYPE: DNA
<213> ORGANISM: Felis catus

<400> SEQUENCE: 961
tagtcgtaga atggagggag                    20

<210> SEQ ID NO 962
<211> LENGTH: 20
<212> TYPE: DNA
<213> ORGANISM: Felis catus

<400> SEQUENCE: 962
tcattagttg tgcacacaat                    20

<210> SEQ ID NO 963
<211> LENGTH: 20
<212> TYPE: DNA
<213> ORGANISM: Felis catus

<400> SEQUENCE: 963
tccacagact gcagcagtta                    20

<210> SEQ ID NO 964
<211> LENGTH: 20
<212> TYPE: DNA
<213> ORGANISM: Felis catus -continued

```
<400> SEQUENCE: 964
tcccatggtg atctccaaac                                               20

<210> SEQ ID NO 965
<211> LENGTH: 20
<212> TYPE: DNA
<213> ORGANISM: Felis catus

<400> SEQUENCE: 965
tcctgggaca tggcaaaggg                                               20

<210> SEQ ID NO 966
<211> LENGTH: 20
<212> TYPE: DNA
<213> ORGANISM: Felis catus

<400> SEQUENCE: 966
tctggtgcct gaggccctcg                                               20

<210> SEQ ID NO 967
<211> LENGTH: 20
<212> TYPE: DNA
<213> ORGANISM: Felis catus

<400> SEQUENCE: 967
tcttaacagc ccaagggttg                                               20

<210> SEQ ID NO 968
<211> LENGTH: 20
<212> TYPE: DNA
<213> ORGANISM: Felis catus

<400> SEQUENCE: 968
tctttggtag atgtcttctg                                               20

<210> SEQ ID NO 969
<211> LENGTH: 20
<212> TYPE: DNA
<213> ORGANISM: Felis catus

<400> SEQUENCE: 969
tgacagatga gtctcaggtg                                               20

<210> SEQ ID NO 970
<211> LENGTH: 20
<212> TYPE: DNA
<213> ORGANISM: Felis catus

<400> SEQUENCE: 970
tgccctcaga ctctcttccc                                               20

<210> SEQ ID NO 971
<211> LENGTH: 20
<212> TYPE: DNA
<213> ORGANISM: Felis catus

<400> SEQUENCE: 971
tggagaacgg actcttatcc                                               20

<210> SEQ ID NO 972
<211> LENGTH: 20
<212> TYPE: DNA
<213> ORGANISM: Felis catus
```

```
<400> SEQUENCE: 972
tggcaattta agggtgactc                                                   20

<210> SEQ ID NO 973
<211> LENGTH: 20
<212> TYPE: DNA
<213> ORGANISM: Felis catus

<400> SEQUENCE: 973
tgtgccaggt ccctgcccac                                                   20

<210> SEQ ID NO 974
<211> LENGTH: 20
<212> TYPE: DNA
<213> ORGANISM: Felis catus

<400> SEQUENCE: 974
tgtttttagt cgtagaatgg                                                   20

<210> SEQ ID NO 975
<211> LENGTH: 20
<212> TYPE: DNA
<213> ORGANISM: Felis catus

<400> SEQUENCE: 975
ttcagactcc ctcctggcac                                                   20

<210> SEQ ID NO 976
<211> LENGTH: 20
<212> TYPE: DNA
<213> ORGANISM: Felis catus

<400> SEQUENCE: 976
ttcccactct taacagccca                                                   20

<210> SEQ ID NO 977
<211> LENGTH: 20
<212> TYPE: DNA
<213> ORGANISM: Felis catus

<400> SEQUENCE: 977
ttctagcagc tgacacgatg                                                   20

<210> SEQ ID NO 978
<211> LENGTH: 20
<212> TYPE: DNA
<213> ORGANISM: Felis catus

<400> SEQUENCE: 978
ttctgtgcgg gaagcgtggg                                                   20

<210> SEQ ID NO 979
<211> LENGTH: 20
<212> TYPE: DNA
<213> ORGANISM: Felis catus

<400> SEQUENCE: 979
ttgcatgact acgggcaccc                                                   20

<210> SEQ ID NO 980
<211> LENGTH: 20
<212> TYPE: DNA
```

```
<213> ORGANISM: Felis catus

<400> SEQUENCE: 980
ttggagtcaa gaaggtgccc                                               20

<210> SEQ ID NO 981
<211> LENGTH: 20
<212> TYPE: DNA
<213> ORGANISM: Felis catus

<400> SEQUENCE: 981
ttgggaacca ggatagtttg                                               20

<210> SEQ ID NO 982
<211> LENGTH: 20
<212> TYPE: DNA
<213> ORGANISM: Felis catus

<400> SEQUENCE: 982
ttggtagatg tcttctgagg                                               20

<210> SEQ ID NO 983
<211> LENGTH: 20
<212> TYPE: DNA
<213> ORGANISM: Felis catus

<400> SEQUENCE: 983
tttaaccgac tgagccaccc                                               20

<210> SEQ ID NO 984
<211> LENGTH: 20
<212> TYPE: DNA
<213> ORGANISM: Felis catus

<400> SEQUENCE: 984
tttacttcct taagggtgag                                               20

<210> SEQ ID NO 985
<211> LENGTH: 20
<212> TYPE: DNA
<213> ORGANISM: Felis catus

<400> SEQUENCE: 985
tttgaaaggc cgaaacaggc                                               20

<210> SEQ ID NO 986
<211> LENGTH: 20
<212> TYPE: DNA
<213> ORGANISM: Felis catus

<400> SEQUENCE: 986
aacaggcagg ctggggtgcc                                               20

<210> SEQ ID NO 987
<211> LENGTH: 20
<212> TYPE: DNA
<213> ORGANISM: Felis catus

<400> SEQUENCE: 987
caggattgct acgtggagaa                                               20

<210> SEQ ID NO 988
<211> LENGTH: 20
```

```
<212> TYPE: DNA
<213> ORGANISM: Felis catus

<400> SEQUENCE: 988
catcctggtc tgactgatcg                                           20

<210> SEQ ID NO 989
<211> LENGTH: 20
<212> TYPE: DNA
<213> ORGANISM: Felis catus

<400> SEQUENCE: 989
ccccgtgtct gtgttctgtg                                           20

<210> SEQ ID NO 990
<211> LENGTH: 20
<212> TYPE: DNA
<213> ORGANISM: Felis catus

<400> SEQUENCE: 990
ctagaggttc ttgctaggga                                           20

<210> SEQ ID NO 991
<211> LENGTH: 20
<212> TYPE: DNA
<213> ORGANISM: Felis catus

<400> SEQUENCE: 991
ctgttcttgg gttctgccag                                           20

<210> SEQ ID NO 992
<211> LENGTH: 20
<212> TYPE: DNA
<213> ORGANISM: Felis catus

<400> SEQUENCE: 992
gaatcaggag cacatgtgag                                           20

<210> SEQ ID NO 993
<211> LENGTH: 20
<212> TYPE: DNA
<213> ORGANISM: Felis catus

<400> SEQUENCE: 993
gatttttttc tttctaggtt                                           20

<210> SEQ ID NO 994
<211> LENGTH: 20
<212> TYPE: DNA
<213> ORGANISM: Felis catus

<400> SEQUENCE: 994
gcaccggtca ggggtctctc                                           20

<210> SEQ ID NO 995
<211> LENGTH: 20
<212> TYPE: DNA
<213> ORGANISM: Felis catus

<400> SEQUENCE: 995
gcggccctct ctccagaaat                                           20

<210> SEQ ID NO 996
```

```
<211> LENGTH: 20
<212> TYPE: DNA
<213> ORGANISM: Felis catus

<400> SEQUENCE: 996
gctggggtgc ccggaggcac                                           20

<210> SEQ ID NO 997
<211> LENGTH: 20
<212> TYPE: DNA
<213> ORGANISM: Felis catus

<400> SEQUENCE: 997
ggaaaatagg ggactaatat                                           20

<210> SEQ ID NO 998
<211> LENGTH: 20
<212> TYPE: DNA
<213> ORGANISM: Felis catus

<400> SEQUENCE: 998
ggttcttgct agggacggag                                           20

<210> SEQ ID NO 999
<211> LENGTH: 20
<212> TYPE: DNA
<213> ORGANISM: Felis catus

<400> SEQUENCE: 999
gttctagcca caaagttaag                                           20

<210> SEQ ID NO 1000
<211> LENGTH: 20
<212> TYPE: DNA
<213> ORGANISM: Felis catus

<400> SEQUENCE: 1000
taactgcatc ttagcacccc                                           20

<210> SEQ ID NO 1001
<211> LENGTH: 20
<212> TYPE: DNA
<213> ORGANISM: Felis catus

<400> SEQUENCE: 1001
tcaaggtttg tgagttcgag                                           20

<210> SEQ ID NO 1002
<211> LENGTH: 20
<212> TYPE: DNA
<213> ORGANISM: Felis catus

<400> SEQUENCE: 1002
tggaatttct tgcatgacta                                           20

<210> SEQ ID NO 1003
<211> LENGTH: 20
<212> TYPE: DNA
<213> ORGANISM: Felis catus

<400> SEQUENCE: 1003
tggcacaggt gcgtgggtga                                           20
```

```
<210> SEQ ID NO 1004
<211> LENGTH: 20
<212> TYPE: DNA
<213> ORGANISM: Felis catus

<400> SEQUENCE: 1004
tgggagtggg caggtctctg                                               20

<210> SEQ ID NO 1005
<211> LENGTH: 20
<212> TYPE: DNA
<213> ORGANISM: Felis catus

<400> SEQUENCE: 1005
tgtcagtgca gagcctgaca                                               20

<210> SEQ ID NO 1006
<211> LENGTH: 20
<212> TYPE: DNA
<213> ORGANISM: Felis catus

<400> SEQUENCE: 1006
tgtgagttgc tctcaagtgg                                               20

<210> SEQ ID NO 1007
<211> LENGTH: 20
<212> TYPE: DNA
<213> ORGANISM: Felis catus

<400> SEQUENCE: 1007
ttttctgttt gtgtcttcag                                               20

<210> SEQ ID NO 1008
<211> LENGTH: 20
<212> TYPE: DNA
<213> ORGANISM: Felis catus

<400> SEQUENCE: 1008
tttttatgac gtcttttttg                                               20

<210> SEQ ID NO 1009
<211> LENGTH: 20
<212> TYPE: DNA
<213> ORGANISM: Felis catus

<400> SEQUENCE: 1009
aactgcatct tagcaccccc                                               20

<210> SEQ ID NO 1010
<211> LENGTH: 20
<212> TYPE: DNA
<213> ORGANISM: Felis catus

<400> SEQUENCE: 1010
aaggccgaaa caggcaggct                                               20

<210> SEQ ID NO 1011
<211> LENGTH: 20
<212> TYPE: DNA
<213> ORGANISM: Felis catus

<400> SEQUENCE: 1011
aaggtttgtg agttcgagcg                                               20
```

<210> SEQ ID NO 1012
<211> LENGTH: 20
<212> TYPE: DNA
<213> ORGANISM: Felis catus

<400> SEQUENCE: 1012 aatagggag agttagttgg					20

<210> SEQ ID NO 1013
<211> LENGTH: 20
<212> TYPE: DNA
<213> ORGANISM: Felis catus

<400> SEQUENCE: 1013
acaatagggg agagttagtt					20

<210> SEQ ID NO 1014
<211> LENGTH: 20
<212> TYPE: DNA
<213> ORGANISM: Felis catus

<400> SEQUENCE: 1014
acaggccttt ggagcttctg					20

<210> SEQ ID NO 1015
<211> LENGTH: 20
<212> TYPE: DNA
<213> ORGANISM: Felis catus

<400> SEQUENCE: 1015
acaggtgcgt gggtgacggg					20

<210> SEQ ID NO 1016
<211> LENGTH: 20
<212> TYPE: DNA
<213> ORGANISM: Felis catus

<400> SEQUENCE: 1016
acatacagac catgcagtca					20

<210> SEQ ID NO 1017
<211> LENGTH: 20
<212> TYPE: DNA
<213> ORGANISM: Felis catus

<400> SEQUENCE: 1017
actcaggtga tgacctgagt					20

<210> SEQ ID NO 1018
<211> LENGTH: 20
<212> TYPE: DNA
<213> ORGANISM: Felis catus

<400> SEQUENCE: 1018
agaaaatgtt ccgtctgtct					20

<210> SEQ ID NO 1019
<211> LENGTH: 20
<212> TYPE: DNA
<213> ORGANISM: Felis catus

<400> SEQUENCE: 1019
agagtgcaca caagtgggaa					20

-continued

<210> SEQ ID NO 1020
<211> LENGTH: 20
<212> TYPE: DNA
<213> ORGANISM: Felis catus

<400> SEQUENCE: 1020
agatcctggg acatggcaaa                                               20

<210> SEQ ID NO 1021
<211> LENGTH: 20
<212> TYPE: DNA
<213> ORGANISM: Felis catus

<400> SEQUENCE: 1021
agcagctgac acgatgaggg                                               20

<210> SEQ ID NO 1022
<211> LENGTH: 20
<212> TYPE: DNA
<213> ORGANISM: Felis catus

<400> SEQUENCE: 1022
aggccgaaac aggcaggctg                                               20

<210> SEQ ID NO 1023
<211> LENGTH: 20
<212> TYPE: DNA
<213> ORGANISM: Felis catus

<400> SEQUENCE: 1023
aggcctttgg agcttctggg                                               20

<210> SEQ ID NO 1024
<211> LENGTH: 20
<212> TYPE: DNA
<213> ORGANISM: Felis catus

<400> SEQUENCE: 1024
agggacggag cggaatcact                                               20

<210> SEQ ID NO 1025
<211> LENGTH: 20
<212> TYPE: DNA
<213> ORGANISM: Felis catus

<400> SEQUENCE: 1025
aggtgcgtgg gtgacggggg                                               20

<210> SEQ ID NO 1026
<211> LENGTH: 20
<212> TYPE: DNA
<213> ORGANISM: Felis catus

<400> SEQUENCE: 1026
agtaagtcca acctcctctt                                               20

<210> SEQ ID NO 1027
<211> LENGTH: 20
<212> TYPE: DNA
<213> ORGANISM: Felis catus

<400> SEQUENCE: 1027
atctcaagct gaacactttg                                           20

<210> SEQ ID NO 1028
<211> LENGTH: 20
<212> TYPE: DNA
<213> ORGANISM: Felis catus

<400> SEQUENCE: 1028
atgaggcatg aggtgatcct                                           20

<210> SEQ ID NO 1029
<211> LENGTH: 20
<212> TYPE: DNA
<213> ORGANISM: Felis catus

<400> SEQUENCE: 1029
atggtgtcca cccattctca                                           20

<210> SEQ ID NO 1030
<211> LENGTH: 20
<212> TYPE: DNA
<213> ORGANISM: Felis catus

<400> SEQUENCE: 1030
atgtaagcag tcctgggagt                                           20

<210> SEQ ID NO 1031
<211> LENGTH: 20
<212> TYPE: DNA
<213> ORGANISM: Felis catus

<400> SEQUENCE: 1031
atgtcaccct ggcaatttaa                                           20

<210> SEQ ID NO 1032
<211> LENGTH: 20
<212> TYPE: DNA
<213> ORGANISM: Felis catus

<400> SEQUENCE: 1032
atgtgctcat tgagagcatg                                           20

<210> SEQ ID NO 1033
<211> LENGTH: 20
<212> TYPE: DNA
<213> ORGANISM: Felis catus

<400> SEQUENCE: 1033
attagttgtg cacacaatag                                           20

<210> SEQ ID NO 1034
<211> LENGTH: 20
<212> TYPE: DNA
<213> ORGANISM: Felis catus

<400> SEQUENCE: 1034
attcactaat gtttctggat                                           20

<210> SEQ ID NO 1035
<211> LENGTH: 20
<212> TYPE: DNA
<213> ORGANISM: Felis catus

<400> SEQUENCE: 1035
attctctcat ctgcaaaatg                                          20

<210> SEQ ID NO 1036
<211> LENGTH: 20
<212> TYPE: DNA
<213> ORGANISM: Felis catus

<400> SEQUENCE: 1036
atttttttct ttctaggttc                                          20

<210> SEQ ID NO 1037
<211> LENGTH: 20
<212> TYPE: DNA
<213> ORGANISM: Felis catus

<400> SEQUENCE: 1037
caagagctgg gcgtcaagat                                          20

<210> SEQ ID NO 1038
<211> LENGTH: 20
<212> TYPE: DNA
<213> ORGANISM: Felis catus

<400> SEQUENCE: 1038
caaggtttgt gagttcgagc                                          20

<210> SEQ ID NO 1039
<211> LENGTH: 20
<212> TYPE: DNA
<213> ORGANISM: Felis catus

<400> SEQUENCE: 1039 caataggga gagttagttg                                           20

<210> SEQ ID NO 1040
<211> LENGTH: 20
<212> TYPE: DNA
<213> ORGANISM: Felis catus

<400> SEQUENCE: 1040
cacaaagtta agcggcagct                                          20

<210> SEQ ID NO 1041
<211> LENGTH: 20
<212> TYPE: DNA
<213> ORGANISM: Felis catus

<400> SEQUENCE: 1041
cacaggcctt tggagcttct                                          20

<210> SEQ ID NO 1042
<211> LENGTH: 20
<212> TYPE: DNA
<213> ORGANISM: Felis catus

<400> SEQUENCE: 1042
cacaggtgcg tgggtgacgg                                          20

<210> SEQ ID NO 1043
<211> LENGTH: 20
<212> TYPE: DNA
<213> ORGANISM: Felis catus

```
<400> SEQUENCE: 1043
caggcctttg gagcttctgg                                                   20

<210> SEQ ID NO 1044
<211> LENGTH: 20
<212> TYPE: DNA
<213> ORGANISM: Felis catus

<400> SEQUENCE: 1044 cagggtgac agttggagct                                                    20

<210> SEQ ID NO 1045
<211> LENGTH: 20
<212> TYPE: DNA
<213> ORGANISM: Felis catus

<400> SEQUENCE: 1045
caggtgcgtg ggtgacgggg                                                   20

<210> SEQ ID NO 1046
<211> LENGTH: 20
<212> TYPE: DNA
<213> ORGANISM: Felis catus

<400> SEQUENCE: 1046
catacagacc atgcagtcag                                                   20

<210> SEQ ID NO 1047
<211> LENGTH: 20
<212> TYPE: DNA
<213> ORGANISM: Felis catus

<400> SEQUENCE: 1047
catgtgctca ttgagagcat                                                   20

<210> SEQ ID NO 1048
<211> LENGTH: 20
<212> TYPE: DNA
<213> ORGANISM: Felis catus

<400> SEQUENCE: 1048
cattagttgt gcacacaata                                                   20

<210> SEQ ID NO 1049
<211> LENGTH: 20
<212> TYPE: DNA
<213> ORGANISM: Felis catus

<400> SEQUENCE: 1049
ccaggcattt acttccttaa                                                   20

<210> SEQ ID NO 1050
<211> LENGTH: 20
<212> TYPE: DNA
<213> ORGANISM: Felis catus

<400> SEQUENCE: 1050
cccgtgtctg tgttctgtgc                                                   20

<210> SEQ ID NO 1051
<211> LENGTH: 20
<212> TYPE: DNA
<213> ORGANISM: Felis catus
```

<400> SEQUENCE: 1051
ccctcctggc acaggtgcgt                    20

<210> SEQ ID NO 1052
<211> LENGTH: 20
<212> TYPE: DNA
<213> ORGANISM: Felis catus

<400> SEQUENCE: 1052
ccttaaatgt catcctggca                    20

<210> SEQ ID NO 1053
<211> LENGTH: 20
<212> TYPE: DNA
<213> ORGANISM: Felis catus

<400> SEQUENCE: 1053
cctttggagc ttctgggggg                    20

<210> SEQ ID NO 1054
<211> LENGTH: 20
<212> TYPE: DNA
<213> ORGANISM: Felis catus

<400> SEQUENCE: 1054
ctacgtgcag ctgcacccca                    20

<210> SEQ ID NO 1055
<211> LENGTH: 20
<212> TYPE: DNA
<213> ORGANISM: Felis catus

<400> SEQUENCE: 1055
ctagcagctg acacgatgag                    20

<210> SEQ ID NO 1056
<211> LENGTH: 20
<212> TYPE: DNA
<213> ORGANISM: Felis catus

<400> SEQUENCE: 1056
ctctccagaa atcggtctgt                    20

<210> SEQ ID NO 1057
<211> LENGTH: 20
<212> TYPE: DNA
<213> ORGANISM: Felis catus

<400> SEQUENCE: 1057
cttaaatgtc atcctggcag                    20

<210> SEQ ID NO 1058
<211> LENGTH: 20
<212> TYPE: DNA
<213> ORGANISM: Felis catus

<400> SEQUENCE: 1058
cttaacagcc caagggttga                    20

<210> SEQ ID NO 1059
<211> LENGTH: 20
<212> TYPE: DNA

<213> ORGANISM: Felis catus

<400> SEQUENCE: 1059
cttccttctg tatcaattca                                        20

<210> SEQ ID NO 1060
<211> LENGTH: 20
<212> TYPE: DNA
<213> ORGANISM: Felis catus

<400> SEQUENCE: 1060
cttgggagag tatcgcattt                                        20

<210> SEQ ID NO 1061
<211> LENGTH: 20
<212> TYPE: DNA
<213> ORGANISM: Felis catus

<400> SEQUENCE: 1061
ctttggagct tctgggggggg                                       20

<210> SEQ ID NO 1062
<211> LENGTH: 20
<212> TYPE: DNA
<213> ORGANISM: Felis catus

<400> SEQUENCE: 1062
gaaggagtag caggaaacag                                        20

<210> SEQ ID NO 1063
<211> LENGTH: 20
<212> TYPE: DNA
<213> ORGANISM: Felis catus

<400> SEQUENCE: 1063
gacagatgag tctcaggtga                                        20

<210> SEQ ID NO 1064
<211> LENGTH: 20
<212> TYPE: DNA
<213> ORGANISM: Felis catus

<400> SEQUENCE: 1064
gagagagagt gcacacaagt                                        20

<210> SEQ ID NO 1065
<211> LENGTH: 20
<212> TYPE: DNA
<213> ORGANISM: Felis catus

<400> SEQUENCE: 1065
gaggcatgag gtgatcctgg                                        20

<210> SEQ ID NO 1066
<211> LENGTH: 20
<212> TYPE: DNA
<213> ORGANISM: Felis catus

<400> SEQUENCE: 1066
gaggcctggc aggagatcct                                        20

<210> SEQ ID NO 1067
<211> LENGTH: 20

```
<212> TYPE: DNA
<213> ORGANISM: Felis catus

<400> SEQUENCE: 1067
gatctcaagc tgaacacttt                                            20

<210> SEQ ID NO 1068
<211> LENGTH: 20
<212> TYPE: DNA
<213> ORGANISM: Felis catus

<400> SEQUENCE: 1068
gatgggtgag agcagatgga                                            20

<210> SEQ ID NO 1069
<211> LENGTH: 20
<212> TYPE: DNA
<213> ORGANISM: Felis catus

<400> SEQUENCE: 1069
gatttttatc tctttgtctt                                            20

<210> SEQ ID NO 1070
<211> LENGTH: 20
<212> TYPE: DNA
<213> ORGANISM: Felis catus

<400> SEQUENCE: 1070
gcacaggtgc gtgggtgacg                                            20

<210> SEQ ID NO 1071
<211> LENGTH: 20
<212> TYPE: DNA
<213> ORGANISM: Felis catus

<400> SEQUENCE: 1071
gccatcaacg aatattgcat                                            20

<210> SEQ ID NO 1072
<211> LENGTH: 20
<212> TYPE: DNA
<213> ORGANISM: Felis catus

<400> SEQUENCE: 1072
gcctttggag cttctggggg                                            20

<210> SEQ ID NO 1073
<211> LENGTH: 20
<212> TYPE: DNA
<213> ORGANISM: Felis catus

<400> SEQUENCE: 1073
gcttctgggg ggggggtgt                                             20

<210> SEQ ID NO 1074
<211> LENGTH: 20
<212> TYPE: DNA
<213> ORGANISM: Felis catus

<400> SEQUENCE: 1074
ggaaggagta gcaggaaaca                                            20

<210> SEQ ID NO 1075
```

-continued

```
<211> LENGTH: 20
<212> TYPE: DNA
<213> ORGANISM: Felis catus

<400> SEQUENCE: 1075
ggaagggact ccctggcttt                                              20

<210> SEQ ID NO 1076
<211> LENGTH: 20
<212> TYPE: DNA
<213> ORGANISM: Felis catus

<400> SEQUENCE: 1076
ggaatttctt gcatgactac                                              20

<210> SEQ ID NO 1077
<211> LENGTH: 20
<212> TYPE: DNA
<213> ORGANISM: Felis catus

<400> SEQUENCE: 1077
ggagaacgga ctcttatcca                                              20

<210> SEQ ID NO 1078
<211> LENGTH: 20
<212> TYPE: DNA
<213> ORGANISM: Felis catus

<400> SEQUENCE: 1078
ggcacaggtg cgtgggtgac                                              20

<210> SEQ ID NO 1079
<211> LENGTH: 20
<212> TYPE: DNA
<213> ORGANISM: Felis catus

<400> SEQUENCE: 1079
ggcctttgga gcttctgggg                                              20

<210> SEQ ID NO 1080
<211> LENGTH: 20
<212> TYPE: DNA
<213> ORGANISM: Felis catus

<400> SEQUENCE: 1080
gggacggagc ggaatcactg                                              20

<210> SEQ ID NO 1081
<211> LENGTH: 20
<212> TYPE: DNA
<213> ORGANISM: Felis catus

<400> SEQUENCE: 1081
gggagaggtt tggagatgga                                              20

<210> SEQ ID NO 1082
<211> LENGTH: 20
<212> TYPE: DNA
<213> ORGANISM: Felis catus

<400> SEQUENCE: 1082
ggtgcgtggg tgacgggggg                                              20
```

<210> SEQ ID NO 1083
<211> LENGTH: 20
<212> TYPE: DNA
<213> ORGANISM: Felis catus

<400> SEQUENCE: 1083
gtcagtgcag agcctgacac                                          20

<210> SEQ ID NO 1084
<211> LENGTH: 20
<212> TYPE: DNA
<213> ORGANISM: Felis catus

<400> SEQUENCE: 1084
gtcctgagac tccctagta                                           20

<210> SEQ ID NO 1085
<211> LENGTH: 20
<212> TYPE: DNA
<213> ORGANISM: Felis catus

<400> SEQUENCE: 1085
gtgagttgct ctcaagtggc                                          20

<210> SEQ ID NO 1086
<211> LENGTH: 20
<212> TYPE: DNA
<213> ORGANISM: Felis catus

<400> SEQUENCE: 1086
gtgcccggag gcaccggtca                                          20

<210> SEQ ID NO 1087
<211> LENGTH: 20
<212> TYPE: DNA
<213> ORGANISM: Felis catus

<400> SEQUENCE: 1087
gtgcgtgggt gacgggggg                                           20

<210> SEQ ID NO 1088
<211> LENGTH: 20
<212> TYPE: DNA
<213> ORGANISM: Felis catus

<400> SEQUENCE: 1088
gtgttcaaga ggcttgaggt                                          20

<210> SEQ ID NO 1089
<211> LENGTH: 20
<212> TYPE: DNA
<213> ORGANISM: Felis catus

<400> SEQUENCE: 1089
gtgttctgtg cgggaagcgt                                          20

<210> SEQ ID NO 1090
<211> LENGTH: 20
<212> TYPE: DNA
<213> ORGANISM: Felis catus

<400> SEQUENCE: 1090 gttttttagtc gtagaatgga                                         20

```
<210> SEQ ID NO 1091
<211> LENGTH: 20
<212> TYPE: DNA
<213> ORGANISM: Felis catus

<400> SEQUENCE: 1091
tacatttaat tgtatacttt                                                    20

<210> SEQ ID NO 1092
<211> LENGTH: 20
<212> TYPE: DNA
<213> ORGANISM: Felis catus

<400> SEQUENCE: 1092
tacgcacagt tggaaaatag                                                    20

<210> SEQ ID NO 1093
<211> LENGTH: 20
<212> TYPE: DNA
<213> ORGANISM: Felis catus

<400> SEQUENCE: 1093
tacgggcacc cagggcacat                                                    20

<210> SEQ ID NO 1094
<211> LENGTH: 20
<212> TYPE: DNA
<213> ORGANISM: Felis catus

<400> SEQUENCE: 1094
tagcagctga cacgatgagg                                                    20

<210> SEQ ID NO 1095
<211> LENGTH: 20
<212> TYPE: DNA
<213> ORGANISM: Felis catus

<400> SEQUENCE: 1095
tatctccagg acttaaactt                                                    20

<210> SEQ ID NO 1096
<211> LENGTH: 20
<212> TYPE: DNA
<213> ORGANISM: Felis catus

<400> SEQUENCE: 1096
tattctctca tctgcaaaat                                                    20

<210> SEQ ID NO 1097
<211> LENGTH: 20
<212> TYPE: DNA
<213> ORGANISM: Felis catus

<400> SEQUENCE: 1097
tcagactctc ttcccaggaa                                                    20

<210> SEQ ID NO 1098
<211> LENGTH: 20
<212> TYPE: DNA
<213> ORGANISM: Felis catus

<400> SEQUENCE: 1098
tcagttccac tgctgttctt                                                    20
```

<210> SEQ ID NO 1099
<211> LENGTH: 20
<212> TYPE: DNA
<213> ORGANISM: Felis catus

<400> SEQUENCE: 1099
tcatcctggc aggggcgcct          20

<210> SEQ ID NO 1100
<211> LENGTH: 20
<212> TYPE: DNA
<213> ORGANISM: Felis catus

<400> SEQUENCE: 1100
tcccactctt aacagcccaa          20

<210> SEQ ID NO 1101
<211> LENGTH: 20
<212> TYPE: DNA
<213> ORGANISM: Felis catus

<400> SEQUENCE: 1101
tctagcagct gacacgatga          20

<210> SEQ ID NO 1102
<211> LENGTH: 20
<212> TYPE: DNA
<213> ORGANISM: Felis catus

<400> SEQUENCE: 1102
tctgggatgt aagcagtcct          20

<210> SEQ ID NO 1103
<211> LENGTH: 20
<212> TYPE: DNA
<213> ORGANISM: Felis catus

<400> SEQUENCE: 1103
tgagcggttt cctcttcctt          20

<210> SEQ ID NO 1104
<211> LENGTH: 20
<212> TYPE: DNA
<213> ORGANISM: Felis catus

<400> SEQUENCE: 1104
tgaggcatga ggtgatcctg          20

<210> SEQ ID NO 1105
<211> LENGTH: 20
<212> TYPE: DNA
<213> ORGANISM: Felis catus

<400> SEQUENCE: 1105
tgatggagga gggtgagaca          20

<210> SEQ ID NO 1106
<211> LENGTH: 20
<212> TYPE: DNA
<213> ORGANISM: Felis catus

<400> SEQUENCE: 1106

```
tgcatgacta cgggcaccca                                               20

<210> SEQ ID NO 1107
<211> LENGTH: 20
<212> TYPE: DNA
<213> ORGANISM: Felis catus

<400> SEQUENCE: 1107
tgcccggagg caccggtcag                                               20

<210> SEQ ID NO 1108
<211> LENGTH: 20
<212> TYPE: DNA
<213> ORGANISM: Felis catus

<400> SEQUENCE: 1108
tgggaaccag gatagtttga                                               20

<210> SEQ ID NO 1109
<211> LENGTH: 20
<212> TYPE: DNA
<213> ORGANISM: Felis catus

<400> SEQUENCE: 1109
tgggctagag gttcttgcta                                               20

<210> SEQ ID NO 1110
<211> LENGTH: 20
<212> TYPE: DNA
<213> ORGANISM: Felis catus

<400> SEQUENCE: 1110
tggggggggg ggtgtgggct                                               20

<210> SEQ ID NO 1111
<211> LENGTH: 20
<212> TYPE: DNA
<213> ORGANISM: Felis catus

<400> SEQUENCE: 1111
ttaagtttac tgatggagga                                               20

<210> SEQ ID NO 1112
<211> LENGTH: 20
<212> TYPE: DNA
<213> ORGANISM: Felis catus

<400> SEQUENCE: 1112
ttacgcacag ttggaaaata                                               20

<210> SEQ ID NO 1113
<211> LENGTH: 20
<212> TYPE: DNA
<213> ORGANISM: Felis catus

<400> SEQUENCE: 1113
ttacttcctt aagggtgaga                                               20

<210> SEQ ID NO 1114
<211> LENGTH: 20
<212> TYPE: DNA
<213> ORGANISM: Felis catus

<400> SEQUENCE: 1114
```

```
ttgctggtga cccaagagct                                               20

<210> SEQ ID NO 1115
<211> LENGTH: 20
<212> TYPE: DNA
<213> ORGANISM: Felis catus

<400> SEQUENCE: 1115
ttgtttcaga tttggccact                                               20

<210> SEQ ID NO 1116
<211> LENGTH: 20
<212> TYPE: DNA
<213> ORGANISM: Felis catus

<400> SEQUENCE: 1116
tttggagctt ctgggggggg                                               20

<210> SEQ ID NO 1117
<211> LENGTH: 20
<212> TYPE: DNA
<213> ORGANISM: Felis catus

<400> SEQUENCE: 1117
tttgtcctca agagtaggaa                                               20

<210> SEQ ID NO 1118
<211> LENGTH: 20
<212> TYPE: DNA
<213> ORGANISM: Felis catus

<400> SEQUENCE: 1118 ttttttttctt tctaggttcg                                              20

<210> SEQ ID NO 1119
<211> LENGTH: 20
<212> TYPE: DNA
<213> ORGANISM: Felis catus

<400> SEQUENCE: 1119
aaaaatccag gattgctacg                                               20

<210> SEQ ID NO 1120
<211> LENGTH: 20
<212> TYPE: DNA
<213> ORGANISM: Felis catus

<400> SEQUENCE: 1120
aaaggccgaa acaggcaggc                                               20

<210> SEQ ID NO 1121
<211> LENGTH: 20
<212> TYPE: DNA
<213> ORGANISM: Felis catus

<400> SEQUENCE: 1121
aaatcctctc cgtgtctcag                                               20

<210> SEQ ID NO 1122
<211> LENGTH: 20
<212> TYPE: DNA
<213> ORGANISM: Felis catus
```

```
<400> SEQUENCE: 1122
acagagcagt tggctcagca                                              20

<210> SEQ ID NO 1123
<211> LENGTH: 20
<212> TYPE: DNA
<213> ORGANISM: Felis catus

<400> SEQUENCE: 1123 acagggtga cagttggagc                                               20

<210> SEQ ID NO 1124
<211> LENGTH: 20
<212> TYPE: DNA
<213> ORGANISM: Felis catus

<400> SEQUENCE: 1124
acatgtgctc attgagagca                                              20

<210> SEQ ID NO 1125
<211> LENGTH: 20
<212> TYPE: DNA
<213> ORGANISM: Felis catus

<400> SEQUENCE: 1125
acgtagcata tttccaactc                                              20

<210> SEQ ID NO 1126
<211> LENGTH: 20
<212> TYPE: DNA
<213> ORGANISM: Felis catus

<400> SEQUENCE: 1126
actgcttgtg ctggcattgc                                              20

<210> SEQ ID NO 1127
<211> LENGTH: 20
<212> TYPE: DNA
<213> ORGANISM: Felis catus

<400> SEQUENCE: 1127
agagagagag tgcacacaag                                              20

<210> SEQ ID NO 1128
<211> LENGTH: 20
<212> TYPE: DNA
<213> ORGANISM: Felis catus

<400> SEQUENCE: 1128
agatctcaag ctgaacactt                                              20

<210> SEQ ID NO 1129
<211> LENGTH: 20
<212> TYPE: DNA
<213> ORGANISM: Felis catus

<400> SEQUENCE: 1129
agccatcaac gaatattgca                                              20

<210> SEQ ID NO 1130
<211> LENGTH: 20
<212> TYPE: DNA
<213> ORGANISM: Felis catus
```

<400> SEQUENCE: 1130
agctgggaca acagagcagt                                         20

<210> SEQ ID NO 1131
<211> LENGTH: 20
<212> TYPE: DNA
<213> ORGANISM: Felis catus

<400> SEQUENCE: 1131
agcttctggg ggggggggtg                                         20

<210> SEQ ID NO 1132
<211> LENGTH: 20
<212> TYPE: DNA
<213> ORGANISM: Felis catus

<400> SEQUENCE: 1132
aggaagggac tccctggctt                                         20

<210> SEQ ID NO 1133
<211> LENGTH: 20
<212> TYPE: DNA
<213> ORGANISM: Felis catus

<400> SEQUENCE: 1133
aggagccttg tcagttctgg                                         20

<210> SEQ ID NO 1134
<211> LENGTH: 20
<212> TYPE: DNA
<213> ORGANISM: Felis catus

<400> SEQUENCE: 1134
agggctggtc agtgtatttc                                         20

<210> SEQ ID NO 1135
<211> LENGTH: 20
<212> TYPE: DNA
<213> ORGANISM: Felis catus

<400> SEQUENCE: 1135
agtgatttgt agcccaagga                                         20

<210> SEQ ID NO 1136
<211> LENGTH: 20
<212> TYPE: DNA
<213> ORGANISM: Felis catus

<400> SEQUENCE: 1136
atacatttaa ttgtatactt                                         20

<210> SEQ ID NO 1137
<211> LENGTH: 20
<212> TYPE: DNA
<213> ORGANISM: Felis catus

<400> SEQUENCE: 1137 atagggact aatatcggtg                                          20

<210> SEQ ID NO 1138
<211> LENGTH: 20
<212> TYPE: DNA

-continued

<213> ORGANISM: Felis catus

<400> SEQUENCE: 1138
atatgtgagt tgctctcaag					20

<210> SEQ ID NO 1139
<211> LENGTH: 20
<212> TYPE: DNA
<213> ORGANISM: Felis catus

<400> SEQUENCE: 1139
atcatgacct gagccgaagt					20

<210> SEQ ID NO 1140
<211> LENGTH: 20
<212> TYPE: DNA
<213> ORGANISM: Felis catus

<400> SEQUENCE: 1140
atgagagctt tgtgaagaag					20

<210> SEQ ID NO 1141
<211> LENGTH: 20
<212> TYPE: DNA
<213> ORGANISM: Felis catus

<400> SEQUENCE: 1141
atgaggtgat cctgggggaa					20

<210> SEQ ID NO 1142
<211> LENGTH: 20
<212> TYPE: DNA
<213> ORGANISM: Felis catus

<400> SEQUENCE: 1142
attgctggtg acccaagagc					20

<210> SEQ ID NO 1143
<211> LENGTH: 20
<212> TYPE: DNA
<213> ORGANISM: Felis catus

<400> SEQUENCE: 1143
attgtttcag atttggccac					20

<210> SEQ ID NO 1144
<211> LENGTH: 20
<212> TYPE: DNA
<213> ORGANISM: Felis catus

<400> SEQUENCE: 1144
caactattca ctaatgtttc					20

<210> SEQ ID NO 1145
<211> LENGTH: 20
<212> TYPE: DNA
<213> ORGANISM: Felis catus

<400> SEQUENCE: 1145
caatggaaat gaattactgt					20

<210> SEQ ID NO 1146
<211> LENGTH: 20

```
<212> TYPE: DNA
<213> ORGANISM: Felis catus

<400> SEQUENCE: 1146
cacaataggg gagagttagt                                               20

<210> SEQ ID NO 1147
<211> LENGTH: 20
<212> TYPE: DNA
<213> ORGANISM: Felis catus

<400> SEQUENCE: 1147
caggaaacag gggtgacagt                                               20

<210> SEQ ID NO 1148
<211> LENGTH: 20
<212> TYPE: DNA
<213> ORGANISM: Felis catus

<400> SEQUENCE: 1148
caggtgaggg agacatcgca                                               20

<210> SEQ ID NO 1149
<211> LENGTH: 20
<212> TYPE: DNA
<213> ORGANISM: Felis catus

<400> SEQUENCE: 1149
catcacctcc agttggtctt                                               20

<210> SEQ ID NO 1150
<211> LENGTH: 20
<212> TYPE: DNA
<213> ORGANISM: Felis catus

<400> SEQUENCE: 1150
ccaagagctg ggcgtcaaga                                               20

<210> SEQ ID NO 1151
<211> LENGTH: 20
<212> TYPE: DNA
<213> ORGANISM: Felis catus

<400> SEQUENCE: 1151
ccacaaagtt aagcggcagc                                               20

<210> SEQ ID NO 1152
<211> LENGTH: 20
<212> TYPE: DNA
<213> ORGANISM: Felis catus

<400> SEQUENCE: 1152
ccacaggcct ttggagcttc                                               20

<210> SEQ ID NO 1153
<211> LENGTH: 20
<212> TYPE: DNA
<213> ORGANISM: Felis catus

<400> SEQUENCE: 1153
ccatgcagtc aggggctaca                                               20

<210> SEQ ID NO 1154
```

-continued

```
<211> LENGTH: 20
<212> TYPE: DNA
<213> ORGANISM: Felis catus

<400> SEQUENCE: 1154
cccaccattt tctgcttctt                                              20

<210> SEQ ID NO 1155
<211> LENGTH: 20
<212> TYPE: DNA
<213> ORGANISM: Felis catus

<400> SEQUENCE: 1155
ccctggcttt gggaagcttc                                              20

<210> SEQ ID NO 1156
<211> LENGTH: 20
<212> TYPE: DNA
<213> ORGANISM: Felis catus

<400> SEQUENCE: 1156
cctcttcttg cctccctcac                                              20

<210> SEQ ID NO 1157
<211> LENGTH: 20
<212> TYPE: DNA
<213> ORGANISM: Felis catus

<400> SEQUENCE: 1157
cgaattacct tacgcacagt                                              20

<210> SEQ ID NO 1158
<211> LENGTH: 20
<212> TYPE: DNA
<213> ORGANISM: Felis catus

<400> SEQUENCE: 1158
cggactctta tccagggtct                                              20

<210> SEQ ID NO 1159
<211> LENGTH: 20
<212> TYPE: DNA
<213> ORGANISM: Felis catus

<400> SEQUENCE: 1159
ctacgggcac ccagggcaca                                              20

<210> SEQ ID NO 1160
<211> LENGTH: 20
<212> TYPE: DNA
<213> ORGANISM: Felis catus

<400> SEQUENCE: 1160
ctattctctc atctgcaaaa                                              20

<210> SEQ ID NO 1161
<211> LENGTH: 20
<212> TYPE: DNA
<213> ORGANISM: Felis catus

<400> SEQUENCE: 1161
ctcagttcca ctgctgttct                                              20
```

```
<210> SEQ ID NO 1162
<211> LENGTH: 20
<212> TYPE: DNA
<213> ORGANISM: Felis catus

<400> SEQUENCE: 1162
ctcatgcctg aatcctgctt                                              20

<210> SEQ ID NO 1163
<211> LENGTH: 20
<212> TYPE: DNA
<213> ORGANISM: Felis catus

<400> SEQUENCE: 1163
ctcattgaga gcatggggac                                              20

<210> SEQ ID NO 1164
<211> LENGTH: 20
<212> TYPE: DNA
<213> ORGANISM: Felis catus

<400> SEQUENCE: 1164
ctcttatcca gggtcttgga                                              20

<210> SEQ ID NO 1165
<211> LENGTH: 20
<212> TYPE: DNA
<213> ORGANISM: Felis catus

<400> SEQUENCE: 1165
ctgggggggg gggtgtgggc                                              20

<210> SEQ ID NO 1166
<211> LENGTH: 20
<212> TYPE: DNA
<213> ORGANISM: Felis catus

<400> SEQUENCE: 1166 ctgttctttta cacctaaagc                                             20

<210> SEQ ID NO 1167
<211> LENGTH: 20
<212> TYPE: DNA
<213> ORGANISM: Felis catus

<400> SEQUENCE: 1167
cttcccagga agggactccc                                              20

<210> SEQ ID NO 1168
<211> LENGTH: 20
<212> TYPE: DNA
<213> ORGANISM: Felis catus

<400> SEQUENCE: 1168
cttgatggct gctattcctt                                              20

<210> SEQ ID NO 1169
<211> LENGTH: 20
<212> TYPE: DNA
<213> ORGANISM: Felis catus

<400> SEQUENCE: 1169
cttgggatta agtttactga                                              20
```

<210> SEQ ID NO 1170
<211> LENGTH: 20
<212> TYPE: DNA
<213> ORGANISM: Felis catus

<400> SEQUENCE: 1170
ctttggttga cctggcacct                                              20

<210> SEQ ID NO 1171
<211> LENGTH: 20
<212> TYPE: DNA
<213> ORGANISM: Felis catus

<400> SEQUENCE: 1171
gaaggtgagt cagaagaccc                                              20

<210> SEQ ID NO 1172
<211> LENGTH: 20
<212> TYPE: DNA
<213> ORGANISM: Felis catus

<400> SEQUENCE: 1172
gactcaggtg atgacctgag                                              20

<210> SEQ ID NO 1173
<211> LENGTH: 20
<212> TYPE: DNA
<213> ORGANISM: Felis catus

<400> SEQUENCE: 1173
gaggggggca ctgcttgtgc                                              20

<210> SEQ ID NO 1174
<211> LENGTH: 20
<212> TYPE: DNA
<213> ORGANISM: Felis catus

<400> SEQUENCE: 1174
gatgaggcat gaggtgatcc                                              20

<210> SEQ ID NO 1175
<211> LENGTH: 20
<212> TYPE: DNA
<213> ORGANISM: Felis catus

<400> SEQUENCE: 1175
gatgtaagca gtcctgggag                                              20

<210> SEQ ID NO 1176
<211> LENGTH: 20
<212> TYPE: DNA
<213> ORGANISM: Felis catus

<400> SEQUENCE: 1176
gattttccac tctgttgttc                                              20

<210> SEQ ID NO 1177
<211> LENGTH: 20
<212> TYPE: DNA
<213> ORGANISM: Felis catus

<400> SEQUENCE: 1177
gattttttgt ctacctgtag                                              20

<210> SEQ ID NO 1178
<211> LENGTH: 20
<212> TYPE: DNA
<213> ORGANISM: Felis catus

<400> SEQUENCE: 1178
ggagagttag ttgggggtag                                                    20

<210> SEQ ID NO 1179
<211> LENGTH: 20
<212> TYPE: DNA
<213> ORGANISM: Felis catus

<400> SEQUENCE: 1179
ggaggcctgg caggagatcc                                                    20

<210> SEQ ID NO 1180
<211> LENGTH: 20
<212> TYPE: DNA
<213> ORGANISM: Felis catus

<400> SEQUENCE: 1180
gggccaaacc tggagctact                                                    20

<210> SEQ ID NO 1181
<211> LENGTH: 20
<212> TYPE: DNA
<213> ORGANISM: Felis catus

<400> SEQUENCE: 1181
ggggggggcc gtctccatcc                                                    20

<210> SEQ ID NO 1182
<211> LENGTH: 20
<212> TYPE: DNA
<213> ORGANISM: Felis catus

<400> SEQUENCE: 1182
gggtgagaca gggccaaacc                                                    20

<210> SEQ ID NO 1183
<211> LENGTH: 20
<212> TYPE: DNA
<213> ORGANISM: Felis catus

<400> SEQUENCE: 1183
ggtccctgcc cacaggcctt                                                    20

<210> SEQ ID NO 1184
<211> LENGTH: 20
<212> TYPE: DNA
<213> ORGANISM: Felis catus

<400> SEQUENCE: 1184
ggtcttggat ggactagtca                                                    20

<210> SEQ ID NO 1185
<211> LENGTH: 20
<212> TYPE: DNA
<213> ORGANISM: Felis catus

<400> SEQUENCE: 1185
ggtgttcaag aggcttgagg                                          20

<210> SEQ ID NO 1186
<211> LENGTH: 20
<212> TYPE: DNA
<213> ORGANISM: Felis catus

<400> SEQUENCE: 1186
gtagaatgga gggagaggtt                                          20

<210> SEQ ID NO 1187
<211> LENGTH: 20
<212> TYPE: DNA
<213> ORGANISM: Felis catus

<400> SEQUENCE: 1187
gtcatcctgg cagggcgcc                                           20

<210> SEQ ID NO 1188
<211> LENGTH: 20
<212> TYPE: DNA
<213> ORGANISM: Felis catus

<400> SEQUENCE: 1188
gtctgggatg taagcagtcc                                          20

<210> SEQ ID NO 1189
<211> LENGTH: 20
<212> TYPE: DNA
<213> ORGANISM: Felis catus

<400> SEQUENCE: 1189
gtcttttttg cggtggccaa                                          20

<210> SEQ ID NO 1190
<211> LENGTH: 20
<212> TYPE: DNA
<213> ORGANISM: Felis catus

<400> SEQUENCE: 1190
gtgagcggtt tcctcttcct                                          20

<210> SEQ ID NO 1191
<211> LENGTH: 20
<212> TYPE: DNA
<213> ORGANISM: Felis catus

<400> SEQUENCE: 1191
gtgcagctgc accccagggc                                          20

<210> SEQ ID NO 1192
<211> LENGTH: 20
<212> TYPE: DNA
<213> ORGANISM: Felis catus

<400> SEQUENCE: 1192
gttaaaaaaa aatgtcaccc                                          20

<210> SEQ ID NO 1193
<211> LENGTH: 20
<212> TYPE: DNA
<213> ORGANISM: Felis catus

<400> SEQUENCE: 1193
gtttccttca ataattttca                                               20

<210> SEQ ID NO 1194
<211> LENGTH: 20
<212> TYPE: DNA
<213> ORGANISM: Felis catus

<400> SEQUENCE: 1194
tagaaaatgt tccgtctgtc                                               20

<210> SEQ ID NO 1195
<211> LENGTH: 20
<212> TYPE: DNA
<213> ORGANISM: Felis catus

<400> SEQUENCE: 1195
tagggacgga gcggaatcac                                               20

<210> SEQ ID NO 1196
<211> LENGTH: 20
<212> TYPE: DNA
<213> ORGANISM: Felis catus

<400> SEQUENCE: 1196
tagtaagtcc aacctcctct                                               20

<210> SEQ ID NO 1197
<211> LENGTH: 20
<212> TYPE: DNA
<213> ORGANISM: Felis catus

<400> SEQUENCE: 1197
tagtccctta aatgtcatcc                                               20

<210> SEQ ID NO 1198
<211> LENGTH: 20
<212> TYPE: DNA
<213> ORGANISM: Felis catus

<400> SEQUENCE: 1198
tattcactaa tgtttctgga                                               20

<210> SEQ ID NO 1199
<211> LENGTH: 20
<212> TYPE: DNA
<213> ORGANISM: Felis catus

<400> SEQUENCE: 1199
tcaagatggg tgagagcaga                                               20

<210> SEQ ID NO 1200
<211> LENGTH: 20
<212> TYPE: DNA
<213> ORGANISM: Felis catus

<400> SEQUENCE: 1200
tccccttgtg cccaccttga                                               20

<210> SEQ ID NO 1201
<211> LENGTH: 20
<212> TYPE: DNA
<213> ORGANISM: Felis catus

<400> SEQUENCE: 1201
tccctcctgg cacaggtgcg 20

<210> SEQ ID NO 1202
<211> LENGTH: 20
<212> TYPE: DNA
<213> ORGANISM: Felis catus

<400> SEQUENCE: 1202
tcctggcagg ggcgcctggg 20

<210> SEQ ID NO 1203
<211> LENGTH: 20
<212> TYPE: DNA
<213> ORGANISM: Felis catus

<400> SEQUENCE: 1203
tctcactcct ttacctccca 20

<210> SEQ ID NO 1204
<211> LENGTH: 20
<212> TYPE: DNA
<213> ORGANISM: Felis catus

<400> SEQUENCE: 1204
tctctccaga aatcggtctg 20

<210> SEQ ID NO 1205
<211> LENGTH: 20
<212> TYPE: DNA
<213> ORGANISM: Felis catus

<400> SEQUENCE: 1205
tcttgggaga gtatcgcatt 20

<210> SEQ ID NO 1206
<211> LENGTH: 20
<212> TYPE: DNA
<213> ORGANISM: Felis catus

<400> SEQUENCE: 1206
tgacctggca ccttggtatg 20

<210> SEQ ID NO 1207
<211> LENGTH: 20
<212> TYPE: DNA
<213> ORGANISM: Felis catus

<400> SEQUENCE: 1207
tgagagcact taagcacctt 20

<210> SEQ ID NO 1208
<211> LENGTH: 20
<212> TYPE: DNA
<213> ORGANISM: Felis catus

<400> SEQUENCE: 1208
tgatgttttt agtcgtagaa 20

<210> SEQ ID NO 1209
<211> LENGTH: 20
<212> TYPE: DNA
<213> ORGANISM: Felis catus

<400> SEQUENCE: 1209
tgatttttat ctctttgtct                                        20

<210> SEQ ID NO 1210
<211> LENGTH: 20
<212> TYPE: DNA
<213> ORGANISM: Felis catus

<400> SEQUENCE: 1210
tgcgggaagc gtgggaggcc                                        20

<210> SEQ ID NO 1211
<211> LENGTH: 20
<212> TYPE: DNA
<213> ORGANISM: Felis catus

<400> SEQUENCE: 1211
tgctcaaatt gtttcagatt                                        20

<210> SEQ ID NO 1212
<211> LENGTH: 20
<212> TYPE: DNA
<213> ORGANISM: Felis catus

<400> SEQUENCE: 1212
tggagggaga ggtttggaga                                        20

<210> SEQ ID NO 1213
<211> LENGTH: 20
<212> TYPE: DNA
<213> ORGANISM: Felis catus

<400> SEQUENCE: 1213
tggcaggaga tcctgggaca                                        20

<210> SEQ ID NO 1214
<211> LENGTH: 20
<212> TYPE: DNA
<213> ORGANISM: Felis catus

<400> SEQUENCE: 1214
tggttgttca gactccctcc                                        20

<210> SEQ ID NO 1215
<211> LENGTH: 20
<212> TYPE: DNA
<213> ORGANISM: Felis catus

<400> SEQUENCE: 1215
tgtaggagcc ttgtcagttc                                        20

<210> SEQ ID NO 1216
<211> LENGTH: 20
<212> TYPE: DNA
<213> ORGANISM: Felis catus

<400> SEQUENCE: 1216
tgtggagctc caactcacaa                                        20

<210> SEQ ID NO 1217
<211> LENGTH: 20
<212> TYPE: DNA

```
<213> ORGANISM: Felis catus

<400> SEQUENCE: 1217
tgtgttctgt gcgggaagcg                                              20

<210> SEQ ID NO 1218
<211> LENGTH: 20
<212> TYPE: DNA
<213> ORGANISM: Felis catus

<400> SEQUENCE: 1218
ttaagcacct ttggttgacc                                              20

<210> SEQ ID NO 1219
<211> LENGTH: 20
<212> TYPE: DNA
<213> ORGANISM: Felis catus

<400> SEQUENCE: 1219
ttagacacat cacctccagt                                              20

<210> SEQ ID NO 1220
<211> LENGTH: 20
<212> TYPE: DNA
<213> ORGANISM: Felis catus

<400> SEQUENCE: 1220
ttatctccag gacttaaact                                              20

<210> SEQ ID NO 1221
<211> LENGTH: 20
<212> TYPE: DNA
<213> ORGANISM: Felis catus

<400> SEQUENCE: 1221
ttatgacgtc tttttttgcgg                                             20

<210> SEQ ID NO 1222
<211> LENGTH: 20
<212> TYPE: DNA
<213> ORGANISM: Felis catus

<400> SEQUENCE: 1222
ttgcacagtt aggtcgattt                                              20

<210> SEQ ID NO 1223
<211> LENGTH: 20
<212> TYPE: DNA
<213> ORGANISM: Felis catus

<400> SEQUENCE: 1223
ttgggcacaa gtaaggtttt                                              20

<210> SEQ ID NO 1224
<211> LENGTH: 20
<212> TYPE: DNA
<213> ORGANISM: Felis catus

<400> SEQUENCE: 1224
tttaaacatt tatatcagta                                              20

<210> SEQ ID NO 1225
<211> LENGTH: 20
```

```
<212> TYPE: DNA
<213> ORGANISM: Felis catus

<400> SEQUENCE: 1225
tttgggaagc ttctggtttt                                               20

<210> SEQ ID NO 1226
<211> LENGTH: 4516
<212> TYPE: DNA
<213> ORGANISM: Felis catus
<220> FEATURE:
<221> NAME/KEY: modified_base
<222> LOCATION: (1994)..(1994)
<223> OTHER INFORMATION: a, c, t, g, unknown or other
<220> FEATURE:
<221> NAME/KEY: modified_base
<222> LOCATION: (1996)..(1996)
<223> OTHER INFORMATION: a, c, t, g, unknown or other
<220> FEATURE:
<221> NAME/KEY: modified_base
<222> LOCATION: (2927)..(2927)
<223> OTHER INFORMATION: a, c, t, g, unknown or other
<220> FEATURE:
<221> NAME/KEY: modified_base
<222> LOCATION: (2929)..(2929)
<223> OTHER INFORMATION: a, c, t, g, unknown or other
<220> FEATURE:
<221> NAME/KEY: modified_base
<222> LOCATION: (3615)..(3664)
<223> OTHER INFORMATION: a, c, t, g, unknown or other

<400> SEQUENCE: 1226
ggcaacagct cgtgcaaagg ccctggcgtg gtcaagaagc agaaaggaga cccgtgaggg    60
aggagagaat ggcaggagta gatgcagaaa agcagcaggt cttcggtggg gcgctggtta   120
cgcagagcac acgacggtcc caggccacag aagcagtctg gcttttcctc ggattgtatc   180
tccagagaga taatggtgtg aatactatga acagtataga gaaactcaaa ggaagaagcc   240
agttgggggg aaatgatatt tctgtgtctg cctgaggtgc tattaaagtg accaggtgag   300
gggcgcctgg gtggcgcagt cggttaagcg tccggcttca gccaggtcac gatctcgcgg   360
tccgtgagtt cgagcccgc gtcaggctct gggctgatgg ctcggagcct ggagcctgtt   420
tccgattctg tgtctccctc tctctctgcc cctcccctgc tcatgctctg tctctctctg   480
tcccaaaaat aaataaacat tgaaaaaaaa attttaaaaa aaaaaaaaaa gaagaaaaaa   540
aaaaataaag tgaccaggtg acaggactcg gtcaagagac gactgaaacc tgggcaccag   600
catgtagggg agggttcagg gctccagaat cagattcagg agactggctc aagggaggcc   660
actgagcagg tcaaggacac agattatgac gaaggcaggg caggagccac cagagaccgg   720
cctccttttg gtacttgcta gctgtgagtc cactagctaa gcactgggtt tcctgaaaaa   780
tccgtaagtt gagaccagac catcttcaag gtcacatgta atgacaggct gacattggcc   840
atcattcggg aggcctgact tgggagactc tcttgcccct ttccccagtc aacctagaaa   900
atttcagttc tgaaattact ggtgtcagct gacacttgga cagagccctc aagacgggga   960
aggggagcca aggtagcgtc atctgttgac tcggggactt aggatcctgc ccacacatac  1020
atctcctccc tccacagccc ccaggcagtt ctgagaagca gcccagagag gcctggcggt  1080
gcctcctgga aaaggatgtt agacgcagcc ctcccaccct gccctactgt tgcagccaca  1140
gcaggtataa aagggttcca ggctggggag ggagcacctg ccactgcatc atgaagggg   1200 ctcgtgttct cgtgcttctc tgggctgcct tgctcttgat ctgggtgga agtaggtgtc   1260 tgggacatga gtgtctgggg acacagattc tccagggggtt ctaacacctt cccagggcac  1320
```

```
ttctgagcat ggcgggaagg ggaagggaag aatgtgtcct gatgaaggtc tttcaaaagg      1380
gagggtcagc ttgtctttgt gttccagatt gtgaaatttg cccagccgtg aagagggatg      1440
ttgacctatt cctgatggga acccctgaca aatatgttga gcaagtggca caatacaatg      1500
cacgacctgt agtattggca aatgccagaa acctgaagaa ctgcgttgat gcaaaaatga      1560
cagaagagga taaggagaat gctctcagcg tgctggtggg tctagctctg tgtctgtgcc      1620
tctgacgcct gtctgggggg tctgctcagg gcagtgcagg agggggttg ctcatgtttg       1680 ttctccacca tggcccttcc ctgggaatct gggaggagaa agacgccatg gctggggaag      1740
tagaggggat catgtgggga agactcagcc taccccctcaa gctttggggc tggcccaggc     1800
tgctcaacgc tgcttggcca ccagcttggg ggtctgcagg ccctcctgtg tccctggcat      1860
cacttggcct cagtgtcagg ccctcagctc tggccttcct gactccagcc tctccagcac      1920
gtgagactgg atcttcaaac tgtttgcact aggtgcttcc tatctccaaa cgtcagttcc      1980
tttctcttag abandnsctg agcaattatg ccatgaatca tatgcttgtt aggaagagcc       2040
tcctgggcag tggcaacagc tcgtgcaaag gccctggcgt ggtcaagaag cagaaaggag      2100
acccgtgagg gaggagagaa tggcaggagt agatgcagaa aagcagcagg tcttcggtgg      2160
ggcgctggtt acgcagagca cacgacggtc ccaggccaca gaagcagtct ggcttttcct      2220
cggattgtat ctccagagag ataatggtgt gaatactatg aacagtatag agaaactcaa      2280
aggaagaagc cagttggggg gaaatgatat tcctgtgtct gcctgaggtg ctattaaagt      2340
gaccaggtga caggactcgg tcaagagacg actagaacct gggcaccagc atgtagggga      2400
gggctcaggg ctccagaatc agattcagga gactggctca agggaggcca ctgagcaggt      2460
caaggacaca gattatgacg aaggcagggc aggagccacc agagaccggc ctccttttgg      2520
tacttgctag ctgtgagtcc actagctaag cactgggttt cctgaaaaat ccgtaagttg      2580
agaccagacc atcttcaagg tcacatgtaa tgacaggctg acattggcca tcattcggga      2640
ggcctgactt gggagactct cttgccccctt tccccagtca acctagaaaa tttcagttct      2700
gaaattactg gtgtcagctg acacttggac agagccctca agacggggaa ggggagccaa      2760
ggtagcgtca tctgttgact cggggactta ggatcctgcc cacacataca tctcctccct      2820
ccacagcccc caggcagttc tgagaagcag cccagagagg cctggcggtg cctcctggaa      2880
aaggatgtta gacgcagccc tcccacccctg ccctactgtt gcgabandns aagaggataa     2940
ggagaatgct ctcagcgtgc tggtgggtct agctctgtgt ctgtgcctct gacgcctgtc      3000 tgggggtct gctcagggca gtgcaggagg ggggttgctc atgtttgttc tccaccatgg        3060
cccttccctg ggaatctggg aggagaaaga cgccatggct ggggaagtag agggatcat       3120 gtggggaaga ctcagcctac ccctcaagct ttggggctgg cccaggctgc tcaacgctgc      3180
ttggccaccg gcttgggggt ctgcaggccc tcctgtgtcc ctggcatcac ttggcctcag      3240
tgtcaggccc tcagctctgg ccttcctgac tccagcctct ccagcacgtg agactggatc      3300
ttcaaactgt ttgcactagg tgcttcctat ctccaaacgt cagttccttt tctcttaact      3360
cctcaagttc catattccac ccccccccca aaaaaaaacc ctcatttgtc ttcattccct      3420
gggtcccaga gggccattct gtgcctcaaa tactgagaga gaggaggagg ggaggggaga      3480
agaggggcgg ggcagggagg gacgagggga ggtgagatgg ggcagcttcc aaaagccctc      3540
cccctgccct gccattctgt gcctcacata ccaagagaga ggatgatgga aggggagggg      3600
aggggagggg agggnnnnnn nnnnnnnnnn nnnnnnnnnn nnnnnnnnnn nnnnnnnnnn      3660
nnnngcttcc atccccacca cctgagcact ccccccagaaa agagtctgct gaacttacac     3720
```

```
tgcagggctt ccccccaggag gggtatctct gtgatcattt tggtgaagag gctgaggaaa    3780
ggttcccaga ggggatctct ctctctctct ctctctctct ctctctctct ctctgtggag    3840
cacgtcatgg ggacaggaga ggaaggccac cttgcccaga gtgagacctg gctcttggcc    3900 tatgcccac  cactctgacc cccagggtct ggccggaggc tacttctgaa atggagcact    3960
gcccccatgg tagcaagggg agtccagagg tcataagcag gttgtggggc agagaccctt    4020
ctcatcaccc tcccatatgt gacccagggt gtatattcca ccactccccc accatacata    4080
ctgaaaagtt cttgggctta cagaaggaaa gctgtcaccc agatgagtgg gccaggtctt    4140
ccaatgtcat agatgaagac tcaccctggt ccacagcaag tgtagggagt gaggggcacc    4200
ccacccaaag gtgagaaggt gatgagcaac gggcagtttg tcctcaccaa gacacaacca    4260
gccccccaac tgctgctaga ctcgcacaga actccctggg gactgatggc acctatgaca    4320
tctggacgct ttctgtgtaa tccctcccct ctggctgcct tccaaacagc cagatggctg    4380
tctgacatcc aaacctcaga tagcttgaaa ggtaaatatc aggaacctaa gggtgacgct    4440
tttgatctct gattcacaca tgagatcata aaagccccgc cccacttccc cgtggtctga    4500
cctaaattcg cccaaa                                                    4516

<210> SEQ ID NO 1227
<211> LENGTH: 4416
<212> TYPE: DNA
<213> ORGANISM: Felis catus

<400> SEQUENCE: 1227
tggttccgct ggcagaaccc aagaacagca gtggaactga gagttcctgc agaaaggttg      60
gcctcctcag aagacatcta ccaaagaagc agaaaatggt ggggcgcctg ggtggctcag     120
tcggttaaag tgtccaactt cggctcaggt catgatctca cagtttgtgg gtctgagacc     180
cgtgtcaggc tctgcactga cagctcagaa cctggagcct gctttggatt ctctctctct     240
ctctctctct ctctctctgc ccttcccact tgtgtgcact ctctctctct ttctctcaaa     300
ataaaacaat taagaaattt tttaaaaacg taaagacaga aaataggcaa ataccactga     360
gacacggaga ggatttgtga taaacccact caggtcatca cctgagtcac ccttaaattg     420
ccagggtgac attttttttt aacgtttatt tttaagagag agggtgagcg cttgcacacg     480
tgcaagtggg ggaggggcag agagagggag acacagactc caaagcagga ttcaggcatg     540
agctgtcagc acagggcctg atgccccgct cgaactcaca aaccttgaga tcatgacctg     600
agctgaagtc agtcacctaa ccgactgagc caccccaggcg cccctgccag gatgacattt     660
aagggactag aggctctgct gctgtgacaa atgccagagt tggaaatatg ctacgtggac     720 aacatttta tccttctgtg gtgatgaatc ctggggttac atgtatgtga tttaatttaa     780
tcctcacact taatccccat tttgcagatg agagaatagc ccaaggaaga ggaaaccgct     840
cacatgtgct cctgattcag cctgcctcca gtcccatgc tctcaatgag cacatgtcac     900 ctcccttgc catgtcccag gatctcctgc caggcctccc acgcttcccg cacagaacac     960
agacacgggg cacccggggg tgctaagatg cagttatttt attctagtca gcctgattga    1020
gagtgaatta ggtgaggaca ggtgtctgga ttccagcttt aggtgtaaag aacaggacag    1080
gaggatgggg ctcagaaggg gcatcagcgg caaagattca tctccccaaa gtgttcagct    1140
tgagatcttc tacggtgttc tgaactgctt cacccatgca atattcgttg atggctatct    1200
gggagagagt aagacgagga gggacagaag acctgagcgc atggcagcgc tatccattcc    1260
```

```
cccaggatca cctcatgcct catccccagt gattccgctc cgtccctagc aagaacctct   1320
agcccacaga ccgatttctg gagagagggc cgcgatcagt cagaccagga tggagacggc   1380
ccccccccg  tcacccacgc acctgtgcca ggagggagtc tgaacaacca gtgagggagg   1440
caagaagagg agaagattct ggagggcgcg atggggctg  ggcctgggtg aggggcaagg   1500
tagctgagtc tgggtccatg cgatgtctcc ctcacctgag actcatctgt caggtgtact   1560
ggatgtatgg aatgtgtatg tgtgtgttgt gaacaatccc atgtgccctg ggtgcccgta   1620
gtcatgcaag aaattccact tcttcacaaa gctctcattt tacagaatca gcacttaacg   1680
gcaagtagag gtaagagaca gactaaccaa aatcgaccta actgtgcaac aagaaaaata   1740
acagaaaaag atagttcacc agaaatacac tgaccagccc tggggtgcag ctgcacgtag   1800
ctaggagctg cctcgagggc ctcaggcacc agaacaacag agtggaaaat ctgactttag   1860
accctgaatt gatacagaag gaagtgagac tctgaaccaa aggaatagca gccatcaagg   1920
tgggcacaag gggaagtaaa acagaagcca aaaaccagaa gcttcccaaa gccagggagt   1980
cccttcctgg gaagagagtc tgagggcagg tgccttagtt tcaatattcc tccaccagaa   2040
ctgacaaggc tcctacatgt gcaggagctg aatgaagaac tttctctttc ctgtggaagg   2100
ctaaaatcct actcctgcaa ttctgacacc ccgaacctag aaagaaaaaa atcctacgag   2160
tcaacacgct ttctatgcca caccgatatt agtcccctat tttccaactg tgcgtaaggt   2220
aattcgcaca aagggacac  gtgtggtaga agaacaggct gggtgtgcac atggcgtgag   2280
gttgcgtatt ctatgtgctg tagagcggag caaaggttta tgtgctcgat tgtttatagc   2340
tcttacctgc catgtagccc ctgactgcat ggtctgtatg tggaatatta caatctgctg   2400
cacgcgcaac gtgaaggttg gggaggcggg gaaggaaagg aaattaccat gactagtcca   2460
tccaagaccc tggataagag tccgttctcc acgtagcaat cctggatttt tttcatggct   2520
gttctctctg gttcagtagc attgactttt gtgagggaca agtccaacag taattcattt   2580
ccattggcca ccgcaaaaaa gacgtcataa aaaatgggc  aagtttccgc tgaagacaca   2640
aacagaaaac accttcacaa aagaatcagc agagcaggag gttcctgttt gcccgccact   2700
tgagagcaac tcacatatat ccagggtctt ctgactcacc ttccgcagag acctgcccac   2760
tcccaggact gcttacatcc cagacagacg gaacattttc tatgaggcac tctcagcaga   2820
agagagcagc cggagagacc cctgaccggt gcctccgggc accccagcct gcctgtttcg   2880
gcctttcaaa taagcaccac taccccccaac taactctccc ctattgtgtg cacaactaat   2940
gatccctcca tctccaaacc tctccctcca ttctacgact aaaaacatca gggggttct    3000
gcaggactcc tggacaatga tctcccagct gccgcttaac tttgtggcta gaacctgttt   3060
ggagatcacc atgggaggta aaggagtgag ataagagcagg gcaaggatca ggaaggtcct   3120
ctgtccctcc atctgctctc acccatcttg acgcccagct cttgggtcac cagcaatgcc   3180
agcacaagca gtgcccccct catcgtgtca gctgctagaa tgctctgctc aggacaggat   3240
ttctgctgct ttataaacta ctagcacctt aagcccagcc cacacccccc ccccagaag   3300
ctccaaaggc ctgtgggcag ggacctggca catgtgggtg gctccctcaa cccttgggct   3360
gttaagagtg ggaagccctt cctactcttg aggacaaagc tcttggagag gatgtggttt   3420
tttcttttgcc aaagaccaac tggaggtgat gtgtctaagt gattccatgc tgagccaact   3480
gctctgttgt cccagctcca actgtcaccc ctgtttcctg ctactccttc cctcaaacta   3540
tcctggttcc caaatgcgat actctcccaa gacaaagaga taaaaatcac aggagggtc    3600
aaggacagat ctacaccact acaggtagac aaaaaaatcat ccaaaaacct tacttgtgcc   3660
```

```
caagtttaag tcctggagat aagtatgggg tgctagaccc acctcaagcc tcttgaacac    3720
cttaactgct gcagtctgtg gatcaagccc tgagaatggg tggacaccat ccttgggcta    3780
caaatcactc cctactaggg gagtctcagg acgcttgggc atgtaggcct cctcaagggc    3840
tggtaacgct ctaaattagg atcatgtcac ctgcttccct ctcaccctta aggaagtaaa    3900
tgcctgggca ccttcttgac tccaagtagc tccaggtttg gccctgtctc accctcctcc    3960
atcagtaaac ttaatcccaa gaggaggttg gacttactag cccatccaga aacattagtg    4020
aatagttgtg gggttgtaca gtttgtctct tatgtccatt gtgagttgga gctccacata    4080
ccaaggtgcc aggtcaacca aggtgctta agtgctctca agagctaaac tcaaccttct      4140
aatctaggaa agtagtttat tggcacaaac atgacgagat agtccatgaa aattattgaa    4200
ggaaactccc agtggccaaa tctgaaacaa tttgagcaaa caaaagaaat aacattgtat    4260
tggttgataa cccaaagtat acaattaaat gtatgagtcc atactgatat aaatgtttaa    4320
ataaataaat aaggagataa gagacagata ttctttacaa aagcattcta gataatacac    4380
ataggtactc tcccttaagg aggtggagct tattgc                              4416

<210> SEQ ID NO 1228
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1228
gttggaacca ttcaaaacag catagcaagt taaataagg ctagtccgtt atcaacttga     60
aaaagtggca ccgagtcggt gcttttttt                                      88

<210> SEQ ID NO 1229
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1229
ttggaaccat tcaaaacagc atagcaagtt aaaataaggc tagtccgtta tcaacttgaa    60
aaagtggcac cgagtcggtg cttttttt                                       87

<210> SEQ ID NO 1230
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1230
gttggaacca ttcaaaacag catagcaagt taaataagg ctagtccgtt atcaacttga     60
aaaagtggca ccgagtcggt gcttttt                                        87

<210> SEQ ID NO 1231
<211> LENGTH: 67
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 1231
atagcaagtt aaaataaggc tagtccgtta tcaacttgaa aaagtggcac cgagtcggtg     60
cttttt                                                               67

<210> SEQ ID NO 1232
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1232
tagcaagtta aaataaggct agtccgttat caacttgaaa agtggcacc gagtcggtgc      60 ttttt                                                                65

<210> SEQ ID NO 1233
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1233
atagcaagtt aaaataaggc tagtccgtta tcaacttgaa aaagtggcac cgagtcggtg     60
ctttt                                                                65

<210> SEQ ID NO 1234
<211> LENGTH: 20
<212> TYPE: RNA
<213> ORGANISM: Felis catus

<400> SEQUENCE: 1234
ggugucugga uuccagcuuu                                                 20

<210> SEQ ID NO 1235
<211> LENGTH: 20
<212> TYPE: RNA
<213> ORGANISM: Felis catus

<400> SEQUENCE: 1235
cuguucuuua caccuaaagc                                                 20

<210> SEQ ID NO 1236
<211> LENGTH: 20
<212> TYPE: RNA
<213> ORGANISM: Felis catus

<400> SEQUENCE: 1236
accuugccca gagugagacc                                                 20

<210> SEQ ID NO 1237
<211> LENGTH: 20
<212> TYPE: RNA
<213> ORGANISM: Felis catus

<400> SEQUENCE: 1237
ccaagagcca ggucucacuc                                                 20

```
<210> SEQ ID NO 1238
<211> LENGTH: 20
<212> TYPE: RNA
<213> ORGANISM: Felis catus

<400> SEQUENCE: 1238
gacuagucca uccaagaccc                                               20

<210> SEQ ID NO 1239
<211> LENGTH: 20
<212> TYPE: RNA
<213> ORGANISM: Felis catus

<400> SEQUENCE: 1239
cggacucuua uccagggucu                                               20

<210> SEQ ID NO 1240
<211> LENGTH: 20
<212> TYPE: RNA
<213> ORGANISM: Felis catus

<400> SEQUENCE: 1240
caaugcacga ccuguaguau                                               20

<210> SEQ ID NO 1241
<211> LENGTH: 20
<212> TYPE: RNA
<213> ORGANISM: Felis catus

<400> SEQUENCE: 1241
cuggcauuug ccaauacuac                                               20

<210> SEQ ID NO 1242
<211> LENGTH: 20
<212> TYPE: RNA
<213> ORGANISM: Felis catus

<400> SEQUENCE: 1242
aaaaaaaaaa uaaagugacc                                               20

<210> SEQ ID NO 1243
<211> LENGTH: 20
<212> TYPE: RNA
<213> ORGANISM: Felis catus

<400> SEQUENCE: 1243
aaaaaugaca gaagaggaua                                               20
```